US007981418B2

(12) United States Patent
Amler et al.

(10) Patent No.: US 7,981,418 B2
(45) Date of Patent: Jul. 19, 2011

(54) PREDICTING RESPONSE TO A HER INHIBITOR

(75) Inventors: Lukas C. Amler, Foster City, CA (US);
Merrill Birkner, Menlo Park, CA (US);
Chin-Yu Lin, Redwood City, CA (US);
Joachim Moecks, Mannheim (DE);
Andreas Strauss, Penzberg (DE)

(73) Assignees: Genentech, Inc., South San Francisco, CA (US); Hoffmann-La Roche Inc., Nutley, NJ (US)

( * ) Notice: Subject to any disclaimer, the term of this patent is extended or adjusted under 35 U.S.C. 154(b) by 397 days.

(21) Appl. No.: 12/074,229

(22) Filed: Mar. 1, 2008

(65) Prior Publication Data

US 2010/0008975 A1 Jan. 14, 2010

Related U.S. Application Data

(60) Provisional application No. 61/029,748, filed on Feb. 19, 2008, provisional application No. 60/912,053, filed on Apr. 16, 2007, provisional application No. 60/892,640, filed on Mar. 2, 2007.

(51) Int. Cl.
*A61K 39/395* (2006.01)
(52) U.S. Cl. .......................... 424/138.1; 435/6
(58) Field of Classification Search .................. None
See application file for complete search history.

(56) References Cited

U.S. PATENT DOCUMENTS

| 4,485,045 | A | * | 11/1984 | Regen |
| 4,544,545 | A | * | 10/1985 | Ryan et al. |
| 4,676,980 | A | * | 6/1987 | Segal et al. |
| 4,816,567 | A | * | 3/1989 | Cabilly et al. |
| 4,892,538 | A | * | 1/1990 | Aebischer et al. |
| 4,933,294 | A | * | 6/1990 | Waterfield et al. |
| 4,935,341 | A | * | 6/1990 | Bargmam et al. |
| 4,943,533 | A | * | 7/1990 | Mendelsohn et al. |
| 4,968,603 | A | * | 11/1990 | Slamon |
| 5,013,556 | A | * | 5/1991 | Woodle et al. |
| 5,183,884 | A | * | 2/1993 | Kraus et al. |
| 5,208,020 | A | * | 5/1993 | Chari et al. |
| 5,212,290 | A | * | 5/1993 | Vogelstein et al. |
| 5,229,275 | A | * | 7/1993 | Goroff |
| 5,264,586 | A | * | 11/1993 | Nicolaou et al. |
| 5,283,187 | A | * | 2/1994 | Aebischer et al. |
| 5,288,477 | A | * | 2/1994 | Bacus |
| 5,401,638 | A | * | 3/1995 | Carney et al. |
| 5,480,968 | A | * | 1/1996 | Kraus et al. |
| 5,500,362 | A | * | 3/1996 | Robinson et al. |
| 5,514,554 | A | * | 5/1996 | Bacus |
| 5,545,806 | A | * | 8/1996 | Lonberg et al. |
| 5,545,807 | A | * | 8/1996 | Surani et al. |
| 5,565,332 | A | * | 10/1996 | Hoogenboom et al. |
| 5,567,610 | A | * | 10/1996 | Borrebaeck et al. |
| 5,569,825 | A | * | 10/1996 | Lonberg et al. |
| 5,571,894 | A | * | 11/1996 | Wels et al. |
| 5,573,905 | A | * | 11/1996 | Lerner et al. |
| 5,587,458 | A | * | 12/1996 | King et al. |
| 5,589,369 | A | * | 12/1996 | Seldman et al. |
| 5,591,669 | A | * | 1/1997 | Krimpenfort et al. |
| 5,604,107 | A | * | 2/1997 | Carney et al. |
| 5,625,126 | A | * | 4/1997 | Lonberg et al. |
| 5,633,425 | A | * | 5/1997 | Lonberg et al. |
| 5,641,869 | A | * | 6/1997 | Vandlen et al. |
| 5,641,870 | A | * | 6/1997 | Rinderknetcht et al. |
| 5,648,237 | A | * | 7/1997 | Carter |
| 5,661,016 | A | * | 8/1997 | Lonberg et al. |
| 5,677,171 | A | * | 10/1997 | Hudziak et al. |
| 5,705,157 | A | * | 1/1998 | Greene |
| 5,712,374 | A | * | 1/1998 | Kuntsmann et al. |
| 5,714,586 | A | * | 2/1998 | Kunstmann et al. |
| 5,720,937 | A | * | 2/1998 | Hudziak et al. |
| 5,720,954 | A | * | 2/1998 | Hudziak et al. |
| 5,725,856 | A | * | 3/1998 | Hudziak et al. |
| 5,731,168 | A | * | 3/1998 | Carter et al. |
| 5,739,277 | A | * | 4/1998 | Presta et al. |
| 5,747,261 | A | * | 5/1998 | King et al. |
| 5,770,195 | A | * | 6/1998 | Hudziak et al. |
| 5,772,997 | A | * | 6/1998 | Hudziak et al. |
| 5,773,001 | A | * | 6/1998 | Hamann et al. |
| 5,783,186 | A | * | 7/1998 | Arakawa et al. |
| 5,783,404 | A | * | 7/1998 | Koski et al. |
| 5,804,396 | A | * | 9/1998 | Plowman et al. |
| 5,821,337 | A | * | 10/1998 | Carter et al. |
| 5,824,311 | A | * | 10/1998 | Greene et al. |
| 5,837,234 | A | * | 11/1998 | Gentile et al. |

(Continued)

FOREIGN PATENT DOCUMENTS

EP 404 097 A2 6/1990

(Continued)

OTHER PUBLICATIONS

Amler (Expert Opin Biol Ther, 2010, 10:1343-1355).*
Amler et al I (2008 ASCO Molecular Marker, abstract 25, 4 pages).*
Amler et al II (J Clinical Oncology, 2008, 26:May 20 suppl; abstract 5552, 4 pages).*
Bossenmaier et al (Proceedings Amer Cancer Res, 2004, vol. 45, abstract #5342, 2 pages).*
Genentech Press Release, Jan. 4, 2007, 3 pages.*
Aasland, R., et al., *Br. J. Cancer*-57:358-363 (1988).
Agus, D.B., et al., *Cancer Celll*-2:127-137 (2002).
Agus, D.B., et al., *Pro Am Soc Clin Oncol*-22:192 (2003).
Allison, D.E., et al, *Pro Am Soc Clin Oncol*-22:197 (2003).
Anderson, W.F., et al., *Science*-256:808-813 (1992).

(Continued)

*Primary Examiner* — Laura B Goddard
(74) *Attorney, Agent, or Firm* — Wendy M. Lee

(57) ABSTRACT

The present application describes the use of low HER3 as a selection criterion for treating patients with a HER inhibitor, such as pertuzumab.
It also describes the use of high HER2:HER3 ratio as a selection criterion for treating cancer patients, such as ovarian cancer patients, with a HER inhibitor, such as pertuzumab.
In addition, the application describes the use of high HER3 as a selection criterion for treating cancer patients with a chemotherapeutic agent, for instance gemcitabine.

64 Claims, 68 Drawing Sheets

U.S. PATENT DOCUMENTS

| | | | |
|---|---|---|---|
| 5,837,243 | A * | 11/1998 | Deo et al. |
| 5,846,749 | A * | 12/1998 | Slamon et al. |
| 5,856,089 | A * | 1/1999 | Wang et al. |
| 5,877,305 | A * | 3/1999 | Huston et al. |
| 5,891,996 | A * | 4/1999 | Mateo de Acosta de Rio et al. |
| 5,910,486 | A * | 6/1999 | Curiel et al. |
| 5,922,845 | A * | 7/1999 | Deo et al. |
| 5,925,519 | A * | 7/1999 | Jensen et al. |
| 5,939,531 | A * | 8/1999 | Wels et al. |
| 5,977,322 | A * | 11/1999 | Marks et al. |
| 5,985,553 | A * | 11/1999 | King et al. |
| 5,994,071 | A * | 11/1999 | Ross et al. |
| 6,015,567 | A * | 1/2000 | Hudziak et al. |
| 6,028,059 | A * | 2/2000 | Curiel et al. |
| 6,054,297 | A * | 4/2000 | Carter et al. |
| 6,075,181 | A * | 6/2000 | Kucherlapati et al. |
| 6,123,939 | A * | 9/2000 | Shawver et al. |
| 6,127,526 | A * | 10/2000 | Blank |
| 6,150,584 | A * | 11/2000 | Kucherlapati et al. |
| 6,165,464 | A * | 12/2000 | Hudziak et al. |
| 6,194,551 | B1 * | 2/2001 | Idusogie et al. |
| 6,214,388 | B1 * | 4/2001 | Benz et al. |
| 6,242,195 | B1 * | 6/2001 | Idusogie et al. |
| 6,267,958 | B1 * | 7/2001 | Andya et al. |
| 6,270,765 | B1 * | 8/2001 | Deo et al. |
| 6,333,169 | B1 * | 12/2001 | Hudziak et al. |
| 6,333,348 | B1 * | 12/2001 | Vogel et al. |
| 6,333,398 | B1 * | 12/2001 | Blank |
| 6,339,142 | B1 * | 1/2002 | Basey et al. |
| 6,358,682 | B1 * | 3/2002 | Jaffee et al. |
| 6,387,371 | B1 * | 5/2002 | Hudziak et al. |
| 6,395,272 | B1 * | 5/2002 | Deo et al. |
| 6,399,063 | B1 * | 6/2002 | Hudziak et al. |
| 6,403,630 | B1 * | 6/2002 | Dannenberg et al. |
| 6,407,213 | B1 * | 6/2002 | Carter et al. |
| 6,417,168 | B1 * | 7/2002 | Greene et al. |
| 6,417,335 | B1 * | 7/2002 | Basey et al. |
| 6,458,356 | B1 * | 10/2002 | Arakawa et al. |
| 6,489,447 | B1 * | 12/2002 | Basey et al. |
| 6,512,097 | B1 * | 1/2003 | Marks et al. |
| 6,528,624 | B1 * | 3/2003 | Idusogie et al. |
| 6,538,124 | B1 * | 3/2003 | Idusogie et al. |
| 6,573,043 | B1 * | 6/2003 | Cohen et al. |
| 6,582,919 | B2 * | 6/2003 | Dannenberg |
| 6,602,670 | B2 * | 8/2003 | Dannenberg |
| 6,602,684 | B1 * | 8/2003 | Umana et al. |
| 6,627,196 | B1 * | 9/2003 | Baughman et al. |
| 6,632,979 | B2 * | 10/2003 | Erickson et al. |
| 6,685,940 | B2 * | 2/2004 | Andya et al. |
| 6,719,971 | B1 * | 4/2004 | Carter et al. |
| 6,737,056 | B1 * | 5/2004 | Presta |
| 6,767,541 | B2 * | 7/2004 | Slamon et al. |
| 6,797,814 | B2 * | 9/2004 | Blank |
| 6,800,738 | B1 | 10/2004 | Carter et al. |
| 6,821,515 | B1 | 11/2004 | Cleland et al. |
| 6,982,321 | B2 | 1/2006 | Winter |
| 7,087,409 | B2 | 8/2006 | Barbas, III et al. |
| 2002/0004587 | A1 | 1/2002 | Miller et al. |
| 2002/0031515 | A1 | 3/2002 | Caligiuri et al. |
| 2002/0051785 | A1 | 5/2002 | Slamon et al. |
| 2002/0064785 | A1 | 5/2002 | Mass |
| 2002/0076408 | A1 | 6/2002 | Buchsbaum |
| 2002/0076695 | A1 | 6/2002 | Ross |
| 2002/0090662 | A1 | 7/2002 | Ralph |
| 2002/0136719 | A1 | 9/2002 | Shenoy et al. |
| 2002/0141993 | A1 | 10/2002 | Ashkenazi |
| 2002/0142328 | A1 | 10/2002 | Danenberg |
| 2002/0155527 | A1 | 10/2002 | Stuart et al. |
| 2002/0192211 | A1 | 12/2002 | Hudziak et al. |
| 2002/0192652 | A1 | 12/2002 | Danenberg et al. |
| 2003/0022918 | A1 | 1/2003 | Horak et al. |
| 2003/0059790 | A1 | 3/2003 | Jaffee et al. |
| 2003/0068318 | A1 | 4/2003 | O'Brien et al. |
| 2003/0086924 | A1 | 5/2003 | Sliwkowski, et al. |
| 2003/0103973 | A1 | 6/2003 | Rockwell et al. |
| 2003/0108545 | A1 | 6/2003 | Rockwell et al. |
| 2003/0134344 | A1 | 7/2003 | Mass |
| 2003/0144252 | A1 | 7/2003 | Furr |
| 2003/0147884 | A1 | 8/2003 | Paton et al. |
| 2003/0152572 | A1 | 8/2003 | Homma et al. |
| 2003/0152987 | A1 | 8/2003 | Cohen et al. |
| 2003/0157097 | A1 | 8/2003 | Noguchi et al. |
| 2003/0157108 | A1 | 8/2003 | Presta |
| 2003/0165840 | A1 | 9/2003 | Danenberg |
| 2003/0170234 | A1 | 9/2003 | Hellman |
| 2003/0175845 | A1 | 9/2003 | Kalbag |
| 2003/0190689 | A1 | 10/2003 | Crosby et al. |
| 2003/0202973 | A1 | 10/2003 | Pieczenik |
| 2003/0211530 | A1 | 11/2003 | Danenberg |
| 2003/0228663 | A1 | 12/2003 | Lowman et al. |
| 2004/0013667 | A1 | 1/2004 | Kelsey et al. |
| 2004/0082047 | A1 | 4/2004 | Emery et al. |
| 2004/0093621 | A1 | 5/2004 | Shitara et al. |
| 2004/0106161 | A1 | 6/2004 | Bossenmaier et al. |
| 2004/0132097 | A1 | 7/2004 | Bacus et al. |
| 2004/0138160 | A1 | 7/2004 | Naito et al. |
| 2004/0236078 | A1 * | 11/2004 | Carter et al. |
| 2004/0248151 | A1 * | 12/2004 | Bacus et al. |
| 2004/0258685 | A1 * | 12/2004 | Brunetta et al. |
| 2005/0002928 | A1 * | 1/2005 | Hellman |
| 2005/0014934 | A1 * | 1/2005 | Hinton et al. |
| 2005/0180970 | A1 * | 8/2005 | Ledbetter et al. |
| 2005/0186216 | A1 * | 8/2005 | Ledbetter et al. |
| 2006/0013819 | A1 * | 1/2006 | Kelsey ................ 424/155.1 |

FOREIGN PATENT DOCUMENTS

| | | |
|---|---|---|
| EP | 656 367 A1 | 8/1992 |
| EP | 616 812 A1 | 3/1993 |
| EP | 599 274 A1 | 11/1993 |
| EP | 659 439 A2 | 12/1994 |
| EP | 412 116 B1 | 11/1995 |
| EP | 494 135 B1 | 4/1996 |
| EP | 711 565 A1 | 5/1996 |
| EP | 502 812 B1 | 8/1996 |
| EP | 554 441 B1 | 1/1999 |
| EP | 1 006 194 A2 | 6/2000 |
| EP | 444 181 B1 | 10/2001 |
| EP | 1 357 132 A2 | 10/2003 |
| WO | WO 87/07646 | 12/1987 |
| WO | WO 89/10412 | 11/1989 |
| WO | WO 91/00360 | 1/1991 |
| WO | WO 91/02062 | 2/1991 |
| WO | WO 91/05264 | 4/1991 |
| WO | WO 91/10741 | 7/1991 |
| WO | WO 92/00373 | 1/1992 |
| WO | WO 93/03741 | 3/1993 |
| WO | WO 93/08829 | 5/1993 |
| WO | WO 93/11161 | 6/1993 |
| WO | WO 93/12220 | 6/1993 |
| WO | WO 93/16185 | 8/1993 |
| WO | WO 93/21232 | 10/1993 |
| WO | WO 93/21319 | 10/1993 |
| WO | WO 93/25673 | 12/1993 |
| WO | WO 94/00136 | 1/1994 |
| WO | WO 94/04690 | 3/1994 |
| WO | WO 94/11026 | 5/1994 |
| WO | WO 96/07321 | 3/1996 |
| WO | WO 96/16673 | 6/1996 |
| WO | WO 96/30347 | 10/1996 |
| WO | WO 96/33735 | 10/1996 |
| WO | WO 96/33978 | 10/1996 |
| WO | WO 96/33980 | 10/1996 |
| WO | WO 96/34096 | 10/1996 |
| WO | WO 96/40210 | 12/1996 |
| WO | WO 96/40789 | 12/1996 |
| WO | WO 97/00271 | 1/1997 |
| WO | WO 97/20858 | 6/1997 |
| WO | WO 97/30087 | 8/1997 |
| WO | WO 97/38731 | 10/1997 |
| WO | WO 97/38983 | 10/1997 |
| WO | WO 98/02463 | 1/1998 |
| WO | WO 98/17797 | 4/1998 |
| WO | WO 98/18489 | 5/1998 |
| WO | WO 98/24893 | 6/1998 |
| WO | WO 98/33914 | 8/1998 |
| WO | WO 98/43960 | 10/1998 |
| WO | WO 98/45479 | 10/1998 |

| | | |
|---|---|---|
| WO | WO 98/50433 | 11/1998 |
| WO | WO 98/58964 | 12/1998 |
| WO | WO 99/06378 | 2/1999 |
| WO | WO 99/06396 | 2/1999 |
| WO | WO 99/09016 | 2/1999 |
| WO | WO 99/19488 | 4/1999 |
| WO | WO 99/22764 | 5/1999 |
| WO | WO 99/31140 | 6/1999 |
| WO | WO 99/48527 | 9/1999 |
| WO | WO 99/51642 | 10/1999 |
| WO | WO 99/55367 | 11/1999 |
| WO | WO 00/42072 A3 | 7/2000 |
| WO | WO 00/61145 | 10/2000 |
| WO | WO 00/69460 | 11/2000 |
| WO | WO 00/78347 A1 | 12/2000 |
| WO | WO 01/00238 A1 | 1/2001 |
| WO | WO 01/00244 A2 | 1/2001 |
| WO | WO 01/00245 A2 | 1/2001 |
| WO | WO 01/05425 A2 | 1/2001 |
| WO | WO 01/09187 A2 | 2/2001 |
| WO | WO 01/15730 A1 | 3/2001 |
| WO | WO 01/20033 A1 | 3/2001 |
| WO | WO 01/21192 A2 | 3/2001 |
| WO | WO 01/32155 A2 | 5/2001 |
| WO | WO 01/53354 A2 | 7/2001 |
| WO | WO 01/56604 A1 | 8/2001 |
| WO | WO 01/64246 A2 | 9/2001 |
| WO | WO 01/76586 A1 | 10/2001 |
| WO | WO 01/76630 A1 | 10/2001 |
| WO | WO 01/87334 A1 | 11/2001 |
| WO | WO 01/87336 A1 | 11/2001 |
| WO | WO 01/89566 A1 | 11/2001 |
| WO | WO 02/05791 A2 | 1/2002 |
| WO | WO 02/09754 A1 | 2/2002 |
| WO | WO 02/11677 A2 | 2/2002 |
| WO | WO 02/44413 A2 | 6/2002 |
| WO | WO 02/45653 A2 | 6/2002 |
| WO | WO 02/055106 A2 | 7/2002 |
| WO | WO 02/087619 A1 | 7/2002 |
| WO | WO 02/070008 A1 | 9/2002 |
| WO | WO 02/089842 A1 | 11/2002 |
| WO | WO 03/006509 A2 | 1/2003 |
| WO | WO 03/011878 A2 | 2/2003 |
| WO | WO 03/012072 A2 | 2/2003 |
| WO | WO 03/028638 A2 | 4/2003 |
| WO | WO 03/041736 A2 | 5/2003 |
| WO | WO 03/086467 A1 | 10/2003 |
| WO | WO 03/087131 A2 | 10/2003 |
| WO | WO 04/000094 A2 | 12/2003 |
| WO | WO 2004/008099 A2 | 1/2004 |
| WO | WO 2004/024866 A2 | 3/2004 |
| WO | WO 2004/048525 A2 | 6/2004 |
| WO | WO 2004/053497 A2 | 6/2004 |
| WO | WO 2004/063709 A2 | 7/2004 |
| WO | WO 2004/087207 A2 | 10/2004 |
| WO | WO 2004/092219 | 10/2004 |
| WO | WO 2007/019899 A2 | 2/2007 |
| WO | WO 2008/064884 A1 | 6/2008 |

OTHER PUBLICATIONS

Arteaga, C.L., et al., *Cancer Research*-54:3758-3765 (1994).
Bacus, S.S., et al., *Cancer Research*-52:2580-2589 (1992).
Bacus, S.S., et al., *Molecular Carcinogenesis*-3:350-362 (1990).
Barbas, C.F., et al., *Proc Nat. Acad. Sci, USA*-91:3809-3813 (1994).
Baselga, J., et al., *Pharmac. Ther.*-64:127-154 (1994).
Baselga, J., et al., *J. Clin. Oncol.*-14(3):737-744 (1996).
Boerner, P., et al., *J. Immunol.*-147(1):86-95 (1991).
Borst, M.P., et al., *Gynecol. Oncol.*-38:364-366 (1990).
Brennan, M., et al., *Science*-229:81-83 (1985).
Brenner, S., et al., *Nature Biotechnology*-18:630-634 (2000).
Brodeur, B.R., et al., *Monoclonal Antibody Production Techniques and Applications*, pp. 51-63 (Marcel Dekker, Inc., New York, 1987).
Bruggemann, M., et al., *Year in Immuno.*-7:33-40 (1993).
Capel, P.J.A., et al., *Immunomethods*-4:25-34 (1994).
Caron, P.C., et al., *J. Exp. Med.*-176:1191-1195 (1992).
Carpenter, G., *Ann. Rev. Biochem.*-56:881-914 (1987).
Carraway, K.L., et al., *Nature*-387:512-516 (1997).
Carraway, K.L., et al., *Cell*-78:5-8 (1994).
Carter, P., et al., *Bio/Technology*-10:163-167 (1992).
Carter, P., et al., *Proc. Natl. Acad. Sci. USA*, 89:4285-4289 (1992).
Chang, H., et al., *Nature*-387:509-512 (1997).
Chari, R.V.J., et al., *Cancer Research*-52:127-131 (1992).
Cho, H-S., et al., *Nature*-421:756-760 (2003).
Chothia, C., et al., *J. Mol. Biol.*,-196:901-917 (1987).
Clackson, T., et al., *Nature*-352:624-628 (1991).
Clynes, R., et al., *PNAS (USA)*-95:652-656 (1998).
Cohen, J.A., et al., *Oncogene*-4:81-88 (1989).
Cook, P.W., et al., *Mol. Cell. Biol.*-11(5):2547-2557 (1991).
Cronin, M., et al., *Am. J. Pathol.*-164(1):35-42 (2004).
Cunningham, B.C., et al., *Science*-244:1081-1085 (1989).
Daëron, M., *Annu. Rev. Immunol.*-15:203-234 (1997).
De Andrés, B., et al., *BioTechniques*-18:42-44 (1995).
De Haas, M.,-et al., *J. Lab. Clin. Med.*-126:330-341 (1995).
Dieffenbach, C.W., et al., "General Concepts for PCR Primer Design" in *PCR Primer, A Laboratory Manual*, Cold Spring Harbor Laboratory Press, New York, 1995, pp. 133-155.
Drebin, J.A., et al., *Oncogene*-2:273-277 (1988).
Drebin, J.A., et al., *Cell*-41:695-706 (1985).
D'Souza, B., et al., *Proc. Natl. Acad. Sci. USA*-91:7202-7206 (1994).
Earp, H.S., et al., *Breast Cancer Research and Treatment*-35:115-132 (1995).
Epstein, D.A., et al., *Proc. Natl. Acad. Sci. USA*-82:3688-3692 (1985).
Falls, D.L., et al., *Cell*-72:801-815 (1993).
Fellouse, F.A., *Proc. Nat. Acad. Sci. USA*-101(34):12467-12472 (2004).
Fendly, B.M., et al., *Cancer Research*-50:1550-1558 (1990).
Fishwild, D.M., et al., *Nature Biotechnology*-14:845-851 (1996).
Franklin, M.C., et al., *Cancer Cell*-5:317-328 (2004).
Fukushige, S-I., et al., *Mol Cell Biol.*-6(3):955-958 (1986).
Gabizon, A., et al., *J. National Cancer Inst.*-81(19):1484-1488 (1989).
Garrett, T.P.J., et al., *Mol. Cell*-11:495-505 (2003).
Gazzano-Santoro, H., et al., *J. Immunol. Methods*-202:163-171 (1997).
Ghetie, V., et al., *Immunol. Today*-18(12):592-598 (1997).
Ghetie, V., et al., *Nature Biotechnology*-15(7):637-640 (1997).
Godfrey, T.E., et al., *J. Molec. Diagnostics*-2(2):84-91 (2000).
Goding, *Monoclonal Antibodies: Principles and Practice*, pp. 59-103 (Academic Press, 1986).
Griffiths, A.D., et al., *EMBO J.*-12(2):725-734 (1993).
Groenen, L.C., et al., *Growth Factors*-11:235-257 (1994).
Gruber, M., et al, *J. Immunol.*-152:5368-5374 (1994).
Gu, K., et al., *Cancer Lett.*-99:185-189 (1996).
Guerin, M., et al., *Oncogene Res.*-3:21-31 (1988).
Guyer, R.L., et al., *J. Immunol.*-117(2):587-595 (1976).
Hammerling, G.J., et al., in: *Monoclonal Antibodies and T-Cell Hybridomas* 563-587 (Elsevier, N.Y., 1981).
Hancock, M.C., et al., *Cancer Research*-51:4575-4580 (1991).
Harari, D., et al., *Oncogene*-18:2681-2689 (1999).
Harari , D., et al., *Oncogene*-19:6102-6114 (2000).
Harris, W.J., *Biochem. Soc. Transactions*-23:1035-1038 (1995).
Harwerth, I-M., et al., *J. Biol. Chem.*-267(21)15160-15167 (1992).
Hawkins, R.E., et al., *J. Mol. Biol.*-226:889-896 (1992).
Heid, C.A., et al., *Genome Research*-6:986-994 (1996).
Higashiyama, S., et al., *Science*-251:936-939 (1991).
Hinman, L.M., et al., *Cancer Research*-53:3336-3342 (1993).
Hinton, P.R., et al., *J. Biol. Chem.*-279(8):6213-6216 (2004).
Ho, W-H., et al., *J. Biol. Chem.*-270(24):14523-14532 (1995).
Hod, Y., *Biotechniques*-13(6):852-853 (1992).
Hollinger, P., et al., *Proc. Natl. Acad. Sci. USA*-90:6444-6448 (1993).
Holmes, W.E., et al., *Science*-256:1205-1210 (1992).
Hongo, J.S., et al., *Hybridoma*,-14 (3):253-260 (1995).
Hoogenboom, H.R., et al.,, *J. Mol. Biol.*-227:381-388 (1992).
Hudson, P.J., et al., *Nat. Med.*-9(1):129-134 (2003).
Hudziak, R.M. et al., *Mol. Cell. Biol.*-9(3):1165-1172 (1989).
Hudziak, R.M., et al., *Proc. Natl. Acad. Sci. USA*-84:7159-7163 (1987).
Humphrey, P.A., et al., *PNAS (USA)*-87:4207-4211 (1990).
Hwang, K.J., et al., *Proc. Natl. Acad. Sci. USA*-77(7):4030-4034 (1980).

Idusogie, E.E., et al., *J. Immunol.*-164:4178-4184 (2000).
Innis, M.A., et al., *PCR Protocols*-3-11(1990).
Jackson, J.R., et al., *J. Immunol.*-154(7):3310-3319 (1995).
Jakobovits, A., et al., *Nature*-362:255-258 (1993).
Jakobovits, A., et al., *Proc. Natl. Acad. Sci. USA*-90:2551-2555 (1993).
Jazaeri, A.A.,et al., *Clin. Cancer Res.*-11(17):6300-6310 (2005).
Johns, T.G., et al., *J. Biol. Chem.*-279(29):30375-30384 (2004).
Johnson, K.S.,et al., *Current Opinion in Structural Biology*-3:564-571 (1993).
Jones, P.T., et al., *Nature*-321:522-525 (1986).
Kabat, E.A., et al., *Sequences of Proteins of Immunological Interest*, Fifth Edition, National Institute of Health, Bethesda, MD (1991) (647-669).
Kannan, S., et al., *J. Biol. Chem.*-272(6):3330-3335 (1997).
Kasprzyk, P.G., et al., *Cancer Research*-52:2771-2776 (1992).
Kent, W.J., *Genome Res.*-12(4):656-664 (2002).
Kern, J.A., et al., *Cancer Research*-50:5184-5191 (1990).
Kim, J-K., et al., *J. Immunol.*-24:2429-2434 (1994).
Kimura, H., et al., *Nature*-348:257-260 (1990).
King, C.R., et al., *Science*-299:974-976 (1985).
Klapper, L.N.,et al., *Oncogene*-14:2099-2109 (1997).
Kohler, et al., *Nature*-256:495-497 (1975).
Komurasaki, T., et al., *Oncogene*-15:2841-2848 (1997).
Kostelny, S.A., et al., *J. Immunol.*-148(5):1547-1553(1992).
Kotts, C,E,., et al., *In Vitro*-26(3):59A (1990).
Kozbor, D., et al., *J. Immunol.*-133(6):3001-3005 (1984).
Kraus, M.H., et al., *PNAS (USA)*-86:9193-9197 (1989).
Kumar, R., et al., *Mol. Cell. Biol.*-11(2):979-986 (1991).
Lee, C.V., et al., *J. Immunol. Methods*-284:119-132 (2004).
Lee, D.C., et al., *Pharm. Rev.*-47(1):51-85 (1995).
Lee, C.V., et al., *J. Mol. Biol.*-340:1073-1093 (2004).
Lehninger, A.L., in *Biochemistry*, second ed., pp. 73-75, Worth Publishers, New York (1975).
Lemke, G., *Molec. & Cell. Neurosci.*-7:247-262 (1996).
Levi, A.D.O., et al., *Journal of Neuroscience*-15(2):1329-1340 (1995).
Lewis, G.D., et al., *Cancer Immunol. Immunother.*-37:255-263 (1993).
Lewis, G.D., et al., *Cancer Research*-56:1457-1465 (1996).
Li, J.,et al., *Proc. Natl. Acad. Sci. USA*-103(10):3557-3562 (2006).
Lode, H.N., et al., *Cancer Research*-58:2925-2928 (1998).
Lonberg, N., et al., Intern. Rev. Immunol.,-13:65-93 (1995).
Lonberg, N., et al., *Nature*-368:856-859 (1994).
Ma, X-J., et al., *Cancer Cell*-5:607-616 (2004).
Maier, L.A., et al., *Cancer Research*-51:5361-5369 (1991).
Malik, M.A., et al. *Pro Am Soc Cancer Res*-44:150 (2003).
Marchionni, M.A., et al., *Nature*-362:312-318 (1993).
Marks, J.D., et al., *Bio/Technology*-10:779-783 (1992).
Marks, J.D., et al., *J. Mol. Biol.*-222:581-597 (1991).
Marquardt et al., *Science*-223:1079-1082 (1984).
Martin, F.J., et al., *J. Biol. Chem.*-257(1):286-288 (1982).
Masui, H., et al., *Cancer Research*-44:1002-1007 (1984).
McCafferty, J., et al., *Nature*-348:552-554 (1990).
McCann, A., et al., *Cancer*-65:88-92 (1990).
McKenzie, S.J., et al., *Oncogene*-4:543-548 (1989).
Milstein, C., et al., *Nature*-305(6):537-540 (1983).
Misener, S., et al., *Bioinformatics Methods and Protocols: Methods in Molecular Biology.* Humana Press, Totowa, N.J., pp. 365-386 (2000).
Molina, M.A., et al., *Cancer Research*-61:4744-4749 (2001).
Morimoto, K., et al., *Journal of Biochemical and Biophysical Methods*-24:107-117 (1992).
Morrison, S.L., et al., *Proc. Natl. Acad. Sci., USA*-81:6851-6855 (1984).
Morrison, S.L., *Nature*-368:812-813 (1994).
Morrissey, T.K., et al., *Proc. Natl. Acad. Sci. USA*-92:1431-1435 (1995).
Mullis, K., et al., *Cold Spring Harbor Symp. Quant. Biol.*-51: 263-273 (1987).
Munson, P.J., et al., *Anal. Biochem.*-107:220-239 (1980).
Myers, J.N., et al., *Metho. Enzym.*-198:277-290 (1991).
Neuberger, M., *Nature Biotechnology*-14:826 (1996).

Nicolaou, K.C., et al., *Angew. Chem Intl. Ed. Engl.*-33(2):183-186 (1994).
Park, J-B., et al., *Cancer Research*-49:6605-6609 (1989).
Parker, R.M.C., et al., *Methods in Molecular Biology*-106:247-283 (1999).
Peles, E., et al., *Cell*-69:205-216 (1992).
Pietras, R.J., et al., *Oncogene*-9:1829-1838 (1994).
Plasterer, T. N., Primerselect: Primer and probe design. *Methods Mol. Biol.*-70:291-302 (1997).
Plowman, G.D., et al., *Proc. Natl. Acad. Sci.*, USA-90:1746-1750 (1993).
Plowman, G.D., et al., *Nature*-366:473-475 (1993).
Plückthun, A., *Immunol. Revs.*,-130:151-188 (1992).
Pluckthün, A., in *The Pharmacology of Monoclonal Antibodies*, vol. 113, Rosenburg and Moore eds., (Springer-Verlag, New York, 1994), pp. 269-315.
Presta, L.G., et al., *J. Immunol.*,-151(5):2623-2632 (1993).
Presta, L.G., *Curr. Op. Struct. Biol.*-2:593-596 (1992).
Ravetch, J.V., et al., *Annu. Rev. Immunol.*-9:457-492 (1991).
Riechmann, L., et al., *Nature*-332:323-327 (1988).
Ross, J.S., et al., *Cancer*-79(11):2162-2170 (1997).
Ross, J.S., et al., *Hum. Pathol.*-28(7):827-833 (1997).
Rupp, G., et al., *Lab Invest.*-56:A67 (1987).
Sadasivan, R., et al., *J. Urol.*-150:126-131 (1993).
Sarup, J.C., et al., *Growth Regulation*-1:72-82 (1991).
Sasada, R., et al., *Biochem. Biophys. Res. Commun.*-190(3):1173-1179 (1993).
Savage, C.R., et al., *J. Biol. Chem.*-247(23):7612-7621 (1972).
Schaefer, G., et al., *Oncogene*-5:1385-1394 (1997).
Schier, R., et al., *Gene*-169:147-155 (1996).
Schena, M., et al., *Proc. Natl. Acad. Sci. USA*-93(2):10614-10619 (1996).
Scott, G.K., et al., *J. Biol. Chem.*-266(22):14300-14305 (1991).
Semba, K., et al., *PNAS (USA)*-82:6497-6501 (1985).
Shalaby, M.R., et al., *J. Exp. Med.*,-175:217-225 (1992).
Shawver, L.K., et al., *Cancer Research*-54:1367-1373 (1994).
Shepard, H.M., et al., *J. Clin. Immunol.*-11(3):117-127 (1991).
Shields, R.L., et al., *J. Biol. Chem.*-9(2):6591-6604 (2001).
Shing, Y., et al., *Science*-259:1604-1607 (1993).
Shopes, B., *J. Immunol.*-148(9):2918-2922 (1992).
Shoyab, M., et al., *Science*-243:1074-1076 (1989).
Sias, P.E., et al., *J. Immunol. Methods*-132:73-80 (1990).
Sidhu, S.S., et al., *J. Mol. Biol.*-338:299-310 (2004).
Sims, M.J., et al., *J. Immunol.*, 151(4):2296-2308 (1993).
Skerra, A., *Curr. Opinion in Immunol.*, 5:256-262 (1993).
Slamon, D.J., et al., *Science*-235:177-182 (1987).
Slamon, D.J., et al., *Science*-244:707-712 (1989).
Sliwkowski, M.X., *Nat Struct Biol*-10(3):158-159 (2003).
Sliwkowsk, M.X., et al., *J. Biol. Chem.*,-269(20):14661-14665 (1994).
Specht, K., et al., Am. *J. Pathol.*-158(2):419-429 (2001).
Stancovski, I., et al., *PNAS (USA)*-88:8691-8695 (1991).
Stevenson, G.T., et al., *Anti-Cancer Drug Design*-3:219-230 (1989).
Stragliotto, G., et al., *Eur. J. Cancer*-32A(4):636-640 (1996).
Suresh, M.R., et al., *Methods in Enzymology*-121:210-228 (1986).
Tagliabue, E., et al., *Int. J. Cancer*-47:933-937 (1991).
Tanner, B., et al., *J. Clin. Oncol.*-24(26):4317-4323 (2006).
Toyoda, H., et al., *J. Biol. Chem.*-270(13):7495-7500 (1995).
Traunecker, A., et al., *EMBO J.*-10(12):3655-3659 (1991).
Tutt, A., et al., *J. Immunol.*-147(1):60-69 (1991).
van Dijk, M.A., et al., *Curr. Opin. Pharmacol.*-5:368-74 (2001).
Vaswani, S.K., *Ann. Allergy, Asthma & Immunol.*-81:105-119 (1998).
Velculescu, V.E., et al., *Science*-270:484-487 (1995).
Velculescu, V.E., et al., *Cell*-88:243-51 (1997).
Verhoeyen, M., et al., *Science*-239:1534-1536 (1988).
Vitetta, E.S., et al., *Cancer Research*-54:5301-5309 (1994).
Vitetta, E.S., et al., *Science*-238:1098-1104 (1987).
Wagner, E., et al., *Proc. Natl. Acad. Sci. USA*-87:3410-3414 (1990).
Waterhouse, P., et al., *Nuc. Acids. Res.*,-21(9):2265-2266 (1993).
Weiner, D.B., et al., *Cancer Research*-50:421-425 (1990).
Weis et al., *Trends in Genetics*-8:263-264 (1992).

Williams, T.M., et al., *Pathobiology*-59:46-52 (1991).
Wolff, E.A., et al., *Cancer Research*-53:2560-2565 (1993).
Wu, X., et al, *J. Clin. Inves.*-95:1897-1905 (1995).
Wu, G.Y., et al., *J. Biol. Chem.*-262(10):4429-4432 (1987).
Xu, F., et al., *Int. J. Cancer*-53:401-408 (1993).
Yamamoto, T., et al., *Nature*-319:230-234 (1986).
Yarden, Y., et al., *Nat Rev Mol Cell Biol*-2:127-137 (2001).

Yelton, D.E., et al., *J. Immunol.*-155:1994-2004 (1995).
Yokota, J., et al., *Lancer*-1:765-767 (1986).
Yonemura, Y., et al., *Cancer Research*-51:1034-1038 (1991).
Zhang, D., et al., *PNAS (USA)*-94:9562-9567 (1997).
Zhau, H.E., et al., *Mol. Carcinog.*,-3:254-257 (1990).

\* cited by examiner

Variable Light

```
              10             20             30             40
2C4    DIVMTQSHKIMSTSVGDRVSITC [KASQDVSIGVA] WYQQRP
       **     ****  *         *                    *
574    DIQMTQSPSSLSASVGDRVTITC [KASQDVSIGVA] WYQQKP
                                  ** ***
hum kI DIQMTQSPSSLSASVGDRVTITC [RASQSISNYLA] WYQQKP 50             60             70             80
2C4    GQSPKLLIY [SASYRYT] GVPDRFTGSGSGTDFTFTISSVQA
       **                      *              *  *
574    GKAPKLLIY [SASYRYT] GVPSRFSGSGSGTDFTLTISSLQP
                 * *****
hum kI GKAPKLLIY [AASSLES] GVPSRFSGSGSGTDFTLTISSLQP 90             100
2C4    EDLAVYYC [QQYYIYPYT] FGGGTKLEIK  (SEQ ID NO:1)
       * *                    *   *
574    EDFATYYC [QQYYIYPYT] FGQGTKVEIK  (SEQ ID NO:3
                  *** *
hum kI EDFATYYC [QQYNSLPWT] FGQGTKVEIK  (SEQ ID NO:5)
```

FIG. 2A

Variable Heavy

```
               10             20             30             40
2C4     EVQLQQSGPELVKPGTSVKISCKAS [GFTFTDYTMD] WVKQS
        **    **  *    ***     *                * *
574     EVQLVESGGGLVQPGGSLRLSCAAS [GFTFTDYTMS] WVRQA
                                      ** * *
hum III EVQLVESGGGLVQPGGSLRLSCAAS [GFTFSSYAMS] WVRQA 50    a         60             70             80
2C4     HGKSLEWIF [DVNPNSGGSIYNQRFKG] KASLTVDRSSRIVYM
        *   *  **                     *** *    **** *
574     PGKGLEWVA [DVNPNSGGSIYNQRFKG] RFTLSVDRSKNTLYL
                   ****** *** ****      *  *
hum III PGKGLEWVA [VISGDGGSTYYADSVKG] RFTISRDNSKNTLYL abc    90             100ab          110
2C4     ELRSLTFEDTAVYYCAR [NLGPSFYFDY] WGQGTTLTVSS (SEQ ID NO:2)
        ***  **                         **
574     QMNSLRAEDTAVYYCAR [NLGPSFYFDY] WGQGTLVTVSS (SEQ ID NO:4)
                           *******
hum III QMNSLRAEDTAVYYCAR [GRVGYSLYDY] WGQGTLVTVSS (SEQ ID NO:6)
```

FIG. 2B

Amino Acid Sequence for Pertuzumab Light Chain

```
  1         10        20        30        40        50        60
  |         |         |         |         |         |         |
DIQMTQSPSSLSASVGDRVTITCKASQDVSIGVAWYQQKPGKAPKLLIYSASYRYTGVPS 70        80        90       100       110       120
            |         |         |         |         |         |
RFSGSGSGTDFTLTISSLQPEDFATYYCQQYYIYPYTFGQGTKVEIKRTVAAPSVFIFPP 130       140       150       160       170       180
            |         |         |         |         |         |
SDEQLKSGTASVVCLLNNFYPREAKVQWKVDNALQSGNSQESVTEQDSKDSTYSLSSTLT 190       200       210
            |         |         |
LSKADYEKHKVYACEVTHQGLSSPVTKSFNRGEC
```

FIG. 3A

Amino Acid Sequence for Pertuzumab Heavy Chain

```
  1         10        20        30        40        50        60
  |         |         |         |         |         |         |
EVQLVESGGGLVQPGGSLRLSCAASGFTFTDYTMDWVRQAPGKGLEWVADVNPNSGGSIY 70        80        90       100       110       120
            |         |         |         |         |         |
NQRFKGRFTLSVDRSKNTLYLQMNSLRAEDTAVYYCARNLGPSFYFDYWGQGTLVTVSSA 130       140       150       160       170       180
            |         |         |         |         |         |
STKGPSVFPLAPSSKSTSGGTAALGCLVKDYFPEPVTVSWNSGALTSGVHTFPAVLQSSG 190       200       210       220       230       240
            |         |         |         |         |         |
LYSLSSVVTVPSSSLGTQTYICNVNHKPSNTKVDKKVEPKSCDKTHTCPPCPAPELLGGP 250       260       270       280       290       300
            |         |         |         |         |        *|
SVFLFPPKPKDTLMISRTPEVTCVVVDVSHEDPEVKFNWYVDGVEVHNAKTKPREEQYNS 310       320       330       340       350       360
            |         |         |         |         |         |
TYRVVSVLTVLHQDWLNGKEYKCKVSNKALPAPIEKTISKAKGQPREPQVYTLPPSREEM 370       380       390       400       410       420
            |         |         |         |         |         |
TKNQVSLTCLVKGFYPSDIAVEWESNGQPENNYKTTPPVLDSDGSFFLYSKLTVDKSRWQ 430       440       448
            |         |         |
QGNVFSCSVMHEALHNHYTQKSLSLSPG
```

FIG. 3B

TRASTUZUMAB
HERCEPTIN
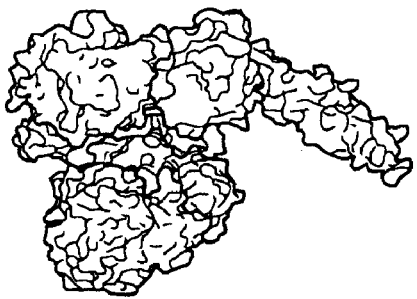
- Binds in IV near JM
- Protects against receptor shedding
- Moderately affects receptor down-modulation
- Slight effect on HER2's role as a coreceptor
PERTUZUMAB
OMNITARG
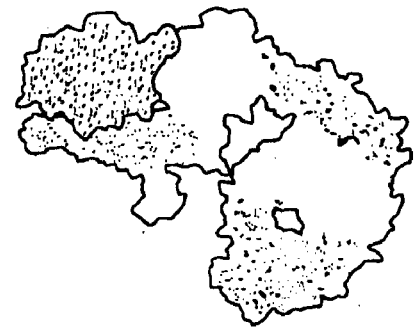
- Binds in II at dimerization interface
- Does not prevent receptor shedding
- Moderately affects receptor down-modulation
- Major effect on HER2's role as a coreceptor
FIG. 6

LIGHT CHAIN

```
1                15                  30                    45
DIQMTQSPSSLSASVGDRVTITCRASQDVNTAVAWYQQKPGKAPK
46               60                  75                    90
LLIYSASFLYSGVPSRFSGSRSGTDFTLTISSLQPEDFATYYCQQ
91              105                 120                   135
HYTTPPTFGQGTKVEIKRTVAAPSVFIFPPSDEQLKSGTASVVCL
136             150                 165                   180
LNNFYPREAKVQWKVDNALQSGNSQESVTEQDSKDSTYSLSSTLT
181             195                 210      214
LSKADYEKHKVYACEVTHQGLSSPVTKSFNRGEC
```

FIG. 7A

HEAVY CHAIN

```
1                           15                          30                          45
EVQLVESGGGLVQPGGSLRLSCAASGFNIKDTYIHWVRQAPGKGL 46                          60                          75                          90
EWVARIYPTNGYTRYADSVKGRFTISADTSKNTAYLQMNSLRAED 91                          105                         120                         135
TAVYYCSRWGGDGFYAMDYWGQGTLVTVSSASTKGPSVFPLAPSS 136                         150                         165                         180
KSTSGGTAALGCLVKDYFPEPVTVSWNSGALTSGVHTFPAVLQSS 181                         195                         210                         225
GLYSLSSVVTVPSSSLGTQTYICNVNHKPSNTKVDKKVEPKSCDK 226                         240                         255                         270
THTCPPCPAPELLGGPSVFLFPPKPKDTLMISRTPEVTCVVVDVS 271                         285                         300                         315
HEDPEVKFNWYVDGVEVHNAKTKPREEQYNSTYRVVSVLTVLHQD 316                         330                         345                         360
WLNGKEYKCKVSNKALPAPIEKTISKAKGQPREPQVYTLPPSREE 361                         375                         390                         405
MTKNQVSLTCLVKGFYPSDIAVEWESNGQPENNYKTTPPVLDSDG 406                         420                         435                         449
SFFLYSKLTVDKSRWQQGNVFSCSVMHEALHNHYTQKSLSLSPG
```

FIG. 7B

```
1                                15                               30                              45
VHSDIQMTQSPSSLSASVGDRVTITCKASQDVSIGVAWYQQKPGK 46                               60                               75                              90
APKLLIYSASYRYTGVPSRFSGSGSGTDFTLTISSLQPEDFATYY 91                               105                              120                             135
CQQYYIYPYTFGQGTKVEIKRTVAAPSVFIFPPSDEQLKSGTASV 136                              150                              165                             180
VCLLNNFYPREAKVQWKVDNALQSGNSQESVTEQDSKDSTYSLSS 181                              195                              210         217
TLTLSKADYEKHKVYACEVTHQGLSSPVTKSFNRGEC
```

FIG. 8A

```
  1 EVQLVESGGGLVQPGGSLRLSCAASGFTFTDYTMDWVRQAPGKGL
 46 EWVADVNPNSGGSIYNQRFKGRFTLSVDRSKNTLYLQMNSLRAED
 91 TAVYYCARNLGPSFYFDYWGQGTLVTVSSASTKGPSVFPLAPSSK
136 STSGGTAALGCLVKDYFPEPVTVSWNSGALTSGVHTFPAVLQSSG
181 LYSLSSVVTVPSSSLGTQTYICNVNHKPSNTKVDKKVEPKSCDKT
226 HTCPPCPAPELLGGPSVFLFPPKPKDTLMISRTPEVTCVVVDVSH
271 EDPEVKFNWYVDGVEVHNAKTKPREEQYNSTYRVVSVLTVLHQDW
316 LNGKEYKCKVSNKALPAPIEKTISKAKGQPREPQVYTLPPSREEM
361 TKNQVSLTCLVKGFYPSDIAVEWESNGQPENNYKTTPPVLDSDGS
406 FFLYSKLTVDKSRWQQGNVFSCSVMHEALHNHYTQKSLSLSPGK
```

FIG. 8B

Note: Dx (+): the Amphi, Her2, Her3 sum score ≥ 70th percentile, Dx (-): Others

Note: Dx (+): the Amphi, Her2, Her3 sum score ≥ 70th percentile, Dx (-): Others

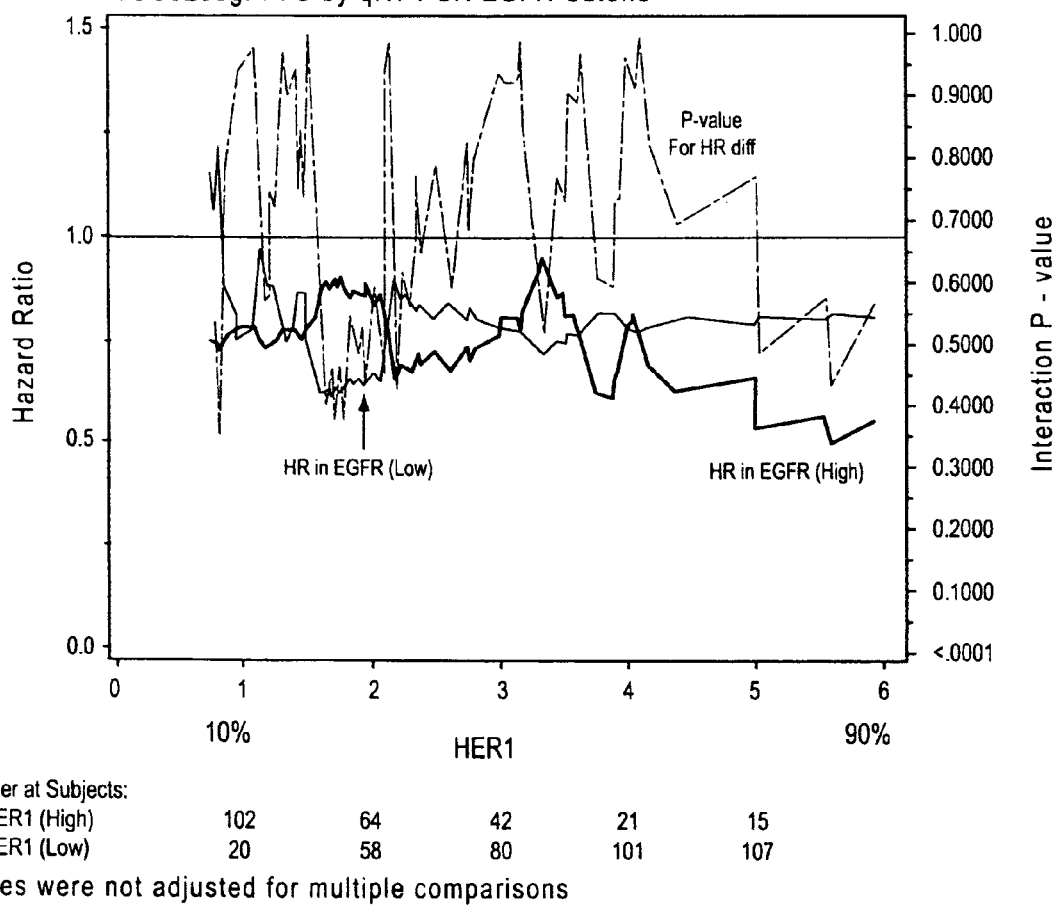

P-values were not adjusted for multiple comparisons

P-values were not adjusted for multiple comparisons

P-values were not adjusted for multiple comparisons

FIG. 17A

| Cutoff | | High HER3 Expression | | | | Low HER3 Expression | | | |
|---|---|---|---|---|---|---|---|---|---|
| %tile | Abs. Value | N | # Events | HR (95%CI) | Logrank P-value | N | # Events | HR (95%CI) | Logrank P-value |
| 20 | 0.99 | 96 | 78 | 1.06 (0.67, 1.65) | 0.8083 | 23 | 16 | 0.09 (0.02, 0.42) | 0.0002 |
| KM → | 1.19 | 91 | 73 | 1.13 (0.71, 1.81) | 0.5875 | 28 | 21 | 0.13 (0.04, 0.45) | 0.0002 |
| 30 | 1.4 | 84 | 66 | 1.28 (0.77, 2.10) | 0.3318 | 35 | 28 | 0.18 (0.06, 0.52) | 0.0004 |
| 35 | 1.57 | 78 | 62 | 1.49 (0.89, 2.51) | 0.1280 | 41 | 32 | 0.16 (0.06, 0.43) | <.0001 |
| 40 | 1.71 | 72 | 58 | 1.55 (0.90, 2.68) | 0.1141 | 47 | 36 | 0.19 (0.08, 0.47) | <.0001 |
| 45 | 1.88 | 66 | 54 | 1.64 (0.94, 2.88) | 0.0817 | 53 | 40 | 0.23 (0.11, 0.50) | <.0001 |
| KM → | 2.28 | 60 | 48 | 1.60 (0.89, 2.87) | 0.1161 | 59 | 46 | 0.30 (0.16, 0.58) | 0.0002 |
| 55 | 2.41 | 54 | 42 | 1.87 (0.97, 3.57) | 0.0565 | 65 | 52 | 0.36 (0.20, 0.65) | 0.0005 |
| 60 | 2.8 | 48 | 37 | 1.88 (0.92, 3.84) | 0.0766 | 71 | 57 | 0.47 (0.27, 0.81) | 0.0060 |
| 65 | 3.14 | 42 | 31 | 1.72 (0.78, 3.75) | 0.1693 | 77 | 63 | 0.57 (0.34, 0.95) | 0.0299 |
| 70 | 3.59 | 36 | 25 | 1.67 (0.72, 3.90) | 0.2270 | 83 | 69 | 0.62 (0.38, 1.00) | 0.0488 |
| 75 | 3.8 | 30 | 19 | 2.00 (0.71, 5.62) | 0.1790 | 89 | 75 | 0.67 (0.42, 1.06) | 0.0898 |
| 80 | 4.29 | 24 | 16 | 2.85 (0.89, 9.20) | 0.0667 | 95 | 78 | 0.59 (0.37, 0.92) | 0.0196 |

FIG. 17B

| Cutoff Value | | High HER3 Expression | | | | Low HER3 Expression | | | |
|---|---|---|---|---|---|---|---|---|---|
| %tile | Abs. Value | N | # Events | HR (95%CI) | Logrank P-value | N | # Events | HR (95%CI) | Logrank P-value |
| KM → | 1.19 | 92 | 74 | 1.16 (0.73, 1.84) | 0.5222 | 30 | 23 | 0.13 (0.04, 0.41) | <.0001 |
| 30 | 1.39 | 86 | 68 | 1.20 (0.74, 1.94) | 0.4674 | 36 | 29 | 0.22 (0.09, 0.56) | 0.0005 |
| 35 | 1.56 | 80 | 64 | 1.37 (0.83, 2.26) | 0.2230 | 42 | 33 | 0.20 (0.09, 0.48) | <.0001 |
| 40 | 1.70 | 74 | 59 | 1.50 (0.88, 2.55) | 0.1381 | 48 | 38 | 0.22 (0.10, 0.50) | <.0001 |
| 45 | 1.87 | 68 | 55 | 1.50 (0.87, 2.61) | 0.1468 | 54 | 42 | 0.29 (0.14, 0.58) | 0.0002 |
| KM → 2.24 | | 61 | 49 | 1.48 (0.83, 2.63) | 0.1809 | 61 | 48 | 0.34 (0.18, 0.63) | 0.0004 |
| 55 | 2.38 | 56 | 44 | 1.74 (0.93, 3.27) | 0.0816 | 66 | 53 | 0.36 (0.20, 0.65) | 0.0005 |
| 60 | 2.75 | 49 | 38 | 1.81 (0.90, 3.67) | 0.0945 | 73 | 59 | 0.48 (0.28, 0.84) | 0.0080 |
| 65 | 3.08 | 43 | 32 | 1.78 (0.82, 3.86) | 0.1382 | 79 | 65 | 0.56 (0.34, 0.94) | 0.0255 |
| 70 | 3.56 | 37 | 26 | 1.73 (0.75, 3.99) | 0.1943 | 85 | 71 | 0.62 (0.38, 1.00) | 0.0459 |
| 75 | 3.77 | 31 | 21 | 1.90 (0.73, 4.93) | 0.1804 | 91 | 76 | 0.65 (0.41, 1.03) | 0.0650 |

FIG. 18A

| qrt-PCR HER3 | n | # of Events | Treatment HR (95% CI) | Log-rank P-value |
|---|---|---|---|---|
| 0 - < 25th percentile | 28 | 21 | 0.13 (0.04, 0.45) | 0.0002 |
| 25 - < 50th percentile | 31 | 25 | 0.42 (0.17, 1.00) | 0.0465 |
| 50 - < 75th percentile | 30 | 29 | 2.11 (0.94, 4.75) | 0.0631 |
| 75 - 100th percentile | 30 | 19 | 2.00 (0.71, 5.62) | 0.1790 |

P-values were not adjusted for multiple comparisons

FIG. 18B

Progression-Free Survival (PFS) Analysis
by HER3 Expression Quartiles

| qRT-PCR HER3 | N | # of Events | Treatment HR (95% CI) | Log-rank P-value |
|---|---|---|---|---|
| 0 - < 25th percentile | 30 | 23 | 0.13 (0.04, 0.41) | <.0001 |
| 25 - < 50th percentile | 31 | 25 | 0.66 (0.29, 1.48) | 0.3181 |
| 50 - < 75th percentile | 30 | 28 | 1.59 (0.73, 3.44) | 0.2318 |
| 75 - 100th percentile | 31 | 21 | 1.90 (0.73, 4.93) | 0.1804 |

FIG. 19A (Part 1)
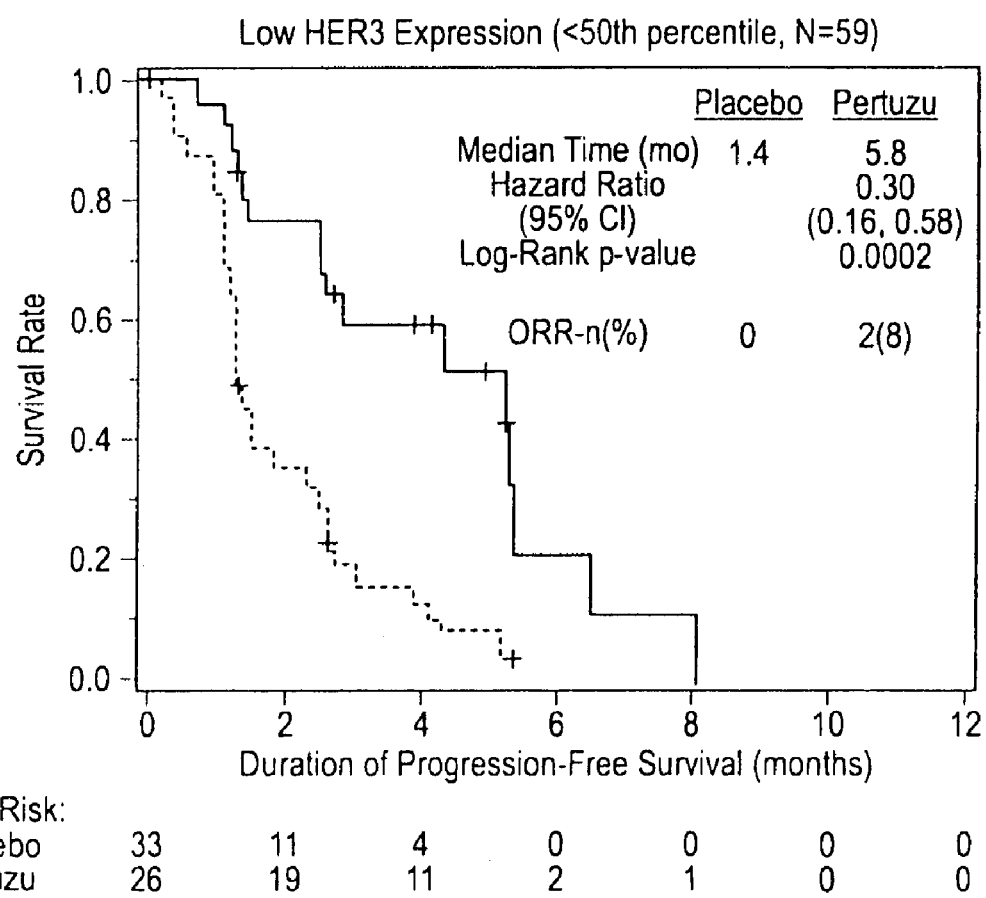
P-value for the difference.....

FIG. 19A (Part 2)
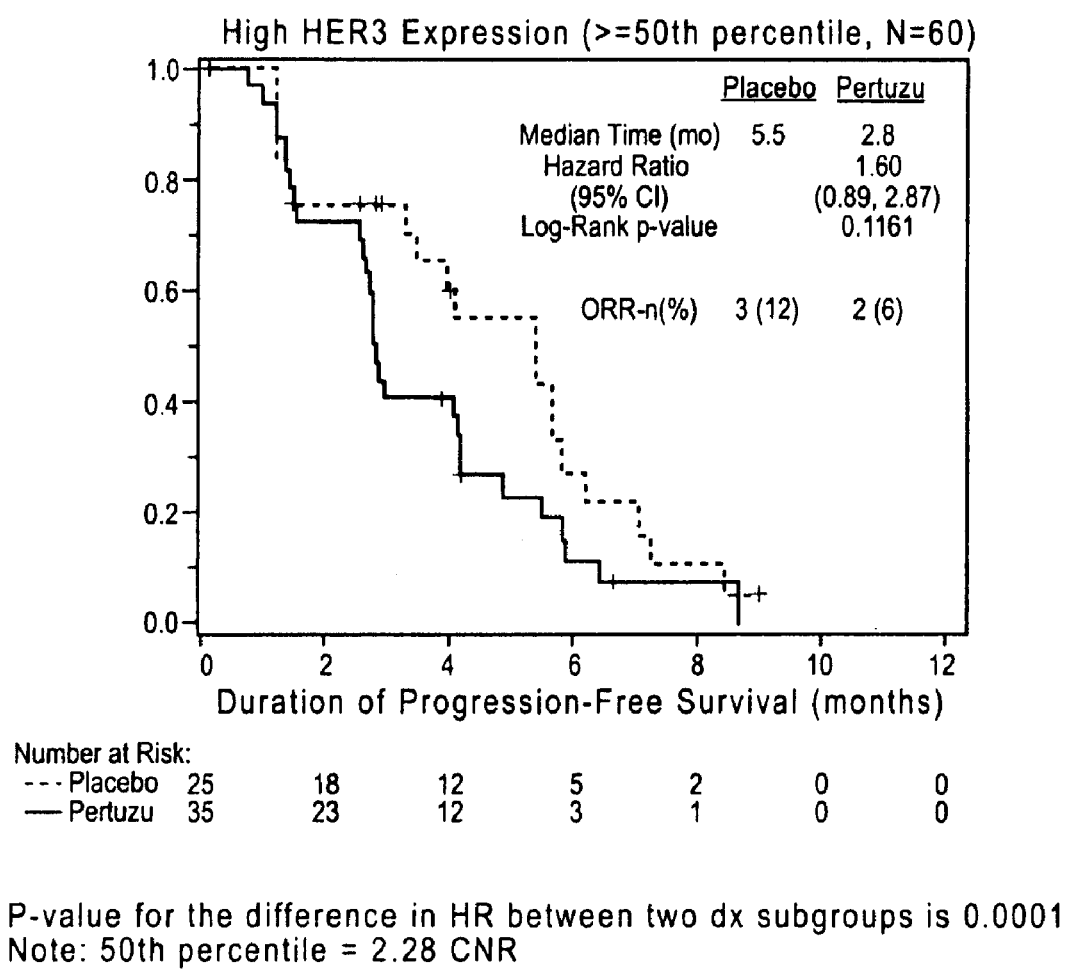
P-value for the difference in HR between two dx subgroups is 0.0001
Note: 50th percentile = 2.28 CNR

FIG. 19B (Part 1)
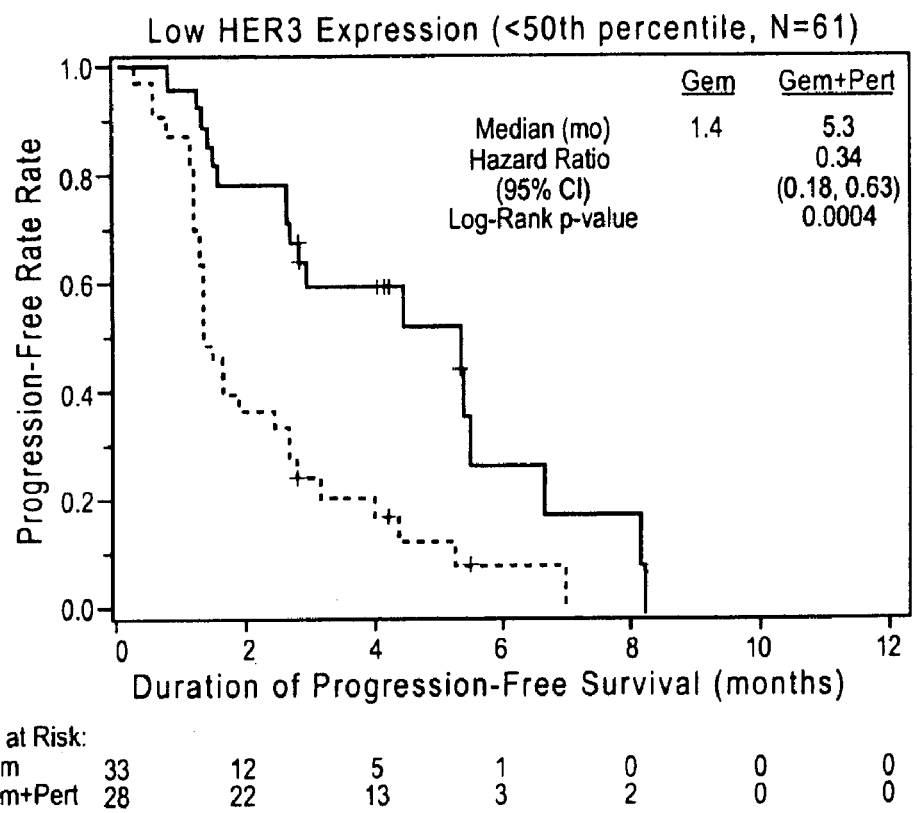
PFS by HER3 qRT-PCR 50/50 split
| All patients | Gem | Gem + Pertuz. |
|---|---|---|
| Median (mo) | 2.6 | 2.9 |
| Hazard Ratio* | | 0.66 |
| (95% CI) | | (0.43, 1.03) |
| P-value* | | 0.07 |
Low HER3 Expression (<50th percentile, N=61)
| | Gem | Gem+Pert |
|---|---|---|
| Median (mo) | 1.4 | 5.3 |
| Hazard Ratio | | 0.34 |
| (95% CI) | | (0.18, 0.63) |
| Log-Rank p-value | | 0.0004 |
Number at Risk:
| | | | | | | | |
|---|---|---|---|---|---|---|---|
| --- Gem | 33 | 12 | 5 | 1 | 0 | 0 | 0 |
| — Gem+Pert | 28 | 22 | 13 | 3 | 2 | 0 | 0 |
P-value for the difference in HR between two dx subgroups is 0.0005
Note: 50th percentile = 2.24 CNR FIG. 19B (Part 2)
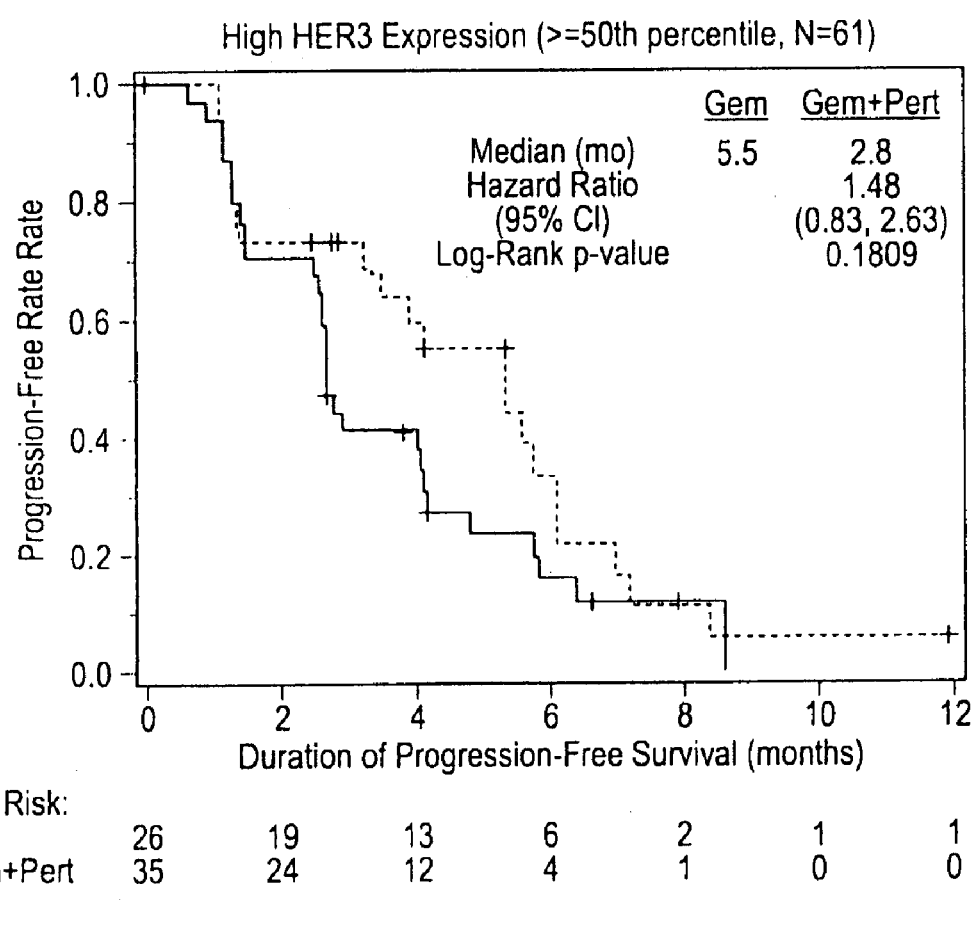
P-value for the difference.....

FIG. 20A
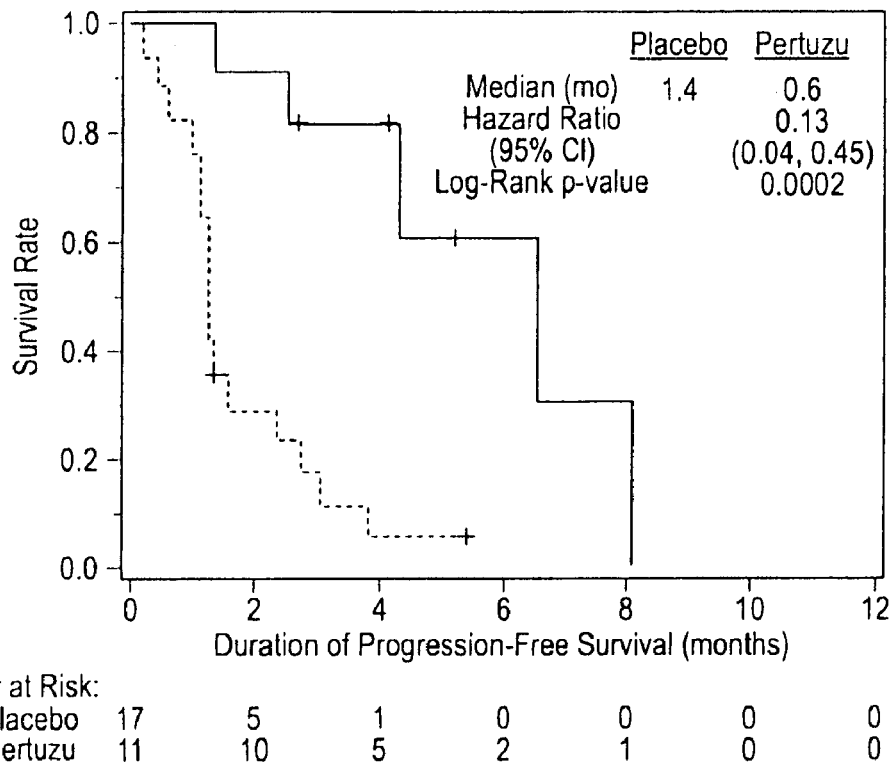
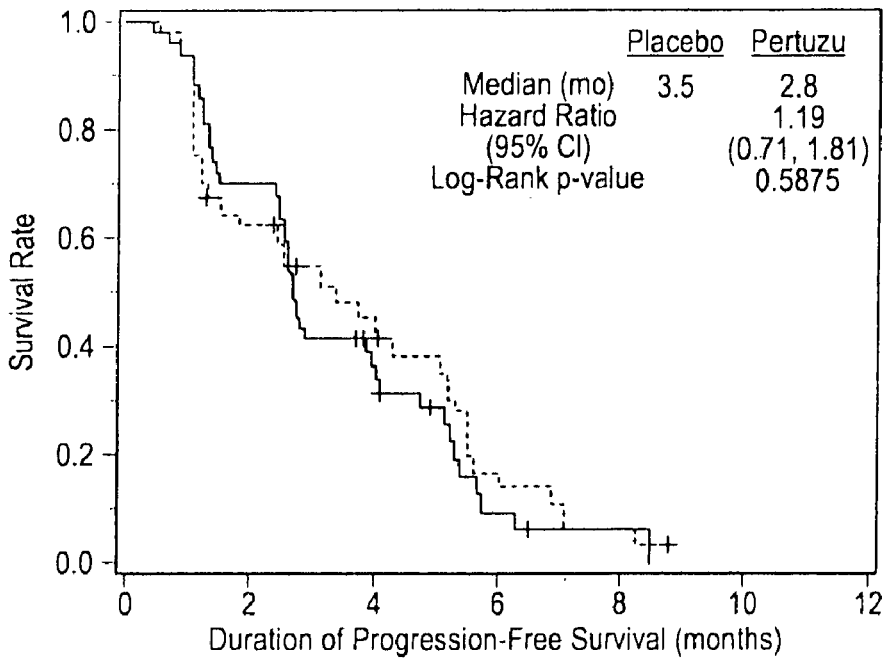

FIG. 20B (Part 1)
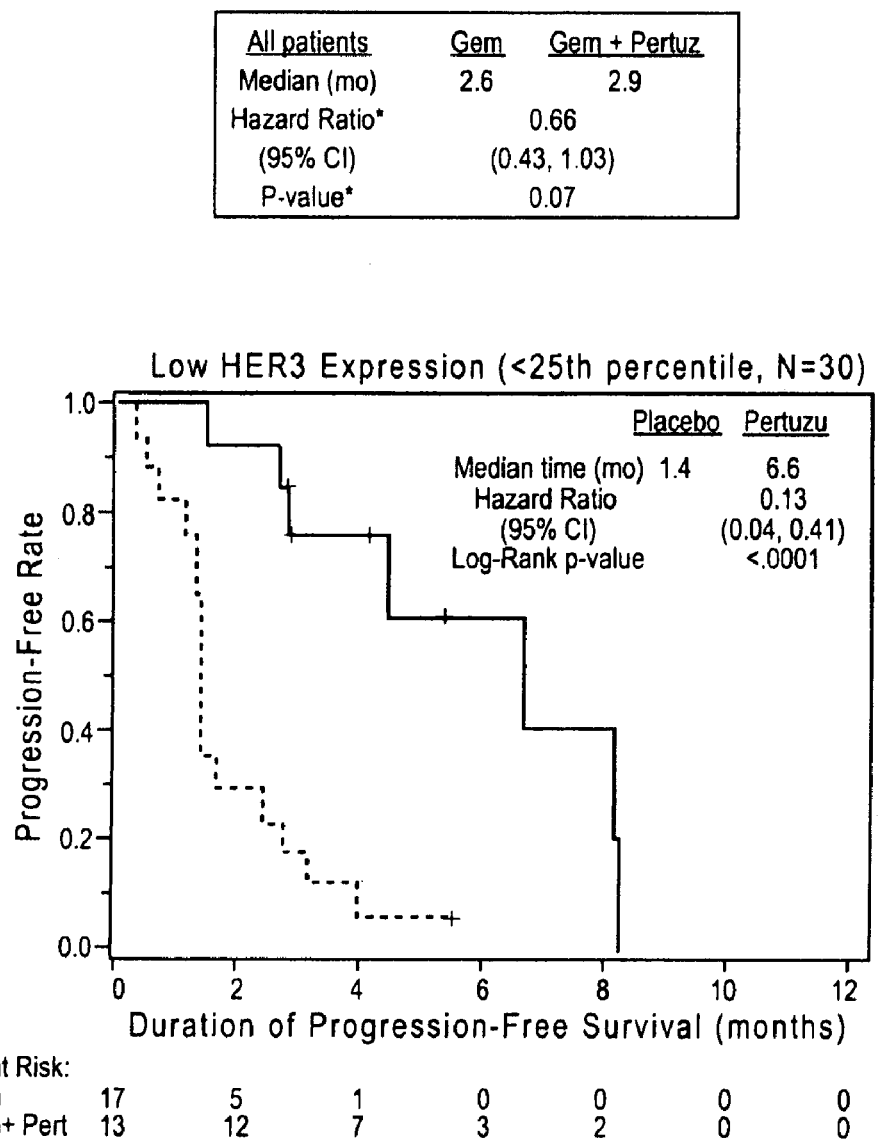

FIG. 20B (Part 2)
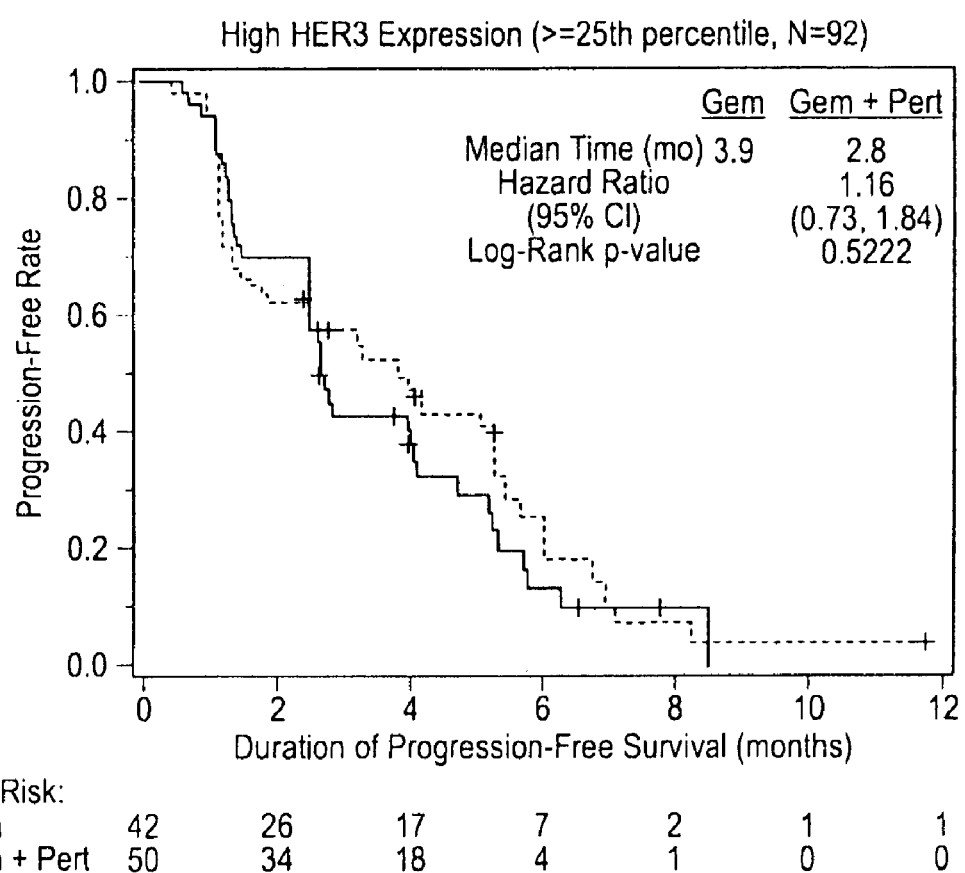
P-value for the difference.....

Preliminary Overall Survival (71 deaths as of April 20, 2007

*Estimated using stratified Cox model and stratified log-rank test by randomization stratification factors (ECOG PS, number of prior regimens for platinum-resistant disease, and disease measurability)

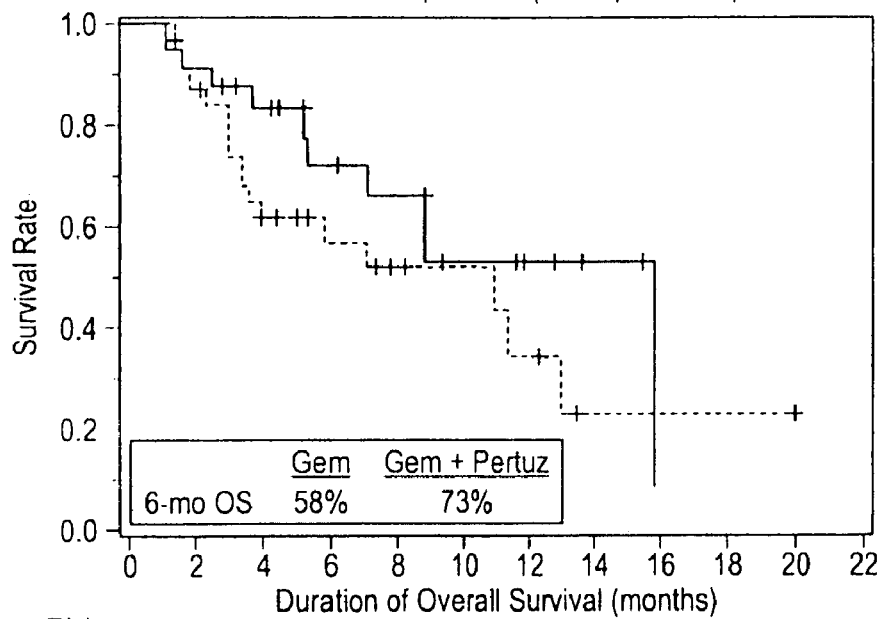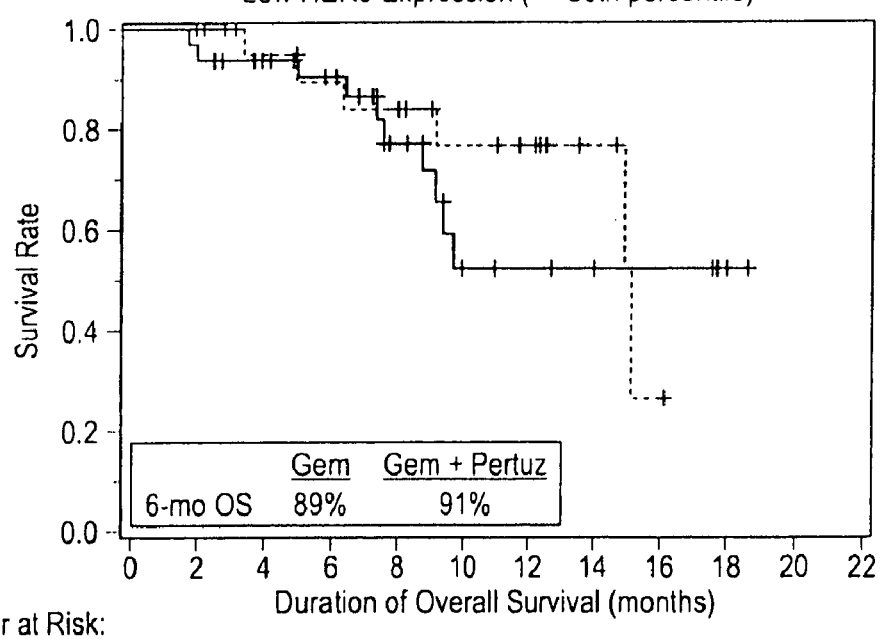
FIG. 22A

FIG. 22B
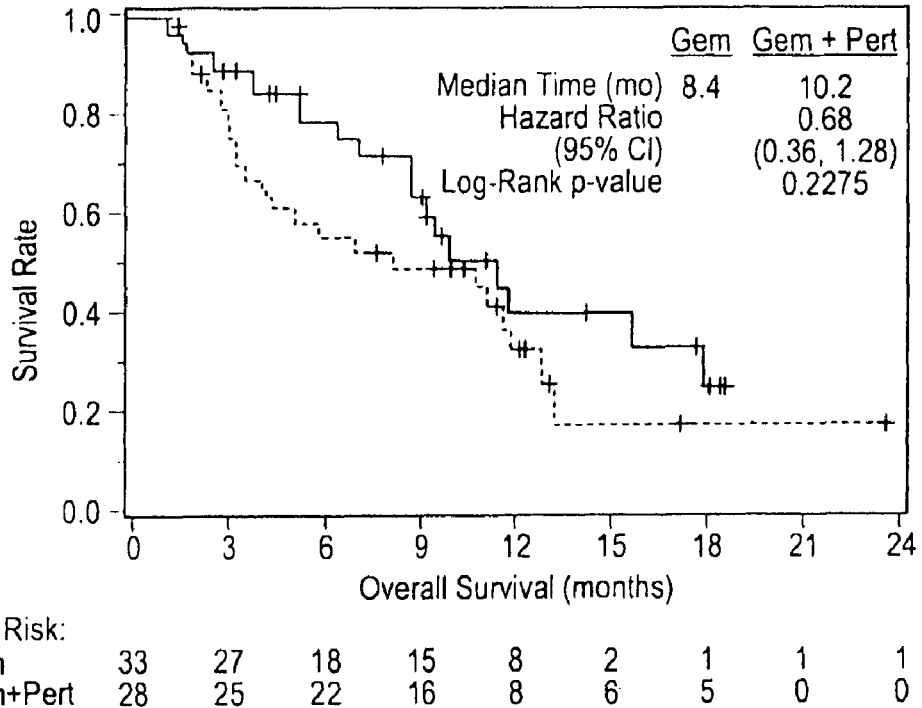
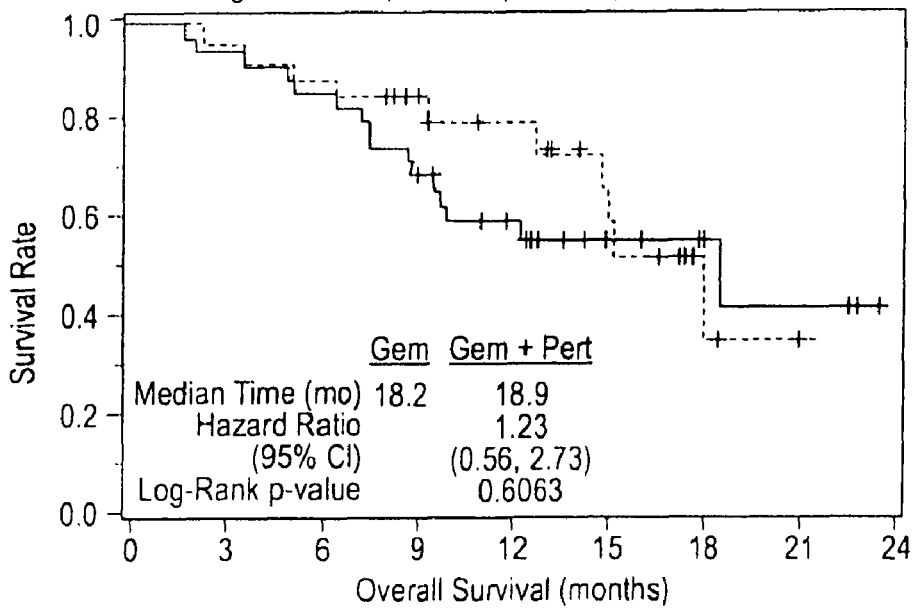

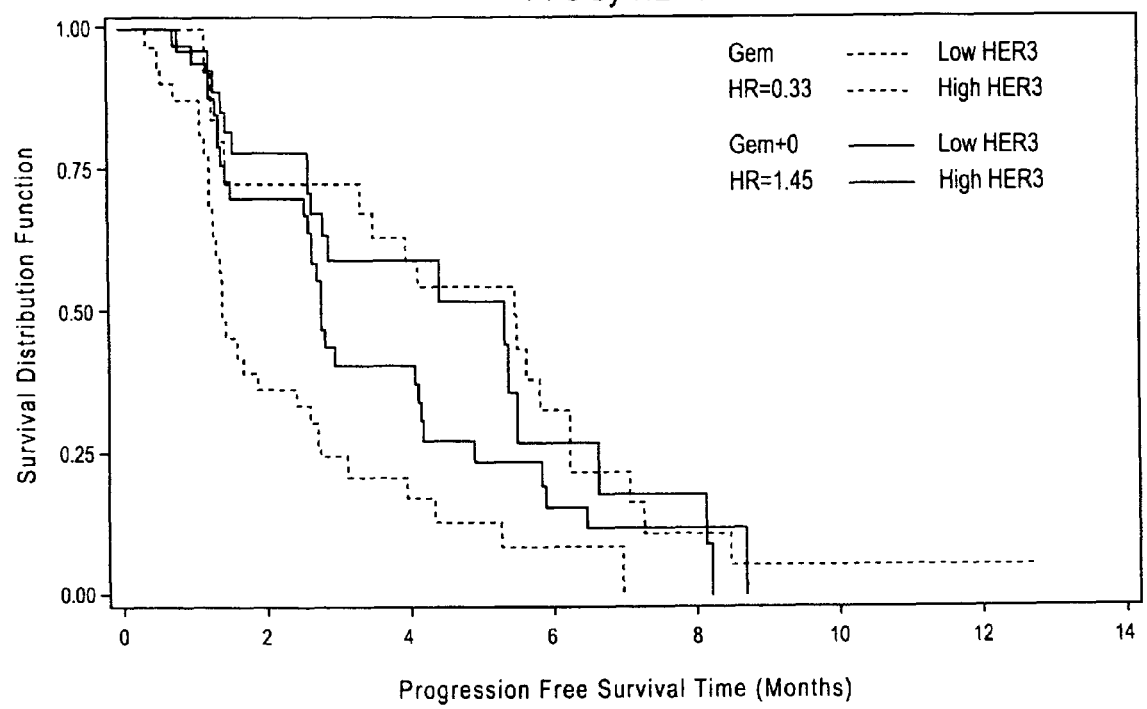

FIG. 24A (Part 1)

Pertuzumab Platinum Resistant Ovarian Cancer:
PFS by qRT-PCR HER3

| Cutoff Value | | HER3high Group | | | | HER3low Group | | | | |
|---|---|---|---|---|---|---|---|---|---|---|
| %tile | Abs. Value | N | # Events | HR (95%CI) | Logrank P-value | N | # Events | HR (95%CI) | Logrank P-value | # Events In Dx(+) |
| 5 | 0.34 | 114 | 91 | 0.81 (0.53, 1.22) | 0.3076 | 5 | 3 | 0.00 (0.00,.) | 0.0389 | 44 |
| 10 | 0.48 | 108 | 87 | 0.84 (0.55, 1.28) | 0.4076 | 11 | 7 | 0.15 (0.02, 1.29) | 0.0497 | 44 |
| 15 | 0.91 | 102 | 83 | 0.92 (0.60, 1.42) | 0.7155 | 17 | 11 | 0.14 (0.03, 0.66) | 0.0048 | 43 |
| 20 | 0.99 | 96 | 78 | 1.06 (0.67, 1.65) | 0.8083 | 23 | 16 | 0.09 (0.02, 0.42) | 0.0002 | 41 |
| 25 | 1.19 | 91 | 73 | 1.13 (0.71, 1.81) | 0.5875 | 28 | 21 | 0.13 (0.04, 0.45) | 0.0002 | 40 |
| 30 | 1.4 | 84 | 66 | 1.28 (0.77, 2.10) | 0.3318 | 35 | 28 | 0.18 (0.06, 0.52) | 0.0004 | 39 |
| 35 | 1.57 | 78 | 62 | 1.49 (0.89, 2.51) | 0.1280 | 41 | 32 | 0.16 (0.06, 0.43) | <.0001 | 38 |
| 40 | 1.71 | 72 | 58 | 1.55 (0.90, 2.68) | 0.1141 | 47 | 36 | 0.19 (0.08, 0.47) | <.0001 | 37 |
| 45 | 1.88 | 66 | 54 | 1.64 (0.94, 2.88) | 0.0817 | 53 | 40 | 0.23 (0.11, 0.50) | <.0001 | 34 |
| 50 | 2.28 | 60 | 48 | 1.60 (0.89, 2.87) | 0.1161 | 59 | 48 | 0.30 (0.16, 0.58) | 0.0002 | 29 |
| 55 | 2.41 | 54 | 42 | 1.87 (0.97, 3.57) | 0.0565 | 65 | 52 | 0.36 (0.20, 0.65) | 0.0005 | 28 |
| 60 | 2.8 | 48 | 37 | 1.88 (0.92, 3.84) | 0.0766 | 71 | 57 | 0.47 (0.27, 0.81) | 0.0060 | 26 |
| 65 | 3.14 | 42 | 31 | 1.72 (0.78, 3.75) | 0.1693 | 77 | 63 | 0.57 (0.34, 0.95) | 0.0299 | 22 |
| 70 | 3.59 | 36 | 25 | 1.67 (0.72, 3.90) | 0.2270 | 83 | 69 | 0.62 (0.38, 1.00) | 0.0488 | 17 |
| 75 | 3.8 | 30 | 19 | 2.00 (0.71, 5.62) | 0.1790 | 89 | 75 | 0.67 (0.42, 1.06) | 0.0898 | 14 |
| 80 | 4.29 | 24 | 16 | 2.85 (0.89, 9.20) | 0.0667 | 95 | 78 | 0.59 (0.37, 0.92) | 0.0196 | 11 |
| 85 | 5.25 | 18 | 13 | 2.53 (0.67, 9.50) | 0.1473 | 101 | 81 | 0.62 (0.40, 0.96) | 0.0324 | 9 |
| 90 | 6.64 | 12 | 9 | 4.73 (0.93, 24.13) | 0.0416 | 107 | 85 | 0.59 (0.38, 0.91) | 0.0151 | 6 |
| 95 | 8.4 | 6 | 5 | 3.35 (0.34, 33.36) | 0.2769 | 113 | 89 | 0.74 (0.49, 1.13) | 0.1582 | 3 |

Note: The HR and Log-rank p-values were not adjusted for multiple comparison

FIG. 24A (Part 2)

| Gem+Omnitarg (n=61) | | | | Gem Alone (n=58) | | | | |
|---|---|---|---|---|---|---|---|---|
| # Events In Dx(-) | HR (95%CI) | Logrank P-value | # Events In Dx(+) | # Events In Dx(-) | HR (95%CI) | Logrank P-value | Interaction P-value |
| 1 | 1.55 (0.21, 11.48) | 0.6559 | 47 | 2 | 0.32 (0.07, 1.38) | 0.1073 | 0.1195 |
| 1 | 2.54 (0.35, 18.64) | 0.3357 | 43 | 6 | 0.73 (0.30, 1.74) | 0.4723 | 0.2021 |
| 2 | 2.80 (0.67, 11.68) | 0.1377 | 40 | 9 | 0.54 (0.26, 1.14) | 0.1001 | 0.0296 |
| 4 | 3.28 (1.16, 9.25) | 0.0174 | 37 | 12 | 0.49 (0.25, 0.98) | 0.0385 | 0.0017 |
| 5 | 2.62 (1.02, 6.69) | 0.0369 | 33 | 16 | 0.40 (0.21, 0.76) | 0.0035 | 0.0007 |
| 6 | 2.17 (0.91, 5.16) | 0.0737 | 27 | 22 | 0.35 (0.19, 0.65) | 0.0006 | 0.0004 |
| 7 | 2.33 (1.03, 5.25) | 0.0355 | 24 | 25 | 0.27 (0.14, 0.52) | <.0001 | <.0001 |
| 8 | 2.55 (1.04, 4.86) | 0.0339 | 21 | 28 | 0.30 (0.16, 0.59) | 0.0002 | <.0001 |
| 11 | 1.96 (0.99, 3.89) | 0.0508 | 20 | 29 | 0.27 (0.14, 0.54) | <.0001 | <.0001 |
| 16 | 1.41 (0.76, 2.62) | 0.2700 | 19 | 30 | 0.25 (0.13, 1.51) | <.0001 | 0.0001 |
| 17 | 1.33 (0.72, 2.44) | 0.3610 | 14 | 35 | 0.25 (0.12, 0.49) | <.0001 | 0.0002 |
| 19 | 1.38 (0.78, 2.50) | 0.2943 | 11 | 38 | 0.36 (0.18, 0.71) | 0.0023 | 0.0020 |
| 23 | 1.06 (0.59, 1.93) | 0.8337 | 9 | 40 | 0.36 (0.17, 0.76) | 0.0050 | 0.0158 |
| 28 | 0.82 (0.44, 1.53) | 0.5400 | 8 | 41 | 0.33 (0.15, 0.71) | 0.0029 | 0.0384 |
| 31 | 0.77 (0.40, 1.49) | 0.4392 | 5 | 44 | 0.29 (0.11, 0.73) | 0.0054 | 0.0528 |
| 34 | 1.40 (0.70, 2.80) | 0.3428 | 5 | 44 | 0.33 (0.13, 0.84) | 0.0146 | 0.0119 |
| 36 | 1.25 (0.60, 2.62) | 0.5534 | 4 | 45 | 0.32 (0.11, 0.92) | 0.0264 | 0.0262 |
| 39 | 2.58 (1.06, 6.23) | 0.0290 | 3 | 46 | 0.26 (0.08, 0.86) | 0.0185 | 0.0020 |
| 42 | 2.57 (0.77, 8.56) | 0.1052 | 2 | 47 | 0.95 (0.23, 3.94) | 0.9478 | 0.3840 |

FIG. 24B (Part 1)

Pertuzumab Platinum Resistant Ovarian Cancer: PFS by qRT-PCR HER3

| Cutoff Value | | Dx(High) Group | | | | Dx(Low) Group | | | |
|---|---|---|---|---|---|---|---|---|---|
| %tile | Abs. Value | N | # Events | HR (95%CI) | Logrank P-value | N | # Events | HR (95%CI) | Logrank P-value | # Events In Dx(High) |
| 20 | 0.99 | 98 | 80 | 1.09 (0.70, 1.70) | 0.6973 | 24 | 17 | 0.08 (0.02, 0.37) | <.0001 | 42 |
| 25 | 1.19 | 92 | 74 | 1.16 (0.73, 1.84) | 0.5222 | 30 | 23 | 0.13 (0.04, 0.41) | <.0001 | 40 |
| 30 | 1.39 | 86 | 68 | 1.20 (0.74, 1.94) | 0.4674 | 36 | 29 | 0.22 (0.09, 0.56) | 0.0005 | 39 |
| 35 | 1.56 | 80 | 64 | 1.37 (0.83, 2.26) | 0.2230 | 42 | 33 | 0.20 (0.09, 0.48) | <.0001 | 38 |
| 40 | 1.70 | 74 | 59 | 1.50 (0.88, 2.55) | 0.1381 | 48 | 38 | 0.22 (0.10, 0.50) | <.0001 | 37 |
| 45 | 1.87 | 68 | 55 | 1.50 (0.87, 2.61) | 0.1468 | 54 | 42 | 0.29 (0.14, 0.58) | 0.0002 | 34 |
| 50 | 2.24 | 61 | 49 | 1.48 (0.83, 2.63) | 0.1809 | 61 | 48 | 0.34 (0.18, 0.63) | 0.0004 | 29 |
| 55 | 2.38 | 56 | 44 | 1.74 (0.93, 3.27) | 0.0816 | 66 | 53 | 0.36 (0.20, 0.65) | 0.0005 | 29 |
| 60 | 2.75 | 49 | 38 | 1.81 (0.90, 3.67) | 0.0945 | 73 | 59 | 0.48 (0.28, 0.84) | 0.0080 | 27 |
| 65 | 3.08 | 43 | 32 | 1.78 (0.82, 3.86) | 0.1382 | 79 | 65 | 0.56 (0.34, 0.94) | 0.0255 | 23 |
| 70 | 3.56 | 37 | 26 | 1.73 (0.75, 3.99) | 0.1943 | 85 | 71 | 0.62 (0.38, 1.00) | 0.0459 | 18 |
| 75 | 3.77 | 31 | 21 | 1.90 (0.73, 4.93) | 0.1804 | 91 | 76 | 0.65 (0.41, 1.03) | 0.0650 | 15 |
| 80 | 4.05 | 25 | 18 | 2.33 (0.82, 6.64) | 0.1053 | 97 | 79 | 0.64 (0.41, 1.00) | 0.0493 | 13 |

Note: The HR and Log-rank p-values were not adjusted for multiple comparison

FIG. 24B (Part 2)

| Gem + Pertuzumab (n=63) | | | | Gem Alone (n=59) | | | | |
|---|---|---|---|---|---|---|---|---|
| # Events In Dx(Low) | HR (95%CI) | Logrank P-value | # Events In Dx(High) | # Events In Dx(Low) | HR (95%CI) | Logrank P-value | Interaction P-value |
| 5 | 3.20 (1.25, 8.23) | 0.0109 | 38 | 12 | 0.47 (0.24, 0.93) | 0.0272 | 0.0007 |
| 7 | 2.34 (1.03, 5.30) | 0.0360 | 34 | 16 | 0.38 (0.20, 0.72) | 0.0020 | 0.0003 |
| 8 | 2.03 (0.93, 4.39) | 0.0683 | 29 | 21 | 0.44 (0.24, 0.79) | 0.0046 | 0.0014 |
| 9 | 2.19 (1.05, 4.56) | 0.0330 | 26 | 24 | 0.37 (0.21, 0.67) | 0.0007 | 0.0001 |
| 10 | 2.14 (1.06, 4.34) | 0.0312 | 22 | 28 | 0.35 (0.19, 0.63) | 0.0004 | <.0001 |
| 13 | 1.84 (0.97, 3.51) | 0.0617 | 21 | 29 | 0.35 (0.19, 0.65) | 0.0005 | 0.0002 |
| 18 | 1.45 (0.80, 2.62) | 0.2230 | 20 | 30 | 0.33 (0.18, 0.62) | 0.0003 | 0.0005 |
| 18 | 1.45 (0.80, 2.62) | 0.2230 | 15 | 35 | 0.31 (0.16, 0.60) | 0.0002 | 0.0004 |
| 20 | 1.33 (0.74, 2.38) | 0.3459 | 11 | 39 | 0.37 (0.19, 0.73) | 0.0030 | 0.0030 |
| 24 | 1.14 (0.64, 2.04) | 0.6516 | 9 | 41 | 0.36 (0.18, 0.76) | 0.0050 | 0.0112 |
| 29 | 0.89 (0.49, 1.62) | 0.6916 | 8 | 42 | 0.33 (0.15, 0.71) | 0.0028 | 0.0295 |
| 32 | 0.89 (0.47, 1.66) | 0.6992 | 6 | 44 | 0.33 (0.14, 0.79) | 0.0086 | 0.0427 |
| 34 | 1.04 (0.54, 2.03) | 0.9069 | 5 | 45 | 0.32 (0.13, 0.83) | 0.0136 | 0.0291 |

FIG. 25 (Part 1)
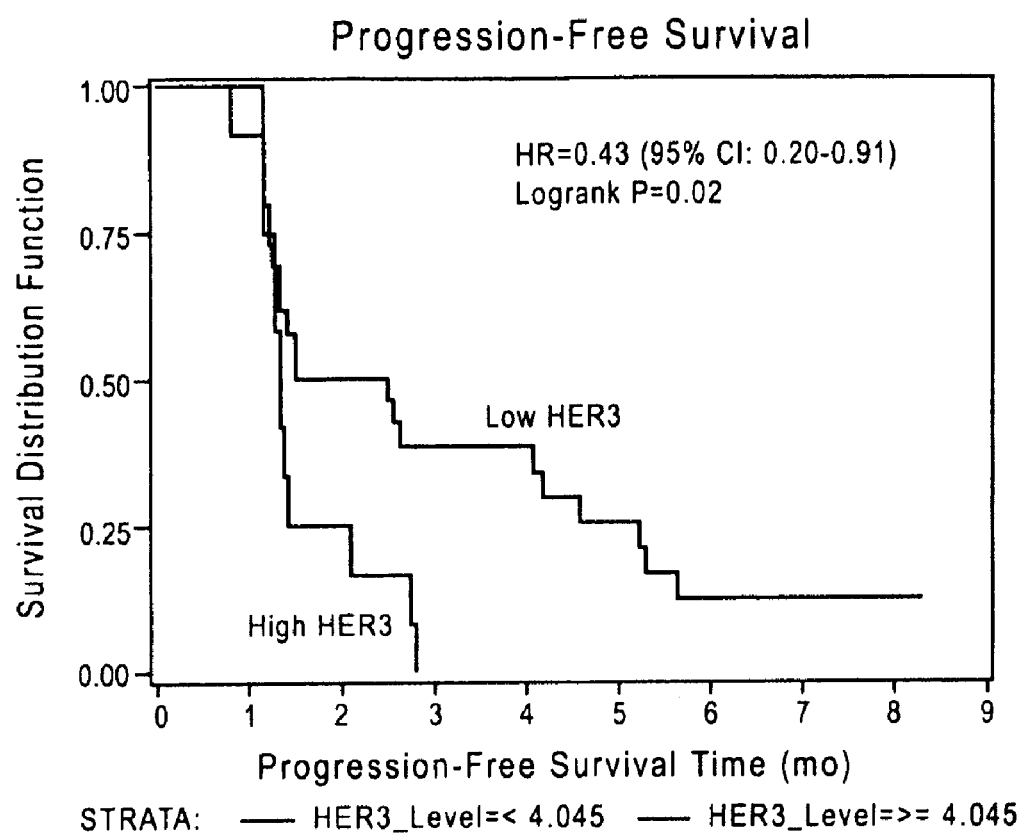
High HER3: HER3 >= 75th percentile
Low HER3: HER3 < 75th percentile
75th percentile = 4.045

FIG. 25 (Part 2)
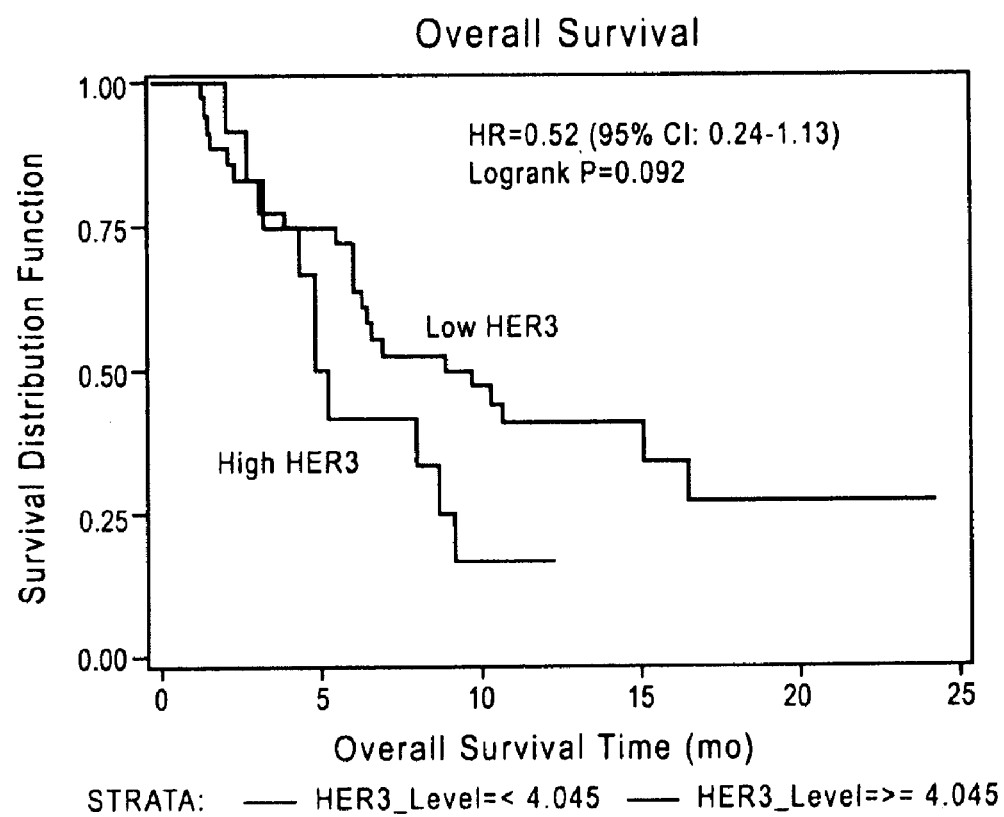

FIG. 29A (Part 1)

PFS by qRT-PCR HER2/HER3 (percentiles)

| Cutoff Value | | Dx (High) Group | | | | Dx (Low) Group | | | |
|---|---|---|---|---|---|---|---|---|---|
| %tile | Abs. Value | N | # Events | HR (95%CI) | Logrank P-value | N | # Events | HR (95%CI) | Logrank P-value | # Events In Dx(High) |
| 20 | 0.74 | 95 | 72 | 0.63 (0.39, 1.02) | 0.0616 | 23 | 21 | 2.04 (0.58, 7.13) | 0.2475 | 26 |
| 25 | 0.82 | 89 | 67 | 0.46 (0.27, 0.76) | 0.0021 | 29 | 26 | 2.85 (1.10, 7.37) | 0.0249 | 24 |
| 30 | 0.90 | 83 | 62 | 0.41 (0.24, 0.69) | 0.0007 | 35 | 31 | 2.52 (1.13, 5.62) | 0.0197 | 22 |
| 35 | 1.06 | 77 | 60 | 0.39 (0.22, 0.68) | 0.0005 | 41 | 33 | 2.51 (1.14, 5.54) | 0.0189 | 20 |
| 40 | 1.13 | 71 | 55 | 0.39 (0.22, 0.69) | 0.0009 | 47 | 38 | 1.91 (0.95, 3.83) | 0.0640 | 18 |
| 45 | 1.26 | 65 | 50 | 0.31 (0.16, 0.61) | 0.0003 | 53 | 43 | 1.93 (0.99, 3.77) | 0.0492 | 14 |
| 50 | 1.53 | 59 | 47 | 0.31 (0.15, 0.61) | 0.0004 | 59 | 46 | 1.71 (0.91, 3.21) | 0.0937 | 13 |
| 55 | 1.70 | 54 | 45 | 0.34 (0.17, 0.68) | 0.0015 | 64 | 48 | 1.44 (0.78, 2.65) | 0.2293 | 13 |
| 60 | 1.86 | 48 | 40 | 0.27 (0.12, 0.57) | 0.0003 | 70 | 53 | 1.35 (0.77, 2.37) | 0.2885 | 12 |
| 65 | 2.15 | 42 | 34 | 0.27 (0.12, 0.62) | 0.0010 | 76 | 59 | 1.10 (0.65, 1.86) | 0.7119 | 11 |
| 70 | 2.49 | 36 | 29 | 0.21 (0.08, 0.54) | 0.0004 | 82 | 64 | 1.13 (0.69, 1.87) | 0.6280 | 8 |
| 75 | 2.62 | 30 | 24 | 0.13 (0.04, 0.46) | 0.0003 | 88 | 69 | 1.08 (0.67, 1.75) | 0.7534 | 6 |
| 80 | 2.92 | 24 | 20 | 0.10 (0.02, 0.43) | 0.0002 | 94 | 73 | 1.06 (0.67, 1.70) | 0.7886 | 4 |

FIG. 29A (Part 2)

| Gem+Omnitarg (n=60) | | | | Gem Alone (n=58) | | | | |
|---|---|---|---|---|---|---|---|---|
| # Events In Dx(Low) | HR (95%CI) | Logrank P-value | # Events In Dx(High) | # Events In Dx(Low) | HR (95%CI) | Logrank P-value | Interaction P-value |
| 17 | 0.57 (0.31, 1.06) | 0.0734 | 46 | 3 | 1.39 (0.43, 4.55) | 0.5881 | 0.1823 |
| 20 | 0.53 (0.29, 0.97) | 0.0370 | 43 | 6 | 4.07 (1.41, 11.74) | 0.0055 | 0.0005 |
| 22 | 0.46 (0.25, 0.84) | 0.0104 | 40 | 9 | 3.04 (1.33, 6.94) | 0.0056 | 0.0002 |
| 24 | 0.49 (0.26, 0.90) | 0.0192 | 40 | 9 | 3.41 (1.50, 7.73) | 0.0019 | 0.0001 |
| 26 | 0.52 (0.28, 0.96) | 0.0340 | 37 | 12 | 2.76 (1.36, 5.59) | 0.0034 | 0.0004 |
| 30 | 0.54 (0.28, 1.03) | 0.0584 | 36 | 13 | 3.21 (1.57, 6.56) | 0.0007 | 0.0001 |
| 31 | 0.57 (0.30, 1.10) | 0.0926 | 34 | 15 | 2.94 (1.50, 5.77) | 0.0010 | 0.0003 |
| 31 | 0.66 (0.34, 1.28) | 0.2161 | 32 | 17 | 2.55 (1.34, 4.83) | 0.0028 | 0.0022 |
| 32 | 0.60 (0.31, 1.18) | 0.1348 | 28 | 21 | 2.60 (1.41, 4.81) | 0.0015 | 0.0009 |
| 33 | 0.56 (0.28, 1.12) | 0.0974 | 23 | 26 | 1.81 (1.00, 3.27) | 0.0447 | 0.0084 |
| 36 | 0.52 (0.24, 1.12) | 0.0895 | 21 | 28 | 2.07 (1.14, 3.76) | 0.0145 | 0.0032 |
| 38 | 0.46 (0.19, 1.10) | 0.0766 | 18 | 31 | 2.11 (1.12, 3.96) | 0.0167 | 0.0035 |
| 40 | 0.42 (0.15, 1.19) | 0.0949 | 16 | 33 | 2.60 (1.36, 4.97) | 0.0026 | 0.0022 |

FIG. 29B (Part 1)

Platinum Resistant Ovarian Cancer:
PFS by qRT-PCR HER2/HER3 Ratio

| Cutoff Value | | | Dx (High) Group | | | | Dx (Low) Group | | | # Events In Dx(High) |
|---|---|---|---|---|---|---|---|---|---|---|
| %tile | Abs. Value | N | # Events | HR (95%CI) | Logrank P-value | N | # Events | HR (95%CI) | Logrank P-value | |
| 20 | 0.76 | 97 | 75 | 0.67 (0.42, 1.06) | 0.0884 | 24 | 21 | 1.70 (0.56, 5.19) | 0.3418 | 29 |
| 25 | 0.83 | 91 | 71 | 0.50 (0.31, 0.82) | 0.0050 | 30 | 25 | 2.53 (0.99, 6.49) | 0.0452 | 27 |
| 30 | 0.91 | 85 | 66 | 0.48 (0.29, 0.80) | 0.0042 | 36 | 30 | 1.98 (0.89, 4.40) | 0.0876 | 25 |
| 35 | 1.06 | 79 | 63 | 0.45 (0.26, 0.77) | 0.0026 | 42 | 33 | 1.99 (0.94, 4.24) | 0.0691 | 23 |
| 40 | 1.13 | 73 | 58 | 0.40 (0.23, 0.71) | 0.0011 | 48 | 38 | 1.76 (0.89, 3.47) | 0.0979 | 21 |
| 45 | 1.26 | 67 | 53 | 0.35 (0.19, 0.65) | 0.0006 | 54 | 43 | 1.78 (0.93, 3.41) | 0.0780 | 17 |
| 50 | 1.54 | 61 | 49 | 0.32 (0.17, 0.63) | 0.0005 | 60 | 47 | 1.63 (0.88, 3.02) | 0.1154 | 15 |
| 55 | 1.73 | 55 | 46 | 0.36 (0.18, 0.70) | 0.0018 | 66 | 50 | 1.37 (0.77, 2.45) | 0.2828 | 15 |
| 60 | 2.04 | 49 | 41 | 0.29 (0.14, 0.60) | 0.0005 | 72 | 55 | 1.35 (0.78, 2.34) | 0.2830 | 13 |
| 65 | 2.17 | 43 | 35 | 0.28 (0.12, 0.61) | 0.0007 | 78 | 61 | 1.13 (0.68, 1.88) | 0.6512 | 13 |
| 70 | 2.50 | 37 | 30 | 0.19 (0.07, 0.48) | 0.0001 | 84 | 66 | 1.16 (0.71, 1.90) | 0.5512 | 10 |
| 75 | 2.65 | 31 | 25 | 0.10 (0.03, 0.37) | <.0001 | 90 | 71 | 1.12 (0.70, 1.80) | 0.6370 | 7 |
| 80 | 2.99 | 25 | 21 | 0.11 (0.03, 0.40) | <.0001 | 96 | 75 | 1.06 (0.67, 1.67) | 0.8088 | 6 |

Note: The HR and Log-rank p-values were not adjusted for multiple comparison

FIG. 29B (Part 2)

| Gem+Pertuzimab (n=63) | | | Gem Alone (n=59) | | | | |
|---|---|---|---|---|---|---|---|
| # Events In Dx(Low) | HR (95%CI) | Logrank P-value | # Events In Dx(High) | # Events In Dx(Low) | HR (95%CI) | Logrank P-value | Interaction P-value |
| 17 | 0.74 (0.40, 1.37) | 0.3323 | 46 | 4 | 1.73 (0.62, 4.87) | 0.2958 | 0.1685 |
| 19 | 0.68 (0.37, 1.24) | 0.2026 | 44 | 6 | 4.34 (1.51, 12.43) | 0.0033 | 0.0022 |
| 21 | 0.65 (0.36, 1.17) | 0.1529 | 41 | 9 | 2.92 (1.28, 6.66) | 0.0075 | 0.0030 |
| 23 | 0.63 (0.35, 1.13) | 0.1204 | 40 | 10 | 2.96 (1.37, 6.42) | 0.0039 | 0.0015 |
| 25 | 0.65 (0.36, 1.17) | 0.1512 | 37 | 13 | 2.87 (1.44, 5.71) | 0.0017 | 0.0011 |
| 29 | 0.66 (0.36, 1.21) | 0.1782 | 36 | 14 | 3.49 (1.70, 7.14) | 0.0003 | 0.0004 |
| 31 | 0.64 (0.34, 1.19) | 0.1566 | 34 | 16 | 3.15 (1.60, 6.19) | 0.0005 | 0.0005 |
| 31 | 0.72 (0.39, 1.35) | 0.3116 | 31 | 19 | 2.64 (1.41, 4.94) | 0.0016 | 0.0033 |
| 33 | 0.62 (0.33, 1.20) | 0.1585 | 28 | 22 | 2.69 (1.47, 4.93) | 0.0009 | 0.0010 |
| 33 | 0.62 (0.33, 1.20) | 0.1585 | 22 | 28 | 2.16 (1.18, 3.96) | 0.0104 | 0.0053 |
| 36 | 0.58 (0.28, 1.18) | 0.1290 | 20 | 30 | 2.64 (1.40, 4.96) | 0.0018 | 0.0010 |
| 39 | 0.42 (0.18, 0.94) | 0.0314 | 18 | 32 | 2.23 (1.19, 4.21) | 0.0100 | 0.0010 |
| 40 | 0.45 (0.19, 1.08) | 0.0694 | 15 | 35 | 2.46 (1.28, 4.74) | 0.0055 | 0.0015 |

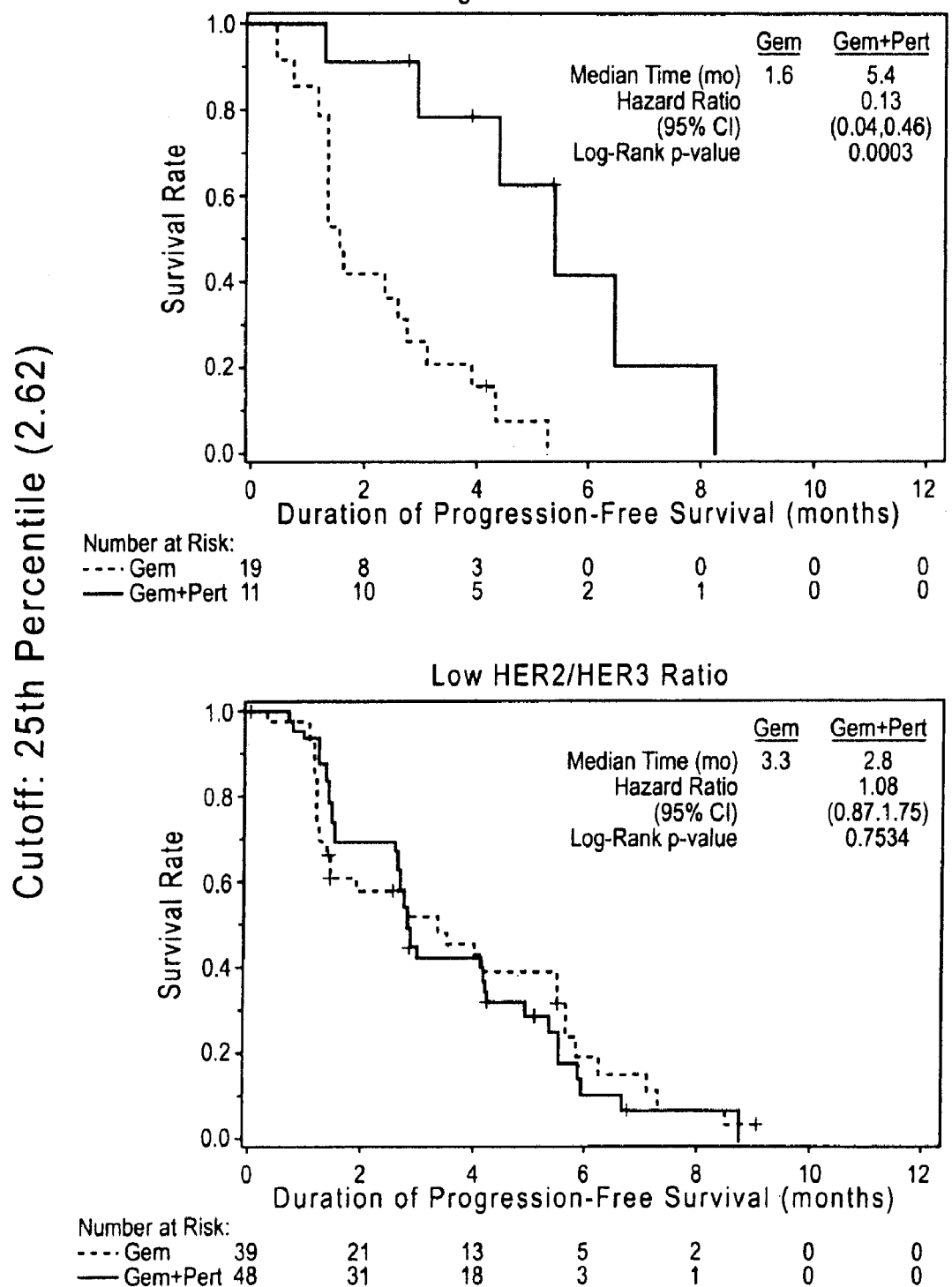

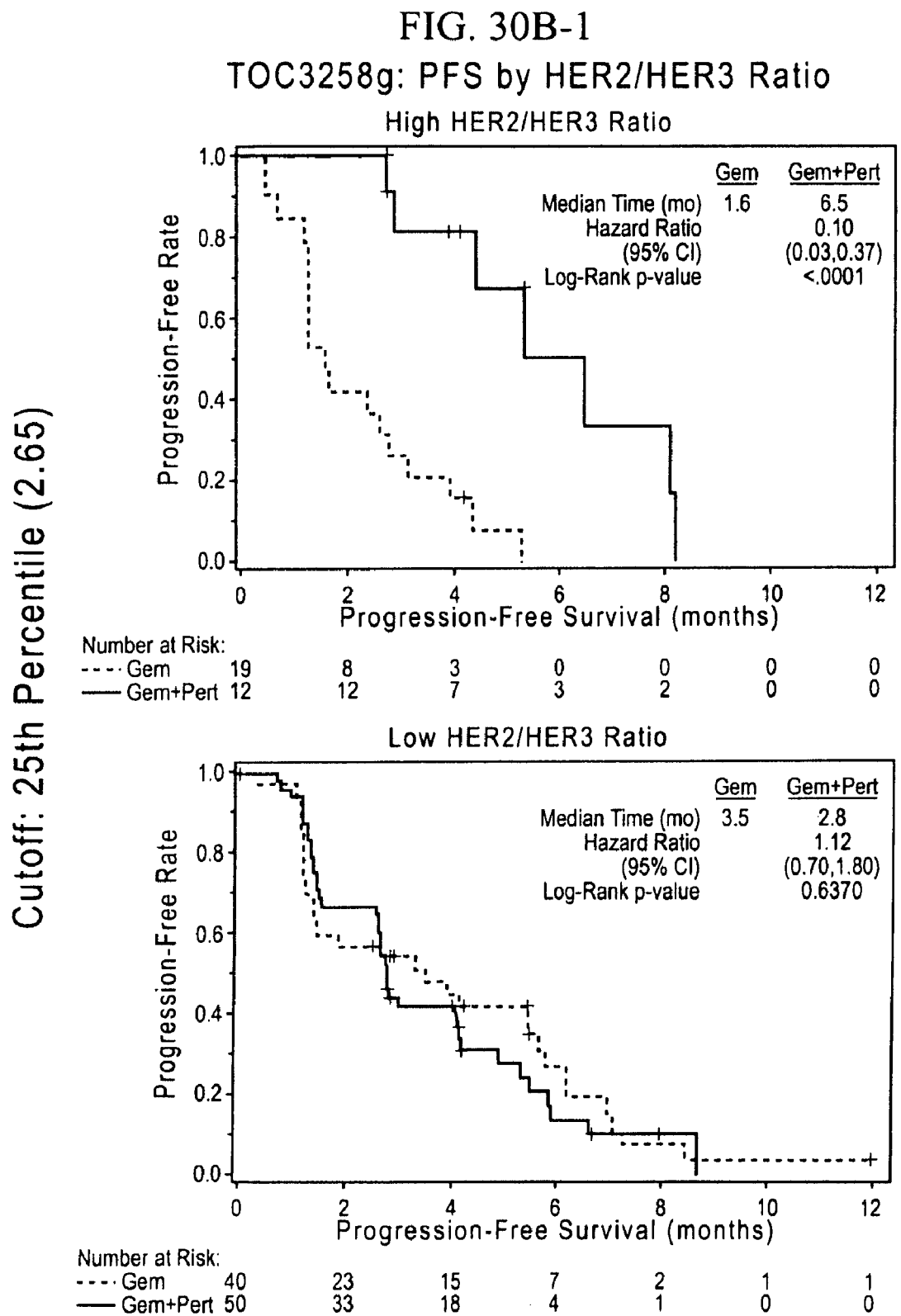

FIG. 31A

| qRT-PCR HER2/HER3 Ratio | Total | | Gem Alone | | | Gem + Omnitarg | | | HR (95%CI) | Logrank P-value |
|---|---|---|---|---|---|---|---|---|---|---|
| | N | # Events | N | # Events | Medium (mo) | N | # Events | Medium (mo) | | |
| 0 - <25th percentile | 29 | 26 | 7 | 6 | 5.5 | 22 | 20 | 2.6 | 2.85 (1.10, 7.37) | 0.0249 |
| 25 - <50th percentile | 30 | 20 | 14 | 9 | 3.7 | 16 | 11 | 4.2 | 1.02 (0.41, 2.54) | 0.9649 |
| 50 - <75th percentile | 29 | 23 | 18 | 16 | 1.3 | 11 | 7 | 5.5 | 0.61 (0.25, 1.52) | 0.2978 |
| 75 - 100th percentile | 30 | 24 | 19 | 18 | 1.6 | 11 | 6 | 5.4 | 0.13 (0.04, 0.46) | 0.0003 |

FIG. 31B

Progression-Free Survival (PFS) Analysis by HER2/HER3 Quartiles

| qRT-PCR HER2/HER3 | N | # Events | HR (95%CI) | Logrank P-value |
|---|---|---|---|---|
| 0 - <25th percentile | 30 | 25 | 2.53 (0.99, 6.49) | 0.0452 |
| 25 - <50th percentile | 30 | 22 | 1.28 (0.52, 3.15) | 0.5952 |
| 50 - <75th percentile | 30 | 24 | 0.76 (0.32, 1.83) | 0.5618 |
| 75 - 100th percentile | 31 | 25 | 0.10 (0.03, 0.37) | <.0001 |

US 7,981,418 B2

PREDICTING RESPONSE TO A HER INHIBITOR

This is a non-provisional application claiming priority under 35 U.S.C. §119 (e) to provisional patent application Ser. Nos. 61/029,748, filed Feb. 19, 2008, 60/912,053, filed Apr. 16, 2007 and 60/892,640, filed Mar. 2, 2007, the entire disclosures of which are hereby incorporated by reference.

FIELD OF THE INVENTION

The present invention concerns the use of low HER3 as a selection criterion for treating cancer patients, such as ovarian cancer patients, with a HER inhibitor, such as pertuzumab.

Also, the invention is related to the use of high HER2:HER3 ratio as a selection criterion for treating cancer patients, such as ovarian cancer patients, with a HER inhibitor, such as pertuzumab.

In addition, the invention relates to the use of high HER3 as a selection criterion for treating cancer patients with a chemotherapeutic agent, for instance gemcitabine.

BACKGROUND OF THE INVENTION

HER Receptors and Antibodies Thereagainst

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science,* 235:177-182 (1987); Slamon et al., *Science,* 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al, *Science,* 229:974 (1985); Yokota et al., *Lancet:* 1:765-767 (1986); Fukushige et al., *Mol Cell Biol.,* 6:955-958 (1986); Guerin et al., *Oncogene Res.,* 3:21-31 (1988); Cohen et al., *Oncogene,* 4:81-88 (1989); Yonemura et al., *Cancer Res.,* 51:1034 (1991); Borst et al., *Gynecol. Oncol.,* 38:364 (1990); Weiner et al., *Cancer Res.,* 50:421-425 (1990); Kern et al., *Cancer Res.,* 50:5184 (1990); Park et al, *Cancer Res.,* 49:6605 (1989); Zhau et al., *Mol. Carcinog.,* 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human HER2 protein products have been described.

Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3): 117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:72 02-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, trastuzumab or HERCEPTIN®; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373

(1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al. *PNAS (USA)* 86:9193-9197 (1989)) and HER4 (EP Pat Appln No 599,274; Plowman et al., *Proc. Natl. Acad. Sci. USA*, 90:1746-1750 (1993); and Plowman et al., *Nature*, 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science*, 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et al *Nature* 387:512-516 (1997)); neuregulin-3 which binds HER4 (Zhang et al. *PNAS* (USA) 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.*, 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.*, 56:1457-1465 (1996) with respect to the HER2-HER3 protein complex. HER4, like HER3, forms an active signaling complex with HER2 (Carraway and Cantley, *Cell* 78:5-8 (1994)).

Patent publications related to HER antibodies include: U.S. Pat. No. 5,677,171, U.S. Pat. No. 5,720,937, U.S. Pat. No. 5,720,954, U.S. Pat. No. 5,725,856, U.S. Pat. No. 5,770,195, U.S. Pat. No. 5,772,997, U.S. Pat. No. 6,165,464, U.S. Pat. No. 6,387,371, U.S. Pat. No. 6,399,063, US2002/0192211A1, U.S. Pat. No. 6,015,567, U.S. Pat. No. 6,333,169, U.S. Pat. No. 4,968,603, U.S. Pat. No. 5,821,337, U.S. Pat. No. 6,054,297, U.S. Pat. No. 6,407,213, U.S. Pat. No. 6,719,971, U.S. Pat. No. 6,800,738, US2004/0236078A1, U.S. Pat. No. 5,648,237, U.S. Pat. No. 6,267,958, U.S. Pat. No. 6,685,940, U.S. Pat. No. 6,821,515, WO98/17797, U.S. Pat. No. 6,127,526, U.S. Pat. No. 6,333,398, U.S. Pat. No. 6,797,814, U.S. Pat. No. 6,339,142, U.S. Pat. No. 6,417,335, U.S. Pat. No. 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,196B1, U.S. Pat. No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. No. 5,985,553, U.S. Pat. No. 5,747,261, U.S. Pat. No. 4,935,341, U.S. Pat. No. 5,401,638, U.S. Pat. No. 5,604,107, WO 87/07646, WO 89/10412, WO91/05264, EP412,116 B1, EP494,135 B1, U.S. Pat. No. 5,824,311, EP444,181 B1, EP 1,006,194 A2, US 2002/0155527A1, WO 91/02062, U.S. Pat. No. 5,571,894, U.S. Pat. No. 5,939,531, EP 502,812 B1, WO 93/03741, EP 554,441 B1, EP 656,367 A1, U.S. Pat. No. 5,288,477, U.S. Pat. No. 5,514,554, U.S. Pat. No. 5,587,458, WO 93/12220, WO 93/16185, U.S. Pat. No. 5,877,305, WO 93/21319, WO 93/21232, U.S. Pat. No. 5,856,089, WO 94/22478, U.S. Pat. No. 5,910,486, U.S. Pat. No. 6,028,059, WO 96/07321, U.S. Pat. No. 5,804,396, U.S. Pat. No. 5,846,749, EP 711,565, WO 96/16673, U.S. Pat. No. 5,783,404, U.S. Pat. No. 5,977,322, U.S. Pat. No. 6,512,097, WO 97/00271, U.S. Pat. No. 6,270,765, U.S. Pat. No. 6,395,272, U.S. Pat. No. 5,837,243, WO 96/40789, U.S. Pat. No. 5,783,186, U.S. Pat. No. 6,458,356, WO 97/20858, WO 97/38731, U.S. Pat. No. 6,214,388, U.S. Pat. No. 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53 354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. No. 5,705,157, U.S. Pat. No. 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467.

Diagnostics

Patients treated with the HER2 antibody trastuzumab are selected for therapy based on HER2 overexpression/amplification. See, for example, WO99/31140 (Paton et al.), US2003/0170234A1 (Hellmann, S.), and US2003/0147884 (Paton et al.); as well as WO01/89566, US2002/0064785, and US2003/0134344 (Mass et al.). See, also, US2003/0152987, Cohen et al., concerning immunohistochemistry (IHC) and fluorescence in situ hybridization (FISH) for detecting HER2 overexpression and amplification.

WO2004/053497 and US2004/024815 μl (Bacus et al.), as well as US 2003/0190689 (Crosby and Smith), refer to determining or predicting response to trastuzumab therapy. US2004/013297A1 (Bacus et al.) concerns determining or predicting response to ABX0303 EGFR antibody therapy. WO2004/000094 (Bacus et al.) is directed to determining response to GW572016, a small molecule, EGFR-HER2 tyrosine kinase inhibitor. WO2004/063709, Amler et al., refers to biomarkers and methods for determining sensitivity to EGFR inhibitor, erlotinib HCl. US2004/0209290, Cobleigh et al., concerns gene expression markers for breast cancer prognosis.

Patients treated with pertuzumab can be selected for therapy based on HER activation or dimerization. Patent publications concerning pertuzumab and selection of patients for therapy therewith include: WO01/00245 (Adams et al.); US2003/0086924 (Sliwkowski, M.); US2004/0013667A1 (Sliwkowski, M.); as well as WO2004/008099A2, and US2004/0106161 (Bossenmaier et al.).

Cronin et al. *Am. J. Path.* 164(1): 35-42 (2004) describes measurement of gene expression in archival paraffin-embedded tissues. Ma et al. *Cancer Cell* 5:607-616 (2004) describes gene profiling by gene oliogonucleotide microarray using isolated RNA from tumor-tissue sections taken from archived primary biopsies.

Pertuzumab (also known as recombinant human monoclonal antibody 2C4; OMNITARG™, Genentech, Inc, South San Francisco) represents the first in a new class of agents known as HER dimerization inhibitors (HDI) and functions to inhibit the ability of HER2 to form active heterodimers with other HER receptors (such as EGFR/HER1, HER3 and HER4) and is active irrespective of HER2 expression levels. See, for example, Harari and Yarden, *Oncogene* 19:6102-14 (2000; Yarden and Sliwkowski *Nat Rev Mol Cell Biol,* 2:127-37 (2001); Sliwkowski *Nat Strcut Biol* 10:158-9 (2003); Cho, et al., *Nature* 421:756-60 (2003); and Malik, et al. *Pro Am Soc Cancer Res* 44:176-7 (2003).

Pertuzumab blockade of the formation of HER2-HER3 heterodimers in tumor cells has been demonstrated to inhibit critical cell signaling, which results in reduced tumor proliferation and survival (Agus et al. *Cancer Cell* 2:127-37 (2002)).

Pertuzumab has undergone testing as a single agent in the clinic with a phase Ia trial in patients with advanced cancers and phase II trials in patients with ovarian cancer and breast cancer as well as lung and prostate cancer. In a Phase I study, patients with incurable, locally advanced, recurrent or metastatic solid tumors that had progressed during or after standard therapy were treated with pertuzumab given intravenously every 3 weeks. Pertuzumab was generally well tolerated. Tumor regression was achieved in 3 of 20 patients evaluable for response. Two patients had confirmed partial responses. Stable disease lasting for more than 2.5 months was observed in 6 of 21 patients (Agus et al. *Pro Am Soc Clin Oncol* 22:192 (2003)). At doses of 2.0-15 mg/kg, the pharmacokinetics of pertuzumab was linear, and mean clearance ranged from 2.69 to 3.74 mL/day/kg and the mean terminal elimination half-life ranged from 15.3 to 27.6 days. Antibodies to pertuzumab were not detected (Allison et al. *Pro Am Soc Clin Oncol* 22:197 (2003)).

Sergina et al. report that the biological marker with which to assess the efficacy of HER tyroskine kinase inhibitors (TKIs) should be the transphosphorylation of HER3 rather than the autophosphorylation. Sergina et al. *Nature* 445(7126): 437-441 (2007).

Jazaeri et al. evaluated gene expression profiles associated with response to chemotherapy in epithelial ovarian cancers. Jazaeri et al. *Clin. Cancer Res. II* (17): 6300-6310 (2005).

Tanner et al. report that HER3 predicts survival in ovarian cancer. Tanner et al. *J. Clin. Oncol.* 24(26):4317-4323 (2006).

SUMMARY OF THE INVENTION

This application relates, at least in part, to the surprising observation that cancer patients (e.g. ovarian cancer patients) whose cancer expresses HER3 at a low level respond better in human clinical trials to a HER dimerization inhibitor than those patients whose cancer expresses HER3 at a high level. Generally, such patients have a high HER2:HER3 ratio (due to the low level of HER3), so evaluating the relative levels of both HER2 and HER3 provides an additional or alternative means for selecting patients for therapy with a HER dimerization inhibitor.

Thus, the invention herein concerns, in a first aspect, a method for treating a patient with a type of cancer which is able to respond to a HER inhibitor, comprising administering a therapeutically effective amount of a HER inhibitor to the patient, wherein the patient's cancer expresses HER3 at a level less than the median level for HER3 expression in the cancer type. Examples of HER inhibitors contemplated include HER antibodies or small molecule inhibitors; HER2 antibodies or small molecule inhibitors; tyrosine kinase inhibitors including but not limited to lapatinib, Tykerb; etc. Most preferably, the HER inhibitor is a HER dimerization inhibitor. Accordingly, the invention provides a method for treating a patient with a type of cancer which is able to respond to a HER dimerization inhibitor, comprising administering a therapeutically effective amount of a HER dimerization inhibitor to the patient, wherein the patient's cancer expresses HER3 at a level less than the median level for HER3 expression in the cancer type.

According to this embodiment, preferably, the patient's cancer expresses HER3 at a level which is less than the $25^{th}$ percentile for HER3 expression in the cancer type. Optionally, such patient's cancer expresses HER2:HER3 at a level greater than $25^{th}$ percentile, preferably greater than the median level, and most preferably greater than the $75^{th}$ percentile for HER2:HER3 expression in the cancer type. The preferred assay for measuring HER3 (and HER2) expression comprises polymerase chain reaction (PCR), most preferably quantitative real time polymerase chain reaction (qRT-PCR).

Preferably the HER dimerization inhibitor is an antibody, most preferably a HER2 antibody such as pertuzumab.

Preferably the cancer type to be treated or diagnosed herein is selected from the group consisting of ovarian cancer, peritoneal cancer, fallopian tube cancer, metastatic breast cancer (MBC), non-small cell lung cancer (NSCLC), prostate cancer, and colorectal cancer. Most preferably, the cancer type treated or diagnosed herein is ovarian cancer, peritoneal cancer, or fallopian tube cancer. The cancer type may be chemotherapy-resistant, platinum-resistant, advanced, refractory, and/or recurrent. The method may extend survival, including progression free survival (PFS) and overall survival (OS) in the patient.

The HER inhibitor may administered as a single anti-tumor agent, or may be combined with one or more other therapies. In one embodiment the HER inhibitor is administered with one or more chemotherapeutic agents, such as gemcitabine, carboplatin, paclitaxel, docetaxel, topotecan, and liposomal doxorubicin, and preferably an antimetabolite, such as gemcitabine. The HER inhibitor may also be combined with trastuzumab, erlotinib, or bevacizumab.

In a further aspect, the invention pertains to a method for treating a patient with ovarian, peritoneal, or fallopian tube cancer comprising administering a therapeutically effective amount of pertuzumab to the patient, wherein the patient's cancer expresses HER3 at a level less than the median level for HER3 expression in ovarian, peritoneal, or fallopian tube cancer.

The invention herein further concerns a method for selecting a therapy for a patient with a type of cancer which is able to respond to a HER inhibitor (e.g. a HER dimerization inhibitor) comprising determining HER3 expression in a cancer sample from the patient and selecting a HER inhibitor (e.g. a HER dimerization inhibitor) as the therapy if the cancer sample expresses HER3 at a level less than the median level for HER3 expression in the cancer type.

In addition, the invention provides an article of manufacture comprising, packaged together, a pharmaceutical composition comprising a HER dimerization inhibitor in a pharmaceutically acceptable carrier and a label stating that the inhibitor or pharmaceutical composition is indicated for treating a patient with a type of cancer which is able to respond to a HER dimerization inhibitor, wherein the patient's cancer expresses HER3 at a level less than the median level for HER3 expression in the cancer type.

In a further aspect, the invention pertains to a method for manufacturing a HER dimerization inhibitor or a pharmaceutical composition thereof comprising combining in a package the inhibitor or pharmaceutical composition and a label stating that the inhibitor or pharmaceutical composition is indicated for treating a patient with a type of cancer which is able to respond to a HER dimerization inhibitor, wherein the patient's cancer expresses HER3 at a level less than the median level for HER3 expression in the cancer type.

In yet another embodiment, the invention provides a method for advertising a HER dimerization inhibitor or a pharmaceutically acceptable composition thereof comprising promoting, to a target audience, the use of the HER dimerization inhibitor or pharmaceutical composition thereof for treating a patient population with a type of cancer, where the patient's cancer expresses HER3 at a level less than the median level for HER3 expression in the cancer type.

Aside from the above inventions, human clinical data provided herein demonstrated that cancer patients (e.g. ovarian cancer patients) whose cancer expresses HER3 at a high level, have a better clinical response to a chemotherapeutic agent, such as gemcitabine, than those patients whose cancer expresses HER3 at a low level.

As to this further aspect of the invention, the invention provides a method for selecting a therapy for a patient with a type of cancer which is likely respond to a chemotherapeutic agent comprising determining HER3 expression in a cancer sample from the patient and selecting a chemotherapeutic agent as the therapy if the cancer sample expresses HER3 at a level greater than the median level for HER3 expression in the cancer type. Preferably the cancer type is ovarian, peritoneal, or fallopian tube cancer, including platinum-resistant ovarian, peritoneal, or fallopian tube cancer, as well as advanced, refractory, or recurrent ovarian cancer. Preferably the selected chemotherapeutic agent is an antimetabolite, such as gemcitabine.

The invention also concerns a method for treating a patient with a type of cancer which is able to respond to a chemotherapeutic agent, comprising administering a therapeutically effective amount of a chemotherapeutic agent to the patient, wherein the patient's cancer expresses HER3 at a level greater than the median level for HER3 expression in the cancer type. Preferably, the patient's cancer expresses HER3 at a level which is greater than the $25^{th}$ percentile for HER3 expression in the cancer type. The preferred assay for measuring HER3 expression comprises polymerase chain reaction (PCR), most preferably quantitative real time polymerase chain reaction (qRT-PCR).

Preferably the chemotherapeutic agent is an antimetabolite, most preferably gemcitabine.

Preferably the cancer type to be treated or diagnosed according to this further aspect of the invention is ovarian cancer, peritoneal cancer, or fallopian tube cancer. The cancer type may be chemotherapy-resistant, platinum-resistant, advanced, refractory, and/or recurrent. The method may extend survival, including progression free survival (PFS) and overall survival (OS) in the patient.

In a further aspect, the invention pertains to a method for treating a patient with ovarian, peritoneal, or fallopian tube cancer comprising administering a therapeutically effective amount of gemcitabine to the patient, wherein the patient's cancer expresses HER3 at a level greater than the median level for HER3 expression in ovarian, peritoneal, or fallopian tube cancer.

The invention also provides an article of manufacture comprising, packaged together, a pharmaceutical composition comprising a chemotherapeutic agent (such as gemcitabine) in a pharmaceutically acceptable carrier and a label stating that the chemotherapeutic agent or pharmaceutical composition is indicated for treating a patient with a type of cancer, wherein the patient's cancer expresses HER3 at a level greater than the median level for HER3 expression in the cancer type.

In yet a further aspect, the invention concerns a method for manufacturing a chemotherapeutic agent (such as gemcitabine) or a pharmaceutical composition thereof comprising combining in a package the chemotherapeutic agent or pharmaceutical composition and a label stating that the chemotherapeutic agent or pharmaceutical composition is indicated for treating a patient with a type of cancer, wherein the patient's cancer expresses HER3 at a level greater than the median level for HER3 expression in the cancer type.

In yet another embodiment, the invention provides a method for advertising a chemotherapeutic agent or a pharmaceutically acceptable composition thereof comprising promoting, to a target audience, the use of the chemotherapeutic agent or pharmaceutical composition thereof for treating a patient population with a type of cancer, where the patient's cancer expresses HER3 at a level greater than the median level for HER3 expression in the cancer type.

The present application provides human clinical data demonstrating that patients with high HER2:HER3 expression respond more favorably to a HER inhibitor, such as pertuzumab. Thus, the invention provides, in another aspect, a means for selecting patients by evaluating HER2 and HER3 expression levels, and excluding from therapy those patients whose cancer expresses HER2:HER3 at a low level.

Thus, the invention also concerns a method for treating a patient with a type of cancer which is able to respond to a HER inhibitor, comprising administering a therapeutically effective amount of a HER inhibitor to the patient, wherein the patient's cancer expresses HER2:HER3 at a level which is greater than the $25^{th}$ percentile for HER2:HER3 expression in the cancer type. Preferably, the patient's cancer expresses HER2:HER3 at a level which is greater than the median, and most preferably greater than the $75^{th}$ percentile, for HER2:HER3 expression in the cancer type.

In addition, a method for treating a patient with ovarian, peritoneal, or fallopian tube cancer is provided which method comprises administering a therapeutically effective amount of pertuzumab to the patient, wherein the patient's cancer expresses HER2:HER3 at a level which is greater than the 25th percentile for HER2:HER3 expression in ovarian, peritoneal, or fallopian tube cancer.

In another aspect, the invention concerns a method for selecting a therapy for a patient with a type of cancer which is able to respond to a HER inhibitor comprising determining HER2 and HER3 expression in a cancer sample from the patient and selecting a HER inhibitor as the therapy if the cancer sample expresses HER2:HER3 at a level which is greater than the 25th percentile for HER2:HER3 expression in the cancer type.

Also, the invention pertains to an article of manufacture comprising, packaged together, a pharmaceutical composition comprising a HER inhibitor in a pharmaceutically acceptable carrier and a label stating that the inhibitor or pharmaceutical composition is indicated for treating a patient with a type of cancer which is able to respond to a HER inhibitor, wherein the patient's cancer expresses HER2:HER3 at a level which is greater than the 25th percentile for HER2:HER3 expression in the cancer type.

Moreover, the invention provides a method for manufacturing a HER inhibitor or a pharmaceutical composition thereof comprising combining in a package the inhibitor or pharmaceutical composition and a label stating that the inhibitor or pharmaceutical composition is indicated for treating a patient with a type of cancer which is able to respond to a HER inhibitor, wherein the patient's cancer expresses HER2:HER3 at a level which is greater than the 25th percentile for HER2:HER3 expression in the cancer type.

In addition, the invention relates to a method for advertising a HER inhibitor or a pharmaceutically acceptable composition thereof comprising promoting, to a target audience, the use of the HER inhibitor or pharmaceutical composition thereof for treating a patient population with a type of cancer, where the patient's cancer expresses HER2:HER3 at a level which is greater than the 25th percentile for HER2:HER3 expression in the cancer type.

BRIEF DESCRIPTION OF THE DRAWINGS

FIGS. 3A and 3B show the amino acid sequences of pertuzumab light chain (FIG. 3A; SEQ ID NO. 13) and heavy chain (FIG. 3B; SEQ ID No. 14). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIG. 6 compares various activities of trastuzumab and pertuzumab.

FIGS. 7A and 7B show the amino acid sequences of trastuzumab light chain (FIG. 7A; SEQ ID No. 15) and heavy chain (FIG. 7B; SEQ ID No. 16), respectively.

FIGS. 8A and 8B depict a variant pertuzumab light chain sequence (FIG. 8A; SEQ ID No. 17) and a variant pertuzumab heavy chain sequence (FIG. 8B; SEQ ID No. 18), respectively.

FIG. 12B is another representation of PFS by wRT-PCR EGFR (HER1) cutoffs, also indicating the number of subjects in the HER1 (High) and HER1 (Low) groups at various EGFR cutoff values.

FIG. 17A summarizes PFS by HER3 subgroups; high HER3 expression subgroup, and low HER3 expression subgroup.

FIG. 17B is an updated version of PFS by qRT-PCR HER3 levels shown in FIG. 17B.

FIG. 18A further demonstrates PFS by HER3 subgroups.

FIG. 18B is an updated version of PFS analysis by HER3 expression quartiles, shown in FIG. 18A.

FIG. 19A shows PFS by HER3 qRT-PCR with a 50/50 split; with low HER3 expression in the less than 50th percentile, and high HER3 expression in the greater than or equal to 50th percentile.

FIG. 19B is an updated version of PFS by HER3 qRT-PCR with a 50/50 split, shown in FIG. 19A.

FIG. 20A shows PFS by HER3 qRT-PCR with a 25/75 split; with low HER3 expression in the less than 25th percentile, and high HER3 expression in the greater than or equal to 25th percentile.

FIG. 20B is an updated version of PFS by HER3 qRT-PCR with a 25/75 split, shown in FIG. 20A.

FIG. 22A illustrates preliminary data for OS by HER3 in qRT-PCR. Data based on 43/119 events.

FIG. 22B is an updated chart of OS data by HER3 in qRT-PCR with a 50/50 split, with 1 or HER3 expression in the less than 50th percentile, and high HER3 expression in the greater than or equal to 25th percentile.

FIG. 23B is an updated chart of PFS by HER3 qRT-PCR comparing high versus low hazart ratios (HR).

FIG. 24A shows the full set of data for pertuzumab platinum resistant ovarian cancer in Example 1, with PFS by qRT-PCR HER3. Note: The HR and Log-rank p-values were not adjusted for multiple comparison.

FIG. 24B is another set of data for pertuzumab platinum resistant ovarian cancer, with PFS by qRT-PCR HER3. Just as in FIG. 24A, the HR and Log-rank p-values were not adjusted for multiple comparison.

FIG. 25 shows PFS and OS by HER3 qRT-PCR for patients treated as in Example 2 with single agent pertuzumab. High HER3 were patients in the greater than and equal to 75th percentile; patients in the low HER3 were those less than the 75th percentile. Median survival for low expressing patients was 3.31 years (95% CI, 1.93-4.69); median survival was 1.80 years for high HER3 expressing patients (95% CI, 0.83 to 2.78).

FIG. 29A provides PFS by HER2:HER3 percentiles for patients treated in Example 1.

FIG. 29B is another figure showing PFS by HER2:HER3 percentiles for patients treated in Example 1. Note: The HRs and log-rank p-values were not adjusted for multiple comparison.

FIG. 31A assesses PFS by HER2:HER3 ratio quartile subgroups, again from Example 1.

FIG. 31B is another summary of PFS analysis by HER2/HER3 quartiles recurrent ovarian cancer.

DETAILED DESCRIPTION OF THE PREFERRED EMBODIMENTS

I. Definitions

A "HER receptor" is a receptor protein tyrosine kinase which belongs to the HER receptor family and includes EGFR, HER2, HER3 and HER4 receptors. The HER receptor will generally comprise an extracellular domain, which may bind an HER ligand and/or dimerize with another HER receptor molecule; a lipophilic transmembrane domain; a conserved intracellular tyrosine kinase domain; and a carboxyl-terminal signaling domain harboring several tyrosine residues which can be phosphorylated. The HER receptor may be a "native sequence" HER receptor or an "amino acid sequence variant" thereof. Preferably the HER receptor is native sequence human HER receptor.

The terms "ErbB1," "HER1", "epidermal growth factor receptor" and "EGFR" are used interchangeably herein and refer to EGFR as disclosed, for example, in Carpenter et al. *Ann. Rev. Biochem.* 56:881-914 (1987), including naturally occurring mutant forms thereof (e.g. a deletion mutant EGFR as in Humphrey et al. *PNAS (USA)* 87:4207-4211 (1990)). erbB1 refers to the gene encoding the EGFR protein product.

The expressions "ErbB2" and "HER2" are used interchangeably herein and refer to human HER2 protein described, for example, in Semba et al., *PNAS (USA)* 82:6497-6501 (1985) and Yamamoto et al. *Nature* 319:230-234 (1986) (Genebank accession number X03363). The term "erbB2" refers to the gene encoding human ErbB2 and "neu" refers to the gene encoding rat p185$^{neu}$. Preferred HER2 is native sequence human HER2.

Figure 1:
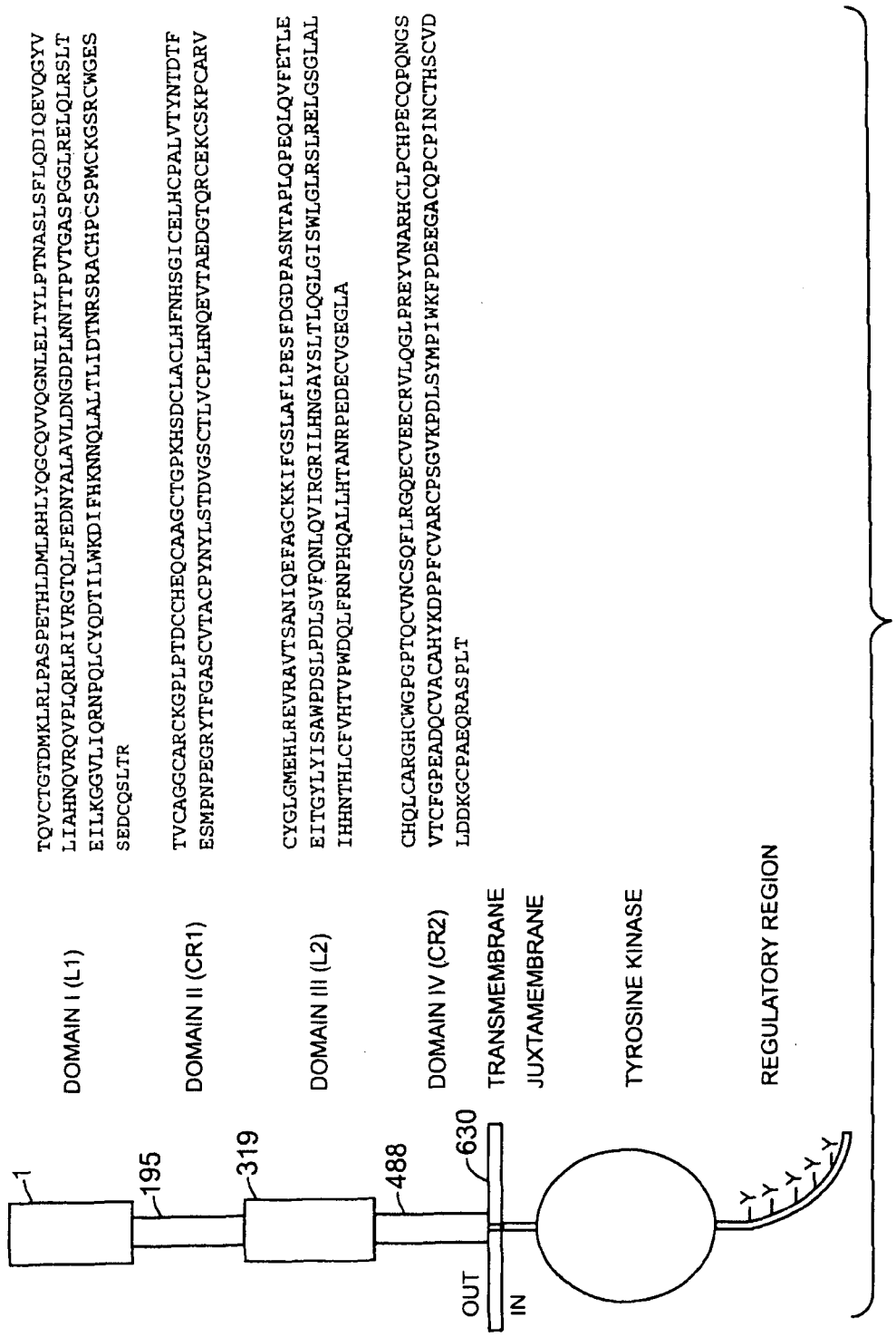
FIG. 1 provides a schematic of the HER2 protein structure, and amino acid sequences for Domains I-IV (SEQ ID Nos. 19-22, respectively) of the extracellular domain thereof.

Herein, "HER2 extracellular domain" or "HER2ECD" refers to a domain of HER2 that is outside of a cell, either anchored to a cell membrane, or in circulation, including fragments thereof. In one embodiment, the extracellular domain of HER2 may comprise four domains: "Domain I" (amino acid residues from about 1-195; SEQ ID NO:19), "Domain II" (amino acid residues from about 196-319; SEQ ID NO:20), "Domain 111" (amino acid residues from about 320-488: SEQ ID NO:21), and "Domain IV" (amino acid residues from about 489-630; SEQ ID NO:22) (residue numbering without signal peptide). See Garrett et al. *Mol. Cell.* 11: 495-505 (2003), Cho et al. *Nature* 421: 756-760 (2003), Franklin et al. *Cancer Cell* 5:317-328 (2004), and Plowman et al. *Proc. Natl. Acad. Sci.* 90:1746-1750 (1993), as well as FIG. 1 herein.

"ErbB3" and "HER3" refer to the receptor polypeptide as disclosed, for example, in U.S. Pat. Nos. 5,183,884 and 5,480, 968 as well as Kraus et al. *PNAS (USA)* 86:9193-9197 (1989).

The terms "ErbB4" and "HER4" herein refer to the receptor polypeptide as disclosed, for example, in EP Pat Appln No 599,274; Plowman et al., *Proc. Natl. Acad. Sci. USA*, 90:1746-1750 (1993); and Plowman et al., *Nature,* 366:473-475 (1993), including isoforms thereof, e.g., as disclosed in WO99/19488, published Apr. 22, 1999.

By "HER ligand" is meant a polypeptide which binds to and/or activates a HER receptor. The HER ligand of particular interest herein is a native sequence human HER ligand such as epidermal growth factor (EGF) (Savage et al., *J. Biol. Chem.* 247:7612-7621 (1972)); transforming growth factor alpha (TGF-α) (Marquardt et al., *Science* 223:1079-1082 (1984)); amphiregulin also known as schwanoma or keratinocyte autocrine growth factor (Shoyab et al. *Science* 243:1074-1076 (1989); Kimura et al. *Nature* 348:257-260 (1990); and Cook et al. *Mol. Cell. Biol.* 11:2547-2557 (1991)); betacellulin (Shing et al., *Science* 259:1604-1607 (1993); and Sasada et al. *Biochem. Biophys. Res. Commun.* 190:1173 (1993)); heparin-binding epidermal growth factor (HB-EGF) (Higashiyama et al., *Science* 251:936-939 (1991)); epiregulin (Toyoda et al., *J. Biol. Chem.* 270:7495-7500 (1995); and Komurasaki et al. *Oncogene* 15:2841-2848 (1997)); a heregulin (see below); neuregulin-2 (NRG-2) (Carraway et al., *Nature* 387:512-516 (1997)); neuregulin-3 (NRG-3) (Zhang et al., *Proc. Natl. Acad. Sci.* 94:9562-9567 (1997)); neuregulin-4 (NRG-4) (Harari et al. *Oncogene* 18:2681-89 (1999)); and cripto (CR-1) (Kannan et al. *J. Biol. Chem.* 272(6):3330-3335 (1997)). HER ligands which bind EGFR include EGF, TGF-α, amphiregulin, betacellulin, HB-EGF and epiregulin. HER ligands which bind HER3 include heregulins. HER ligands capable of binding HER4 include betacellulin, epiregulin, HB-EGF, NRG-2, NRG-3, NRG-4, and heregulins.

"Heregulin" (HRG) when used herein refers to a polypeptide encoded by the heregulin gene product as disclosed in U.S. Pat. No. 5,641,869, or Marchionni et al., *Nature,* 362: 312-318 (1993). Examples of heregulins include heregulin-α, heregulin-β1, heregulin-β2 and heregulin-β3 (Holmes et al., *Science,* 256:1205-1210 (1992); and U.S. Pat. No. 5,641, 869); neu differentiation factor (NDF) (Peles et al. *Cell* 69: 205-216 (1992)); acetylcholine receptor-inducing activity (ARIA) (Falls et al. *Cell* 72:801-815 (1993)); glial growth factors (GGFs) (Marchionni et al., *Nature,* 362:312-318 (1993)); sensory and motor neuron derived factor (SMDF) (Ho et al. *J. Biol. Chem.* 270:14523-14532 (1995)); γ-heregulin (Schaefer et al. *Oncogene* 15:1385-1394 (1997)).

A "HER dimmer" herein is a noncovalently associated dimer comprising at least two HER receptors. Such complexes may form when a cell expressing two or more HER receptors is exposed to an HER ligand and can be isolated by immunoprecipitation and analyzed by SDS-PAGE as described in Sliwkowski et al., *J. Biol. Chem.,* 269(20): 14661-14665 (1994), for example. Other proteins, such as a cytokine receptor subunit (e.g. gp130) may be associated with the dimer. Preferably, the HER dimer comprises HER2.

A "HER heterodimer" herein is a noncovalently associated heterodimer comprising at least two different HER receptors, such as EGFR-HER2, HER2-HER3 or HER2-HER4 heterodimers.

Figure 5:
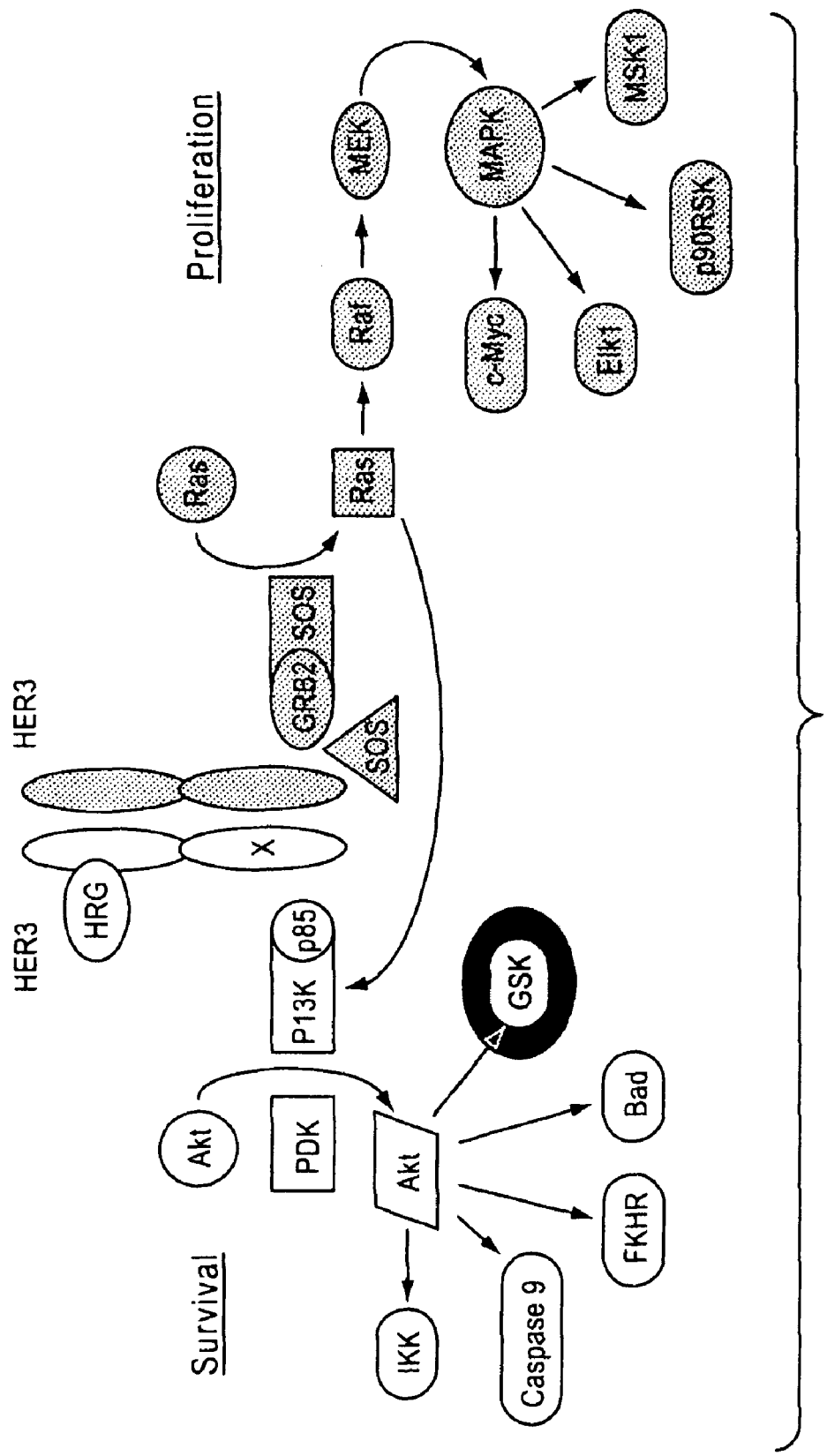
FIG. 5 depicts coupling of HER2/HER3 to the MAPK and Akt pathways.

A "HER inhibitor" is an agent which interferes with HER activation or function. Examples of HER inhibitors include HER antibodies (e.g. EGFR, HER2, HER3, or HER4 antibodies); EGFR-targeted drugs; small molecule HER antagonists; HER tyrosine kinase inhibitors; HER2 and EGFR dual tyrosine kinase inhibitors such as lapatinib/GW572016); antisense molecules (see, for example, WO2004/87207); and/or agents that bind to, or interfere with function of, downstream signaling molecules, such as MAPK or Akt (see FIG. 5). Preferably, the HER inhibitor is an antibody or small molecule which binds to a HER receptor.

Figure 4:
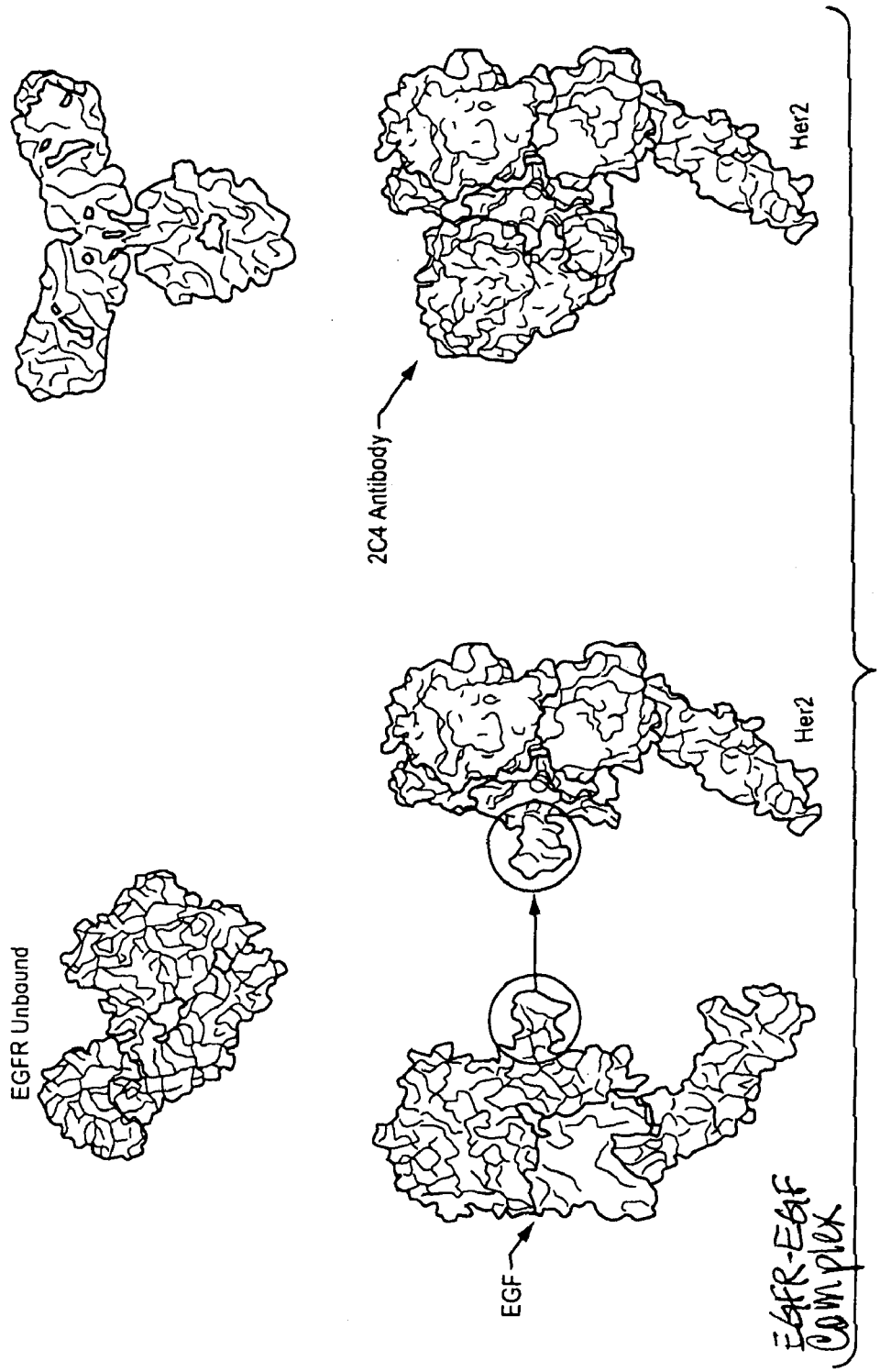
FIG. 4 depicts, schematically, binding of 2C4 at the heterodimeric binding site of HER2, thereby preventing heterodimerization with activated EGFR or HER3.

A "HER dimerization inhibitor" is an agent which inhibits formation of a HER dimer or HER heterodimer. Preferably the HER dimerization inhibitor is a HER2 dimerization inhibitor and/or inhibits HER heterodimerization. Preferably, the HER dimerization inhibitor is an antibody, for example an antibody which binds to HER2 at the heterodimeric binding site thereof. The most preferred HER dimerization inhibitor herein is pertuzumab or MAb 2C4. Binding of 2C4 to the heterodimeric binding site of HER2 is illustrated in FIG. 4. Other examples of HER dimerization inhibitors include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279 (29):30375-30384 (2004)); antibodies which bind to HER3 and inhibit dimerization thereof with one or more other HER receptors; antibodies which bind to HER4 and inhibit dimerization thereof with one or more other HER receptors; peptide dimerization inhibitors (U.S. Pat. No. 6,417,168); antisense dimerization inhibitors; etc.

A "HER2 dimerization inhibitor" is an agent that inhibits formation of a dimer or heterodimer comprising HER2.

A "HER antibody" is an antibody that binds to a HER receptor. Optionally, the HER antibody further interferes with HER activation or function. Preferably, the HER antibody binds to the HER2 receptor. A HER2 antibody of particular interest herein is pertuzumab. Another example of a HER2 antibody is trastuzumab. Examples of EGFR antibodies include cetuximab and ABX0303.

"HER activation" refers to activation, or phosphorylation, of any one or more HER receptors. Generally, HER activation results in signal transduction (e.g. that caused by an intracellular kinase domain of a HER receptor phosphorylating tyrosine residues in the HER receptor or a substrate polypeptide). HER activation may be mediated by HER ligand binding to a HER dimer comprising the HER receptor of interest. HER ligand binding to a HER dimer may activate a kinase domain of one or more of the HER receptors in the dimer and thereby results in phosphorylation of tyrosine residues in one or more of the HER receptors and/or phosphorylation of tyrosine residues in additional substrate polypeptides(s), such as Akt or MAPK intracellular kinases, see, FIG. 5, for example.

"Phosphorylation" refers to the addition of one or more phosphate group(s) to a protein, such as a HER receptor, or substrate thereof.

An antibody which "inhibits HER dimerization" is an antibody which inhibits, or interferes with, formation of a HER dimer. Preferably, such an antibody binds to HER2 at the heterodimeric binding site thereof. The most preferred dimerization inhibiting antibody herein is pertuzumab or MAb 2C4. Binding of 2C4 to the heterodimeric binding site of HER2 is illustrated in FIG. 4. Other examples of antibodies which inhibit HER dimerization include antibodies which bind to EGFR and inhibit dimerization thereof with one or more other HER receptors (for example EGFR monoclonal antibody 806, MAb 806, which binds to activated or "untethered" EGFR; see Johns et al., *J. Biol. Chem.* 279(29):30375-30384 (2004)); antibodies which bind to HER3 and inhibit dimerization thereof with one or more other HER receptors; and antibodies which bind to HER4 and inhibit dimerization thereof with one or more other HER receptors.

Figure 2:
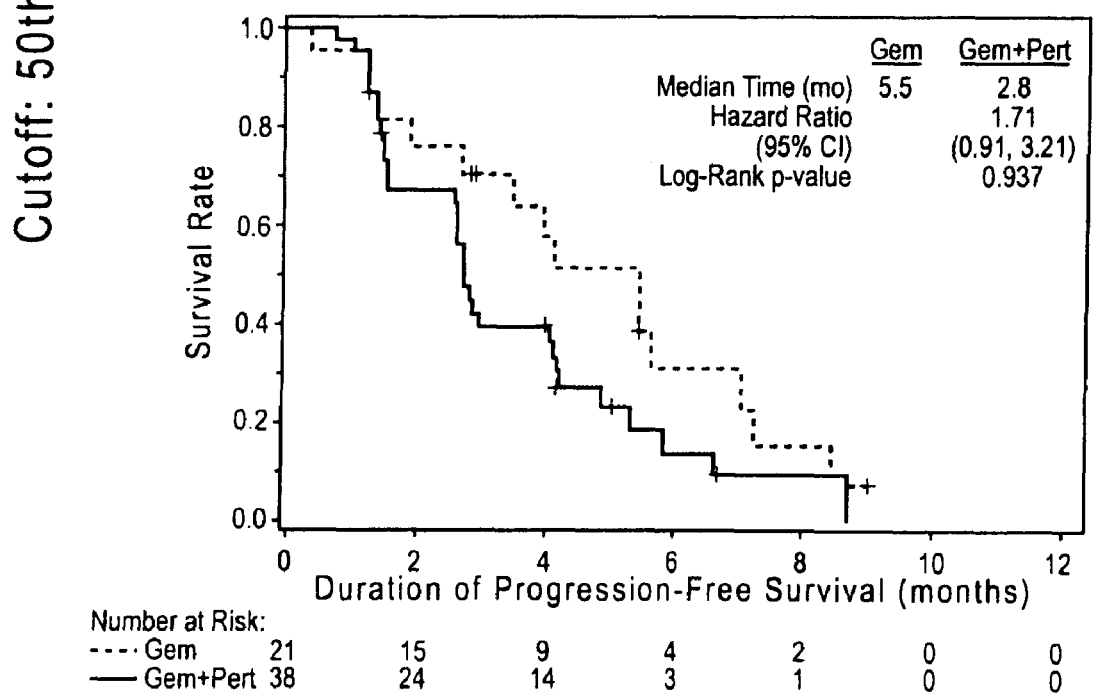
FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 1 and 2, respectively); $V_L$ and $V_H$ domains of variant 574/pertuzumab (SEQ ID Nos. 3 and 4, respectively), and human $V_L$ and $V_H$ consensus frameworks (humκ1, light kappa subgroup 1; humIII, heavy subgroup III) (SEQ ID Nos. 5 and 6, respectively). Asterisks identify differences between variable domains of pertuzumab and murine monoclonal antibody 2C4 or between variable domains of pertuzumab and the human framework. Complementarity Determining Regions (CDRs) are in brackets.

An antibody which "blocks ligand activation of a HER receptor more effectively than trastuzumab" is one which reduces or eliminates HER ligand activation of HER receptor(s) or HER dimer(s) more effectively (for example at least about 2-fold more effectively) than trastuzumab. Preferably, such an antibody blocks HER ligand activation of a HER receptor at least about as effectively as murine monoclonal antibody 2C4 or a Fab fragment thereof, or as pertuzumab or a Fab fragment thereof. One can evaluate the ability of an antibody to block ligand activation of a HER receptor by studying HER dimers directly, or by evaluating HER activation, or downstream signaling, which results from HER dimerization, and/or by evaluating the antibody-HER2 binding site, etc. Assays for screening for antibodies with the ability to inhibit ligand activation of a HER receptor more effectively than trastuzumab are described in Agus et al. *Cancer Cell* 2: 127-137 (2002) and WO01/00245 (Adams et al.). By way of example only, one may assay for: inhibition of HER dimer formation (see, e.g., FIG. 1A-B of Agus et al. *Cancer Cell* 2: 127-137 (2002); and WO01/00245); reduction in HER ligand activation of cells which express HER dimers (WO01/00245 and FIG. 2A-B of Agus et al. *Cancer Cell* 2: 127-137 (2002), for example); blocking of HER ligand binding to cells which express HER dimers (WO01/00245, and FIG. 2E of Agus et al. *Cancer Cell* 2: 127-137 (2002), for example); cell growth inhibition of cancer cells (e.g. MCF7, MDA-MD-134, ZR-75-1, MD-MB-175, T-47D cells) which express HER dimers in the presence (or absence) of HER ligand (WO01/00245 and FIGS. 3A-D of Agus et al. *Cancer Cell* 2:127-137 (2002), for instance); inhibition of downstream signaling (for instance, inhibition of HRG-dependent AKT phosphorylation or inhibition of HRG- or TGFα-dependent MAPK phosphorylation) (see, WO01/00245, and FIG. 2C-D of Agus et al. *Cancer Cell* 2: 127-137 (2002), for example). One may also assess whether the antibody inhibits HER dimerization by studying the antibody-HER2 binding site, for instance, by evaluating a structure or model, such as a crystal structure, of the antibody bound to HER2 (See, for example, Franklin et al. *Cancer Cell* 5:317-328 (2004)).

A "heterodimeric binding site" on HER2, refers to a region in the extracellular domain of HER2 that contacts, or interfaces with, a region in the extracellular domain of EGFR, HER3 or HER4 upon formation of a dimer therewith. The region is found in Domain II of HER2. Franklin et al. *Cancer Cell* 5:317-328 (2004).

The HER2 antibody may "inhibit HRG-dependent AKT phosphorylation" and/or inhibit "HRG- or TGFα-dependent MAPK phosphorylation" more effectively (for instance at least 2-fold more effectively) than trastuzumab (see Agus et al. *Cancer Cell* 2: 127-137 (2002) and WO01/00245, by way of example).

The HER2 antibody may be one which, like pertuzumab, does "not inhibit HER2 ectodomain cleavage" (Molina et al. *Cancer Res.* 61:4744-4749 (2001)). Trastuzumab, on the other hand, can inhibit HER2 ectodomain cleavage.

A HER2 antibody that "binds to a heterodimeric binding site" of HER2, binds to residues in domain II (and optionally also binds to residues in other of the domains of the HER2 extracellular domain, such as domains I and III), and can sterically hinder, at least to some extent, formation of a HER2-EGFR, HER2-HER3, or HER2-HER4 heterodimer. Franklin et al. *Cancer Cell* 5:317-328 (2004) characterize the HER2-pertuzumab crystal structure, deposited with the RCSB Protein Data Bank (ID Code IS78), illustrating an exemplary antibody that binds to the heterodimeric binding site of HER2.

An antibody that "binds to domain II" of HER2 binds to residues in domain II and optionally residues in other domain(s) of HER2, such as domains I and III. Preferably the antibody that binds to domain II binds to the junction between domains I, II and III of HER2.

Protein "expression" refers to conversion of the information encoded in a gene into messenger RNA (mRNA) and then to the protein.

Herein, a sample or cell that "expresses" a protein of interest (such as a HER3 and/or HER2) is one in which mRNA encoding the protein, or the protein, including fragments thereof, is determined to be present in the sample or cell.

A sample, cell, tumor or cancer which "expresses HER3 at a level less than the median level for HER3 expression" in a type of cancer is one in which the level of HER3 expression is considered a "low HER3 level" to a skilled person for that type of cancer. Generally, such level will be in the range from about 0 to less than about 50%, relative to HER3 levels in a population of samples, cells, tumors, or cancers of the same cancer type. For instance the population which is used to arrive at the median expression level may be ovarian cancer samples generally, or subgroupings thereof, such as chemotherapy-resistant ovarian cancer, platinum-resistant ovarian cancer, as well as advanced, refractory or recurrent ovarian cancer. The examples herein, demonstrate how the median expression level can be determined. This may constitute an absolute value of expression. Thus, with reference to FIG. 17 herein, the cut off for platinum-resistant ovarian patients considered to express HER3 at a low level may be about 2.8 or less (less than $60^{th}$ percentile); about 2.41 or less (less than $55^{th}$ percentile); about 2.28 or less (less than $50^{th}$ percentile); about 1.88 or less (less than $45^{th}$ percentile); about 1.71 or less (less than $40^{th}$ percentile); about 1.57 or less (less than $35^{th}$ percentile); about 1.4 or less (less than $30^{th}$ percentile); about 1.19 or less (less than $25^{th}$ percentile); about 0.99 or less (less than $20^{th}$ percentile), etc. Such absolute values will be quantified in an assay under specified assay conditions, such as qRT-PCR disclosed herein, and most preferably the qRT-PCR assay as in Example 1. Preferably, the level of HER3 expression is less than the $50^{th}$ percentile, and most preferably less than the $30^{th}$ or $25^{th}$ percentile.

The expressions "HER2:HER3" or "HER2 to HER3" herein refer to the expression level of HER2 relative to the expression level of HER3 in a sample, cell, tumor or cancer. Such expression level(s) may be quantified using a variety of different techniques such as those disclosed herein. While this may be calculated as a ratio of HER2 expression to HER3 expression, the present invention contemplates various other ways of evaluating the levels of HER2 and HER3 so as to select a patient for therapy herein, including, but not limited to using a decision tree where patients are selected if their expression of HER2 and/or HER3 is over or under certain cut-offs, etc. Such various other means for comparing HER2 to HER3 are encompassed by the phrases "HER2:HER3" or "HER2 to HER3" herein.

A sample, cell, tumor or cancer which "expresses HER2: HER3 a level which is greater than the $25^{th}$ percentile for HER2:HER3 expression" in a type of cancer is one in which the ratio of HER2 expression relative to HER3 expression is not a "low HER2:HER3 level" for that type of cancer. Preferably, such level will be in the range from greater than about 25% to about 100%, relative to HER2:HER3 levels in a population of samples, cells, tumors, or cancers of the same cancer type. For instance, the population which is used to arrive at the such expression levels may be ovarian cancer samples generally, or subgroupings thereof, such as chemotherapy-resistant ovarian cancer, platinum-resistant ovarian cancer, as well as advanced, refractory or recurrent ovarian cancer. The examples herein, demonstrate how the percentile expression levels can be determined. In one embodiment, the HER2:

HER3 level constitutes an absolute value of expression. Thus, with reference to FIG. 29 herein, the cut off for platinum-resistant ovarian patients expressing HER2:HER3 at this level may be about 0.82 or more (greater than $25^{th}$ percentile); about 0.90 or more (greater than $30^{th}$ percentile); about 1.06 or more (greater than $35^{th}$ percentile); about 1.13 or more (greater than $40^{th}$ percentile); about 1.26 or more (greater than $45^{th}$ percentile); about 1.53 or more (greater than $50^{th}$ percentile); about 1.70 or more (greater than $55^{th}$ percentile); about 1.86 or more (greater than $60^{th}$ percentile); about 2.15 or more (greater than $65^{th}$ percentile); about 2.49 or more (greater than $70^{th}$ percentile); about 2.62 or more (greater than $75^{th}$ percentile); about 2.92 or more (greater than $80^{th}$ percentile), etc. Such absolute values will be quantified in an assay under specified assay conditions, such as qRT-PCR disclosed herein, and most preferably the qRT-PCR assay as in Example 1. In one embodiment, the level of HER2:HER3 expression is greater than the $50^{th}$ percentile, preferably greater than the $70^{th}$ percentile, and most preferably greater than the $75^{th}$ percentile. Patients whose cancer expresses HER2:HER3 at levels as described herein may, or may not, overexpress HER2.

The technique of "polymerase chain reaction" or "PCR" as used herein generally refers to a procedure wherein minute amounts of a specific piece of nucleic acid, RNA and/or DNA, are amplified as described in U.S. Pat. No. 4,683,195 issued 28 Jul. 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.,* 51: 263 (1987); Erlich, ed., PCR Technology, (Stockton Press, NY, 1989). As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real time polymerase chain reaction" or "qRT-PCR" refers to a form of PCR wherein the amount of PCR product is measured at each step in a PCR reaction. This technique has been described in various publications including Cronin et al., *Am. J. Pathol.* 164(1):35-42 (2004); and Ma et al., *Cancer Cell* 5:607-616 (2004).

The term "microarray" refers to an ordered arrangement of hybridizable array elements, preferably polynucleotide probes, on a substrate.

The term "polynucleotide," when used in singular or plural, generally refers to any polyribonucleotide or polydeoxyribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The term includes DNAs (including cDNAs) and RNAs that contain one or more modified bases. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of viruses and cells, including simple and complex cells.

The term "oligonucleotide" refers to a relatively short polynucleotide, including, without limitation, single-stranded deoxyribonucleotides, single- or double-stranded ribonucleotides, RNA:DNA hybrids and double-stranded DNAs. Oligonucleotides, such as single-stranded DNA probe oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells and organisms.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced also increases in the proportion of the number of copies made of the particular gene expressed.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures. Hybridization generally depends on the ability of denatured DNA to reanneal when complementary strands are present in an environment below their melting temperature. The higher the degree of desired homology between the probe and hybridizable sequence, the higher the relative temperature which can be used. As a result, it follows that higher relative temperatures would tend to make the reaction conditions more stringent, while lower temperatures less so. For additional details and explanation of stringency of hybridization reactions, see Ausubel et al., *Current Protocols in Molecular Biology,* Wiley Interscience Publishers, (1995).

"Stringent conditions" or "high stringency conditions", as defined herein, typically: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 &gr; g/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

"Moderately stringent conditions" may be identified as described by Sambrook et al., *Molecular Cloning: A Laboratory Manual*, New York: Cold Spring Harbor Press, 1989, and include the use of washing solution and hybridization conditions (e.g., temperature, ionic strength and % SDS) less stringent that those described above. An example of moderately stringent conditions is overnight incubation at 37° C. in a solution comprising: 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C. The skilled artisan will recognize how to adjust the temperature, ionic strength, etc. as necessary to accommodate factors such as probe length and the like.

A "native sequence" polypeptide is one which has the same amino acid sequence as a polypeptide (e.g., HER receptor or HER ligand) derived from nature, including naturally occurring or allelic variants. Such native sequence polypeptides can be isolated from nature or can be produced by recombinant or synthetic means. Thus, a native sequence polypeptide can have the amino acid sequence of naturally occurring human polypeptide, murine polypeptide, or polypeptide from any other mammalian species.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or non-proteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The "variable region" or "variable domain" of an antibody refers to the amino-terminal domains of the heavy or light chain of the antibody. The variable domain of the heavy chain may be referred to as "VH." The variable domain of the light chain may be referred to as "VL." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. *Cellular and Mol. Immunology,* 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. Examples of antibody fragments include Fab, Fab', $F(ab')_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the sc Fv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315. scFv fragments herein specifically include "small modular immunopharmaceuticals" (SMIPs) such as disclosed in US2005/0180970A1 and US2005/0186216 A1 assigned to Trubion.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816, 567; and Morrison et al., *Proc. Natl. Acad. Sci. USA* 81:6851-6855 (1984)). Chimeric antibodies include PRIMATIZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

Humanized HER2 antibodies include huMAb4D5-1, huMAb4D5-2, huMAb4D5-3, huMAb4D5-4, huMAb4D5-5, huMAb4D5-6, huMAb4D5-7 and huMAb4D5-8 or trastuzumab (HERCEPTIN®) as described in Table 3 of U.S. Pat. No. 5,821,337 expressly incorporated herein by reference; humanized 520C9 (WO93/21319); and humanized 2C4 antibodies such as pertuzumab as described herein.

For the purposes herein, "trastuzumab," "HERCEPTIN®," and "huMAb4D5-8" refer to an antibody comprising the light and heavy chain amino acid sequences in SEQ ID NOS. 15 and 16, respectively.

Herein, "pertuzumab" and "OMNITARG™" refer to an antibody comprising the light and heavy chain amino acid sequences in SEQ ID NOS. 13 and 14, respectively.

Differences between trastuzumab and pertuzumab functions are illustrated in FIG. 6.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227:381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147 (1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE technology). See also, for example, Li et al., *Proc. Natl. Acad. Sci. USA*, 103:3557-3562 (2006) regarding human antibodies generated via a human B-cell hybridoma technology.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

Throughout the present specification and claims, the Kabat numbering system is generally used when referring to a residue in the variable domain (approximately, residues 1-107 of the light chain and residues 1-113 of the heavy chain) (e.g, Kabat et al., *Sequences of Immunological Interest.* 5th Ed. Public Health Service, National Institutes of Health, Bethesda, Md. (1991)).

The "EU numbering system" or "EU index" is generally used when referring to a residue in an immunoglobulin heavy chain constant region (e.g., the EU index reported in Kabat et al., *Sequences of Proteins of Immunological Interest,* 5th Ed. Public Health Service, National Institutes of Health, Bethesda, Md. (1991) expressly incorporated herein by reference). Unless stated otherwise herein, references to residues numbers in the variable domain of antibodies means residue numbering by the Kabat numbering system. Unless stated otherwise herein, references to residue numbers in the constant domain of antibodies means residue numbering by the EU numbering system (e.g., see U.S. Provisional Application No. 60/640,323, Figures for EU numbering).

An "affinity matured" antibody is one with one or more alterations in one or more HVRs thereof which result in an improvement in the affinity of the antibody for antigen, compared to a parent antibody which does not possess those alteration(s). In one embodiment, an affinity matured antibody has nanomolar or even picomolar affinities for the target antigen. Affinity matured antibodies may be produced using certain procedures known in the art. For example, Marks et al. *Bio/Technology* 10:779-783 (1992) describes affinity maturation by VH and VL domain shuffling. Random mutagenesis of HVR and/or framework residues is described by, for example, Barbas et al. *Proc Nat. Acad. Sci. USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

The term "Fc region" herein is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

Unless indicated otherwise herein, the numbering of the residues in an immunoglobulin heavy chain is that of the EU index as in Kabat et al., supra. The "EU index as in Kabat" refers to the residue numbering of the human IgG1 EU antibody.

A "functional Fc region" possesses an "effector function" of a native sequence Fc region. Exemplary "effector functions" include C1q binding; CDC; Fc receptor binding; ADCC; phagocytosis; down regulation of cell surface receptors (e.g. B cell receptor; BCR), etc. Such effector functions generally require the Fc region to be combined with a binding domain (e.g., an antibody variable domain) and can be assessed using various assays as disclosed, for example, in definitions herein.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. In some embodiments, an FcR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see, e.g., Daëron, *Annu. Rev. Immunol.* 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, e.g., Ghetie and Ward., *Immunol. Today* 18(12):592-598 (1997); Ghetie et al., *Nature Biotechnology*, 15(7):637-640 (1997); Hinton et al., *J. Biol. Chem.* 279(8):6213-6216 (2004); WO 2004/92219 (Hinton et al.).

Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 (Presta) describes antibody variants with improved or diminished binding to FcRs. See also, e.g., Shields et al. *J. Biol. Chem.* 9(2):6591-6604 (2001).

"Human effector cells" are leukocytes which express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Antibody-dependent cell-mediated cytotoxicity" or "ADCC" refers to a form of cytotoxicity in which secreted Ig bound onto Fc receptors (FcRs) present on certain cytotoxic cells (e.g. NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 or U.S. Pat. No. 6,737,056 (Presta), may be performed. Useful effector cells for such assays include PBMC and NK cells. Alternatively, or additionally, ADCC activity of the molecule of interest may be assessed in vivo, e.g., in an animal model such as that disclosed in Clynes et al. *PNAS* (*USA*) 95:652-656 (1998).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, e.g., as described in Gazzano-Santoro et al., *J. Immunol. Methods* 202:163 (1996), may be performed. Polypeptide variants with altered Fc region amino acid sequences (polypeptides with a variant Fc region) and increased or decreased C1q binding capability are described, e.g., in U.S. Pat. No. 6,194,551 B1 and WO 1999/51642. See also, e.g., Idusogie et al. *J. Immunol.* 164: 4178-4184 (2000).

The term "Fc region-comprising antibody" refers to an antibody that comprises an Fc region. The C-terminal lysine (residue 447 according to the EU numbering system) of the Fc region may be removed, for example, during purification of the antibody or by recombinant engineering of the nucleic acid encoding the antibody. Accordingly, a composition comprising an antibody having an Fc region according to this invention can comprise an antibody with K447, with all K447 removed, or a mixture of antibodies with and without the K447 residue.

The term "main species antibody" herein refers to the antibody structure in a composition which is the quantitatively predominant antibody molecule in the composition. In one embodiment, the main species antibody is a HER2 antibody, such as an antibody that binds to Domain II of HER2, antibody that inhibits HER dimerization more effectively than trastuzumab, and/or an antibody which binds to a heterodimeric binding site of HER2. The preferred embodiment herein of the main species antibody is one comprising the variable light and variable heavy amino acid sequences in SEQ ID Nos. 3 and 4, and most preferably comprising the light chain and heavy chain amino acid sequences in SEQ ID Nos. 13 and 14 (pertuzumab).

An "amino acid sequence variant" antibody herein is an antibody with an amino acid sequence which differs from a main species antibody. Ordinarily, amino acid sequence variants will possess at least about 70% homology with the main species antibody, and preferably, they will be at least about 80%, more preferably at least about 90% homologous with the main species antibody. The amino acid sequence variants possess substitutions, deletions, and/or additions at certain positions within or adjacent to the amino acid sequence of the main species antibody. Examples of amino acid sequence variants herein include an acidic variant (e.g. deamidated antibody variant), a basic variant, an antibody with an amino-terminal leader extension (e.g. VHS-) on one or two light chains thereof, an antibody with a C-terminal lysine residue on one or two heavy chains thereof, etc, and includes combinations of variations to the amino acid sequences of heavy and/or light chains. The antibody variant of particular interest herein is the antibody comprising an amino-terminal leader extension on one or two light chains thereof, optionally further comprising other amino acid sequence and/or glycosylation differences relative to the main species antibody.

A "glycosylation variant" antibody herein is an antibody with one or more carbohydrate moeities attached thereto which differ from one or more carbohydate moieties attached to a main species antibody. Examples of glycosylation variants herein include antibody with a G1 or G2 oligosaccharide structure, instead a G0 oligosaccharide structure, attached to an Fc region thereof, antibody with one or two carbohydrate moieties attached to one or two light chains thereof, antibody with no carbohydrate attached to one or two heavy chains of the antibody, etc, and combinations of glycosylation alterations.

Where the antibody has an Fc region, an oligosaccharide structure may be attached to one or two heavy chains of the antibody, e.g. at residue 299 (298, Eu numbering of residues). For pertuzumab, G0 was the predominant oligosaccharide structure, with other oligosaccharide structures such as G0-F, G-1, Man5, Man6, G1-1, G1(1-6), G1(1-3) and G2 being found in lesser amounts in the pertuzumab composition.

Unless indicated otherwise, a "G1 oligosaccharide structure" herein includes G-1, G1-1, G1(1-6) and G1(1-3) structures.

An "amino-terminal leader extension" herein refers to one or more amino acid residues of the amino-terminal leader sequence that are present at the amino-terminus of any one or more heavy or light chains of an antibody. An exemplary amino-terminal leader extension comprises or consists of three amino acid residues, VHS, present on one or both light chains of an antibody variant.

A "deamidated" antibody is one in which one or more asparagine residues thereof has been derivitized, e.g. to an aspartic acid, a succinimide, or an iso-aspartic acid.

The terms "cancer" and "cancerous" refer to or describe the physiological condition in mammals that is typically characterized by unregulated cell growth. A "cancer type" herein refers to a particular category or indication of cancer. Examples of such cancer types include, but are not limited to, carcinoma, lymphoma, blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, and leukemia or lymphoid malignancies. More particular examples of such cancers include squamous cell cancer (e.g. epithelial squamous cell cancer), lung cancer including small-cell lung cancer (SCLC), non-small cell lung cancer (NSCLC), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumors of the biliary tract, as well as head and neck cancer, as well as subtypes of any of such cancers, including, but not limited to chemotherapy-resistant, platinum-resistant, advanced, refractory, and/or recurrent types thereof.

A "cancer type which is able to respond to a HER inhibitor" is one which when treated with a HER inhibitor, such as a HER2 antibody or small molecule inhibitor, shows a therapeutically effective benefit in the patient therewith according to any of the criteria for therapeutic effectiveness known to the skilled oncologist, including those elaborated herein, but particularly in terms of survival, including progression free survival (PFS) and/or overall survival (OS). Preferably, such cancer is selected from ovarian cancer, peritoneal cancer, fallopian tube cancer, metastatic breast cancer (MBC), non-small cell lung cancer (NSCLC), prostate cancer, and colorectal cancer. Most preferably, the cancer is ovarian, peritoneal, or fallopian tube cancer, including platinum-resistant forms of such cancers, as well as advanced, refractory or recurrent ovarian cancer.

A "cancer type which is able to respond to a HER dimerization inhibitor" is one which when treated with a HER dimerization inhibitor, such as pertuzumab, shows a therapeutically effective benefit in the patient therewith according to any of the criteria for therapeutic effectiveness known to the skilled oncologist, including those elaborated herein, but particularly in terms of survival, including progression free survival (PFS) and/or overall survival (OS). Preferably, such cancer is selected from ovarian cancer, peritoneal cancer, fallopian tube cancer, metastatic breast cancer (MBC), non-small cell lung cancer (NSCLC), prostate cancer, and colorectal cancer. Most preferably, the cancer is ovarian, peritoneal, or fallopian tube cancer, including platinum-resistant forms of such cancers, as well as advanced, refractory or recurrent ovarian cancer.

An "effective response" and similar wording refers to a response to the HER dimerization inhibitor, HER inhibitor or chemotherapeutic agent that is significantly higher than a response from a patient that does not express HER3 at the designated level.

An "advanced" cancer is one which has spread outside the site or organ of origin, either by local invasion or metastasis.

A "refractory" cancer is one which progresses even though an anti-tumor agent, such as a chemotherapeutic agent, is being administered to the cancer patient. An example of a refractory cancer is one which is platinum refractory.

A "recurrent" cancer is one which has regrown, either at the initial site or at a distant site, after a response to initial therapy.

Herein, a "patient" is a human patient. The patient may be a "cancer patient," i.e. one who is suffering or at risk for suffering from one or more symptoms of cancer.

A "tumor sample" herein is a sample derived from, or comprising tumor cells from, a patient's tumor. Examples of tumor samples herein include, but are not limited to, tumor biopsies, circulating tumor cells, circulating plasma proteins, ascitic fluid, primary cell cultures or cell lines derived from tumors or exhibiting tumor-like properties, as well as preserved tumor samples, such as formalin-fixed, paraffin-embedded tumor samples or frozen tumor samples.

A "fixed" tumor sample is one which has been histologically preserved using a fixative.

A "formalin-fixed" tumor sample is one which has been preserved using formaldehyde as the fixative.

An "embedded" tumor sample is one surrounded by a firm and generally hard medium such as paraffin, wax, celloidin, or a resin. Embedding makes possible the cutting of thin sections for microscopic examination or for generation of tissue microarrays (TMAs).

A "paraffin-embedded" tumor sample is one surrounded by a purified mixture of solid hydrocarbons derived from petroleum.

Herein, a "frozen" tumor sample refers to a tumor sample which is, or has been, frozen.

A cancer or biological sample which "displays HER expression, amplification, or activation" is one which, in a diagnostic test, expresses (including overexpresses) a HER receptor, has amplified HER gene, and/or otherwise demonstrates activation or phosphorylation of a HER receptor.

A cancer cell with "HER receptor overexpression or amplification" is one which has significantly higher levels of a HER receptor protein or gene compared to a noncancerous cell of the same tissue type. Such overexpression may be caused by gene amplification or by increased transcription or translation. HER receptor overexpression or amplification may be determined in a diagnostic or prognostic assay by evaluating increased levels of the HER protein present on the surface of a cell (e.g. via an immunohistochemistry assay; IHC). Alternatively, or additionally, one may measure levels of HER-encoding nucleic acid in the cell, e.g. via fluorescent in situ hybridization (FISH; see WO98/45479 published October, 1998), southern blotting, or polymerase chain reaction (PCR) techniques, such as quantitative real time PCR (qRT-PCR). One may also study HER receptor overexpression or amplification by measuring shed antigen (e.g., HER extracellular domain) in a biological fluid such as serum (see, e.g., U.S. Pat. No. 4,933,294 issued Jun. 12, 1990; WO91/05264 published Apr. 18, 1991; U.S. Pat. No. 5,401,638 issued Mar. 28, 1995; and Sias et al. *J. Immunol. Methods* 132: 73-80 (1990)). Aside from the above assays, various in vivo assays are available to the skilled practitioner. For example, one may expose cells within the body of the patient to an antibody which is optionally labeled with a detectable label, e.g. a radioactive isotope, and binding of the antibody to cells in the patient can be evaluated, e.g. by external scanning for radioactivity or by analyzing a biopsy taken from a patient previously exposed to the antibody.

Conversely, a cancer which "does not overexpress or amplify HER receptor" is one which does not have higher than normal levels of HER receptor protein or gene compared to a noncancerous cell of the same tissue type. Antibodies that inhibit HER dimerization, such as pertuzumab, may be used to treat cancer which does not overexpress or amplify HER2 receptor.

Herein, an "anti-tumor agent" refers to a drug used to treat cancer. Non-limiting examples of anti-tumor agents herein include chemotherapeutic agents, HER inhibitors, HER dimerization inhibitors, HER antibodies, antibodies directed against tumor associated antigens, anti-hormonal compounds, cytokines, EGFR-targeted drugs, anti-angiogenic agents, tyrosine kinase inhibitors, growth inhibitory agents and antibodies, cytotoxic agents, antibodies that induce apoptosis, COX inhibitors, farnesyl transferase inhibitors, antibodies that binds oncofetal protein CA 125, HER2 vaccines, Raf or ras inhibitors, liposomal doxorubicin, topotecan, taxane, dual tyrosine kinase inhibitors, TLK286, EMD-7200, pertuzumab, trastuzumab, erlotinib, and bevacizumab.

An "approved anti-tumor agent" is a drug used to treat cancer which has been accorded marketing approval by a regulatory authority such as the Food and Drug Administration (FDA) or foreign equivalent thereof.

Where a HER inhibitor or HER dimerization inhibitor is administered as a "single anti-tumor agent" it is the only anti-tumor agent administered to treat the cancer, i.e. it is not administered in combination with another anti-tumor agent, such as chemotherapy.

By "standard of care" herein is intended the anti-tumor agent or agents that are routinely used to treat a particular form of cancer. For example, for platinum-resistant ovarian cancer, the standard of care is topotecan or liposomal doxorubicin.

A "growth inhibitory agent" when used herein refers to a compound or composition which inhibits growth of a cell, especially a HER expressing cancer cell either in vitro or in vivo. Thus, the growth inhibitory agent may be one which significantly reduces the percentage of HER expressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13.

Examples of "growth inhibitory" antibodies are those which bind to HER2 and inhibit the growth of cancer cells overexpressing HER2. Preferred growth inhibitory HER2 antibodies inhibit growth of SK-BR-3 breast tumor cells in cell culture by greater than 20%, and preferably greater than 50% (e.g. from about 50% to about 100%) at an antibody concentration of about 0.5 to 30 µg/ml, where the growth inhibition is determined six days after exposure of the SK-BR-3 cells to the antibody (see U.S. Pat. No. 5,677,171 issued Oct. 14, 1997). The SK-BR-3 cell growth inhibition assay is described in more detail in that patent and hereinbelow. The preferred growth inhibitory antibody is a humanized variant of murine monoclonal antibody 4D5, e.g., trastuzumab.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). The cell is usually one which overexpresses the HER2 receptor. Preferably the cell is a tumor cell, e.g. a breast, ovarian, stomach, endometrial, salivary gland, lung, kidney, colon, thyroid, pancreatic or bladder cell. In vitro, the cell may be a SK-BR-3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an annexin binding assay using BT474 cells (see below). Examples of HER2 antibodies that induce apoptosis are 7C2 and 7F3.

The "epitope 2C4" is the region in the extracellular domain of HER2 to which the antibody 2C4 binds. In order to screen for antibodies which bind to the 2C4 epitope, a routine cross-blocking assay such as that described in *Antibodies, A Laboratory Manual*, Cold Spring Harbor Laboratory, Ed Harlow and David Lane (1988), can be performed. Preferably the antibody blocks 2C4's binding to HER2 by about 50% or more. Alternatively, epitope mapping can be performed to assess whether the antibody binds to the 2C4 epitope of HER2. Epitope 2C4 comprises residues from Domain II in the extracellular domain of HER2. 2C4 and pertuzumab binds to the extracellular domain of HER2 at the junction of domains I, II and III. Franklin et al. *Cancer Cell* 5:317-328 (2004).

The "epitope 4D5" is the region in the extracellular domain of HER2 to which the antibody 4D5 (ATCC CRL 10463) and trastuzumab bind. This epitope is close to the transmembrane domain of HER2, and within Domain IV of HER2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to assess whether the antibody binds to the 4D5 epitope of HER2 (e.g. any one or more residues in the region from about residue 529 to about residue 625, inclusive of the HER2 ECD, residue numbering including signal peptide).

The "epitope 7C2/7F3" is the region at the N terminus, within Domain 1, of the extracellular domain of HER2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on HER2 (e.g. any one or more of residues in the region from about residue 22 to about residue 53 of the HER2ECD, residue numbering including signal peptide).

"Treatment" refers to both therapeutic treatment and prophylactic or preventative measures. Those in need of treatment include those already with cancer as well as those in which cancer is to be prevented. Hence, the patient to be treated herein may have been diagnosed as having cancer or may be predisposed or susceptible to cancer.

The terms "therapeutically effective amount" or "effective amount" refer to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete respose, CR), improve survival (including overall survival and progression free survival) and/or improve one or more symptoms of cancer (e.g. as assessed by FOSI). Most preferably, the therapeutically effective amount of the drug is effective to improve progression free survival (PFS) and/or overall survival (OS).

"Survival" refers to the patient remaining alive, and includes overall survival as well as progression free survival.

"Overall survival" refers to the patient remaining alive for a defined period of time, such as 1 year, 5 years, etc from the time of diagnosis or treatment.

"Progression free survival" refers to the patient remaining alive, without the cancer progressing or getting worse.

By "extending survival" is meant increasing overall or progression free survival in a treated patient relative to an untreated patient (i.e. relative to a patient not treated with a HER inhibitor, HER dimerization inhibitor, such as pertuzumab), or relative to a patient who does not express HER3 or HER2:HER3 at the designated level, and/or relative to a patient treated with an approved anti-tumor agent (such as topotecan or liposomal doxorubicin, where the cancer is ovarian cancer).

An "objective response" refers to a measurable response, including complete response (CR) or partial response (PR).

By "complete response" or "CR" is intended the disappearance of all signs of cancer in response to treatment. This does not always mean the cancer has been cured.

"Partial response" or "PR" refers to a decrease in the size of one or more tumors or lesions, or in the extent of cancer in the body, in response to treatment.

The term "cytotoxic agent" as used herein refers to a substance that inhibits or prevents the function of cells and/or causes destruction of cells. The term is intended to include radioactive isotopes (e.g. $At^{211}$, $I^{131}$, $I^{125}$, $Y^{90}$, $Re^{186}$, $Re^{188}$, $Sm^{153}$, $Bi^{22}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include alkylating agents such as thiotepa and cyclosphosphamide (CYTOXAN®); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calichearnicin gammall and calicheamicin omegall (see, e.g., Nicolaou et al., *Angew. Chem. Intl. Ed. Engl.*, 33: 183-186 (1994)); CDP323, an oral alpha-4 integrin inhibitor; dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®), liposomal doxorubicin TLC D-99 (MYOCET®), peglylated liposomal doxorubicin (CAELYX®), and deoxydoxorubicin), epirubicin, esorubicin, darubicin, marcellomycin, mitomycins such as mitomycin C, mycophenolic acid, nogalamycin, olivomycins, peplomycin, potfiromycin, puromycin, quelarnycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfonithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL®), albumin-engineered nanoparticle formulation of paclitaxel (ABRAXANE™), and docetaxel (TAXOTERE®); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN®), vincristine (ONCOVIN®), vindesine (ELDISINE®&, FILDESIN®), and vinorelbine (NAVELBINE®); etoposide (VP-16); ifosfamide; mitoxantrone; leucovovin; novantrone; edatrexate; daunomycin; aminopterin; ibandronate; topoisomerase inhibitor RFS 2000; difluoromethylomithine (DMFO); retinoids such as retinoic acid, including bexarotene (TARGRETIN®); bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAX ID® vaccine; topoisomerase 1 inhibitor (e.g., LURTOTECAN®); rmRH (e.g., ABARELIX®); BAY439006 (sorafenib; Bayer); SU-11248 (Pfizer); perifosine, COX-2 inhibitor (e.g. celecoxib or etoricoxib), proteosome inhibitor (e.g. PS341); bortezomib (VELCADE®); CCI-779; tipifamib (R11577); orafenib, ABT510; Bcl-2 inhibitor such as oblimersen sodium (GENASENSE®); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Herein, chemotherapeutic agents include "anti-hormonal agents" or "endocrine therapeutics" which act to regulate, reduce, block, or inhibit the effects of hormones that can promote the growth of cancer. They may be hormones themselves, including, but not limited to: anti-estrogens with mixed agonist/antagonist profile, including, tamoxifen (NOLVADEX®), 4-hydroxytamoxifen, toremifene (FARESTON®), idoxifene, droloxifene, raloxifene (EVISTA®), trioxifene, keoxifene, and selective estrogen receptor modulators (SERMs) such as SERM3; pure anti-estrogens without agonist properties, such as fulvestrant (FASLODEX®), and EM800 (such agents may block estrogen receptor (ER) dimerization, inhibit DNA binding, increase ER turnover, and/or suppress ER levels); aromatase inhibitors, including steroidal aromatase inhibitors such as formestane and exemestane (AROMASIN®), and nonsteroidal aromatase inhibitors such as anastrazole (ARIMIDEX®), letrozole (FEMARA®) and aminoglutethimide, and other aromatase inhibitors include vorozole (RIVISOR®), megestrol acetate (MEGASE®), fadrozole, and 4(5)-imidazoles; lutenizing hormone-releasing hormone agonists, including leuprolide (LUPRON® and ELIGARD®), goserelin, buserelin, and tripterelin; sex steroids, including progestines such as megestrol acetate and medroxyprogesterone acetate, estrogens such as diethylstilbestrol and premarin, and androgens/retinoids such as fluoxymesterone, all transretionic acid and fenretinide; onapristone; anti-progesterones; estrogen receptor down-regulators (ERDs); anti-androgens such as flutamide, nilutamide and bicalutamide; and pharmaceutically acceptable salts, acids or derivatives of any of the above; as well as combinations of two or more of the above.

An "antimetabolite chemotherapeutic agent" is an agent which is structurally similar to a metabolite, but can not be used by the body in a productive manner. Many antimetabolite chemotherapeutic agents interfere with the production of the nucleic acids, RNA and DNA. Examples of antimetabolite chemotherapeutic agents include gemcitabine (GEMZAR®), 5-fluorouracil (5-FU), capecitabine (XELODA™), 6-mercaptopurine, methotrexate, 6-thioguanine, pemetrexed, raltitrexed, arabinosylcytosine ARA-C cytarabine (CYTOSAR-U®), dacarbazine (DTIC-DOME®), azocytosine, deoxycytosine, pyridmidene, fludarabine (FLUDARA®), cladrabine, 2-deoxy-D-glucose etc. The preferred antimetabolite chemotherapeutic agent is gemcitabine.

"Gemcitabine" or "2'-deoxy-2',2'-difluorocytidine monohydrochloride (b-isomer)" is a nucleoside analogue that exhibits antitumor activity. The empirical formula for gemcitabine HCl is C9H11F2N₃O4 A HCl. Gemcitabine HCl is sold by Eli Lilly under the trademark GEMZAR®.

A "platinum-based chemotherapeutic agent" comprises an organic compound which contains platinum as an integral part of the molecule. Examples of platinum-based chemotherapeutic agents include carboplatin, cisplatin, and oxaliplatinum.

By "platinum-based chemotherapy" is intended therapy with one or more platinum-based chemotherapeutic agents, optionally in combination with one or more other chemotherapeutic agents.

By "chemotherapy-resistant" cancer is meant that the cancer patient has progressed while receiving a chemotherapy regimen (i.e. the patient is "chemotherapy refractory"), or the patient has progressed within 12 months (for instance, within 6 months) after completing a chemotherapy regimen.

By "platinum-resistant" cancer is meant that the cancer patient has progressed while receiving platinum-based chemotherapy (i.e. the patient is "platinum refractory"), or the patient has progressed within 12 months (for instance, within 6 months) after completing a platinum-based chemotherapy regimen.

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. The preferred anti-angiogenic factor herein is an antibody that binds to vascular endothelial growth factor (VEGF), such as bevacizumab (AVASTIN®).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO98/50433, Abgenix); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding; and mAb 806 or humanized mAb 806 (Johns et al., J. Biol. Chem. 279(29):30375-30384 (2004)). The anti-EGFR antibody may be conjugated with a cytotoxic agent, thus generating an immunoconjugate (see, e.g., EP659,439A2, Merck Patent GmbH). Examples of small molecules that bind to EGFR include ZD1839 or Gefitinib (IRESSA™; Astra Zeneca); CP-358774 or Erlotinib (TARCEVA™; Genentech/OSI); and AG1478, AG1571 (SU 5271; Sugen); EMD-7200.

A "tyrosine kinase inhibitor" is a molecule which inhibits tyrosine kinase activity of a tyrosine kinase such as a HER receptor. Examples of such inhibitors include the EGFR-targeted drugs noted in the preceding paragraph; small molecule HER2 tyrosine kinase inhibitor such as TAK165 available from Takeda; CP-724,714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; GW572016 (available from Glaxo) an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibits Raf-1 signaling; non-HER targeted TK inhibitors such as Imatinib mesylate (Gleevac™) available from Glaxo; MAPK extracellular regulated kinase 1 inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804,396); tryphostins (U.S. Pat. No. 5,804, 396); ZD6474 (Astra Zeneca); PTK-787 (Novartis/Schering AG); pan-HER inhibitors such as CI-1033 (Pfizer); Affinitac (ISIS 3521; Isis/Lilly); Imatinib mesylate (Gleevac; Novartis); PKI 166 (Novartis); GW2016 (Glaxo SmithKline); CI-1033 (Pfizer); EKB-569 (Wyeth); Semaxinib (Sugen); ZD6474 (AstraZeneca); PTK-787 (Novartis/Schering AG); INC-1C11 (Imclone); or as described in any of the following patent publications: U.S. Pat. No. 5,804,396; WO99/09016 (American Cyanimid); WO98/43960 (American Cyanamid);

WO97/38983 (Warner Lambert); WO99/06378 (Warner Lambert); WO99/06396 (Warner Lambert); WO96/30347 (Pfizer, Inc); WO96/33978 (Zeneca); WO96/3397 (Zeneca); and WO96/33980 (Zeneca).

A "fixed" or "flat" dose of a therapeutic agent herein refers to a dose that is administered to a human patient without regard for the weight (WT) or body surface area (BSA) of the patient. The fixed or flat dose is therefore not provided as a mg/kg dose or a mg/m² dose, but rather as an absolute amount of the therapeutic agent.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

A "maintenance" dose herein refers to one or more doses of a therapeutic agent administered to the patient over a treatment period. Usually, the maintenance doses are administered at spaced treatment intervals, such as approximately every week, approximately every 2 weeks, approximately every 3 weeks, or approximately every 4 weeks.

A "medicament" is an active drug to treat cancer, such as a HER inhibitor, a HER dimerization inhibitor (such as pertuzumab) or a chemotherapeutic agent (such as gemcitabine).

A "target audience" is a group of people or an institution to whom or to which a particular medicament is being promoted or intended to be promoted, as by marketing or advertising, especially for particular uses, treatments, or indications, such as individual patients, patient populations, readers of newspapers, medical literature, and magazines, television or internet viewers, radio or internet listeners, physicians, drug companies, etc.

A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

II. Production of Antibodies

Since, in the preferred embodiment, the HER inhibitor is an antibody, a description follows as to exemplary techniques for the production of HER antibodies used in accordance with the present invention. The HER antigen to be used for production of antibodies may be, e.g., a soluble form of the extracellular domain of a HER receptor or a portion thereof, containing the desired epitope. Alternatively, cells expressing HER at their cell surface (e.g. NIH-3T3 cells transformed to overexpress HER2; or a carcinoma cell line such as SK-BR-3 cells, see Stancovski et al. *PNAS (USA)* 88:8691-869 5 (1991)) can be used to generate antibodies. Other forms of HER receptor useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Various methods for making monoclonal antibodies herein are available in the art. For example, the monoclonal antibodies may be made using the hybridoma method first described by Kohler et al., *Nature*, 256:495 (1975), by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); and Brodeur et al., *Monoclonal Antibody Production Techniques and Applications*, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., *Anal. Biochem.*, 107:220 (1980).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional antibody purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., *Curr. Opinion in Immunol.*, 5:256-262 (1993) and Plückthun, *Immunol. Revs.*, 130: 151-188 (1992).

In a further embodiment, monoclonal antibodies or antibody fragments can be isolated from antibody phage libraries generated using the techniques described in McCafferty et al., *Nature*, 348:552-554 (1990). Clackson et al., *Nature*, 352: 624-628 (1991) and Marks et al., *J. Mol. Biol.*, 222:581-597 (1991) describe the isolation of murine and human antibodies, respectively, using phage libraries. Subsequent publications describe the production of high affinity (nM range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nuc. Acids. Res.*, 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al., *Proc. Natl. Acad. Sci. USA*, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized Antibodies

Methods for humanizing non-human antibodies have been described in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522-525 (1986); Riechmann et al., *Nature*, 332:323-327 (1988); Verhoeyen et al., *Science*, 239:1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework region (FR) for the humanized antibody (Sims et al., *J. Immunol.*, 151:2296 (1993); Chothia et al., *J. Mol. Biol.*, 196:901 (1987)). Another method uses a particular framework region derived from the consensus sequence of all human antibodies of a particular subgroup of light or heavy chains. The same framework may be used for several different humanized antibodies (Carter et al., *Proc. Natl. Acad. Sci. USA*, 89:4285 (1992); Presta et al., *J. Immunol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

WO01/00245 describes production of exemplary humanized HER2 antibodies which bind HER2 and block ligand activation of a HER receptor. The humanized antibody of particular interest herein blocks EGF, TGF-α and/or HRG mediated activation of MAPK essentially as effectively as murine monoclonal antibody 2C4 (or a Fab fragment thereof) and/or binds HER2 essentially as effectively as murine monoclonal antibody 2C4 (or a Fab fragment thereof). The humanized antibody herein may, for example, comprise nonhuman hypervariable region residues incorporated into a human variable heavy domain and may further comprise a framework region (FR) substitution at a position selected from the group consisting of 69H, 71H and 73H utilizing the variable domain numbering system set forth in Kabat et al., *Sequences of Proteins of Immunological Interest,* 5th Ed. Public Health Service, National Institutes of Health, Bethesda, Md. (1991). In one embodiment, the humanized antibody comprises FR substitutions at two or all of positions 69H, 71H and 73H.

An exemplary humanized antibody of interest herein comprises variable heavy domain complementarity determining residues GFTFTDYTMX, where X is preferably D or S (SEQ ID NO:7); DVNPNSGGSIYNQR FKG (SEQ ID NO:8); and/or NLGPSFYFDY (SEQ ID NO:9), optionally comprising amino acid modifications of those CDR residues, e.g. where the modifications essentially maintain or improve affinity of the antibody. For example, the antibody variant of interest may have from about one to about seven or about five amino acid substitutions in the above variable heavy CDR sequences. Such antibody variants may be prepared by affinity maturation, e.g., as described below. The most preferred humanized antibody comprises the variable heavy domain amino acid sequence in SEQ ID NO:4.

The humanized antibody may comprise variable light domain complementarity determining residues KASQD-VSIGVA (SEQ ID NO:10); SASYX$^1$X$^2$X$^3$, where X$^1$ is preferably R or L, X$^2$ is preferably Y or E, and X$^3$ is preferably T or S (SEQ ID NO:11); and/or QQYYIYPYT (SEQ ID NO:12), e.g. in addition to those variable heavy domain CDR residues in the preceding paragraph. Such humanized antibodies optionally comprise amino acid modifications of the above CDR residues, e.g. where the modifications essentially maintain or improve affinity of the antibody. For example, the antibody variant of interest may have from about one to about seven or about five amino acid substitutions in the above variable light CDR sequences. Such antibody variants may be prepared by affinity maturation, e.g., as described below. The most preferred humanized antibody comprises the variable light domain amino acid sequence in SEQ ID NO:3.

The present application also contemplates affinity matured antibodies which bind HER2 and block ligand activation of a HER receptor. The parent antibody may be a human antibody or a humanized antibody, e.g., one comprising the variable light and/or variable heavy sequences of SEQ ID Nos. 3 and 4, respectively (i.e. comprising the VL and/or VH of pertuzumab). The affinity matured antibody preferably binds to HER2 receptor with an affinity superior to that of murine 2C4 or pertuzumab (e.g. from about two or about four fold, to about 100 fold or about 1000 fold improved affinity, e.g. as assessed using a HER2-extracellular domain (ECD) ELISA). Exemplary variable heavy CDR residues for substitution include H28, H30, H34, H35, H64, H96, H99, or combinations of two or more (e.g. two, three, four, five, six, or seven of these residues). Examples of variable light CDR residues for alteration include L28, L50, L53, L56, L91, L92, L93, L94, L96, L97 or combinations of two or more (e.g. two to three, four, five or up to about ten of these residues).

Various forms of the humanized antibody or affinity matured antibody are contemplated. For example, the humanized antibody or affinity matured antibody may be an antibody fragment, such as a Fab, which is optionally conjugated with one or more cytotoxic agent(s) in order to generate an immunoconjugate. Alternatively, the humanized antibody or affinity matured antibody may be an intact antibody, such as an intact IgG1 antibody. The preferred intact IgG1 antibody comprises the light chain sequence in SEQ ID NO:13 and the heavy chain sequence in SEQ ID NO:14.

(iv) Human Antibodies

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA,* 90:2551 (1993); Jakobovits et al., *Nature,* 362:255-258 (1993); Bruggermann et al., *Year in Immuno.,* 7:33 (1993); and U.S. Pat. Nos. 5,591,669, 5,589, 369 and 5,545,807. Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature,* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See, also, U.S. Pat. Nos. 5,565,332 and 5,573,905.

As discussed above, human antibodies may also be generated by in vitro activated B cells (see U.S. Pat. Nos. 5,567,610 and 5,229,275).

Human HER2 antibodies are described in U.S. Pat. No. 5,772,997 issued Jun. 30, 1998 and WO 97/00271 published Jan. 3, 1997.

(v) Antibody Fragments

Various techniques have been developed for the production of antibody fragments comprising one or more antigen binding regions. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody", e.g., as described in U.S. Pat. No. 5,641,870 for example. Such linear antibody fragments may be monospecific or bispecific.

(vi) Bispecific Antibodies

Bispecific antibodies are antibodies that have binding specificities for at least two different epitopes. Exemplary bispecific antibodies may bind to two different epitopes of the HER2 protein. Other such antibodies may combine a HER2 binding site with binding site(s) for EGFR, HER3 and/or HER4. Alternatively, a HER2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the HER2-expressing cell. Bispecific antibodies may also be used to localize cytotoxic agents to cells which express HER2. These antibodies possess a HER2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

WO 96/16673 describes a bispecific HER2/FcγRIII antibody and U.S. Pat. No. 5,837,234 discloses a bispecific HER2/FcγRI antibody IDM1 (Osidem). A bispecific HER2/Fcα antibody is shown in WO98/02463. U.S. Pat. No. 5,821,337 teaches a bispecific HER2/CD3 antibody. MDX-210 is a bispecific HER2-FcγRIII Ab.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in U.S. Pat. No. 5,731,168, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage.

Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the HER2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have also been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147: 60 (1991).

(vii) Other Amino Acid Sequence Modifications

Amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 1 under the heading of "preferred substitutions". If such substitutions result in a change in biological activity, then more substantial changes, denominated "exemplary substitutions" in Table 1, or as further described below in reference to amino acid classes, may be introduced and the products screened.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in *Biochemistry*, second ed., pp. 73-75, Worth Publishers, New York (1975)):

(1) non-polar: Ala (A), Val (V), Leu (L), Ile (I), Pro (P), Phe (F), Trp (W), Met (M)

(2) uncharged polar: Gly (G), Ser (S), Thr (T), Cys (C), Tyr (Y), Asn (N), Gln (Q)

(3) acidic: Asp (D), Glu (E)

(4) basic: Lys (K), Arg (R), His (H)

Alternatively, naturally occurring residues may be divided into groups based on common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

A particularly preferred type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and human HER2. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 A1, Presta, L. See also US 2004/0093621 A1 (Kyowa Hakko Kogyo Co., Ltd). Antibodies with a bisecting N-acetylglucosamine (GlcNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase C1q binding and/or CDC.

Antibodies with altered C1q binding and/or complement dependent cytotoxicity (CDC) are described in WO99/51642, U.S. Pat. No. 6,194,551B1, U.S. Pat. No. 6,242,195B1, U.S. Pat. No. 6,528,624B1 and U.S. Pat. No. 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, IgG2, $IgG_3$, or $IgG_4$) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region may have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues).

Engineered antibodies with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

(viii) Screening for Antibodies with the Desired Properties

Techniques for generating antibodies have been described above. One may further select antibodies with certain biological characteristics, as desired.

To identify an antibody which blocks ligand activation of a HER receptor, the ability of the antibody to block HER ligand binding to cells expressing the HER receptor (e.g. in conjugation with another HER receptor with which the HER receptor of interest forms a HER hetero-oligomer) may be determined. For example, cells naturally expressing, or transfected to express, HER receptors of the HER hetero-oligomer may be incubated with the antibody and then exposed to labeled HER ligand. The ability of the antibody to block ligand binding to the HER receptor in the HER hetero-oligomer may then be evaluated.

For example, inhibition of HRG binding to MCF7 breast tumor cell lines by HER2 antibodies may be performed using monolayer MCF7 cultures on ice in a 24-well-plate format essentially as described in WO01/00245. HER2 monoclonal antibodies may be added to each well and incubated for 30 minutes. $^{125}$I-labeled rHRGβ1$_{177-224}$ (25 pm) may then be added, and the incubation may be continued for 4 to 16 hours. Dose response curves may be prepared and an IC$_{50}$ value may be calculated for the antibody of interest. In one embodiment, the antibody which blocks ligand activation of a HER receptor will have an IC$_{50}$ for inhibiting HRG binding to MCF7 cells in this assay of about 50 nM or less, more preferably 10 nM or less. Where the antibody is an antibody fragment such as a Fab fragment, the IC$_{50}$ for inhibiting HRG binding to MCF7 cells in this assay may, for example, be about 100 nM or less, more preferably 50 nM or less.

Alternatively, or additionally, the ability of an antibody to block HER ligand-stimulated tyrosine phosphorylation of a HER receptor present in a HER hetero-oligomer may be assessed. For example, cells endogenously expressing the HER receptors or transfected to expressed them may be incubated with the antibody and then assayed for HER ligand-dependent tyrosine phosphorylation activity using an anti-phosphotyrosine monoclonal (which is optionally conjugated with a detectable label). The kinase receptor activation assay described in U.S. Pat. No. 5,766,863 is also available for determining HER receptor activation and blocking of that activity by an antibody.

In one embodiment, one may screen for an antibody which inhibits HRG stimulation of p180 tyrosine phosphorylation in MCF7 cells essentially as described in WO01/00245. For example, the MCF7 cells may be plated in 24-well plates and monoclonal antibodies to HER2 may be added to each well and incubated for 30 minutes at room temperature; then rHRGβ1$_{177-244}$ may be added to each well to a final concentration of 0.2 nM, and the incubation may be continued for 8 minutes. Media may be aspirated from each well, and reactions may be stopped by the addition of 100 μl of SDS sample buffer (5% SDS, 25 mM DTT, and 25 mM Tris-HCl, pH 6.8). Each sample (25 μl) may be electrophoresed on a 4-12% gradient gel (Novex) and then electrophoretically transferred to polyvinylidene difluoride membrane. Antiphosphotyrosine (at 1 μg/ml) immunoblots may be developed, and the intensity of the predominant reactive band at M$_r$~180,000 may be quantified by reflectance densitometry. The antibody selected will preferably significantly inhibit HRG stimulation of p180 tyrosine phosphorylation to about 0-35% of control in this assay. A dose-response curve for inhibition of HRG stimulation of p180 tyrosine phosphorylation as determined by reflectance densitometry may be prepared and an IC$_{50}$ for the antibody of interest may be calculated. In one embodiment, the antibody which blocks ligand activation of a HER receptor will have an IC$_{50}$ for inhibiting HRG stimulation of p180 tyrosine phosphorylation in this assay of about 50 nM or less, more preferably 10 nM or less. Where the antibody is an antibody fragment such as a Fab fragment, the IC$_{50}$ for inhibiting HRG stimulation of p180 tyrosine phosphorylation in this assay may, for example, be about 100 nM or less, more preferably 50 nM or less.

One may also assess the growth inhibitory effects of the antibody on MDA-MB-175 cells, e.g, essentially as described in Schaefer et al. *Oncogene* 15:1385-1394 (1997). According to this assay, MDA-MB-175 cells may be treated with a HER2 monoclonal antibody (10 μg/mL) for 4 days and stained with crystal violet. Incubation with a HER2 antibody may show a growth inhibitory effect on this cell line similar to that displayed by monoclonal antibody 2C4. In a further embodiment, exogenous HRG will not significantly reverse this inhibition. Preferably, the antibody will be able to inhibit cell proliferation of MDA-MB-175 cells to a greater extent than monoclonal antibody 4D5 (and optionally to a greater extent than monoclonal antibody 7F3), both in the presence and absence of exogenous HRG.

In one embodiment, the HER2 antibody of interest may block heregulin dependent association of HER2 with HER3 in both MCF7 and SK-BR-3 cells as determined in a co-immunoprecipitation experiment such as that described in WO01/00245 substantially more effectively than monoclonal antibody 4D5, and preferably substantially more effectively than monoclonal antibody 7F3.

To identify growth inhibitory HER2 antibodies, one may screen for antibodies which inhibit the growth of cancer cells which overexpress HER2. In one embodiment, the growth inhibitory antibody of choice is able to inhibit growth of SK-BR-3 cells in cell culture by about 20-100% and preferably by about 50-100% at an antibody concentration of about 0.5 to 30 μg/ml. To identify such antibodies, the SK-BR-3 assay described in U.S. Pat. No. 5,677,171 can be performed. According to this assay, SK-BR-3 cells are grown in a 1:1 mixture of F12 and DMEM medium supplemented with 10% fetal bovine serum, glutamine and penicillin streptomycin. The SK-BR-3 cells are plated at 20,000 cells in a 35 mm cell culture dish (2 mls/35 mm dish). 0.5 to 30 μg/ml of the HER2 antibody is added per dish. After six days, the number of cells, compared to untreated cells are counted using an electronic COULTER™ cell counter. Those antibodies which inhibit growth of the SK-BR-3 cells by about 20-100% or about 50-100% may be selected as growth inhibitory antibodies. See U.S. Pat. No. 5,677,171 for assays for screening for growth inhibitory antibodies, such as 4D5 and 3E8.

In order to select for antibodies which induce apoptosis, an annexin binding assay using BT474 cells is available. The BT474 cells are cultured and seeded in dishes as discussed in the preceding paragraph. The medium is then removed and replaced with fresh medium alone or medium containing 10 μg/ml of the monoclonal antibody. Following a three day incubation period, monolayers are washed with PBS and detached by trypsinization. Cells are then centrifuged, resuspended in Ca$^{2+}$ binding buffer and aliquoted into tubes as discussed above for the cell death assay. Tubes then receive labeled annexin (e.g. annexin V-FTIC) (1 μg/ml). Samples may be analyzed using a FACSCAN™ flow cytometer and FACSCONVERT™ CellQuest software (Becton Dickinson). Those antibodies which induce statistically significant levels of annexin binding relative to control are selected as apoptosis-inducing antibodies. In addition to the annexin binding assay, a DNA staining assay using BT474 cells is available. In order to perform this assay, BT474 cells which have been treated with the antibody of interest as described in the preceding two paragraphs are incubated with 9 μg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay. See WO98/17797 for assays for screening for antibodies which induce apoptosis, such as 7C2 and 7F3.

To screen for antibodies which bind to an epitope on HER2 bound by an antibody of interest, a routine cross-blocking assay such as that described in *Antibodies, A Laboratory Manual*, Cold Spring Harbor Laboratory, Ed Harlow and David Lane (1988), can be performed to assess whether the antibody cross-blocks binding of an antibody, such as 2C4 or pertuzumab, to HER2. Alternatively, or additionally, epitope mapping can be performed by methods known in the art and/or one can study the antibody-HER2 structure (Franklin et al. *Cancer Cell* 5:317-328 (2004)) to see what domain(s) of HER2 is/are bound by the antibody.

(ix) Pertuzumab Compositions

In one embodiment of a HER2 antibody composition, the composition comprises a mixture of a main species pertuzumab antibody and one or more variants thereof. The preferred embodiment herein of a pertuzumab main species antibody is one comprising the variable light and variable heavy amino acid sequences in SEQ ID Nos. 3 and 4, and most preferably comprising a light chain amino acid sequence selected from SEQ ID No. 13 and 17, and a heavy chain amino acid sequence selected from SEQ ID No. 14 and 18 (including deamidated and/or oxidized variants of those sequences). In one embodiment, the composition comprises a mixture of the main species pertuzumab antibody and an amino acid sequence variant thereof comprising an amino-terminal leader extension. Preferably, the amino-terminal leader extension is on a light chain of the antibody variant (e.g. on one or two light chains of the antibody variant). The main species HER2 antibody or the antibody variant may be an full length antibody or antibody fragment (e.g. Fab of F(ab')2 fragments), but preferably both are full length antibodies. The antibody variant herein may comprise an amino-terminal leader extension on any one or more of the heavy or light chains thereof. Preferably, the amino-terminal leader extension is on one or two light chains of the antibody. The amino-terminal leader extension preferably comprises or consists of VHS-. Presence of the amino-terminal leader extension in the composition can be detected by various analytical techniques including, but not limited to, N-terminal sequence analysis, assay for charge heterogeneity (for instance, cation exchange chromatography or capillary zone electrophoresis), mass spectrometry, etc. The amount of the antibody variant in the composition generally ranges from an amount that constitutes the detection limit of any assay (preferably N-terminal sequence analysis) used to detect the variant to an amount less than the amount of the main species antibody. Generally, about 20% or less (e.g. from about 1% to about 15%, for instance from 5% to about 15%) of the antibody molecules in the composition comprise an amino-terminal leader extension. Such percentage amounts are preferably determined using quantitative N-terminal sequence analysis or cation exchange analysis (preferably using a high-resolution, weak cation-exchange column, such as a PROPAC WCX-10™ cation exchange column). Aside from the amino-terminal leader extension variant, further amino acid sequence alterations of the main species antibody and/or variant are contemplated, including but not limited to an antibody comprising a C-terminal lysine residue on one or both heavy chains thereof, a deamidated antibody variant, etc.

Moreover, the main species antibody or variant may further comprise glycosylation variations, non-limiting examples of which include antibody comprising a G1 or G2 oligosaccharide structure attached to the Fc region thereof, antibody comprising a carbohydrate moiety attached to a light chain thereof (e.g. one or two carbohydrate moieties, such as glucose or galactose, attached to one or two light chains of the antibody, for instance attached to one or more lysine residues), antibody comprising one or two non-glycosylated heavy chains, or antibody comprising a sialidated oligosaccharide attached to one or two heavy chains thereof etc.

The composition may be recovered from a genetically engineered cell line, e.g. a Chinese Hamster Ovary (CHO) cell line expressing the HER2 antibody, or may be prepared by peptide synthesis.

(x) Immunoconjugates

The invention also pertains to immunoconjugates comprising an antibody conjugated to a cytotoxic agent such as a chemotherapeutic agent, toxin (e.g. a small molecule toxin or an enzymatically active toxin of bacterial, fungal, plant or animal origin, including fragments and/or variants thereof), or a radioactive isotope (i.e., a radioconjugate).

Chemotherapeutic agents useful in the generation of such immunoconjugates have been described above. Conjugates of an antibody and one or more small molecule toxins, such as a calicheamicin, a maytansine (U.S. Pat. No. 5,208,020), a trichothene, and CC1065 are also contemplated herein.

In one preferred embodiment of the invention, the antibody is conjugated to one or more maytansine molecules (e.g. about 1 to about 10 maytansine molecules per antibody molecule). Maytansine may, for example, be converted to May-SS-Me which may be reduced to May-SH3 and reacted with modified antibody (Chari et al. *Cancer Research* 52: 127-131 (1992)) to generate a maytansinoid-antibody immunoconjugate.

Another immunoconjugate of interest comprises an antibody conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N-acetyl-$\gamma_1^1$, PSAG and $\theta^1_1$ (Hinman et al. *Cancer Research* 53: 3336-3342 (1993) and Lode et al. *Cancer Research* 58: 2925-2928 (1998)). See, also, U.S. Pat. Nos. 5,714,586; 5,712,374; 5,264,586; and 5,773,001 expressly incorporated herein by reference.

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g. a ribonuclease or a DNA endonuclease such as a deoxyribonuclease; DNase).

A variety of radioactive isotopes are available for the production of radioconjugated HER2 antibodies. Examples include $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu.

Conjugates of the antibody and cytotoxic agent may be made using a variety of bifunctional protein coupling agents such as N-succinimidyl-3-2-pyridyldithiol) propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52: 127-131 (1992)) may be used.

Alternatively, a fusion protein comprising the antibody and cytotoxic agent may be made, e.g. by recombinant techniques or peptide synthesis.

Other immunoconjugates are contemplated herein. For example, the antibody may be linked to one of a variety of nonproteinaceous polymers, e.g., polyethylene glycol, polypropylene glycol, polyoxyalkylenes, or copolymers of polyethylene glycol and polypropylene glycol. The antibody also may be entrapped in microcapsules prepared, for example, by coacervation techniques or by interfacial polymerization (for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules), or in macroemulsions. Such techniques are disclosed in *Remington's Pharmaceutical Sciences,* 16th edition, Oslo, A., Ed., (1980).

The antibodies disclosed herein may also be formulated as immunoliposomes. Liposomes containing the antibody are prepared by methods known in the art, such as described in Epstein et al., *Proc. Natl. Acad. Sci. USA*, 82:3688 (1985); Hwang et al., *Proc. Natl. Acad. Sci. USA*, 77:4030 (1980); U.S. Pat. Nos. 4,485,045 and 4,544,545; and WO97/38731 published Oct. 23, 1997. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *J. Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

III. Diagnostic Methods

In a first aspect, the invention herein provides a method for selecting a therapy for a patient with a type of cancer (e.g. ovarian cancer) which is able to respond to a HER inhibitor or HER dimerization inhibitor (e.g. pertuzumab) comprising determining HER3 expression in a cancer sample from the patient and selecting a HER inhibitor or HER dimerization inhibitor as the therapy if the cancer sample expresses HER3 at a level less than the median level for HER3 expression in the cancer type and/or if the cancer sample expresses HER2: HER3 at a level which is greater than the $25^{th}$ percentile (or greater than the median level) for HER2:HER3 expression in the cancer type.

In a second aspect, the invention provides a method for selecting a therapy for a patient with a type of cancer (e.g. ovarian cancer) which is able to respond to a chemotherapeutic agent comprising determining HER3 expression in a cancer sample from the patient and selecting a chemotherapeutic agent (e.g. gemcitabine) as the therapy if the cancer sample expresses HER3 at a level greater than the median level for HER3 expression in the cancer type.

The median or percentile expression level can be determined essentially contemporaneously with measuring HER3 expression (or HER2 and HER3 expression), or may have been determined previously.

Prior to the therapeutic methods described below, HER3 expression level(s), and optionally HER2 expression level(s), in the patient's cancer is/are assessed. Generally, a biological sample is obtained from the patient in need of therapy, which sample is subjected to one or more diagnostic assay(s), usually at least one in vitro diagnostic (IVD) assay. However, other forms of evaluating HER3 and/or HER2 expression, such as in vivo diagnosis, are expressly contemplated herein. The biological sample is usually a tumor sample, preferably from ovarian cancer, peritoneal cancer, fallopian tube cancer, metastatic breast cancer (MBC), non-small cell lung cancer (NSCLC), prostate cancer, or colorectal cancer tumor sample.

The biological sample herein may be a fixed sample, e.g. a formalin fixed, paraffin-embedded (FFPE) sample, or a frozen sample.

Various methods for determining expression of mRNA or protein include, but are not limited to, gene expression profiling, polymerase chain reaction (PCR) including quantitative real time PCR (qRT-PCR), microarray analysis, serial analysis of gene expression (SAGE), MassARRAY, Gene Expression Analysis by Massively Parallel Signature Sequencing (MPSS), proteomics, immunohistochemistry (IHC), etc. Preferably mRNA is quantified. Such mRNA analysis is preferably performed using the technique of polymerase chain reaction (PCR), or by microarray analysis. Where PCR is employed, a preferred form of PCR is quantitative real time PCR (qRT-PCR). The preferred qRT-PCR assay is that as described in Example 1 below.

The steps of a representative protocol for profiling gene expression using fixed, paraffin-embedded tissues as the RNA source, including mRNA isolation, purification, primer extension and amplification are given in various published journal articles (for example: Godfrey et al. *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR. Finally, the data are analyzed to identify the best treatment option(s) available to the patient on the basis of the characteristic gene expression pattern identified in the tumor sample examined.

Various exemplary methods for determining gene expression will now be described in more detail.

(i) Gene Expression Profiling

In general, methods of gene expression profiling can be divided into two large groups: methods based on hybridization analysis of polynucleotides, and methods based on sequencing of polynucleotides. The most commonly used methods known in the art for the quantification of mRNA expression in a sample include northern blotting and in situ hybridization (Parker & Barnes, *Methods in Molecular Biology* 106:247-283 (1999)); RNAse protection assays (Hod, Biotechniques 13:852-854 (1992)); and polymerase chain reaction (PCR) (Weis et al., *Trends in Genetics* 8:263-264 (1992)). Alternatively, antibodies may be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE), and gene expression analysis by massively parallel signature sequencing (MPSS).

(ii) Polymerase Chain Reaction (PCR)

Of the techniques listed above, a sensitive and flexible quantitative method is PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. Thus RNA can be isolated from a variety of primary tumors, including breast, lung, colon, prostate, brain, liver, kidney, pancreas, spleen, thymus, testis, ovary, uterus, etc., tumor, or tumor cell lines, with pooled DNA from healthy donors. If the source of mRNA is a primary tumor, mRNA can be extracted, for example, from frozen or archived paraffin-embedded and fixed (e.g. formalin-fixed) tissue samples. General methods for mRNA extraction are well known in the art and are disclosed in standard textbooks of molecular biology, including Ausubel et al., *Current Protocols of Molecular Biology*, John Wiley and Sons (1997). Methods for RNA extraction from paraffin embedded tissues are disclosed, for example, in Rupp and Locker, *Lab Invest.* 56:A67 (1987), and De Andrés et al., *BioTechniques* 18:42044 (1995). In particular, RNA isolation can be performed using purification kit, buffer set and protease from commercial manufacturers, such as Qiagen, according to the manufacturer's instructions. For example, total RNA from cells in culture can be isolated using Qiagen RNeasy mini-columns. Other commercially available RNA isolation kits include MASTERPURE® Complete DNA and RNA Purification Kit (EPICENTRE®, Madison, Wis.), and Paraffin Block RNA Isolation Kit (Ambion, Inc.). Total RNA from tissue samples can be isolated using RNA Stat-60 (Tel-Test). RNA prepared from tumor can be isolated, for example, by cesium chloride density gradient centrifugation.

As RNA cannot serve as a template for PCR, the first step in gene expression profiling by PCR is the reverse transcription of the RNA template into cDNA, followed by its exponential amplification in a PCR reaction. The two most commonly used reverse transcriptases are avilo myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GENEAMP™ RNA PCR kit (Perkin Elmer, Calif., USA), following the manufacturer's instructions. The derived cDNA can then be used as a template in the subsequent PCR reaction. Although the PCR step can use a variety of thermostable DNA-dependent DNA polymerases, it typically employs the Taq DNA polymerase, which has a 5'-3' nuclease activity but lacks a 3'-5' proofreading endonuclease activity. Thus, TAQMAN® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN® PCR can be performed using commercially available equipment, such as, for example, ABI PRISM 7700® Sequence Detection System® (Perkin-Elmer-Applied Biosystems, Foster City, Calif., USA), or Lightcycler (Roche Molecular Biochemicals, Mannheim, Germany). In a preferred embodiment, the 5' nuclease procedure is run on a real-time quantitative PCR device such as the ABI PRISM 7700® Sequence Detection System. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

5'-Nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

To minimize errors and the effect of sample-to-sample variation, PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and P-actin.

A more recent variation of the PCR technique is quantitative real time PCR (qRT-PCR), which measures PCR product accumulation through a dual-labeled fluorigenic probe (i.e., TAQMAN® probe). Real time PCR is compatible both with quantitative competitive PCR, where internal competitor for each target sequence is used for normalization, and with quantitative comparative PCR using a normalization gene contained within the sample, or a housekeeping gene for PCR. For further details see, e.g. Held et al., *Genome Research* 6:986-994 (1996).

The steps of a representative protocol for profiling gene expression using fixed, paraffin-embedded tissues as the RNA source, including mRNA isolation, purification, primer extension and amplification are given in various published journal articles (for example: Godfrey et al., *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR.

According to one aspect of the present invention, PCR primers and probes are designed based upon intron sequences present in the gene to be amplified. In this embodiment, the first step in the primer/probe design is the delineation of intron sequences within the genes. This can be done by publicly available software, such as the DNA BLAT software developed by Kent, W., *Genome Res.* 12(4):656-64 (2002), or by the BLAST software including its variations. Subsequent steps follow well established methods of PCR primer and probe design.

In order to avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as Primer Express (Applied Biosystems); MGB assay-by-design (Applied Biosystems); Primer3 (Rozen and Skaletsky (2000) Primer3 on the WWW for general users and for biologist programmers. In: Krawetz S, Misener S (eds) *Bioinformatics Methods and Protocols: Methods in Molecular Biology*. Humana Press, Totowa, N.J., pp 365-386).

Factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50 and 80° C., e.g. about 50 to 70° C. are typically preferred.

For further guidelines for PCR primer and probe design see, e.g. Dieffenbach et al., "General Concepts for PCR Primer Design" in *PCR Primer, A Laboratory Manual*, Cold Spring Harbor Laboratory Press, New York, 1995, pp. 133-155; Innis and Gelfand, "Optimization of PCRs" in *PCR Protocols, A Guide to Methods and Applications*, CRC Press, London, 1994, pp. 5-11; and Plasterer, T. N. Primerselect: Primer and probe design. *Methods Mol. Biol.* 70:520-527 (1997), the entire disclosures of which are hereby expressly incorporated by reference.

The preferred conditions, primers, probes, and internal reference (G6PDH) are as described in Example 1 below.

(iii) Microarrays

Differential gene expression can also be identified, or confirmed using the microarray technique. Thus, the expression profile of breast cancer-associated genes can be measured in either fresh or paraffin-embedded tumor tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. Just as in the PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):106-149 (1996)). Microarray analysis can be performed by commercially available equipment, following manufacturer's protocols, such as by using the Affymetrix GENCHIP™ technology, or Incyte's microarray technology.

The development of microarray methods for large-scale analysis of gene expression makes it possible to search systematically for molecular markers of cancer classification and outcome prediction in a variety of tumor types.

(iv) Serial Analysis of Gene Expression (SAGE)

Serial analysis of gene expression (SAGE) is a method that allows the simultaneous and quantitative analysis of a large number of gene transcripts, without the need of providing an individual hybridization probe for each transcript. First, a short sequence tag (about 10-14 bp) is generated that contains sufficient information to uniquely identify a transcript, provided that the tag is obtained from a unique position within each transcript. Then, many transcripts are linked together to form long serial molecules, that can be sequenced, revealing the identity of the multiple tags simultaneously. The expression pattern of any population of transcripts can be quantitatively evaluated by determining the abundance of individual tags, and identifying the gene corresponding to each tag. For more details see, e.g. Velculescu et al., *Science* 270:484-487 (1995); and Velculescu et al., *Cell* 88:243-51 (1997).

(v) MassARRAY Technology

The MassARRAY (Sequenom, San Diego, Calif.) technology is an automated, high-throughput method of gene expression analysis using mass spectrometry (MS) for detection. According to this method, following the isolation of RNA, reverse transcription and PCR amplification, the cDNAs are subjected to primer extension. The cDNA-derived primer extension products are purified, and dispensed on a chip array that is pre-loaded with the components needed for MALTI-TOF MS sample preparation. The various cDNAs present in the reaction are quantitated by analyzing the peak areas in the mass spectrum obtained.

(vi) Gene Expression Analysis by Massively Parallel Signature Sequencing (MPSS)

This method, described by Brenner et al., *Nature Biotechnology* 18:630-634 (2000), is a sequencing approach that combines non-gel-based signature sequencing with in vitro cloning of millions of templates on separate 5 micrometer diameter microbeads. First, a microbead library of DNA templates is constructed by in vitro cloning. This is followed by the assembly of a planar array of the template—containing microbeads in a flow cell at a high density (typically greater than 3×106 microbeads/cm2). The free ends of the cloned templates on each microbead are analyzed simultaneously, using a fluorescence-based signature sequencing method that does not require DNA fragment separation. This method has been shown to simultaneously and accurately provide, in a single operation, hundreds of thousands of gene signature sequences from a yeast cDNA library.

(vii) Immunohistochemistry

Immunohistochemistry methods are also suitable for detecting the expression levels of the prognostic markers of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

(viii) Proteomics

The term "proteome" is defined as the totality of the proteins present in a sample (e.g. tissue, organism, or cell culture) at a certain point of time. Proteomics includes, among other things, study of the global changes of protein expression in a sample (also referred to as "expression proteomics"). Proteomics typically includes the following steps: (1) separation of individual proteins in a sample by 2-D gel electrophoresis (2-D PAGE); (2) identification of the individual proteins recovered from the gel, e.g. my mass spectrometry or N-terminal sequencing, and (3) analysis of the data using bioinformatics. Proteomics methods are valuable supplements to other methods of gene expression profiling, and can be used, alone or in combination with other methods, to detect the products of the prognostic markers of the present invention.

(ix) General Description of mRNA Isolation, Purification and Amplification

The steps of a representative protocol for profiling gene expression using fixed, paraffin-embedded tissues as the RNA source, including mRNA isolation, purification, primer extension and amplification are given in various published journal articles (for example: Godfrey et al *J. Molec. Diagnostics* 2: 84-91 (2000); Specht et al., *Am. J. Pathol.* 158: 419-29 (2001)). Briefly, a representative process starts with cutting about 10 microgram thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by PCR. Finally, the data are analyzed to identify the best treatment option(s) available to the patient on the basis of the characteristic gene expression pattern identified in the tumor sample examined.

In one embodiment, the patient treated herein, aside from expressing HER3 at a certain level and/or expressing HER2:HER3 at a certain level, the patient further does not overexpress HER2. HER2 overexpression may be analyzed by IHC, e.g. using the HERCEPTEST® (Dako). Parrafin embedded tissue sections from a tumor biopsy may be subjected to the IHC assay and accorded a HER2 protein staining intensity criteria as follows:

Score 0 no staining is observed or membrane staining is observed in less than 10% of tumor cells.

Score 1+ a faint/barely perceptible membrane staining is detected in more than 10% of the tumor cells. The cells are only stained in part of their membrane.

Score 2+ a weak to moderate complete membrane staining is observed in more than 10% of the tumor cells.

Score 3+ a moderate to strong complete membrane staining is observed in more than 10% of the tumor cells.

Those tumors with 0 or 1+ scores for HER2 overexpression assessment may be characterized as not overexpressing HER2, whereas those tumors with 2+ or 3+ scores may be characterized as overexpressing HER2.

Tumors overexpressing HER2 may be rated by immunohistochemical scores corresponding to the number of copies of HER2 molecules expressed per cell, and can been determined biochemically:

0=0-10,000 copies/cell,
1+=at least about 200,000 copies/cell,
2+=at least about 500,000 copies/cell,
3+=at least about 2,000,000 copies/cell.

Overexpression of HER2 at the 3+ level, which leads to ligand-independent activation of the tyrosine kinase (Hudziak et al., *Proc. Natl. Acad. Sci. USA*, 84:7159-7163 (1987)), occurs in approximately 30% of breast cancers, and in these patients, relapse-free survival and overall survival are diminished (Slamon et al., *Science*, 244:707-712 (1989); Slamon et al., *Science*, 235:177-182 (1987)). Alternatively, or additionally, FISH assays such as the INFORM™ (sold by Ventana, Ariz.) or PATHVISION™ (Vysis, Ill.) may be carried out on formalin-fixed, paraffin-embedded tumor tissue to determine the extent (if any) of HER2 amplification in the tumor.

HER3 and/or HER2 expression may also be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

IV. Pharmaceutical Formulations

Therapeutic formulations of the HER inhibitor, HER dimerization inhibitor, or chemotherapeutic agent used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. (1980)), generally in the form of lyophilized formulations or aqueous solutions. Antibody crystals are also contemplated (see US Pat Appln 2002/0136719). Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Lyophilized antibody formulations are described in WO 97/04801, expressly incorporated herein by reference.

The preferred pertuzumab formulation for therapeutic use comprises 30 mg/mL pertuzumab in 20 mM histidine acetate, 120 mM sucrose, 0.02% polysorbate 20, at pH 6.0. An alternate pertuzumab formulation comprises 25 mg/mL pertuzumab, 10 mM histidine-HCl buffer, 240 mM sucrose, 0.02% polysorbate 20, pH 6.0.

The formulation herein may also contain more than one active compound as necessary for the particular indication being treated, preferably those with complementary activities that do not adversely affect each other. Various drugs which can be combined with the HER inhibitor, or HER dimerization inhibitor are described in the Treatment Section below. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

Accordingly, a method for manufacturing a HER inhibitor, or HER dimerization inhibitor (such as pertuzumab), or a pharmaceutical composition thereof is provided, which method comprises combining in a package the inhibitor or pharmaceutical composition and a label stating that the inhibitor or pharmaceutical composition is indicated for treating a patient with a type of cancer (for example, ovarian cancer) which is able to respond to the inhibitor, wherein the patient's cancer expresses HER3 at a level less than the median level for HER3 expression in the cancer type and/or if the patient's cancer sample expresses HER2:HER3 at a level which is greater than the $25^{th}$ percentile for HER2:HER3 expression in the cancer type.

In addition, a method for manufacturing a chemotherapeutic agent (such as gemcitabine) or a pharmaceutical composition thereof is provided, wherein the method comprises combining in a package the chemotherapeutic agent or pharmaceutical composition and a label stating that the chemotherapeutic agent or pharmaceutical composition is indicated for treating a patient with a type of cancer (exemplified by ovarian cancer), wherein the patient's cancer expresses HER3 at a level greater than the median level for HER3 expression in the cancer type.

V. Treatment with HER Inhibitors

The invention herein provides a method for treating a patient with a type cancer which is able to respond to a HER inhibitor or HER dimerization inhibitor, comprising administering a therapeutically effective amount of the inhibitor to the patient, wherein the patient's cancer expresses HER3 at a level less than the median level for HER3 expression in the cancer type and/or if the cancer sample expresses HER2:HER3 at a level which is greater than the $25^{th}$ percentile for HER2:HER3 expression in the cancer type. Preferably the patient's cancer expresses HER3 at a level which is less than the $25^{th}$ percentile for HER3 expression in the cancer type and/or expresses HER2:HER3 at a level which is greater than the median level (most preferably greater than the $75^{th}$ percentile for HER2:HER3 expression) in the cancer type.

In a particularly preferred embodiment, the invention provides a method for treating a patient with ovarian, peritoneal, or fallopian tube cancer comprising administering a therapeutically effective amount of pertuzumab to the patient, wherein the patient's cancer expresses HER3 at a level less than the median level for HER3 expression in ovarian, peritoneal, or fallopian tube cancer and/or wherein the patient's cancer sample expresses HER2:HER3 at a level which is greater than the $25^{th}$ percentile for HER2:HER3 expression in ovarian, peritoneal, or fallopian tube cancer. In this embodiment, preferably the patient's cancer expresses HER3 at a level which is less than the $25^{th}$ percentile for HER3 expression in ovarian, peritoneal, or fallopian tube cancer and/or expresses HER2:HER3 at a level which is greater than the median level (most preferably greater than the $75^{th}$ percentile for HER2:HER3 expression) in ovarian, peritoneal, or fallopian tube cancer.

In another aspect, the invention provides a method for selecting a therapy for a patient with a type of cancer which is able to respond to a chemotherapeutic agent comprising determining HER3 expression in a cancer sample from the patient and selecting a chemotherapeutic agent as the therapy if the cancer sample expresses HER3 at a level greater than the median level for HER3 expression in the cancer type. In this embodiment, preferably the cancer type is ovarian, peritoneal, or fallopian tube cancer, including platinum-resistant ovarian, peritoneal, or fallopian tube cancer, as well as advanced, refractory and/or recurrent ovarian cancer. The chemotherapeutic agent is preferably an antimetabolite, such as gemcitabine. Thus, in this embodiment, high HER3 correlates with improved response to therapy with a chemotherapeutic agent, such as gemcitabine.

Examples of various cancer types that can be treated with a HER inhibitor or HER dimerization inhibitor are listed in the definition section above. Preferred cancer types include ovarian cancer; peritoneal cancer; fallopian tube cancer; breast cancer, including metastatic breast cancer (MBC); lung cancer, including non-small cell lung cancer (NSCLC); prostate cancer; and colorectal cancer. In one embodiment, the cancer which is treated is advanced, refractory, recurrent, chemotherapy-resistant, and/or platinum-resistant cancer.

Therapy with the HER inhibitor, HER dimerization inhibitor and/or chemotherapeutic agent preferably extends survival, including progression free survival (PFS) and/or overall survival (OS). In one embodiment, therapy with the HER inhibitor or HER dimerization inhibitor extends survival at least about 20% more than survival achieved by administering an approved anti-tumor agent, or standard of care, for the cancer being treated.

In the preferred embodiment, the method involves treating a patient with ovarian, peritoneal, or fallopian tube cancer. The patient may have advanced, refractory, recurrent, chemotherapy-resistant, and/or platinum-resistant ovarian, peritoneal or fallopian tube cancer. Administration of pertuzumab to the patient may, for example, extend survival at least about 20% more than survival achieved by administering topotecan or liposomal doxorubicin to such a patient.

The HER inhibitor, or HER dimerization inhibitor and/or chemotherapeutic agent is administered to a human patient in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

For the prevention or treatment of cancer, the dose of HER inhibitor, HER dimerization inhibitor and/or chemotherapeutic agent will depend on the type of cancer to be treated, as defined above, the severity and course of the cancer, whether the antibody is administered for preventive or therapeutic purposes, previous therapy, the patient's clinical history and response to the drug, and the discretion of the attending physician.

In one embodiment, a fixed dose of inhibitor is administered. The fixed dose may suitably be administered to the patient at one time or over a series of treatments. Where a fixed dose is administered, preferably it is in the range from about 20 mg to about 2000 mg of the inhibitor. For example, the fixed dose may be approximately 420 mg, approximately 525 mg, approximately 840 mg, or approximately 1050 mg of the inhibitor, such as pertuzumab.

Where a series of doses are administered, these may, for example, be administered approximately every week, approximately every 2 weeks, approximately every 3 weeks, or approximately every 4 weeks, but preferably approximately every 3 weeks. The fixed doses may, for example, continue to be administered until disease progression, adverse event, or other time as determined by the physician. For example, from about two, three, or four, up to about 17 or more fixed doses may be administered.

In one embodiment, one or more loading dose(s) of the antibody are administered, followed by one or more maintenance dose(s) of the antibody. In another embodiment, a plurality of the same dose are administered to the patient.

According to one preferred embodiment of the invention, a fixed dose of HER dimerization inhibitor (e.g. pertuzumab) of approximately 840 mg (loading dose) is administered, followed by one or more doses of approximately 420 mg (maintenance dose(s)) of the antibody. The maintenance doses are preferably administered about every 3 weeks, for a total of at least two doses, up to 17 or more doses.

According to another preferred embodiment of the invention, one or more fixed dose(s) of approximately 1050 mg of the HER dimerization inhibitor (e.g. pertzumab) are administered, for example every 3 weeks. According to this embodiment, one, two or more of the fixed doses are administered, e.g. for up to one year (17 cycles), and longer as desired.

In another embodiment, a fixed dose of approximately 1050 mg of the HER dimerization inhibitor (e.g. pertuzumab) is administered as a loading dose, followed by one or more maintenance dose(s) of approximately 525 mg. About one, two or more maintenance doses may be administered to the patient every 3 weeks according to this embodiment.

While the HER inhibitor, HER dimerization inhibitor or chemotherapeutic agent may be administered as a single antitumor agent, the patient is optionally treated with a combination of the inhibitor (or chemotherapeutic agent), and one or more (additional) chemotherapeutic agent(s). Exemplary chemotherapeutic agents herein include: gemcitabine, carboplatin, paclitaxel, docetaxel, topotecan, and/or liposomal doxorubicin. Preferably at least one of the chemotherapeutic agents is an antimetabolite chemotherapeutic agent such as gemcitabine. The combined administration includes coadministration or concurrent administration, using separate formulations or a single pharmaceutical formulation, and consecutive administration in either order, wherein preferably there is a time period while both (or all) active agents simultaneously exert their biological activities. Thus, the antimetabolite chemotherapeutic agent may be administered prior to, or following, administration of the inhibitor. In this embodiment, the timing between at least one administration of the antimetabolite chemotherapeutic agent and at least one administration of the inhibitor is preferably approximately 1 month or less, and most preferably approximately 2 weeks or less. Alternatively, the antimetabolite chemotherapeutic agent and the inhibitor are administered concurrently to the patient, in a single formulation or separate formulations. Treatment with the combination of the chemotherapeutic agent (e.g. antimetabolite chemotherapeutic agent such as gemcitabine) and the inhibitor (e.g. pertuzumab) may result in a synergistic, or greater than additive, therapeutic benefit to the patient.

Particularly desired chemotherapeutic agents for combining with the inhibitor, e.g. for therapy of ovarian cancer, include: an antimetabolite chemotherapeutic agent such as gemcitabine; a platinum compound such as carboplatin; a taxoid such as paclitaxel or docetaxel; topotecan; or liposomal doxorubicin.

An antimetabolite chemotherapeutic agent, if administered, is usually administered at dosages known therefor, or optionally lowered due to combined action of the drugs or negative side effects attributable to administration of the antimetabolite chemotherapeutic agent. Preparation and dosing schedules for such chemotherapeutic agents may be used according to manufacturers' instructions or as determined empirically by the skilled practitioner. Where the antimetabolite chemotherapeutic agent is gemcitabine, preferably, it is administered at a dose between about 600 mg/m$^2$ to 1250 mg/m² (for example approximately 1000 mg/m²), for instance, on days 1 and 8 of a 3-week cycle.

Aside from the inhibitor and antimetabolite chemotherapeutic agent, other therapeutic regimens may be combined therewith. For example, a second (third, fourth, etc) chemotherapeutic agent(s) may be administered, wherein the second chemotherapeutic agent is either another, different antimetabolite chemotherapeutic agent, or a chemotherapeutic agent that is not an antimetabolite. For example, the second chemotherapeutic agent may be a taxane (such as paclitaxel or docetaxel), capecitabine, or platinum-based chemotherapeutic agent (such as carboplatin, cisplatin, or oxaliplatin), anthracycline (such as doxorubicin, including, liposomal doxorubicin), topotecan, pemetrexed, vinca alkaloid (such as vinorelbine), and TLK 286. "Cocktails" of different chemotherapeutic agents may be administered.

Other therapeutic agents that may be combined with the inhibitor and/or chemotherapeutic agent include any one or more of: a second, different HER inhibitor, HER dimerization inhibitor (for example, a growth inhibitory HER2 antibody such as trastuzumab, or a HER2 antibody which induces apoptosis of a HER2-overexpressing cell, such as 7C2, 7F3 or humanized variants thereof); an antibody directed against a different tumor associated antigen, such as EGFR, HER3, HER4; anti-hormonal compound, e.g., an anti-estrogen compound such as tamoxifen, or an aromatase inhibitor; a cardioprotectant (to prevent or reduce any myocardial dysfunction associated with the therapy); a cytokine; an EGFR-targeted drug (such as TARCEVA® IRESSA® or cetuximab); an anti-angiogenic agent (especially bevacizumab sold by Genentech under the trademark AVASTIN™); a tyrosine kinase inhibitor; a COX inhibitor (for instance a COX-1 or COX-2 inhibitor); non-steroidal anti-inflammatory drug, celecoxib (CELEBREX®); farnesyl transferase inhibitor (for example, Tipifarnib/ZARNESTRA® R115777 available from Johnson and Johnson or Lonafarnib SCH66336 available from Schering-Plough); antibody that binds oncofetal protein CA 125 such as Oregovomab (MoAb B43.13); HER2 vaccine (such as HER2AutoVac vaccine from Pharmexia, or APC8024 protein vaccine from Dendreon, or HER2 peptide vaccine from GSK/Corixa); another HER targeting therapy (e.g. trastuzumab, cetuximab, ABX-EGF, EMD7200, gefitinib, erlotinib, CP724714, CI1033, GW572016, IMC-11F8, TAK165, etc); Raf and/or ras inhibitor (see, for example, WO 2003/86467); doxorubicin HCl liposome injection (DOXIL®); topoisomerase 1 inhibitor such as topotecan; taxane; HER2 and EGFR dual tyrosine kinase inhibitor such as lapatinib/GW572016; TLK286 (TELCYTA®); EMD-7200; a medicament that treats nausea such as a serotonin antagonist, steroid, or benzodiazepine; a medicament that prevents or treats skin rash or standard acne therapies, including topical or oral antibiotic; a medicament that treats or prevents diarrhea; a body temperature-reducing medicament such as acetaminophen, diphenhydramine, or meperidine; hematopoietic growth factor, etc.

Suitable dosages for any of the above coadministered agents are those presently used and may be lowered due to the combined action (synergy) of the agent and inhibitor.

In addition to the above therapeutic regimes, the patient may be subjected to surgical removal of cancer cells and/or radiation therapy.

Where the inhibitor is an antibody, preferably the administered antibody is a naked antibody. However, the inhibitor administered may be conjugated with a cytotoxic agent. Preferably, the conjugated inhibitor and/or antigen to which it is bound is/are internalized by the cell, resulting in increased therapeutic efficacy of the conjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases and DNA endonucleases.

The present application contemplates administration of the inhibitor by gene therapy. See, for example, WO96/07321 published Mar. 14, 1996 concerning the use of gene therapy to generate intracellular antibodies.

There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:44294432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

VI. Articles of Manufacture

In another embodiment of the invention, an article of manufacture containing materials useful for the treatment of the diseases or conditions described above is provided. The article of manufacture comprises a container and a label or package insert on or associated with the container. Suitable containers include, for example, bottles, vials, syringes, etc. The containers may be formed from a variety of materials such as glass or plastic. The container holds or contains a composition which is effective for treating the disease or condition of choice and may have a sterile access port (for example the container may be an intravenous solution bag or a vial having a stopper pierceable by a hypodermic injection needle). At least one active agent in the composition is the HER dimerization inhibitor, such as pertuzumab, or chemotherapeutic agent, such as gemcitabine.

The article of manufacture may further comprise a second container comprising a pharmaceutically-acceptable diluent buffer, such as bacteriostatic water for injection (BWFI), phosphate-buffered saline, Ringer's solution and dextrose solution. The article of manufacture may further include other materials desirable from a commercial and user standpoint, including other buffers, diluents, filters, needles, and syringes.

The kits and articles of manufacture of the present invention also include information, for example in the form of a package insert or label, indicating that the composition is used for treating cancer where the patient's cancer expresses HER3 and/or HER2:HER3 at a defined level depending on the drug. The insert or label may take any form, such as paper or on electronic media such as a magnetically recorded medium (e.g., floppy disk) or a CD-ROM. The label or insert may also include other information concerning the pharmaceutical compositions and dosage forms in the kit or article of manufacture.

Generally, such information aids patients and physicians in using the enclosed pharmaceutical compositions and dosage forms effectively and safely. For example, the following information regarding the HER dimerization inhibitor or chemotherapeutic agent may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references and patent information.

In a specific embodiment of the invention, an article of manufacture is provided comprising, packaged together, a pharmaceutical composition comprising a HER inhibitor, or HER dimerization inhibitor in a pharmaceutically acceptable carrier and a label stating that the inhibitor or pharmaceutical composition is indicated for treating a patient with a type of cancer which is able to respond to a HER inhibitor, or HER dimerization inhibitor, wherein the patient's cancer expresses HER3 at a level less than the median level for HER3 expression in the cancer type and/or if the patient's cancer sample expresses HER2:HER3 at a level which is greater than the $25^{th}$ percentile for HER2:HER3 expression in the cancer type.

In an optional embodiment of this inventive aspect, the article of manufacture herein further comprises a container comprising a second medicament, wherein the HER inhibitor or HER dimerization inhibitor is a first medicament, and which article further comprises instructions on the package insert for treating the patient with the second medicament, in an effective amount. The second medicament may be any of those set forth above, with an exemplary second medicament being another HER2 antibody or a chemotherapeutic agent.

In another aspect, an article of manufacture is provided which comprises, packaged together, a pharmaceutical composition comprising a chemotherapeutic agent (such as gemcitabine) in a pharmaceutically acceptable carrier and a label stating that the chemotherapeutic agent or pharmaceutical composition is indicated for treating a patient with a type of cancer, wherein the patient's cancer expresses HER3 at a level greater than the median level for HER3 expression in the cancer type.

The package insert is on or associated with the container. Suitable containers include, for example, bottles, vials, syringes, etc. The containers may be formed from a variety of materials such as glass or plastic. The container holds or contains a composition that is effective for treating cancer type may have a sterile access port (for example the container may be an intravenous solution bag or a vial having a stopper pierceable by a hypodermic injection needle). At least one active agent in the composition is the HER inhibitor, HER dimerization inhibitor, or chemotherapeutic agent. The label or package insert indicates that the composition is used for treating cancer in a subject eligible for treatment with specific guidance regarding dosing amounts and intervals of inhibitor and any other medicament being provided. The article of manufacture may further comprise an additional container comprising a pharmaceutically acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

Many alternative experimental methods known in the art may be successfully substituted for those specifically described herein in the practice of this invention, as for example described in many of the excellent manuals and textbooks available in the areas of technology relevant to this invention (e.g. *Using Antibodies, A Laboratory Manual*, edited by Harlow, E. and Lane, D., 1999, Cold Spring Harbor Laboratory Press, (e.g. ISBN 0-87969-544-7); Roe B. A. et. al. 1996, *DNA Isolation and Sequencing (Essential Techniques Series)*, John Wiley & Sons. (e.g. ISBN 0-471-97324-0); *Methods in Enzymology: Chimeric Genes and Proteins*, 2000, ed. J. Abelson, M. Simon, S. Emr, J. Thorner. Academic Press; *Molecular Cloning: a Laboratory Manual*, 2001, 3rd Edition, by Joseph Sambrook and Peter MacCallum, (the former Maniatis Cloning manual) (e.g. ISBN 0-87969-577-3); *Current Protocols in Molecular Biology*, Ed. Fred M. Ausubel, et. al. John Wiley & Sons (e.g. ISBN 0-471-50338-X); *Current Protocols in Protein Science*, Ed. John E. Coligan, John Wiley & Sons (e.g. ISBN 0471-11184-8); and *Methods in Enzymology: Guide to protein Purification*, 1990, Vol. 182, Ed. Deutscher, M. P., Acedemic Press, Inc. (e.g. ISBN 0-12-213585-7)), or as described in the many university and commercial websites devoted to describing experimental methods in molecular biology.

VII. Methods of Advertising

The invention herein also encompasses a method for advertising a HER inhibitor, HER dimerization inhibitor (for instance pertuzumab) or a pharmaceutically acceptable composition thereof comprising promoting, to a target audience, the use of the inhibitor or pharmaceutical composition thereof for treating a patient population with a type of cancer (such as ovarian cancer), where the patient's cancer expresses HER3 at a level less than the median level for HER3 expression in the cancer type and/or where the patient's cancer sample expresses HER2:HER3 at a level which is greater than the $25^{th}$ percentile for HER2:HER3 expression in the cancer type.

In yet another embodiment, the invention provides a method for advertising a chemotherapeutic agent (such as gemcitabine) or a pharmaceutically acceptable composition thereof comprising promoting, to a target audience, the use of the chemotherapeutic agent or pharmaceutical composition thereof for treating a patient population with a type of cancer (such as ovarian cancer), where the patient's cancer expresses HER3 at a level greater than the median level for HER3 expression in the cancer type.

Advertising is generally paid communication through a non-personal medium in which the sponsor is identified and the message is controlled. Advertising for purposes herein includes publicity, public relations, product placement, sponsorship, underwriting, and sales promotion. This term also includes sponsored informational public notices appearing in any of the print communications media designed to appeal to a mass audience to persuade, inform, promote, motivate, or otherwise modify behavior toward a favorable pattern of purchasing, supporting, or approving the invention herein.

The advertising and promotion of the diagnostic method herein may be accomplished by any means. Examples of advertising media used to deliver these messages include television, radio, movies, magazines, newspapers, the internet, and billboards, including commercials, which are messages appearing in the broadcast media. Advertisements also include those on the seats of grocery carts, on the walls of an airport walkway, and on the sides of buses, or heard in telephone hold messages or in-store PA systems, or anywhere a visual or audible communication can be placed.

More specific examples of promotion or advertising means include television, radio, movies, the internet such as webcasts and webinars, interactive computer networks intended to reach simultaneous users, fixed or electronic billboards and other public signs, posters, traditional or electronic literature such as magazines and newspapers, other media outlets, presentations or individual contacts by, e.g., e-mail, phone, instant message, postal, courier, mass, or carrier mail, in-person visits, etc.

The type of advertising used will depend on many factors, for example, on the nature of the target audience to be reached, e.g., hospitals, insurance companies, clinics, doctors, nurses, and patients, as well as cost considerations and the relevant jurisdictional laws and regulations governing advertising of medicaments and diagnostics. The advertising may be individualized or customized based on user characterizations defined by service interaction and/or other data such as user demographics and geographical location.

VIII. Deposit of Materials

The following hybridoma cell lines have been deposited with the American Type Culture Collection, 10801 University Boulevard, Manassas, Va. 20110-2209, USA (ATCC):

| Antibody Designation | ATCC No. | Deposit Date |
| --- | --- | --- |
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |
| 2C4 | ATCC HB-12697 | Apr. 8, 1999 |

Further details of the invention are illustrated by the following non-limiting Examples. The disclosures of all citations in the specification are expressly incorporated herein by reference.

Example 1

Pertuzumab and Gemcitabine for Therapy of Platinum-Resistant Ovarian Cancer, Primary Peritoneal Carcinoma, or Fallopian Tube Carcinoma This example provides the results for a phase III clinical trial evaluating the safety, tolerability, and efficacy of pertuzumab in combination with gemcitabine in patients with platinum-resistant ovarian cancer, primary peritoneal carcinoma, or fallopian tube carcinoma. Pertuzumab represents a new class of targeted agents called HER dimerization inhibitors (HDIs) that inhibit dimerization of HER2 with EGFR, HER3 and HER4, and inhibit signaling through MAP and PI3 kinase. Pertuzumab binds at the dimer-dimer interaction site, has a major effect on the role of HER2 as a co-receptor, prevents EGFR/HER2 and HER3/HER2 dimerization, and inhibits multiple HER-mediated signaling pathways.

Figure 9:
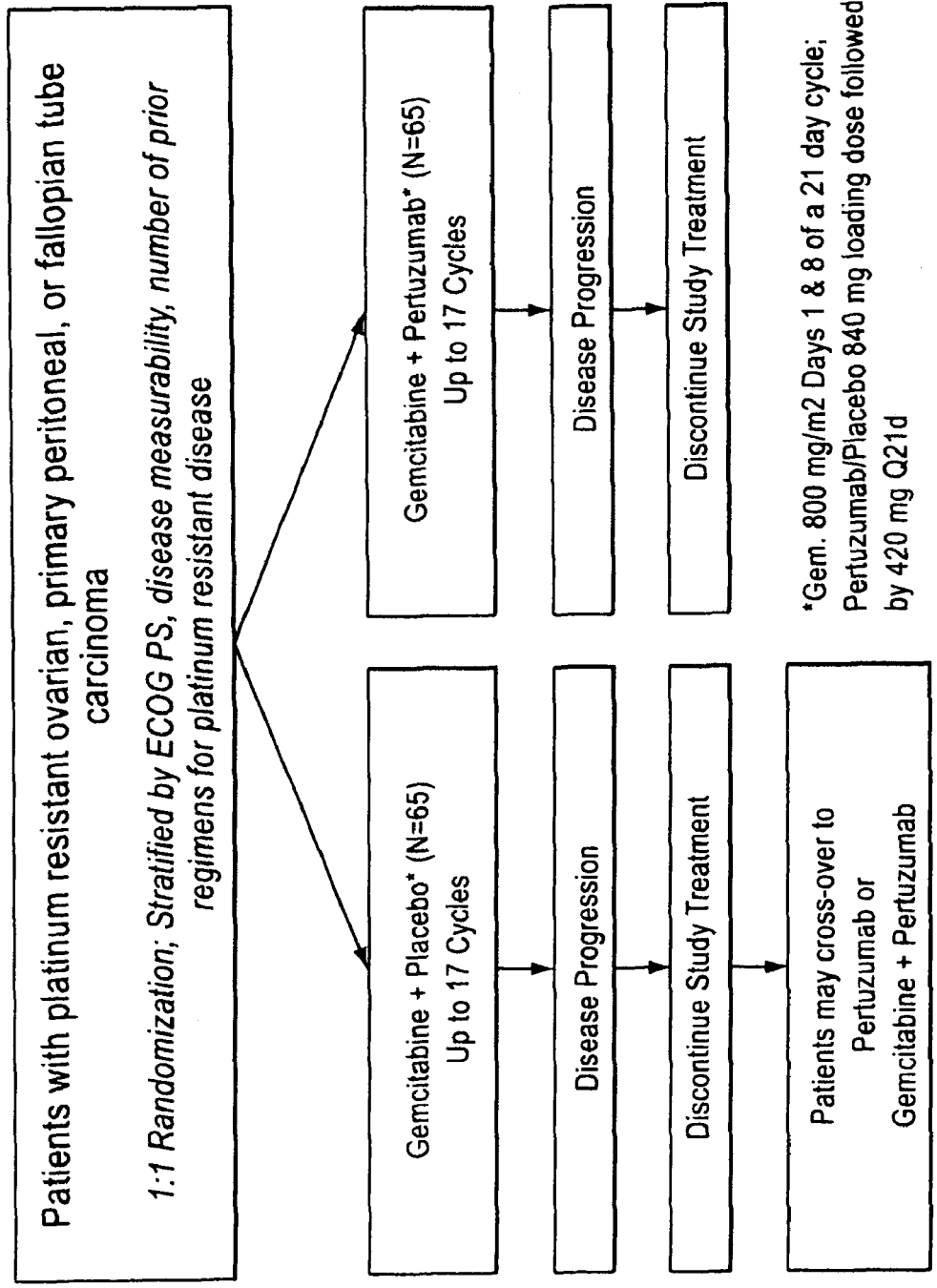
FIG. 9 depicts the study design/schemata for the clinical trial in Example 1 involving patients with platinum resistant ovarian, primary peritoneal, or fallopian tube carcinoma treated with either gemcitabine and placebo or gemcitabine and pertuzumab.

The effect of pertuzumab and gemcitabine on progression free survival (PFS) and overall survival (OS), was evaluated in all patients, and in the subset of patients whose tumors contained markers that indicated activation of HER2. The study design/schema is shown in FIG. 9.

Patients who had progressed while receiving, or within 6 months of receiving, a platinum-based chemotherapy regimen were eligible for this study. Patients were randomized to receive either gemcitabine in combination with pertuzumab, or gemcitabine in combination with placebo. Patients treated herein included those who had not received a previous salvage regimen treatment for platinum-resistant disease prior to study entry, and those who had received one prior regimen for platinum-resistant disease.

Gemcitabine was administered at 1000 mg/m$^2$ on days 1 and 8 of each 21 day cycle. Gemcitabine was infused first over 30 minutes. Dose reductions were permitted for toxicity. Placebo or pertuzumab was administered on day 1 of the 21 day cycle. Subjects randomized to receive pertuzumab were administered an initial loading dose of 840 mg (Cycle 1) followed by 420 mg in Cycles 2 and beyond. Subjects randomized to receive placebo were administered placebo in the same volume as administered with pertuzumab arm for Cycle 1, Cycles 2 and beyond. Subjects without progressive disease received treatment for up to 17 cycles, or 1 year. Patients had standard gemcitabine dose reduction and held doses as a result of cytopenias. Pertuzumab also was held for any held Day 1 gemcitabine doses. Subsequent doses were at the reduced doses and were not increased. If dose reduction or holding a dose was required in more than 4 occasions, or if doses were held for more than 3 weeks, then gemcitabine was discontinued and with the approval of the treating physician and medical monitor, blinded drug was continued until disease progression. If Day 8 gemcitabine doses were held, then the Day 8 dose was omitted and the subsequent treatment was commenced with the next cycle (Day 22 of the previous cycle).

Gemcitabine was held and dose reduced as recommended by the following table:

| Absolute Granulocyte Count ($\times 10^6$/L) | | Platelet Count ($\times 10^6$/L) | % full dose |
| --- | --- | --- | --- |
| >1000 | And | >100,000 | 100 |
| 500-999 | Or | 50,000-99,000 | 75 |
| <500 | Or | <50,000 | Hold |

Subsequent doses for any patient requiring dose reduction were at the reduced dose. If doses were held for more than 3 weeks as a result of cytopenias, patients were assumed to have unacceptable toxicity and discontinued gemcitabine. If there were no other additional grade III or IV toxicities, continuation of blinded drug was at the discretion of the physician and medical monitor. Hematological toxicity of gemcitabine has been related to rate of dose administration. Gemcitabine was given over 30 minutes regardless of total dose. The use of colony-stimulating agents for NCI-CTC Grade 2 cytopenias were used at the discretion of the treating physician.

The option for crossover to single agent pertuzumab was offered. A loading dose of 840 mg was administered at the next cycle due with continuation of 420 mg with subsequent cycles every 21 days.

Response was assessed at the end of Cycles 2, 4, 6, 8, 12 and 17. Measurable disease was assessed using the Response Evaluation Criteria for Solid Tumors (RECIST), by clinical evaluation and CT scan or equivalent. Response for subjects with evaluable disease was assessed according to changes to CA-125 and clinical and radiologic evidence of disease. Responses were confirmed 4-8 weeks after the initial documentation of response. The following outcome measures were assessed.

Primary Efficacy Endpoint

Progression free survival, as determined by investigator assessment using RECIST or CA-125 changes, following initiation of assigned study treatment of all subjects in each arm.

Progression free survival, as determined by investigator assessment using RECIST or CA-125 changes following initiation of assigned study treatment in each arm in the following subgroups:

Subjects with detectable markers of HER2 activation.
Subjects with no detectable markers of HER2 activation.
Secondary Efficacy Endpoints
Objective response (PR or CR)
Duration of response
Survival time
Freedom from progression at 4 months These endpoints were assessed in all subjects in each arm and in the following subgroups:

Subjects with detectable markers of HER2 activation.
Subjects with no detectable markers of HER2 activation.

To prevent or treat possible nausea and vomiting, the patient was premedicated with serotonin antagonists, steroids, and/or benzodiazepines. To prevent or treat possible rash, standard acne therapies, including topical and/or oral antibiotics were used. Other possible concomitant medications were any prescription medications or over-the-counter preparations used by a subject in the interval beginning 7 days prior to Day 1 and continuing through the last day of the follow-up period. Subjects who experienced infusion-associated temperature elevations to >38.5° C. or other infusion-associated symptoms were treated symptomatically with acetaminophen, diphenhydramine, or meperidine. Non-experimental hematopoietic growth factors were administered for NCI-CTC Grade 2 cytopenias.

Figure 27:
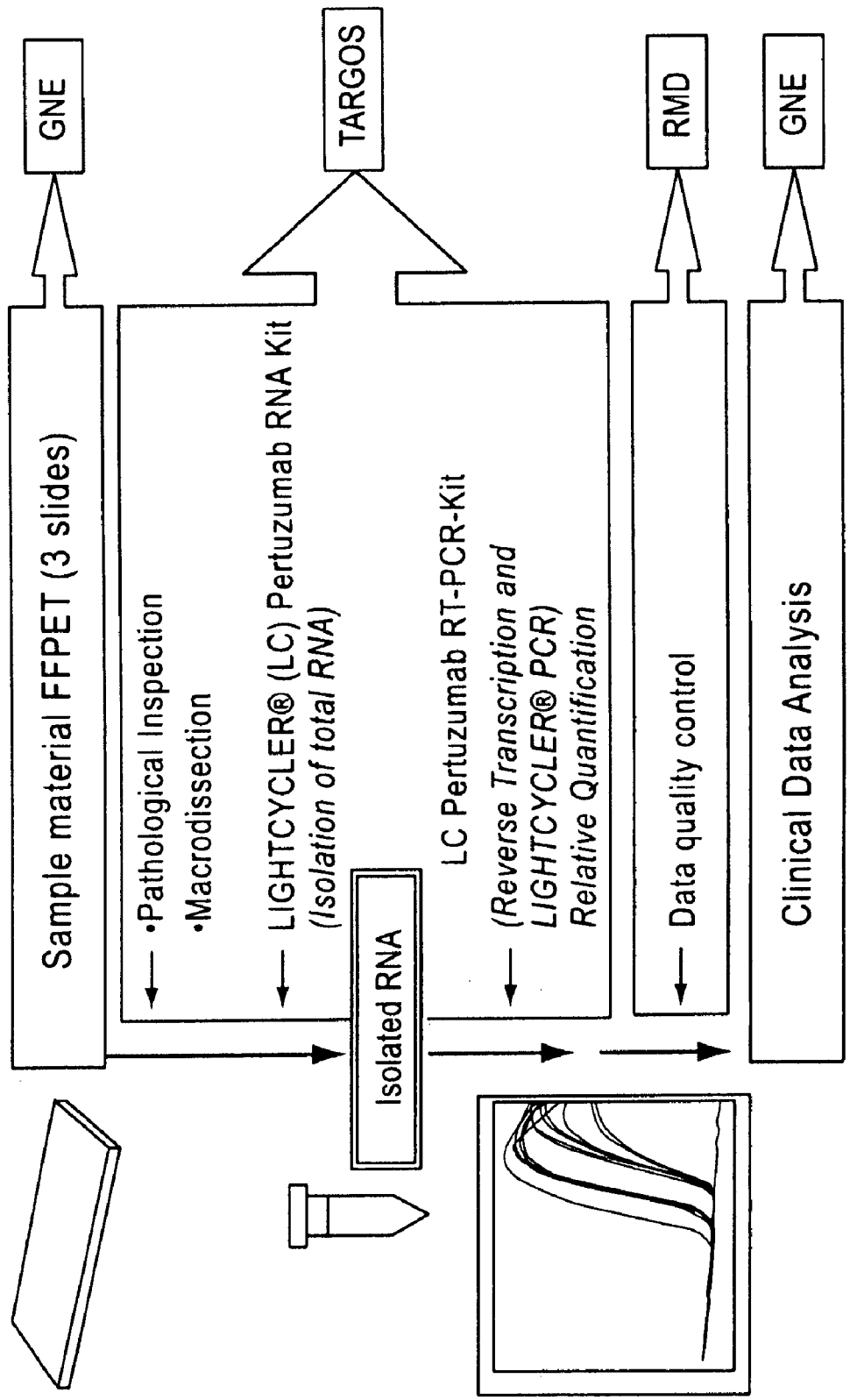
FIG. 27 shows LIGHTCYCLER® 2.0 pertuzumab qRT-PCR in vitro diagnostic (IVD) assay workflow.
Figure 28:
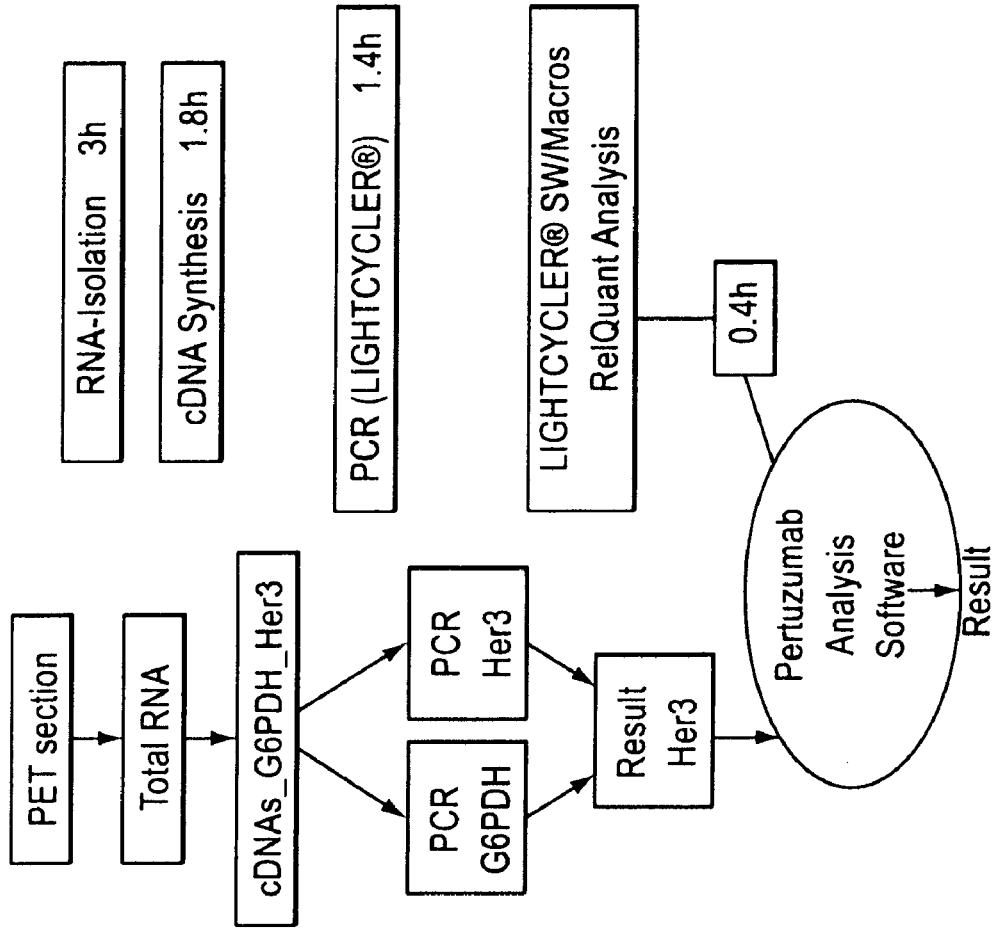
FIG. 28 shows pertuzumab IVD assay workflow and analysis with one marker and reference.

Formalin-fixed, paraffin embedded tissue (FFPET) samples obtained from the patients in this clinical trial were analyzed for EGFR, HER2, HER3, two HER ligands (amphiregulin and betacellulin), and G6PDH (a housekeeping gene) by qRT-PCR. The qRT-PCR assay was performed by TARGOS Molecular Pathology GmbH (Kassel, Germany) using Roche Diagnostic's lab lot kits. The workflow and analysis for performing the qRT-PCR assay on the clinical samples are depicted in FIGS. 27 and 28 herein.

mRNA analysis of EGFR, HER2, HER3, amphiregulin, and betacellulin was performed in duplicate. To allow quantitative data analysis G6PDH was also analyzed as an internal reference. Primer and probes were designed to amplify only mRNA, not DNA. qRT-PCR was conducted separately for each marker and G6PDH as a two-step procedure.

In the first step, cDNA was reverse transcribed from 5 µl of total RNA using AMV reverse transcriptase and specific priming for each marker and G6PDH. Temperature profile was 10 min./25° C. for annealing, 60 min./42° C. for reverse transcription and 5 min./94° C. for enzyme inactivation.

In the second step, a 100-120 bp fragment of marker and G6PDH mRNA was amplified from 5 µl cDNA using the LIGHTCYCLER® instrument (Roche Applied Science, Mannheim, Germany). Amplicons were detected by fluorescence using specific pairs of labeled hybridization probes (principle of fluorescence resonance energy transfer). All reagents used for qRT-PCR were from Roche Applied Science, Mannheim, Germany. Temperature profile was 10 min./95° for initial denaturation, and 45 cycles of (10 sec./62° C. for annealing, 9 sec./72° C. for elongation, 10 sec./95° C. for denaturation). See table below for primer/probe sequences used.

| Name | Sequence |
| --- | --- |
| G6PDH cDNA Primer | 5'-tgc gga tgt cag cca ctg tg-3' (SEQ ID NO: 23) |
| G6PDH forw. Primer | 5'-ggg tgc atc ggg tga cct g-3' (SEQ ID NO: 24) |
| G6PDH rev. Primer | 5'-agc cac tgt gag gcg gga-3' (SEQ ID NO: 25) |
| G6PDH Fluos Probe | 5'-ggt gtt ttc ggg cag aag gcc atc c-Fluos-3' (SEQ ID NO: 26) |
| G6PDH LC Red Probe | 5'-LCred 640-aac agc cac cag atg gtg ggg tag atc tt-3' (SEQ ID NO: 27) |
| EGFR cDNA Primer | 5'-ccg tca atg tag tgg gca cac-3' (SEQ ID NO: 28) |
| EGFR forw. Primer | 5'-ggg tga gcc aag gga gtt tg-3' (SEQ ID NO: 29) |
| EGFR rev. Primer | 5'-gca cac tgg ata cag ttg tct ggt c-3' (SEQ ID NO: 30) |
| EGFR LC Fluos Probe | 5'-tgt gca ggt gat gtt cat ggc ctg agg-Fluos-3' (SEQ ID NO: 31) |
| EGFR LC Red Probe | 5'-LCred 640-cac tct ggg tgg cac tgt atg cac tc-3' (SEQ ID NO: 32) |
| HER2 cDNA Primer | 5'-gga cct gcc tca ctt ggt tg-3' (SEQ ID NO: 33) |
| HER2 forw. Primer | 5'-cag gtg gtg cag gga aac ct-3' (SEQ ID NO: 34) |
| HER2 rev. Primer | 5'-ctg cct cac ttg gtt gtg agc-3' (SEQ ID NO: 35) |
| HER2 Fluos Probe | 5'-caa tgc cag cct gtc ctt cct gca g-Fluos-3' (SEQ ID NO: 36) |
| HER2 LC Red Probe | 5'-LCred 640-tat cca gga ggt gca ggg cta cgt gc-3' (SEQ ID NO: 37) |
| HER3 cDNA Primer | 5'-gtg tcc atg tga caa agc tta tcg-3' (SEQ ID NO: 38) |
| HER3 forw. Primer | 5'-gat ggg aag ttt gcc atc ttc g-3' (SEQ ID NO: 39) |
| HER3 rev. Primer | 5'-tct caa tat aaa cac ccc ctg aca g-3' (SEQ ID NO: 40) |
| HER3-Fluos Probe | 5'-aac acc aac tcc agc cac gct ctg-Fluos-3' (SEQ ID NO: 41) |
| HER3 LC Red Probe | 5'-LCred 640-agc tcc gct tga ctc agc tca ccg-3' (SEQ ID NO: 42) |

-continued

| Name | Sequence |
| --- | --- |
| Amphiregulin cDNA Primer | 5'-ctt gtc gaa gtt tc-3' (SEQ ID NO: 43) |
| Amphiregulin forw. Primer | 5'-cca tag ctg cct tta tgt ctg c-3' (SEQ ID NO: 44) |
| Amphiregulin rev. Primer | 5'-ctt tcg ttc ctc agc ttc tcc ttc-3' (SEQ ID NO: 45) |
| Amphiregulin Fluos Probe | 5'-tga tcc tca cag ctg ttg ctg tta-Fluos-3' (SEQ ID NO: 46) |
| Amphregulin LC Red Probe | 5'-LC red tac agt cca gct tag aag aca ata cgt cag gaa-3' (SEQ ID NO: 47) |
| Betacellulin cDNA Primer | 5'-gtc aac tct ctc aca c-3' (SEQ ID NO: 48) |
| Betacellulin forw. Primer | 5'-tct agg tgc ccc aag c-3' (SEQ ID NO: 49) |
| Betacellulin rev. Primer | 5'-tag cct tca tca cag aca cag-3' (SEQ ID NO: 50) |
| Betacellulin Fluos Probe | 5'-gca tta ctg cat caa agg gag atg ccg-Fluos-3' (SEQ ID NO: 51) |
| Betacellulin LC Red Probe | 5'-LCred 640-tcg tgg tgg ccg agc aga cg-3' (SEQ ID NO: 52) |

A calibrator RNA (purified RNA from HT29 cell line) was included in each run to allow for relative quantification, positive and negative controls were used to check the workflow and reagents.

Data analysis was conducted using the LIGHTCYCLER® Relative Quantification Software (Roche Applied Science, Mannheim, Germany) according to the manufacturer's instructions. The result was a "calibrator normalized ratio" of each marker for each patient sample. qRT-PCR values were available for 119/130 patients (92%). Dynamic range was: EGFR—about 10 fold, HER2—about 10 fold, HER3—about 20 fold. The principle of "relative quantification" was used. Gene expression (mRNA level) in a sample was quantified relatively referring to the expression of a housekeeping gene of the same sample (reference=G6PDH). This relative gene expression is then normalized to the relative gene expression in the calibratoer. For each marker a "calibrator normalized ratio" is calculated as below:

$$\text{Calibrator Normalized Ratio} = \frac{\frac{\text{Concentration of target}}{\text{Concentration of reference}}(\text{sample})}{\frac{\text{Concentration of target}}{\text{Concentration of reference}}(\text{calibrator})}$$

Target=gene of interest

Reference=house keeping gene (G6PDH)

Calibrator=HT29 colorectal cancer cell line RNA

Figure 10A:
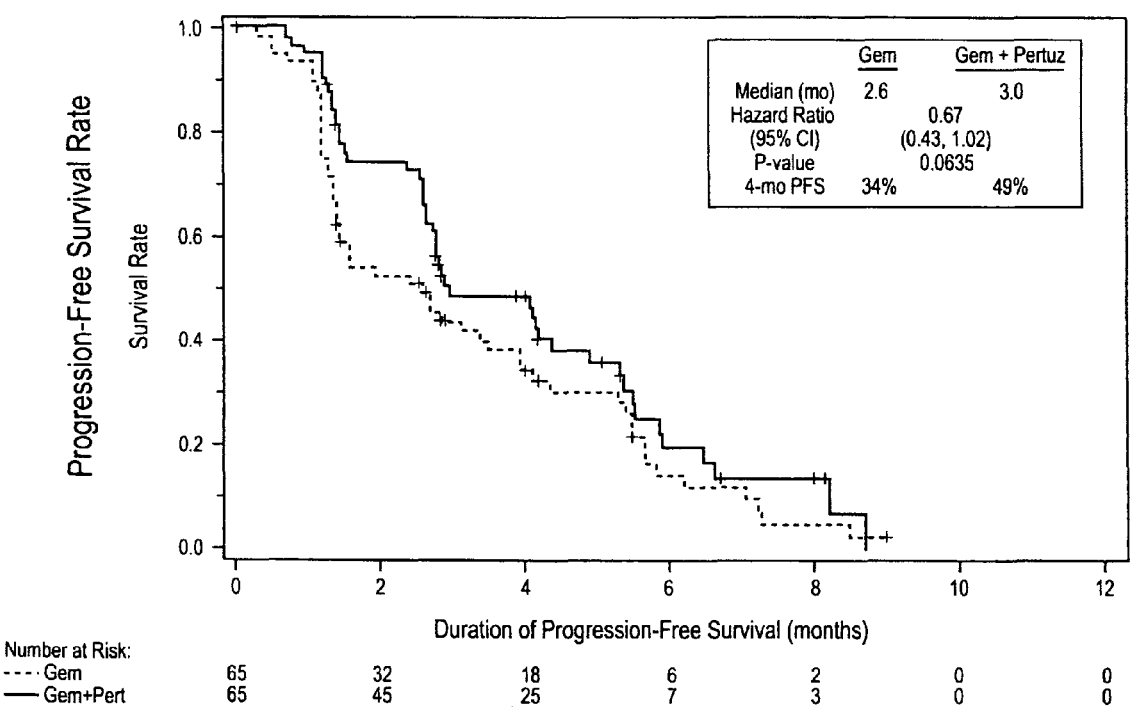
FIG. 10A depicts progression-free survival (PFS) for all patients from the study in Example 1.
Figure 10B:
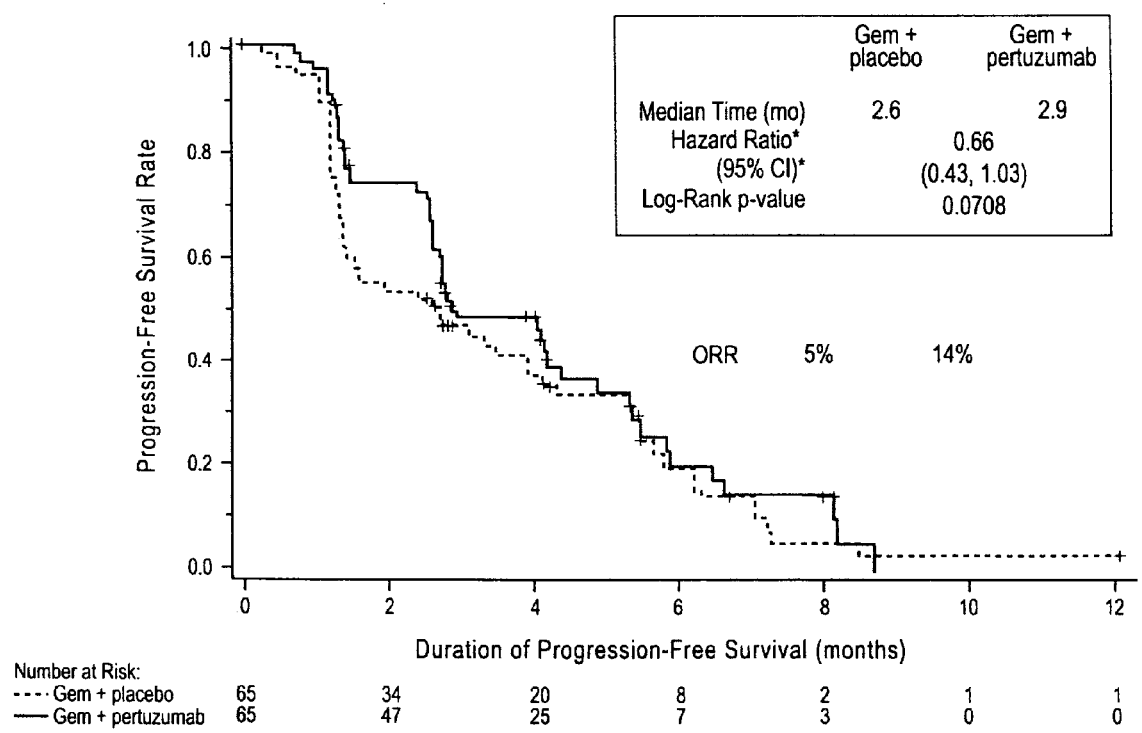
FIG. 10B is an updated version of FIG. 10A. PFS has been estimates using stratified Cox model and stratified long mk test by randomization stratification factors (ECOG PS, number of prior regimens for platinum-resistant disease, and disease measurability).

The efficacy results were assessed at 7.1 months median follow-up (range 1.3-20.3). There were 101 progression free survival (PFS) events at that time. FIGS. 10A and B represent PFS in all patients treated with either gemcitabine and placebo, or gemcitabine and pertuzumab. P-values were estimated using stratified Cox model and stratified log-rank test by randomization stratification factors (ECOG PS, number of prior regimens for platinum resistant disease, and disease measurability).

Figure 11A:
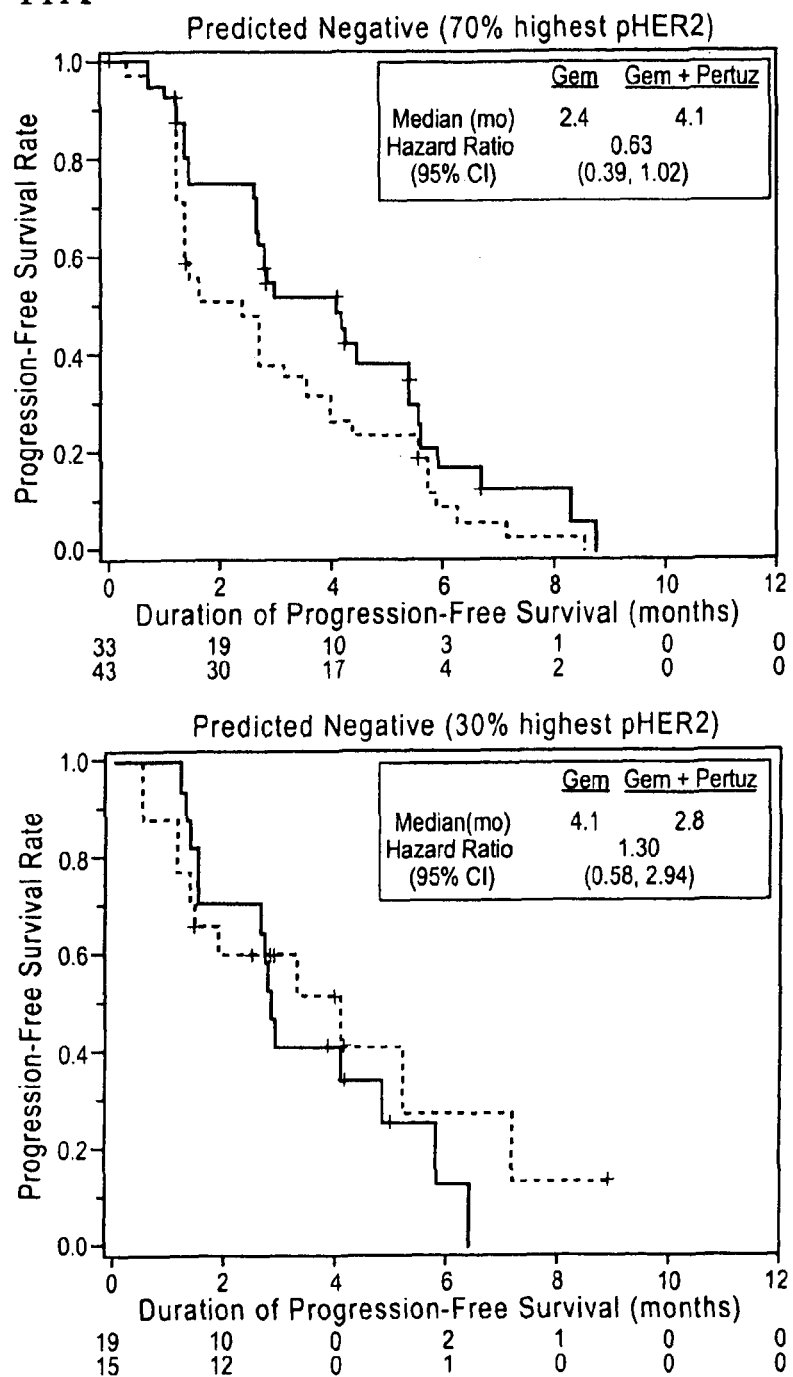
FIG. 11A represents PFS by predicted pHER2 status.
Figure 11B:
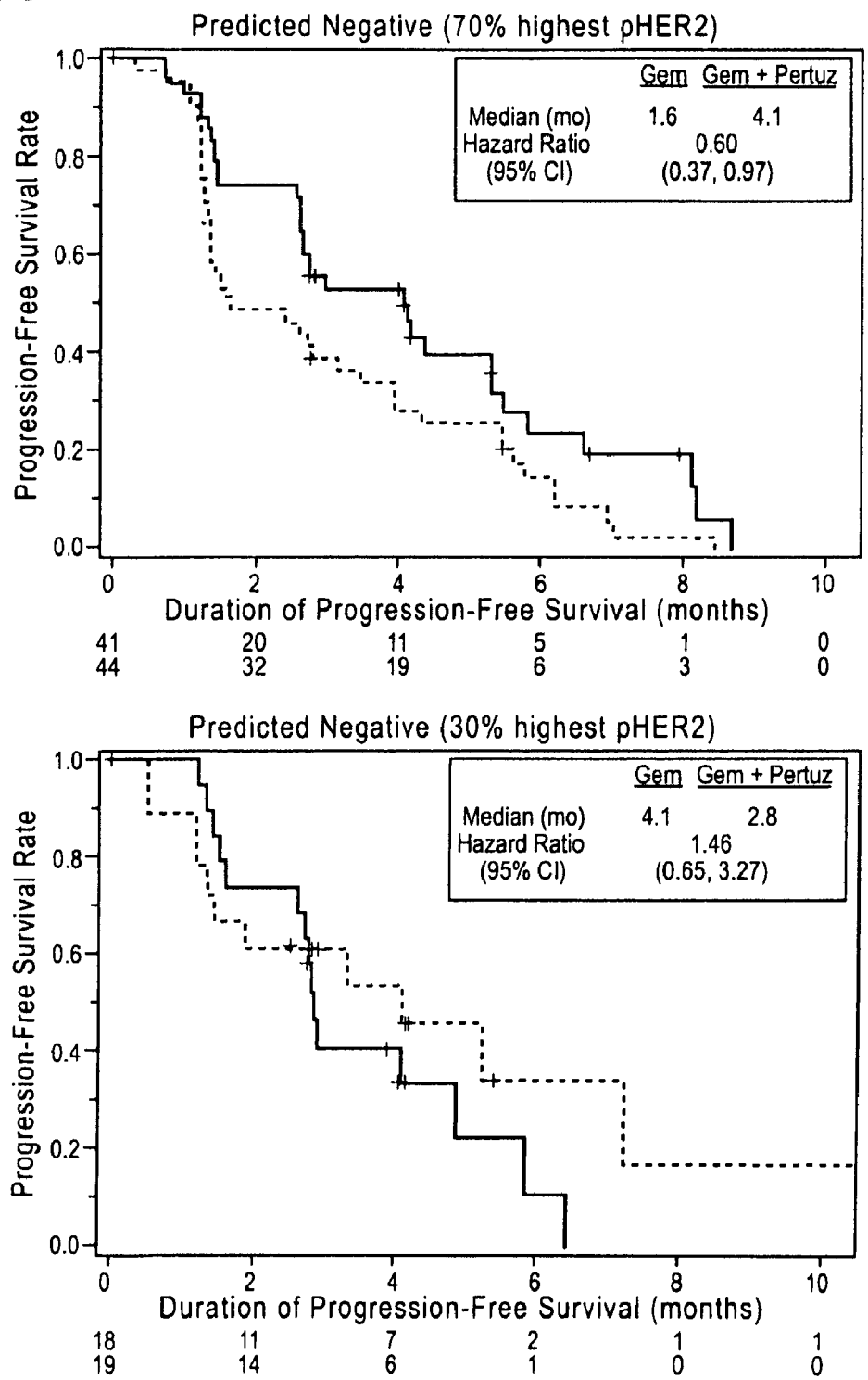
FIG. 11B is an updated version of FIG. 11A.

PFS by predicted pHER2 status is shown in FIGS. 11A and B, comparing PFS in patients predicted negative for pHER2, and those predicted positive for pHER2. A predictive algorithm was developed using 80 commercially obtained ovarian cancer samples. A combination of HER2, HER3 and amphiregulin expression predicts the 30% highest pHER samples with an accuracy of 80%. Patients were predicted positive for pHER2 if amphiregulin, HER2, and HER3 were greater than and equal to the $70^{th}$ percentile, others were considered negative for pHER2.

Figure 12A:
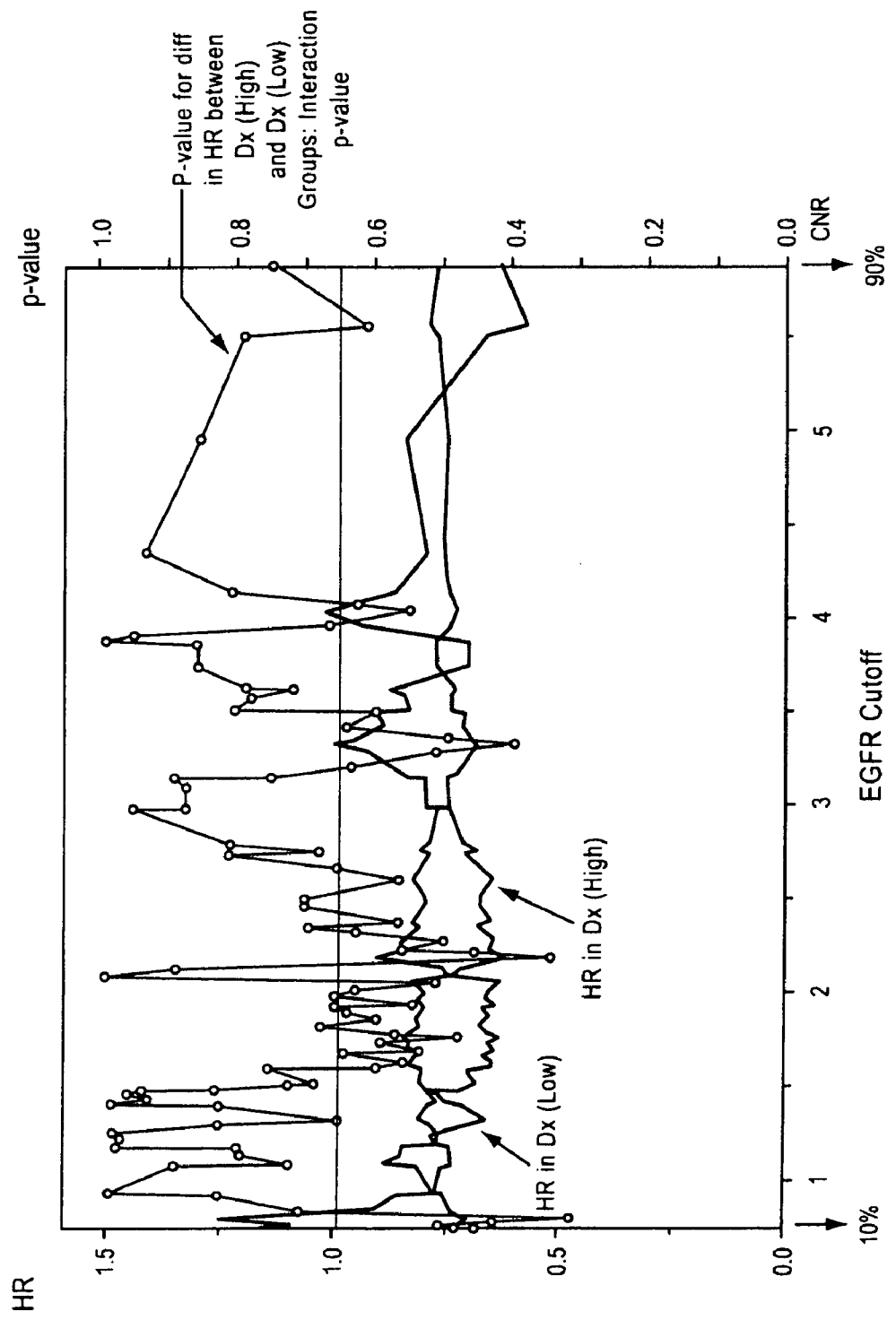
FIG. 12A represents PFS by qRT-PCR EGFR (HER1) cutoffs.
Figure 13A:
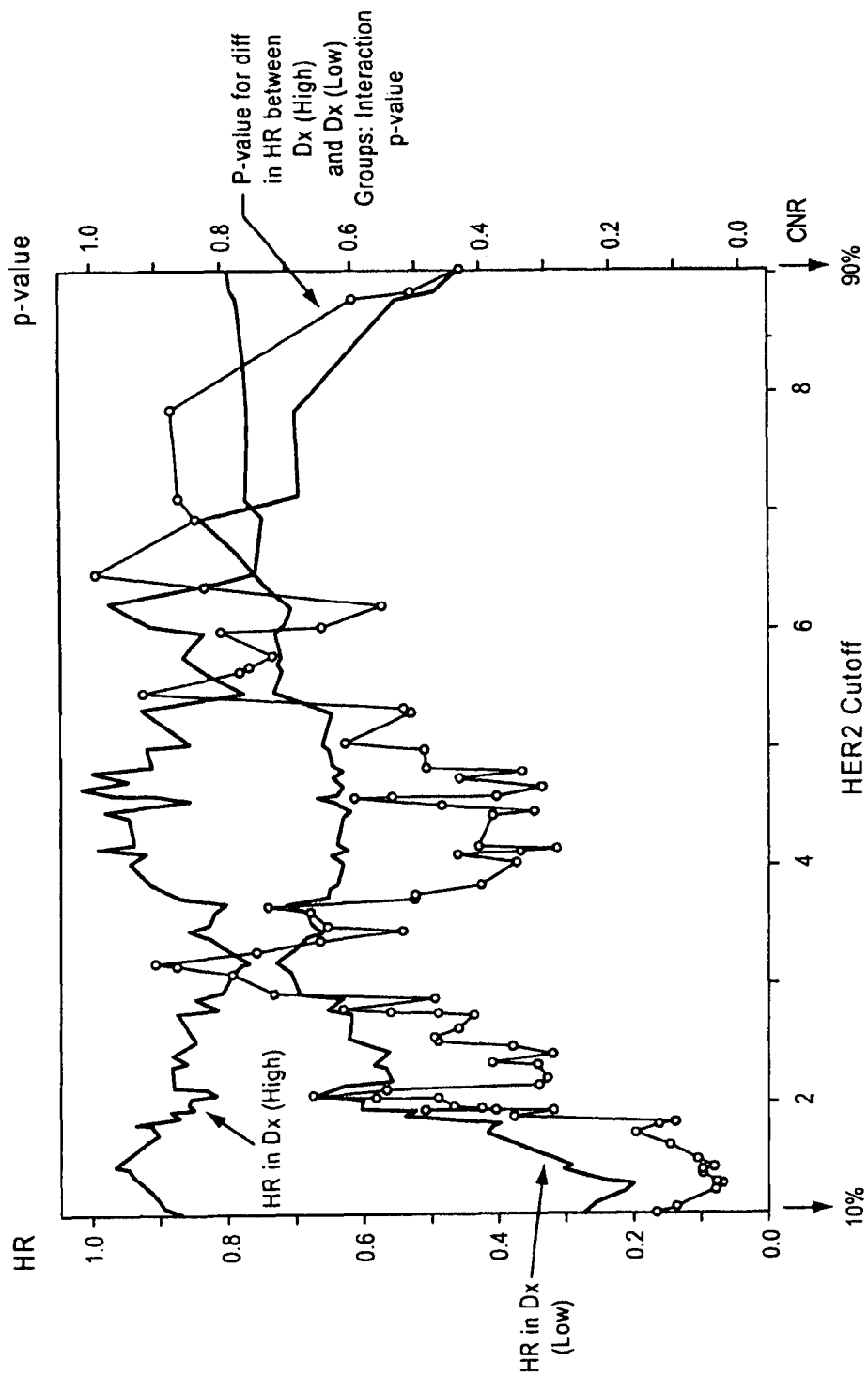
FIG. 13A represents PFS by qRT-PCR HER2 cutoffs.
Figure 13B:
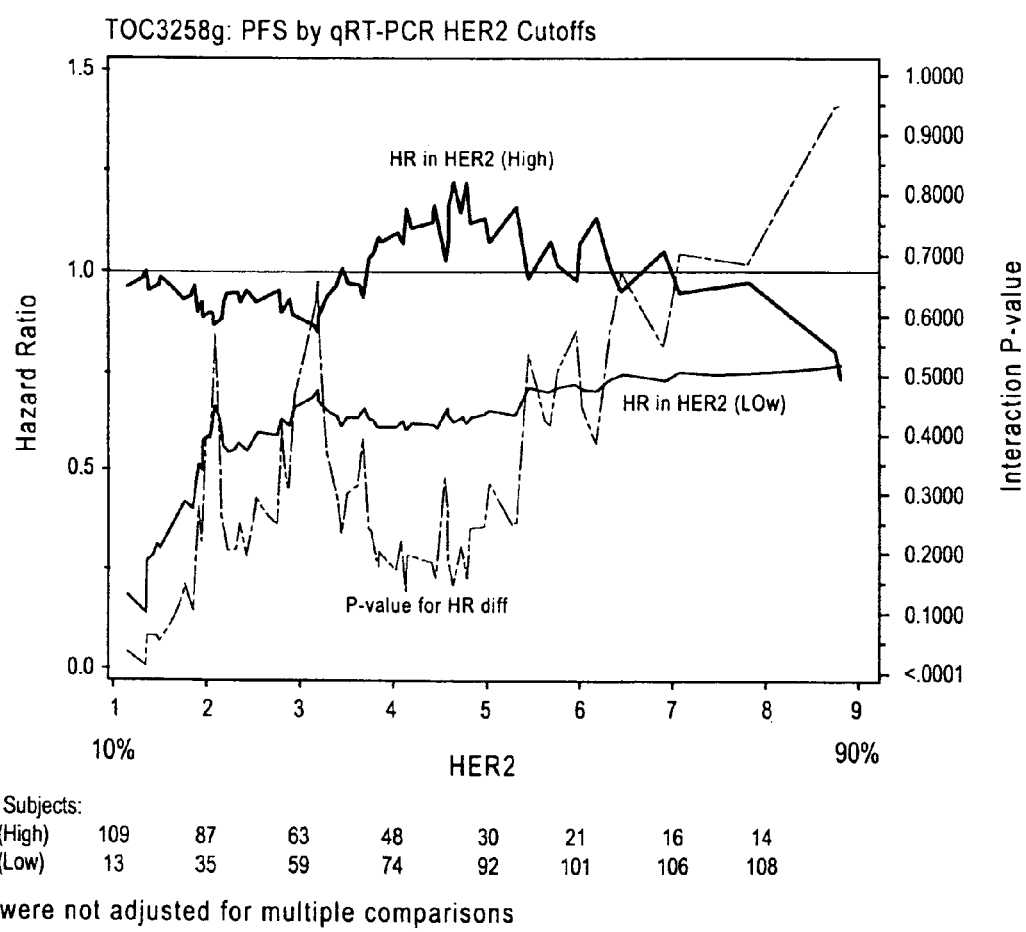
FIG. 13B is another representation of PFS by qRT-PCR HER2 cutoffs, also indicating the number of subjects in the HER1 (High) and HER1 (Low) groups at various HER2 cutoff values.
Figure 14A:
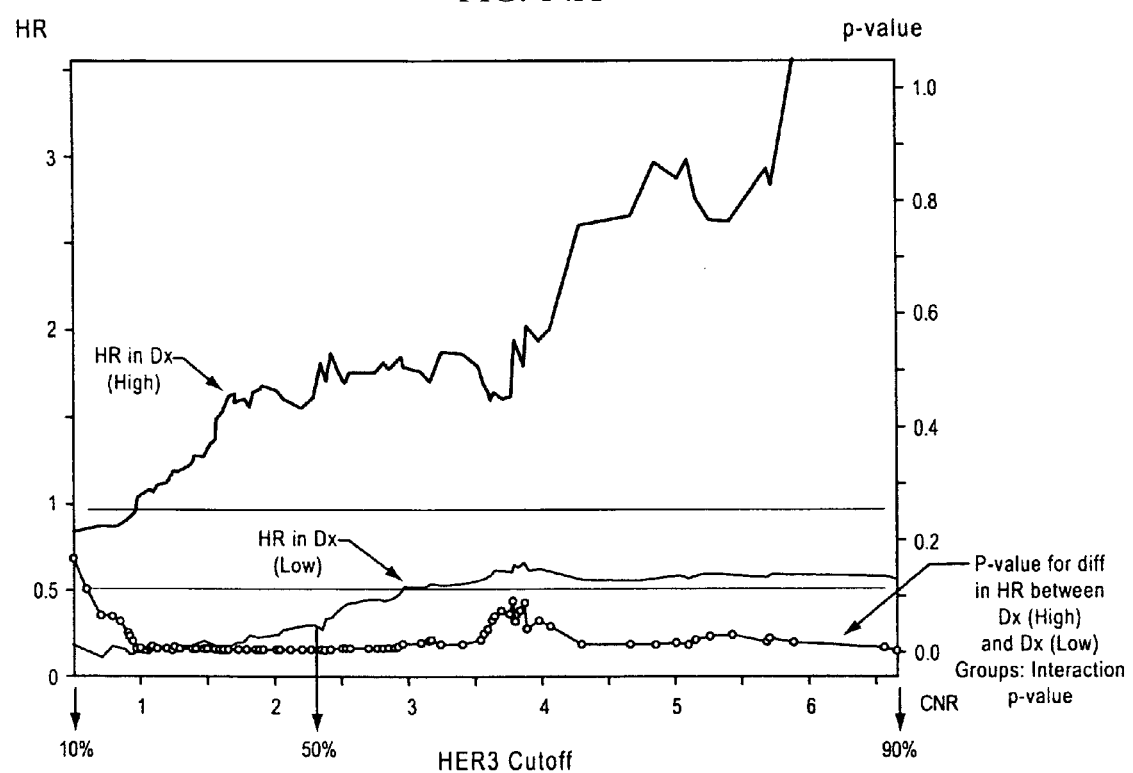
FIG. 14A represents PFS by qRT-PCR HER3 cutoffs.
Figure 14B:
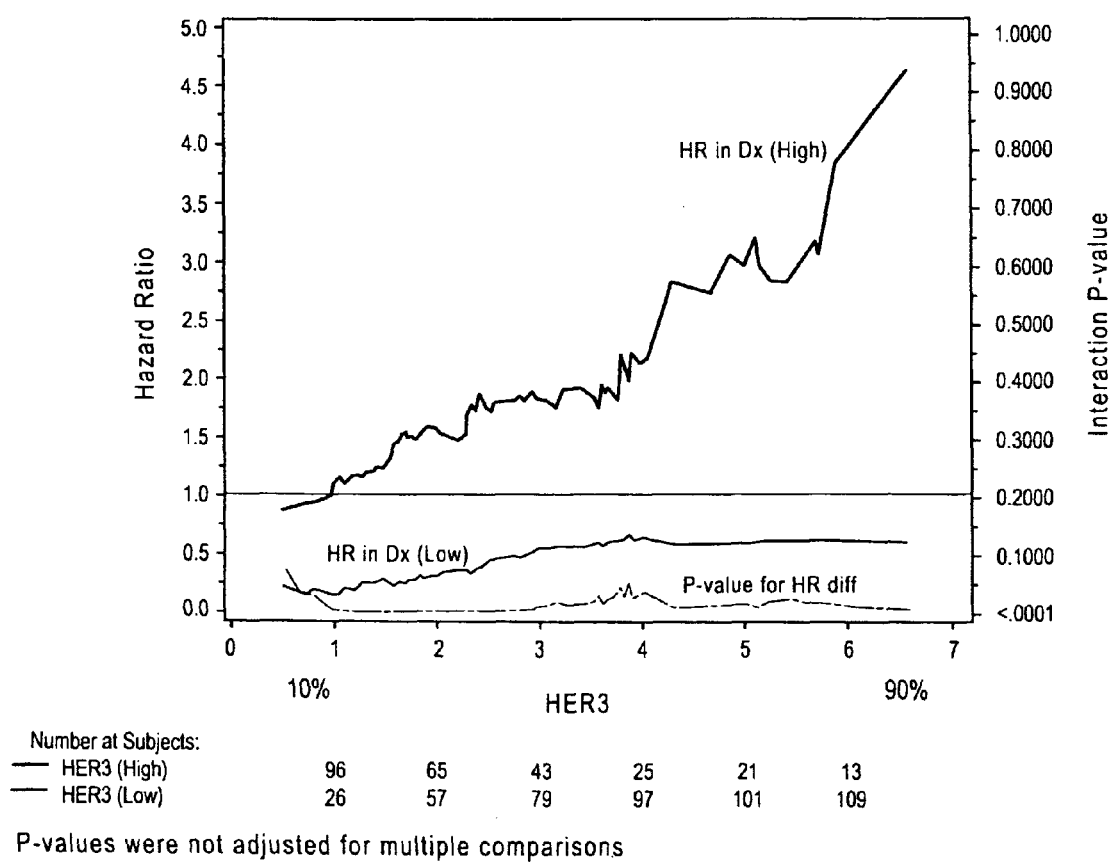
FIG. 14B is another representation of PFS by qRT-PCR HER3 cutoffs, also indicating the number of subjects in the HER3 (High) and HER3 (Low) groups at various HER3 cutoff values.
Figure 15A:
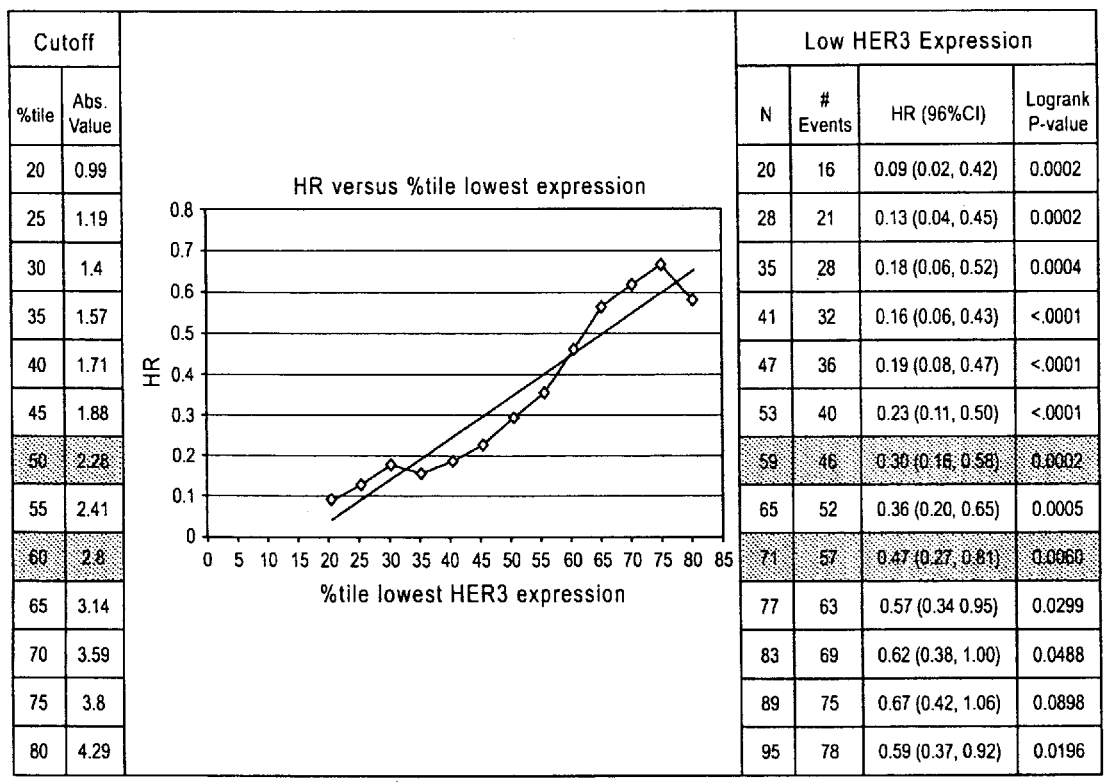
FIG. 15A shows PFS by HER3 subgroups. Pertuzumab activity is greatest in patients with low HER3 expressing tumors and tends to increase as HER3 gene expression level decreases.
Figure 15B:
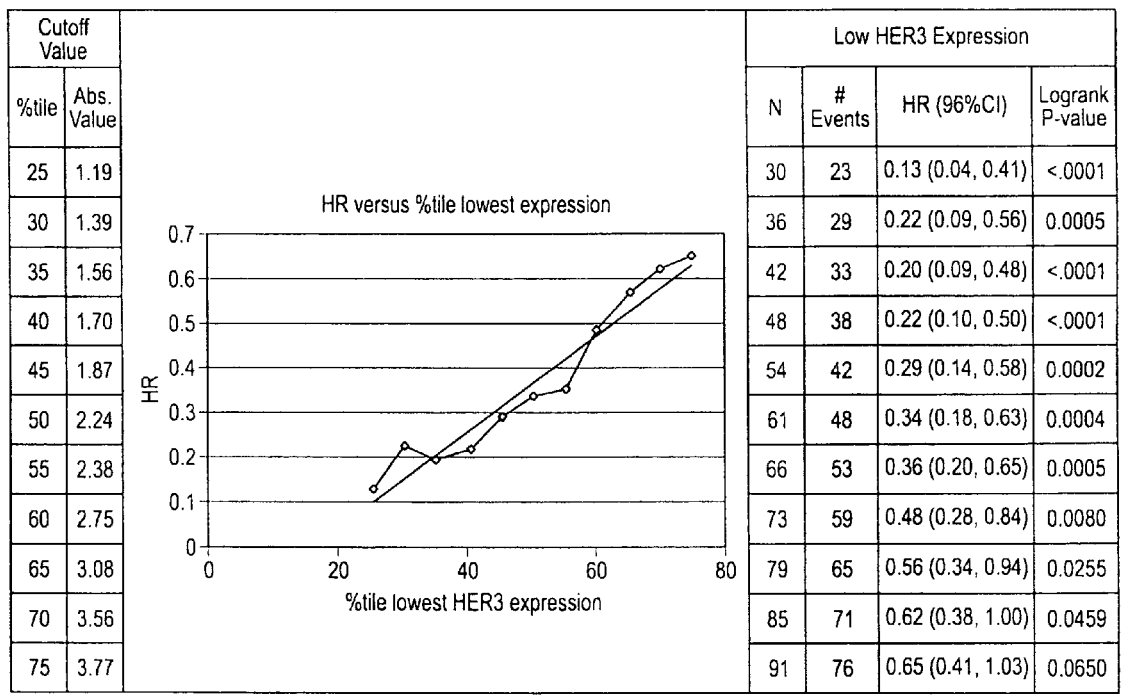
FIG. 15B is another representation of PFS by qRT-PCR HER3 levels.

FIGS. 12A and B represent PFS based on qRT-PCR EGFR cutoffs; FIGS. 13A and B PFS based on qRT-PCR HER2 cutoffs; and FIGS. 14A and B PFS by qRT-PCR HER3 cutoffs. Patients with low HER3 had better outcome in terms of PFS. These data are shown in more detail in FIGS. 15A and B. As shown in those figures, pertuzumab activity is greatest in patients with HER3 low expressing tumors and tends to increase as HER3 gene expressing level decreases. These figures include the absolute value for HER3 expression as quantified in the qRT-PCR assay.

Figure 16A:
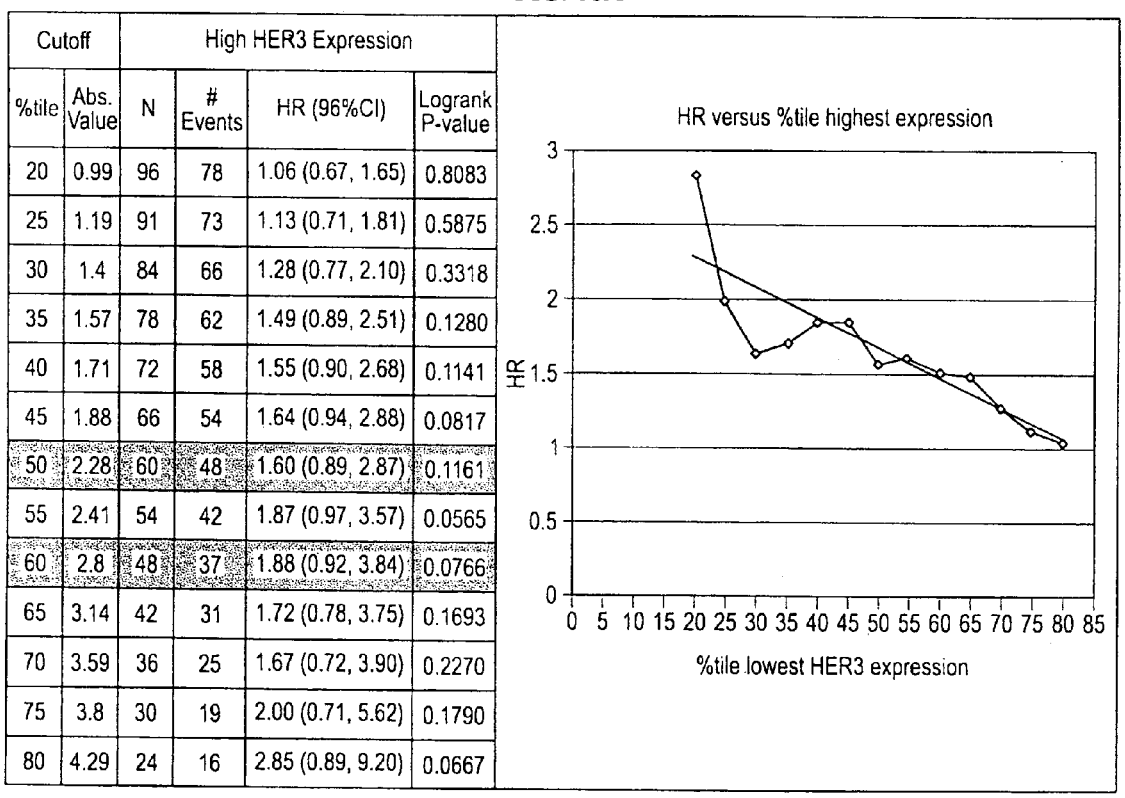
FIG. 16A demonstrates PFS by HER3 subgroups. The data show there may be a negative interaction between pertuzumab and gemcitabine in patients with HER3 high expressing tumors.
Figure 16B:
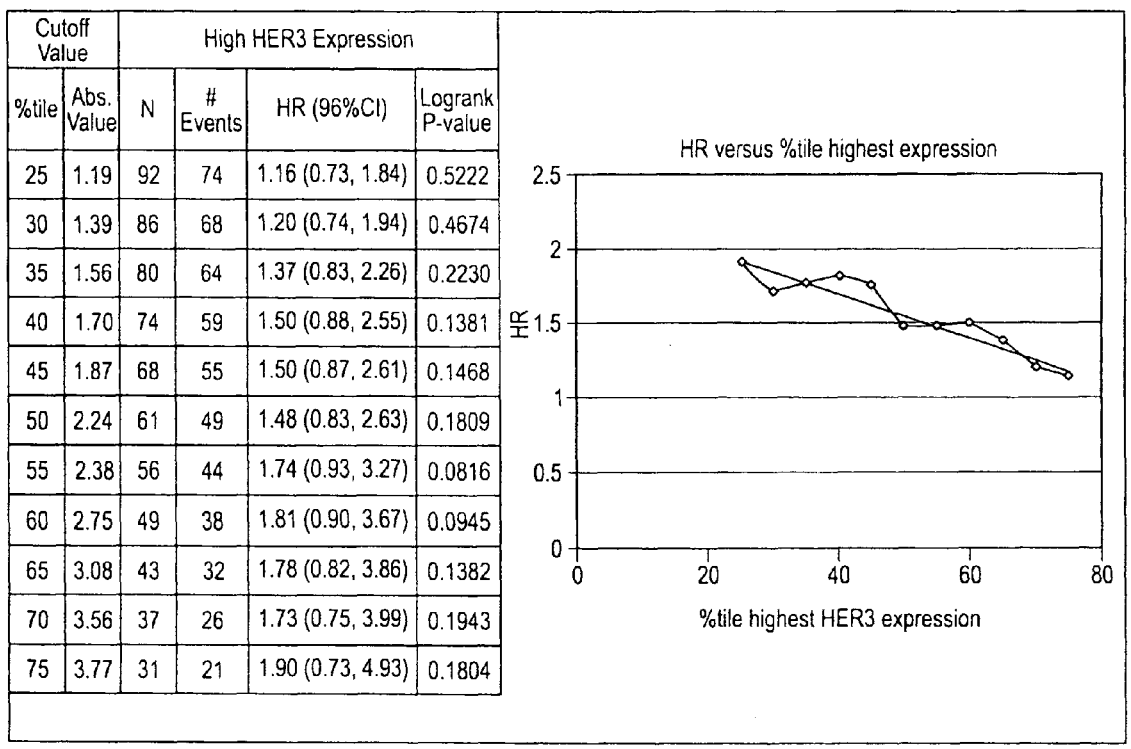
FIG. 16B is another representation of PFS by qRT-PCR HER3 levels. The data further conform that there may be a negative interaction between pertuzumab and gemcitabine in patients with HER3 high expressing tumors.

FIGS. 16A and B illustrate PFS by HER3 subgroups. These data show that there may be a negative interaction between pertuzumab and gemcitabine in patients with high HER3 expressing tumors.

FIGS. 17A and B are further tables summarizing the data for PFS by HER3 subgroups for both high HER3 expression and low HER3 expression. FIGS. 18A and B represent PFS by HER3 subgroups based on four different percentiles. Patients in the 0 to less than $50^{th}$ percentile, and particularly the 0 to $25^{th}$ percentile for HER3 expression have an improved hazard ration (HR) for PFS. (Lower HRs correlate with improved outcome as measured by PFS.)

FIGS. 19A and B provide the data showing PFS by HER3 qRT-PCR with a 50/50 split. Low HER3 expressing patients (less than $50^{th}$ percentile) have an increased duration of PFS as measured in months compared to high HER3 expressing patients (greater than and equal to $50^{th}$ percentile). This correlation is more pronounced in FIGS. 20A and B where low HER3 expressing patients were characterized as those in the less than $25^{th}$ percentile, and high HER3 expressing patients were those in the greater than or equal to $25^{th}$ percentile. The P-value for the difference in HR between the two diagnostic subgroups was 0.0007. The $25^{th}$ percentile is equal to 1.19 CNR.

Figure 21A:
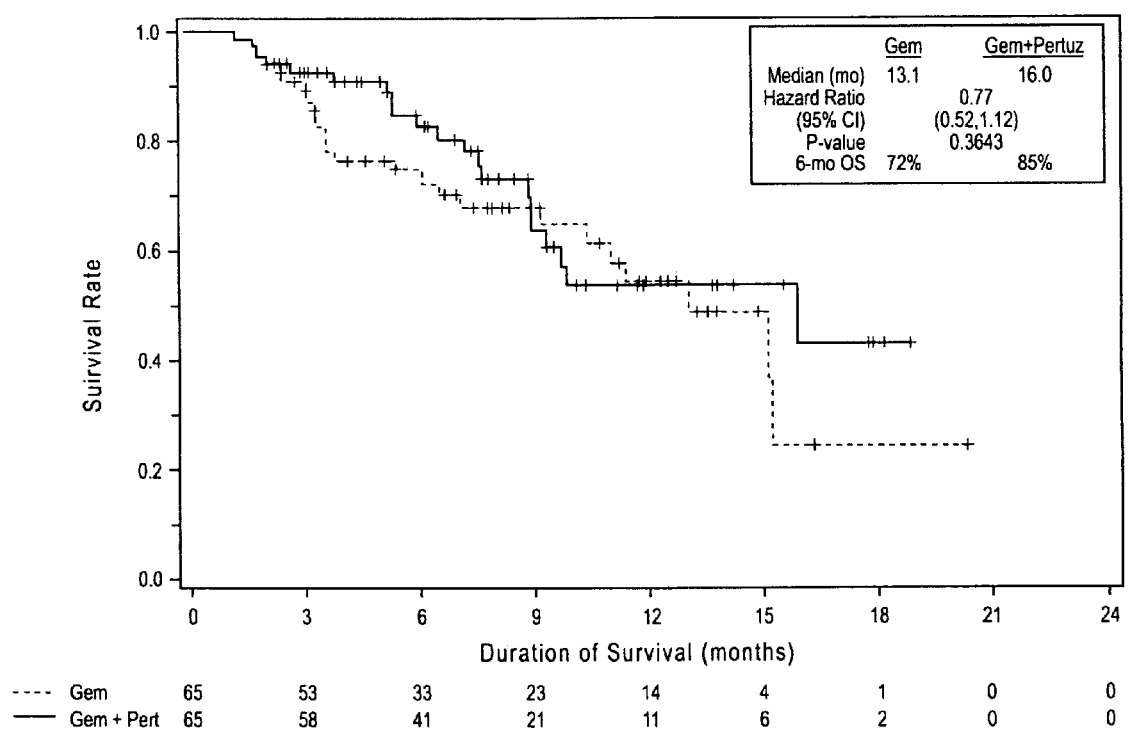
FIG. 21A shows preliminary data for overall survival (OS) in all patients. Data based on 46/130 events.
Figure 21B:
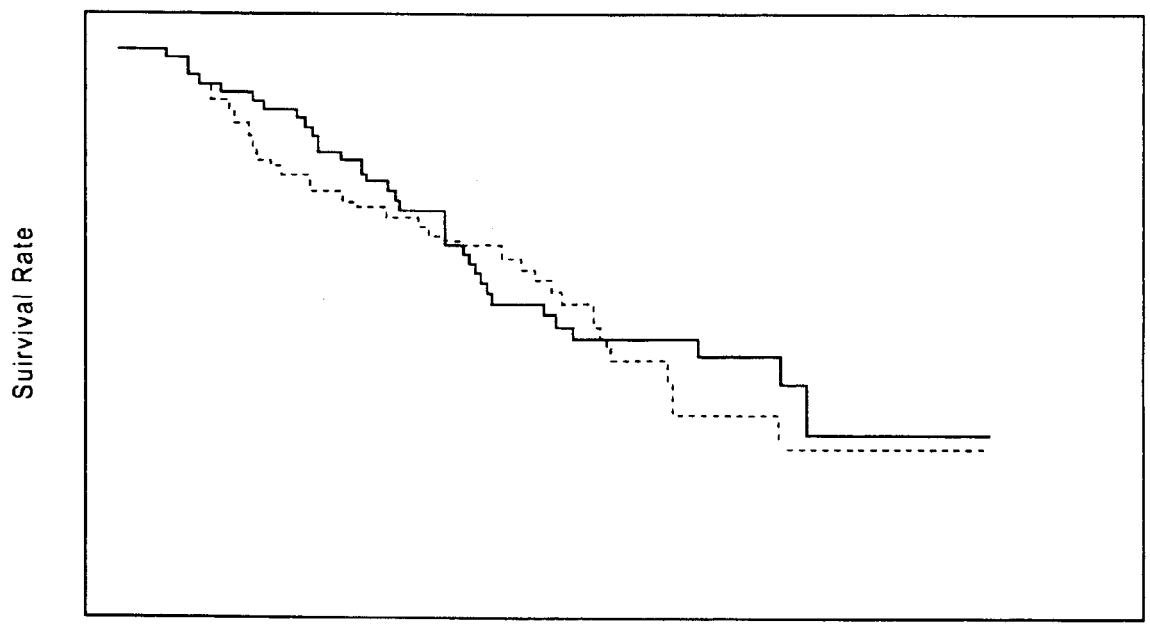
FIG. 21B is an updated chart of OS data, estimated stratified Cox model and stratified log rank-test by randomization stratification factors (ECOG PS, number of prior regimens for platinum-resistant disease, and disease measurability).

Preliminary data is available for overall survival (OS). Such data for all patients are provided in FIGS. 21A and B. FIGS. 22A and B compare OS by HER3 qRT-PCR comparing low HER3 expression (less than $50^{th}$ percentile) and high HER3 expression (greater than or equal to the $50^{th}$ percentile).

Figure 23A:
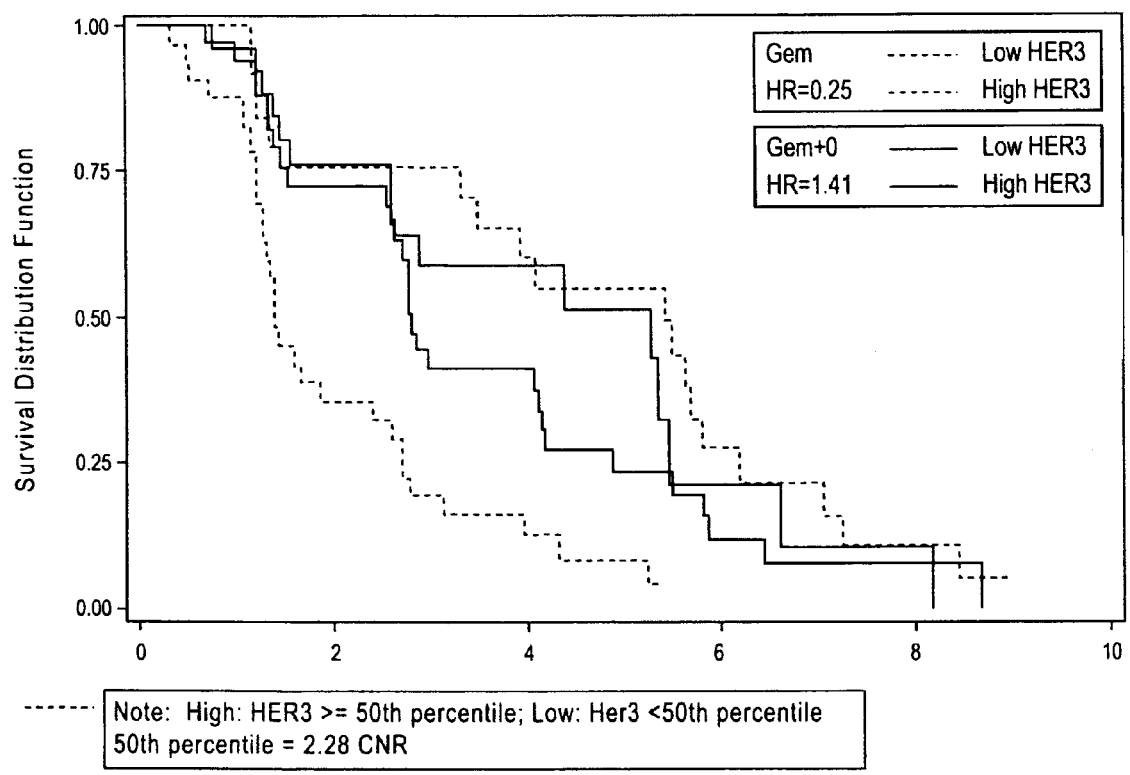
FIG. 23A demonstrates PFS by HER3 qRT-PCR comparing high versus low hazard ratios (HR).

FIGS. 23A and B illustrate PFS by HER3 qRT-PCR with 50/50 split, high versus low hazard ratio (HR). The complete set of PFS data including percentiles from 5% to 95% are shown in FIGS. 24A and B.

Figure 26A:
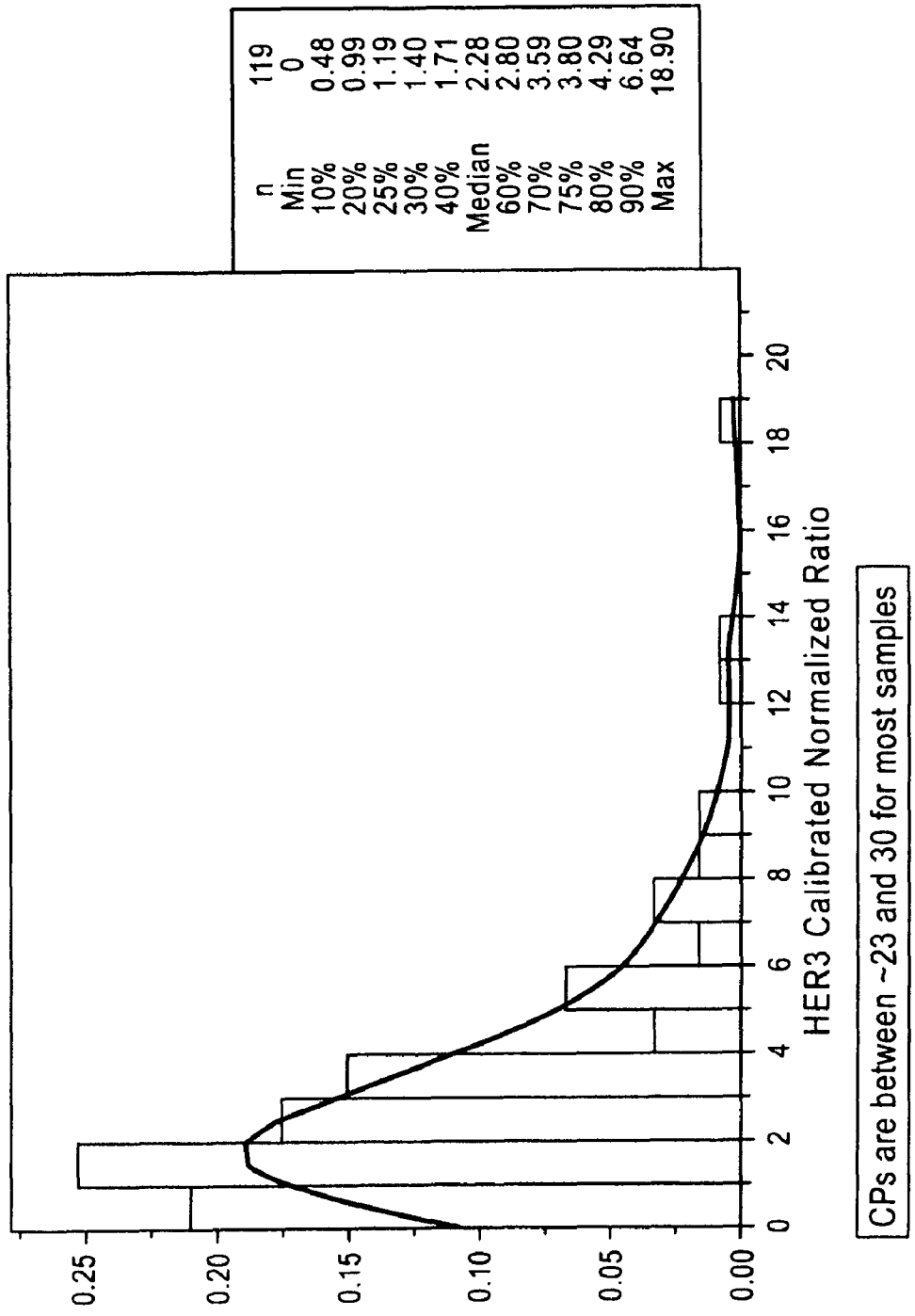
FIG. 26A shows HER3 calibrated normalized ratio; expression range is about 20-80 fold. CPs are between about 23 and 30 for most samples.
Figure 26B:
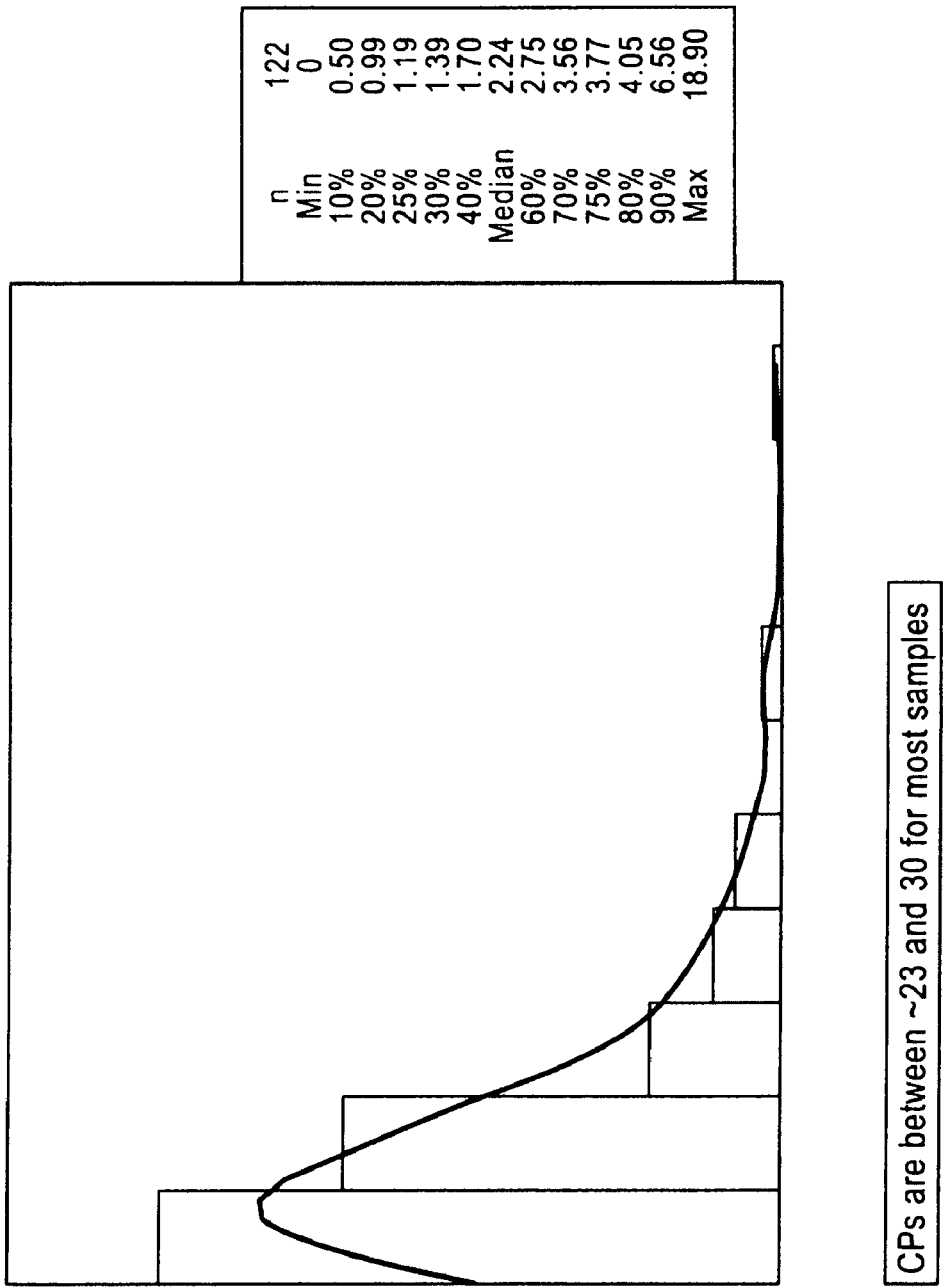
FIG. 26B is another figure shown HER3 calibrated normalized ratio; expression range is about 20-80 fold. CPs are between about 23 and 30 for most samples.

HER3 calibrated normalized ratio expression range is shown in FIG. 26. This range is about 20-80 fold.

Figure 30A:
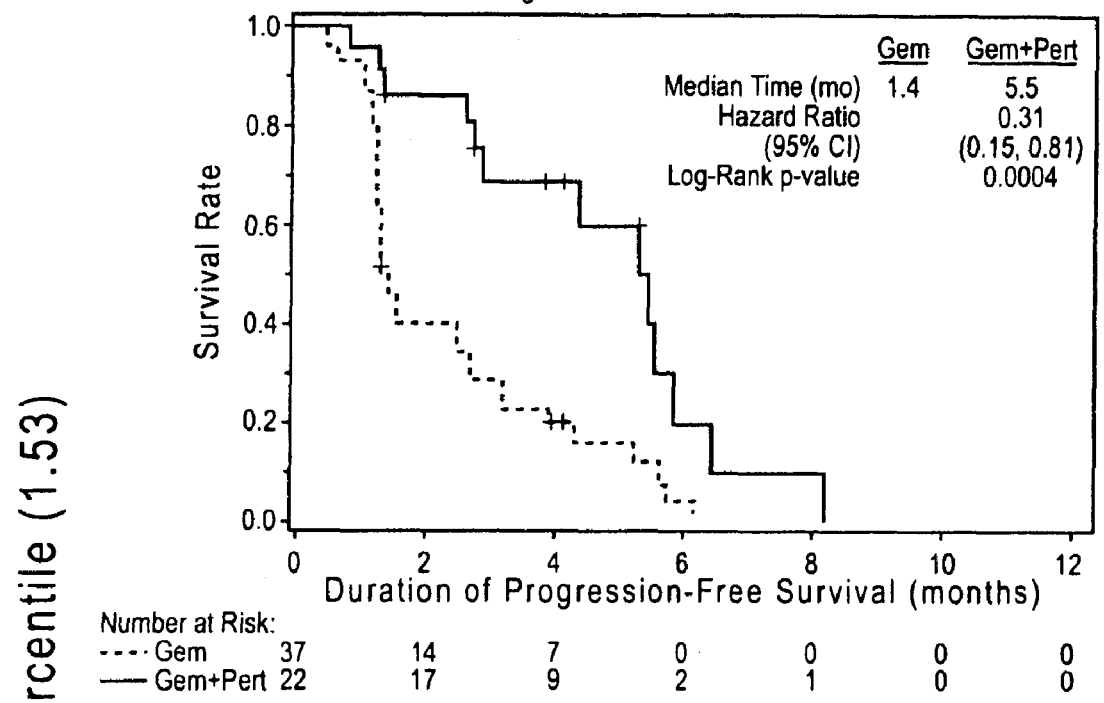
FIG. 30A evaluates PFS by HER2:HER3 ratio for Example 1 using Kaplan Meyer plots specifically for patients with HER2 to HER3 ratios of higher than the median, or higher than the 75th percentile.
Figure 30B:
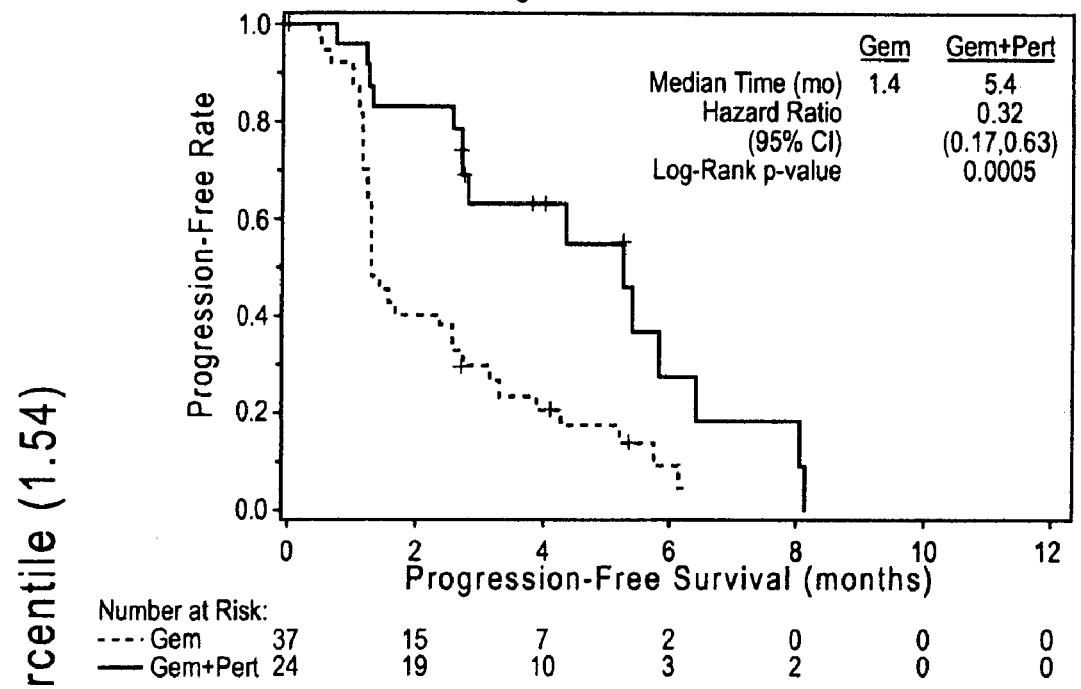
FIG. 30B is an updated showing of PFS by HER2:HER3 ratio for Example 1 using Kaplan Meyer plots specifically for patients with HER2 to HER3 ratios of higher than the median, or higher than the 75th percentile.
Figure 2:
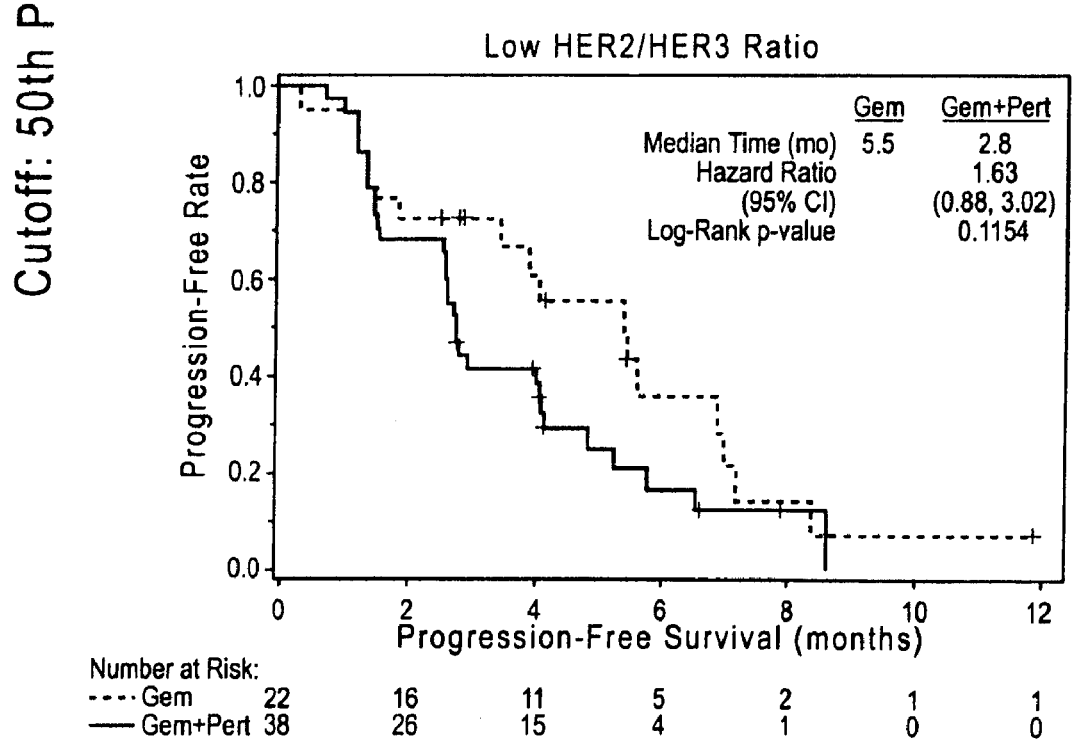
Figures 1, 32:
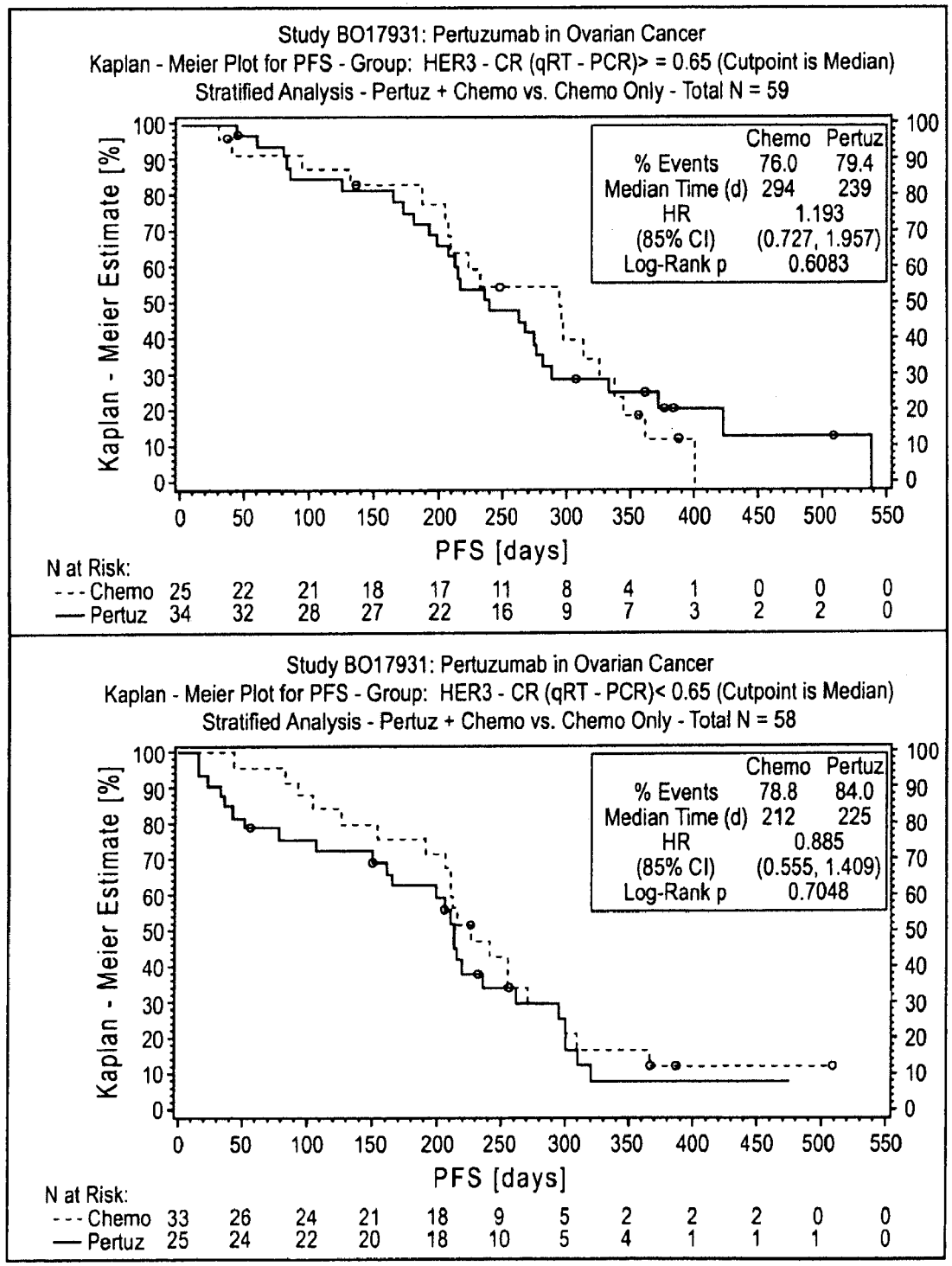
FIG. 32 shows Kaplan-Meier plots for PFS for subjects with ovarian cancer having HER3 levels less than median and equal to or more than median, respectively, treated as described in Example 3.
Figures 2, 32:
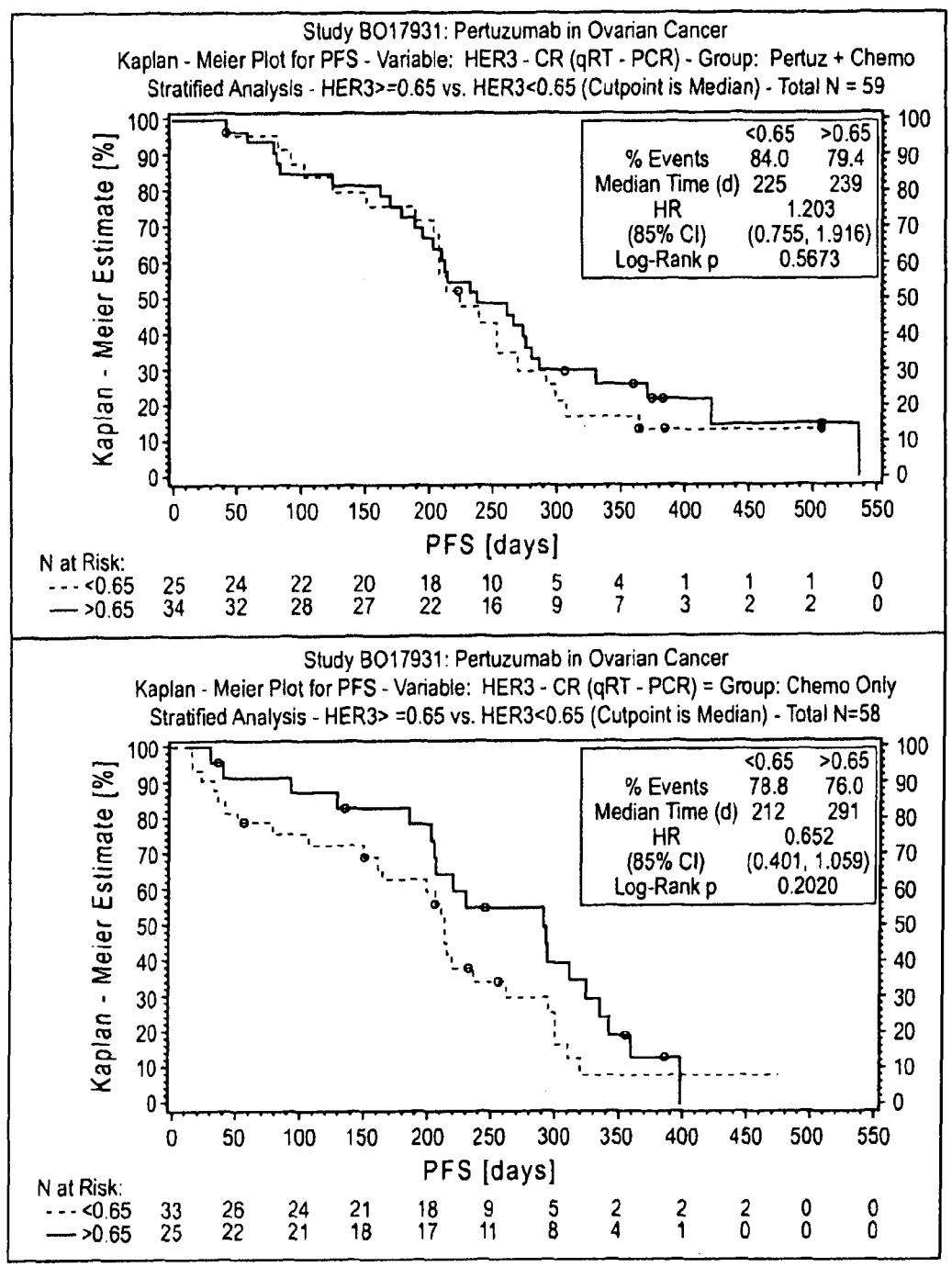
Figure 33:
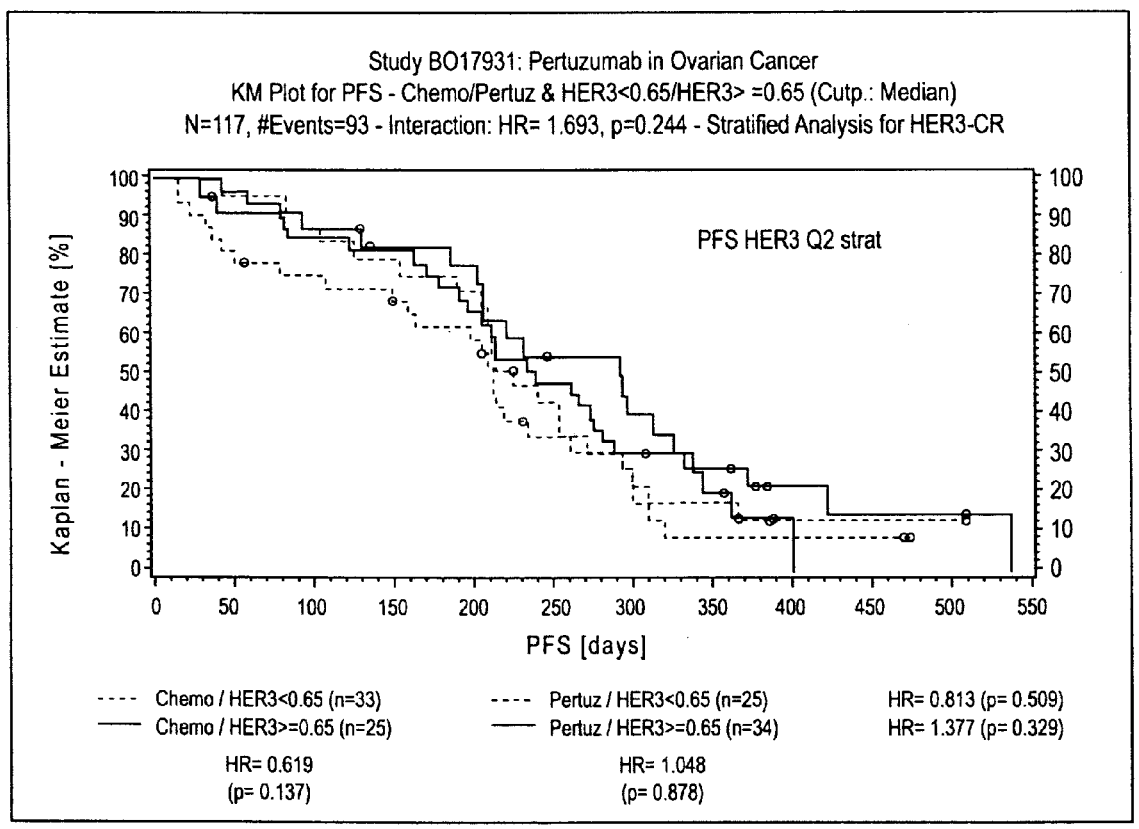
FIG. 33 shows a PFS Kaplan-Meier plot for subjects with ovarian cancer, treated with chemotherapy or pertuzumab in patient group with HER3 levels less than median and equal to or more than median, respectively.
Figures 1, 34:
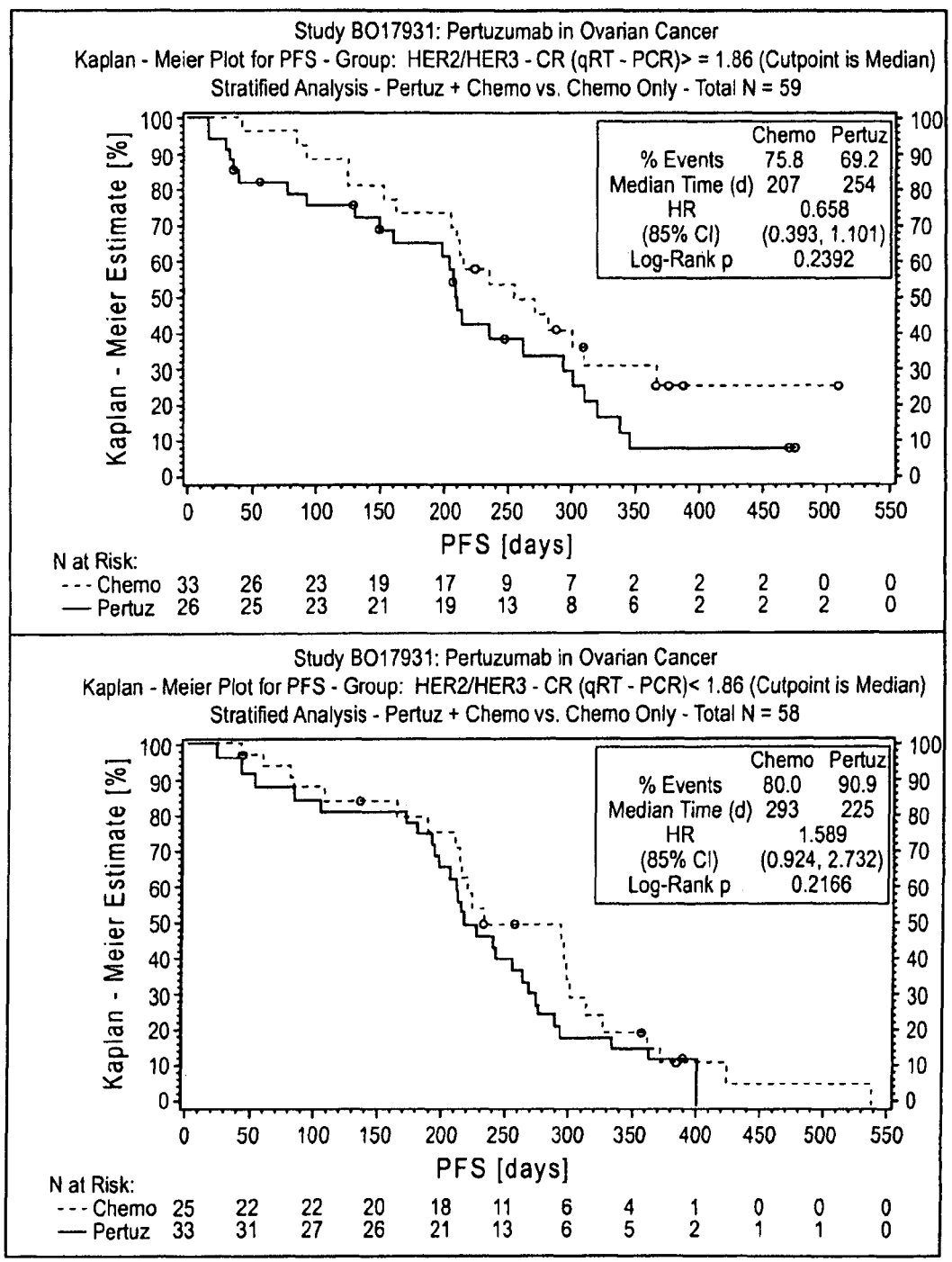
FIG. 34 shows PFS Kaplan-Meier plots for subjects with ovarian cancer, treated with pertuzumab and chemotherapy or with pertuzumab alone, for HER2/HER3 ratios below median and equal to or more than median, respectively.
Figures 2, 34:
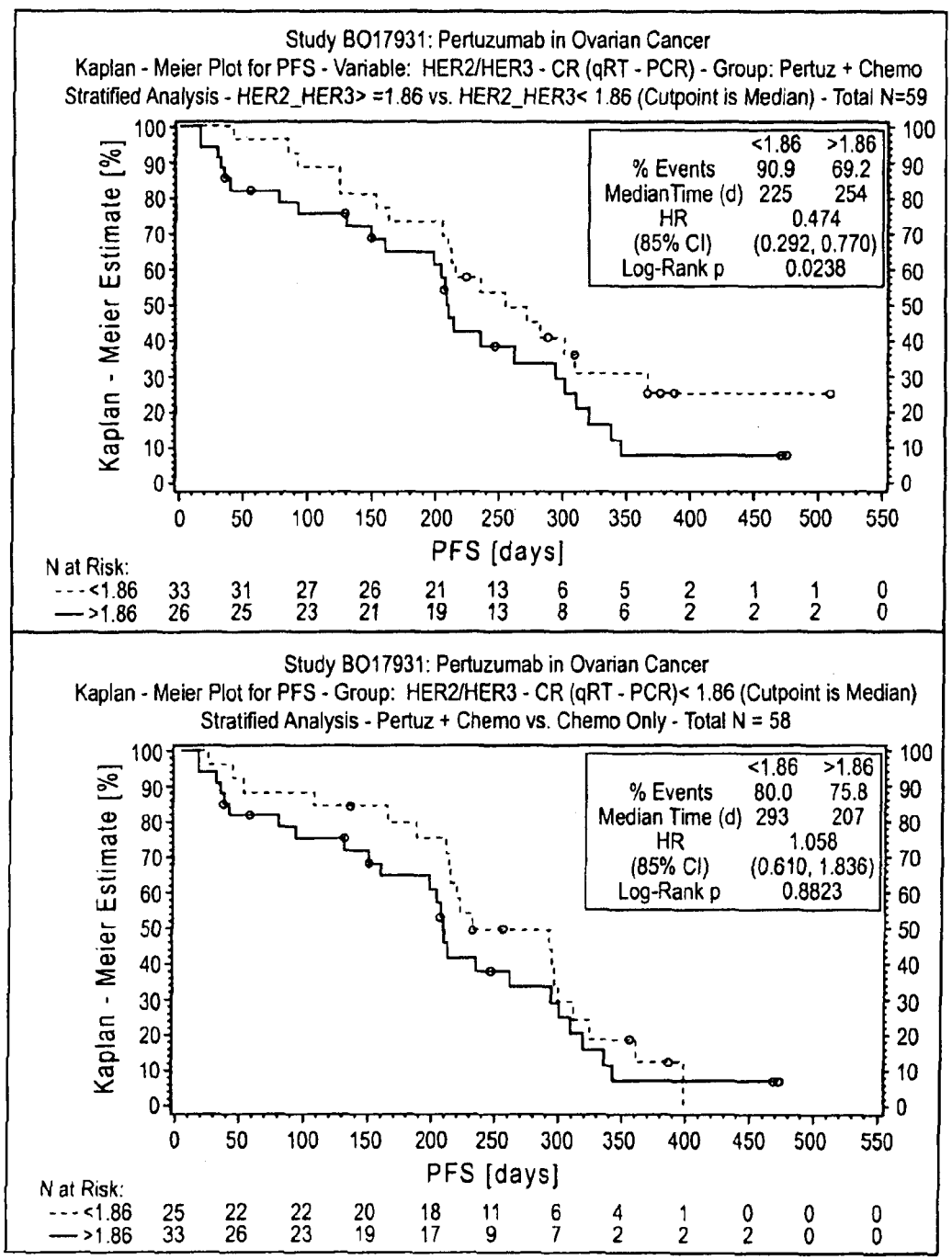
Figure 35:
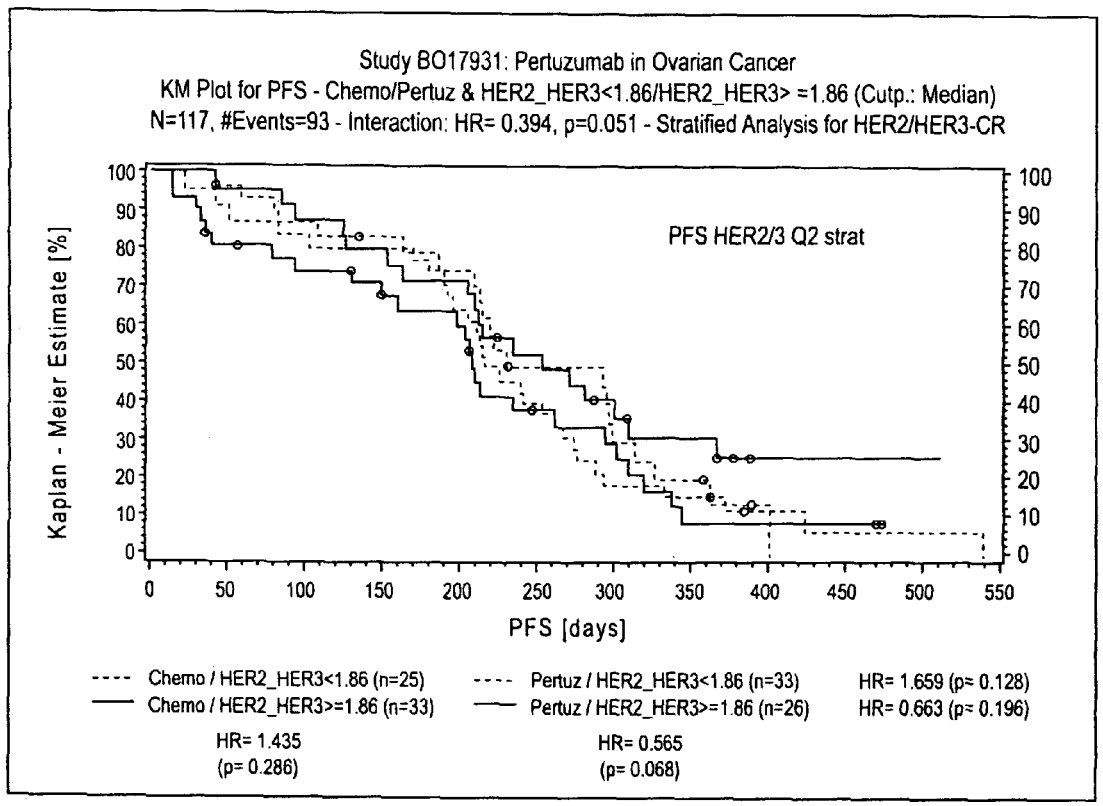
FIG. 35 shows a PFS Kaplan-Meier plot for subjects with ovarian cancer, treated with chemotherapy or pertuzumab, for HER2/HER3 ratios below median and equal to or more than median, respectively.

The PFS results were further assessed with respect to HER2:HER3 ratio. The results of these further analyses are depicted in FIGS. 29 to 31. As these figures show, pertuzumab activity is greatest in patients with a high HER2:HER3 ratio.

Conclusions

Pertuzumab activity is greatest in patients with HER3 low expressing cancer and tends to increase as HER3 gene expression level decreases. Pertuzumab activity is also greatest in patients with high HER2:HER3 expressing cancer and tends to increase as HER2:HER3 gene expression level increases. Most patients with low HER3 expression level that responded to pertuzumab therapy also had a high HER2:HER3 ratio.

There may be a negative interaction between pertuzumab and gemcitabine in patient with HER3 high expressing tumors.

HER3 expression may be prognostic on the background of chemotherapy with high expressing tumors doing better.

The results were surprising and unexpected.

Example 2

Pertuzumab for Therapy of Advanced, Refractory, or Recurrent Ovarian Cancer

This example concerns a single arm, open label, multi-center phase II clinical trial of ovarian cancer patients. Patients with advanced, refractory, or recurrent ovarian cancer were treated with pertuzumab, a humanized HER2 antibody.

Patients with relapsed ovarian cancer were enrolled to receive therapy with "low dose" single agent pertuzumab; pertuzumab was administered intravenously (IV) with a loading of 840 mg followed by 420 mg every 3 weeks.

A second cohort of patients was treated with "high dose" pertuzumab; 1050 mg every 3 weeks, administered as a single agent.

Tumor assessments were obtained after 2, 4, 6, 8, 12 and 16 cycles. Response Rate (RR) by RECIST was the primary endpoint. Safety and tolerability were additionally evaluated. Secondary endpoints were TTP, duration of response, duration of survival, pharmacokinetics (PK), and FOSI (cohort 2).

qRT-PCR assays were performed on archived formalin fixed paraffin embedded tissue. Assay data is available for 46/117 patients. PFS and OS by HER3 qRT-PCR with 25/75 selected as best split is shown in FIG. 25. Here high HER3 expressors were in the greater than and equal to 75$^{th}$ percentile, while low HER3 expressors were in the less than 75$^{th}$ percentile.

Again, patients with low HER3 expression treated with pertuzumab displayed better outcomes in terms of PFS and OS.

Example 3

Pertuzumab for Therapy of Platinum-Resistant Recurrent Ovarian Cancer

In this randomized, open-label Phase II clinical study, the efficacy and safety of pertuzumab treatment in combination with carboplatin-based standard chemotherapy was investigated in patients with platinum-sensitive recurrent ovarian cancer. The target sample size is 100-500 individuals. Target sample size is 148.

Inclusion Criteria:
histologically confirmed ovarian, primary peritoneal, or fallopian tube cancer;
only 1 previous regimen, which must be platinum-based;
platinum-sensitive disease which is defined by a progression-free interval of greater than 6 months after completion of platinum-based chemotherapy.

Exclusion Criteria:
previous radiotherapy;
previous treatment with an anti-cancer vaccine or any targeted therapy;
major surgery or traumatic injury within 4 weeks of study;
history or evidence of central nervous system metastases.

The results are shown in FIGS. 32-35. The results of this trial further confirm that pertuzumab activity is greatest in patients with HER3 low expressing cancer and tends to increase as HER3 gene expression level decreases. Pertuzumab activity is also greatest in patients with high HER2:HER3 expressing cancer and tends to increase as HER2:HER3 gene expression level increases. Most patients with low HER3 expression level that responded to pertuzumab therapy also had a high HER2:HER3 ratio.

There may be a negative interaction between pertuzumab and gemcitabine in patient with HER3 high expressing tumors.

HER3 expression may be prognostic on the background of chemotherapy with high expressing tumors doing better.

Example 4

HER Pathway Gene Expression Analysis in a Phase II Study of Pertuzumab+Gemcitabine Vs. Gemcitabine+Placebo in Patients with Platinum-Resistant Epithelial Ovarian Cancer Background: A randomized phase II trial (N=130) of pertuzumab+gemcitabine vs. gemcitabine vs. placebo in patients with platinum-resistant (CDDP-R) epithelial ovarian cancer (EOC) suggested that pertuzumab could prolong PFS(HR 0.66, 95% CI 0.43, 1.03) and that the duration of PFS may be associated with HER3 gene expression (see Examples 2 and 3).

Methods: Patients with CDDP-R EOC were randomized to G+P or G+placebo. Treatment was given until progression or until unacceptable toxicity. The primary endpoint was PFS. A secondary objective was to evaluate efficacy outcomes in patients with HER2 activation-related expression profiles. A qRT-PCR assay using archival formalin-fixed paraffin-embedded tissue (FFPET), preformed as described above, allowed mRNA expression analysis of HER pathway genes, including HER1, HER2, HER3, amphiregulin, and betacellulin. Outcomes were described by low gene expression (<median) and by high gene expression (≧median).

Results: Of the 5 biomarkers tested, only HER3 gene expression suggested a patient subgroup with a differential PFS and OS outcome based upon low vs. high results. Final PFS and OS outcomes for all patients and by qRT-PCR HER3 outcomes are as follows:

|  | G + P | G + Placebo | Hazard Ratio (95% CI) |
|---|---|---|---|
| PFS (median months) | | | |
| All Patients (n = 130) | 2.9 | 2.6 | 0.66* (0.43, 1.03) |
| Low HER3 (N = 61) | 5.3 | 1.4 | 0.34 (0.18, 0.63) |
| High HER3 (N = 61) | 2.8 | 5.5 | 1.48 (0.83, 2.63) |
| OS (median months) | | | |
| All Patients (n = 130) | 13.0 | 13.1 | 0.91* (0.58, 1.41) |
| Low HER3 (N = 61) | 11.8 | 8.4 | 0.62 (0.35, 1.11) |
| High HER3 (N = 61) | 16.1 | 18.2 | 1.59 (0.8, 3.2) |

*All-patient analyses were stratified by ECOG status, disease measurability and # prior regimens for CDDP-R disease.

Conclusions: This exploratory analysis suggests that low tumor HER3 gene expression levels can be used prognostic indicators in patients with CDDP-R EOC. Pertuzumab treatment may add to gemcitabine's clinical activity in patients whose tumors have low HER3 gene expression. These data suggest that HER3 mRNA expression levels may be used as a prognostic and predictive diagnostic biomarker.

What is claimed is:

1. A method for treating a patient with ovarian, peritoneal, or fallopian tube cancer, comprising administering to the patient a therapeutically effective amount of a HER2 dimerization inhibitor antibody that binds to a heterodimeric binding site of HER2, wherein the patient's cancer has been determined to express HER3 at a level less than the median level for HER3 expression in the cancer type.

2. The method of claim 1 wherein the patient's cancer has been determined to express HER3 at a level which is less than the 25$^{th}$ percentile for HER3 expression in the cancer type.

3. The method of claim 1 or claim 2 wherein HER3 expression has been determined using polymerase chain reaction (PCR).

4. The method of claim 3 wherein the PCR is quantitative reverse transcription polymerase chain reaction (qRT-PCR).

5. The method of claim 1 wherein the antibody has been determined to bind to a junction between domains I, II and III of HER2 extracellular domain.

6. The method of claim 1 wherein the HER2 antibody comprises the variable light and variable heavy amino acid sequences in SEQ ID Nos. 3 and 4, respectively.

7. The method of claim 6 wherein the HER2 antibody is pertuzumab.

8. The method of claim 1 or claim 7 wherein the HER2 antibody is a naked antibody.

9. The method of claim 1 or claim 7 wherein the HER2 antibody is an intact antibody.

10. The method of claim 1 or claim 7 wherein the HER2 antibody is an antibody fragment comprising an antigen binding region.

11. The method of claim 1 or claim 7 wherein the cancer type is platinum-resistant.

12. The method of claim 1 or claim 7 wherein the cancer type is advanced, refractory, or recurrent ovarian cancer.

13. The method of claim 1 or claim 7 which extends progression free survival (PFS) in the patient.

14. The method of claim 1 or claim 7 which extends overall survival (OS) in the patient.

15. The method of claim 1 or claim 7 wherein the HER2 dimerization inhibitor antibody is administered as a single anti-tumor agent.

16. The method of claim 1 or claim 7 comprising administering a second therapeutic agent to the patient.

17. The method claim 16 wherein the second therapeutic agent is selected from the group consisting of chemotherapeutic agent, HER antibody, antibody directed against a tumor associated antigen, anti-hormonal compound, cardioprotectant, cytokine, EGFR-targeted drug, anti-angiogenic agent, tyrosine kinase inhibitor, COX inhibitor, non-steroidal anti-inflammatory drug, farnesyl transferase inhibitor, antibody that binds oncofetal protein CA 125, HER2 vaccine, HER targeting therapy, Raf or ras inhibitor, liposomal doxorubicin, topotecan, taxane, dual tyrosine kinase inhibitor, TLK286, EMD-7200, a medicament that treats nausea, a medicament that prevents or treats skin rash or standard acne therapy, a medicament that treats or prevents diarrhea, a body temperature-reducing medicament, and a hematopoietic growth factor.

18. The method of claim 17 wherein the second therapeutic agent is a chemotherapeutic agent.

19. The method of claim 18 wherein the chemotherapeutic agent is selected from the group consisting of gemcitabine, carboplatin, paclitaxel, docetaxel, topotecan, and liposomal doxorubicin.

20. The method of claim 18 wherein the chemotherapeutic agent is an antimetabolite.

21. The method of claim 20 wherein the antimetabolite chemotherapeutic agent is gemcitabine.

22. The method of claim 16 wherein the second therapeutic agent is trastuzumab, erlotinib, or bevacizumab.

23. The method of claim 1 or claim 7 wherein the patient's cancer expresses HER2:HER3 at a level which is greater than the $25^{th}$ percentile for HER2:HER3 expression in the cancer type.

24. The method of claim 23 wherein the patient's cancer expresses HER2:HER3 at a level which is greater than the median level for HER2:HER3 expression in the cancer type.

25. The method of claim 24 wherein the patient's cancer expresses HER2:HER3 at a level which is greater than the $75^{th}$ percentile for HER2:HER3 expression in the cancer type.

26. A method for treating a patient with ovarian, peritoneal, or fallopian tube cancer comprising administering a therapeutically effective amount of pertuzumab to the patient, wherein the patient's cancer expresses has been determined to express HER3 at a level less than the median level for HER3 expression in ovarian, peritoneal, or fallopian tube cancer.

27. The method of claim 26 wherein the patient's cancer has been determined to express HER3 at a level which is less than the $25^{th}$ percentile for HER3 expression in ovarian, peritoneal, or fallopian tube cancer.

28. The method of claim 26 or claim 27 wherein HER3 expression has been determined using polymerase chain reaction (PCR).

29. The method of claim 28 wherein the PCR is quantitative reverse transcription polymerase chain reaction (qRT-PCR).

30. The method of claim 26 or claim 27 which extends progression free survival (PFS).

31. The method of claim 26 or claim 27 which extends overall survival (OS).

32. The method of claim 26 or claim 27 wherein the patient has ovarian cancer.

33. The method of claim 32 wherein the ovarian cancer is platinum-resistant ovarian cancer.

34. The method of claim 32 wherein the patient has advanced, refractory, or recurrent ovarian cancer.

35. The method of claim 26 or claim 27 further comprising administering a chemotherapeutic agent to the patient.

36. The method of claim 35 wherein the chemotherapeutic agent is selected from the group consisting of gemcitabine, carboplatin, paclitaxel, docetaxel, topotecan, and liposomal doxorubicin.

37. The method of claim 36 wherein the chemotherapeutic agent is an antimetabolite chemotherapeutic agent.

38. The method of claim 37 wherein the antimetabolite chemotherapeutic agent is gemcitabine.

39. The method of claim 26 or claim 27 wherein the patient's cancer expresses HER2:HER3 at a level which is greater than the $25^{th}$ percentile for HER2:HER3 expression in the cancer type.

40. The method of claim 39 wherein the patient's cancer expresses HER2:HER3 at a level which is greater than the median level for HER2:HER3 expression in the cancer type.

41. The method of claim 40 wherein the patient's cancer expresses HER2:HER3 at a level which is greater than the $75^{th}$ percentile for HER2:HER3 expression in ovarian, peritoneal, or fallopian tube cancer.

42. A method for treating a patient with a type of ovarian, peritoneal, or fallopian tube cancer, comprising administering a therapeutically effective amount of a HER2 dimerization inhibitor antibody that binds to a heterodimeric binding site of HER2 to the patient, wherein the patient's cancer has been determined to express HER2:HER3 at a level which is greater than the $25^{th}$ percentile for HER2:HER3 expression in the cancer type.

43. The method of claim 42 wherein the patient's cancer has been determined to express HER2:HER3 at a level which is greater than the median level for HER2:HER3 expression in the cancer type.

44. The method of claim 43 wherein the patient's cancer has been determined to express HER2:HER3 at a level which is greater than the $75^{th}$ percentile for HER2:HER3 expression in the cancer type.

45. The method of claim 42, 43 or 44 wherein HER2 and HER3 expression has been determined using polymerase chain reaction (PCR).

46. The method of claim 45 wherein the PCR is quantitative reverse transcription polymerase chain reaction (qRT-PCR).

47. The method of claim 42 wherein the HER2 antibody binds to a junction between domains I, II and III of HER2 extracellular domain.

48. The method of claim 47 wherein the HER2 antibody comprises the variable light and variable heavy amino acid sequences in SEQ ID Nos. 3 and 4, respectively.

49. The method of claim 48 wherein the HER2 antibody is pertuzumab.

50. The method of claim 42 or claim 49 wherein the HER2 antibody is a naked antibody.

51. The method of claim 42 or claim 49 wherein the HER2 antibody is an intact antibody.

52. The method of claim 42 or claim 49 wherein the HER2 antibody is an antibody fragment comprising an antigen binding region.

53. The method of claim 42 or claim 49 wherein the cancer type is platinum-resistant.

54. The method of claim 42 or claim 49 wherein the cancer type is advanced, refractory, or recurrent ovarian cancer.

55. The method of claim 42 or claim 49 which extends progression free survival (PFS) in the patient.

56. The method of claim 42 or claim 49 which extends overall survival (OS) in the patient.

57. The method of claim 42 or claim 49 wherein the HER2 dimerization inhibitor antibody is administered as a single anti-tumor agent.

58. The method of claim 42 or claim 49 comprising administering a second therapeutic agent to the patient.

59. The method claim 58 wherein the second therapeutic agent is selected from the group consisting of chemotherapeutic agent, HER antibody, antibody directed against a tumor associated antigen, anti-hormonal compound, cardioprotectant, cytokine, EGFR-targeted drug, anti-angiogenic agent, tyrosine kinase inhibitor, COX inhibitor, non-steroidal anti-inflammatory drug, farnesyl transferase inhibitor, antibody that binds oncofetal protein CA 125, HER2 vaccine, HER targeting therapy, Raf or ras inhibitor, liposomal doxorubicin, topotecan, taxane, dual tyrosine kinase inhibitor, TLK286, EMD-7200, a medicament that treats nausea, a medicament that prevents or treats skin rash or standard acne therapy, a medicament that treats or prevents diarrhea, a body temperature-reducing medicament, and a hematopoietic growth factor.

60. The method of claim 58 wherein the second therapeutic agent is a chemotherapeutic agent.

61. The method of claim 60 wherein the chemotherapeutic agent is selected from the group consisting of gemcitabine, carboplatin, paclitaxel, docetaxel, topotecan, and liposomal doxorubicin.

62. The method of claim 60 wherein the chemotherapeutic agent is an antimetabolite.

63. The method of claim 62 wherein the antimetabolite chemotherapeutic agent is gemcitabine.

64. The method of claim 58 wherein the second therapeutic agent is trastuzumab, erlotinib, or bevacizumab.

\* \* \* \* \*

UNITED STATES PATENT AND TRADEMARK OFFICE
CERTIFICATE OF CORRECTION

PATENT NO. : 7,981,418 B2  
APPLICATION NO. : 12/074229  
DATED : July 19, 2011  
INVENTOR(S) : Amler et al.

Page 1 of 1

It is certified that error appears in the above-identified patent and that said Letters Patent is hereby corrected as shown below:

In column 109, line 43, claim 26 delete "expresses".

In column 110, line 20, claim 42 delete "a type of".

Signed and Sealed this
Eighteenth Day of October, 2011

David J. Kappos
*Director of the United States Patent and Trademark Office*

SEQUENCE LISTING

<160> NUMBER OF SEQ ID NOS: 52

<210> SEQ ID NO 1
<211> LENGTH: 107
<212> TYPE: PRT
<213> ORGANISM: Mus musculus

<400> SEQUENCE: 1

Asp Thr Val Met Thr Gln Ser His Lys Ile Met Ser Thr Ser Val Gly
1               5                   10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105

<210> SEQ ID NO 2
<211> LENGTH: 119
<212> TYPE: PRT
<213> ORGANISM: Mus Musculus

<400> SEQUENCE: 2

Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
    50                  55                  60

Lys Gly Lys Ala Ser Leu Thr Val Asp Arg Ser Ser Arg Ile Val Tyr
65                  70                  75                  80

Met Glu Leu Arg Ser Leu Thr Phe Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115

<210> SEQ ID NO 3
<211> LENGTH: 107
<212> TYPE: PRT
<213> ORGANISM: Artificial Sequence
<220> FEATURE:
<223> OTHER INFORMATION: Sequence is synthesized

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

```
Val Ala Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
                100                 105

<210> SEQ ID NO 4
<211> LENGTH: 119
<212> TYPE: PRT
<213> ORGANISM: Artificial Sequence
<220> FEATURE:
<223> OTHER INFORMATION: Sequence is synthesized

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
                100                 105                 110

Thr Leu Val Thr Val Ser Ser
        115

<210> SEQ ID NO 5
<211> LENGTH: 107
<212> TYPE: PRT
<213> ORGANISM: Artificial Sequence
<220> FEATURE:
<223> OTHER INFORMATION: Sequence is synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Ala Trp Tyr Gln Gln Lys Pro Gly Lys Ala Pro Lys Leu Leu Ile
            35                  40                  45

Tyr Ala Ala Ser Ser Leu Glu Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Trp
                85                  90                  95

Thr Phe Gly Gln Gly Thr Lys Val Glu Ile Lys
                100                 105
```

<210> SEQ ID NO 6
<211> LENGTH: 119
<212> TYPE: PRT
<213> ORGANISM: Artificial Sequence
<220> FEATURE:
<223> OTHER INFORMATION: Sequence is synthesized

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Val Gly Tyr Ser Leu Tyr Asp Tyr Trp Gly Gln Gly
            100                 105                 110

Thr Leu Val Thr Val Ser Ser
        115

<210> SEQ ID NO 7
<211> LENGTH: 10
<212> TYPE: PRT
<213> ORGANISM: Artificial Sequence
<220> FEATURE:
<223> OTHER INFORMATION: Humanized Antibody Sequence
<220> FEATURE:
<221> NAME/KEY: VARIANT
<222> LOCATION: 10
<223> OTHER INFORMATION: Xaa = preferably Asp or Ser
<220> FEATURE:
<221> NAME/KEY: VARIANT
<222> LOCATION: 10
<223> OTHER INFORMATION: Xaa = Any Amino Acid

<400> SEQUENCE: 7

Gly Phe Thr Phe Thr Asp Tyr Thr Met Xaa
1               5                   10

<210> SEQ ID NO 8
<211> LENGTH: 17
<212> TYPE: PRT
<213> ORGANISM: Artificial Sequence
<220> FEATURE:
<223> OTHER INFORMATION: Humanized Antibody Sequence

<400> SEQUENCE: 8

Asp Val Asn Pro Asn Ser Gly Gly Ser Ile Tyr Asn Gln Arg Phe Lys
1               5                   10                  15

Gly

<210> SEQ ID NO 9
<211> LENGTH: 10
<212> TYPE: PRT
<213> ORGANISM: Artificial Sequence
<220> FEATURE:
<223> OTHER INFORMATION: Humanized Antibody Sequence

<400> SEQUENCE: 9

-continued

```
Asn Leu Gly Pro Ser Phe Tyr Phe Asp Tyr
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Humanized Antibody Sequence

<400> SEQUENCE: 10

Lys Ala Ser Gln Asp Val Ser Ile Gly Val Ala
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Humanized Antibody Sequence
<220> FEATURE:
<221> NAME/KEY: VARIANT
<222> LOCATION: 5
<223> OTHER INFORMATION: Xaa is preferably Arg or Leu
<220> FEATURE:
<221> NAME/KEY: VARIANT
<222> LOCATION: 6
<223> OTHER INFORMATION: Xaa is preferably Tyr or Glu
<220> FEATURE:
<221> NAME/KEY: VARIANT
<222> LOCATION: 7
<223> OTHER INFORMATION: Xaa is preferably Thr or Ser

<400> SEQUENCE: 11

Ser Ala Ser Tyr Xaa Xaa Xaa
1               5

<210> SEQ ID NO 12
<211> LENGTH: 9
<212> TYPE: PRT
<213> ORGANISM: Artificial Sequence
<220> FEATURE:
<223> OTHER INFORMATION: Humanized Antibody Sequence

<400> SEQUENCE: 12

Gln Gln Tyr Tyr Ile Tyr Pro Tyr Thr
1               5

<210> SEQ ID NO 13
<211> LENGTH: 214
<212> TYPE: PRT
<213> ORGANISM: Artificial Sequence
<220> FEATURE:
<223> OTHER INFORMATION: Sequence is synthesized

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 14
<211> LENGTH: 448
<212> TYPE: PRT
<213> ORGANISM: Artificial Sequence
<220> FEATURE:
<223> OTHER INFORMATION: Sequence is synthesized

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
```

```
                225                 230                 235                 240
Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                    405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 15
<211> LENGTH: 214
<212> TYPE: PRT
<213> ORGANISM: Artificial Sequence
<220> FEATURE:
<223> OTHER INFORMATION: Sequence is synthesized

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 16
<211> LENGTH: 449
<212> TYPE: PRT
<213> ORGANISM: Artificial Sequence
<220> FEATURE:
<223> OTHER INFORMATION: Sequence is synthesized

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly

<210> SEQ ID NO 17
<211> LENGTH: 217
<212> TYPE: PRT
<213> ORGANISM: Artificial Sequence
<220> FEATURE:
<223> OTHER INFORMATION: Sequence is synthesized

<400> SEQUENCE: 17

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
                20                  25                  30

Ser Ile Gly Val Ala Trp Tyr Gln Gln Lys Pro Gly Lys Ala Pro Lys
            35                  40                  45

Leu Leu Ile Tyr Ser Ala Ser Tyr Arg Tyr Thr Gly Val Pro Ser Arg
50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
                100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
210                 215
```

<210> SEQ ID NO 18
<211> LENGTH: 449
<212> TYPE: PRT
<213> ORGANISM: Artificial Sequence
<220> FEATURE:
<223> OTHER INFORMATION: Sequence is synthesized

<400> SEQUENCE: 18

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 19
<211> LENGTH: 195
<212> TYPE: PRT
<213> ORGANISM: Homo sapiens

<400> SEQUENCE: 19

Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
            20                  25                  30

Val Val Gln Gly Asn Leu Glu Leu Thr Tyr Leu Pro Thr Asn Ala Ser
        35                  40                  45

Leu Ser Phe Leu Gln Asp Ile Gln Glu Val Gln Gly Tyr Val Leu Ile
    50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg
        195

<210> SEQ ID NO 20
<211> LENGTH: 124
<212> TYPE: PRT
<213> ORGANISM: Homo sapiens

<400> SEQUENCE: 20

Thr Val Cys Ala Gly Gly Cys Ala Arg Cys Lys Gly Pro Leu Pro Thr
1               5                   10                  15

Asp Cys Cys His Glu Gln Cys Ala Ala Gly Cys Thr Gly Pro Lys His
            20                  25                  30

Ser Asp Cys Leu Ala Cys Leu His Phe Asn His Ser Gly Ile Cys Glu
        35                  40                  45
```

```
Leu His Cys Pro Ala Leu Val Thr Tyr Asn Thr Asp Thr Phe Glu Ser
        50                  55                  60

Met Pro Asn Pro Glu Gly Arg Tyr Thr Phe Gly Ala Ser Cys Val Thr
 65                  70                  75                  80

Ala Cys Pro Tyr Asn Tyr Leu Ser Thr Asp Val Gly Ser Cys Thr Leu
                85                  90                  95

Val Cys Pro Leu His Asn Gln Glu Val Thr Ala Glu Asp Gly Thr Gln
            100                 105                 110

Arg Cys Glu Lys Cys Ser Lys Pro Cys Ala Arg Val
            115                 120

<210> SEQ ID NO 21
<211> LENGTH: 169
<212> TYPE: PRT
<213> ORGANISM: Homo sapiens

<400> SEQUENCE: 21

Cys Tyr Gly Leu Gly Met Glu His Leu Arg Glu Val Arg Ala Val Thr
 1               5                  10                  15

Ser Ala Asn Ile Gln Glu Phe Ala Gly Cys Lys Lys Ile Phe Gly Ser
                20                  25                  30

Leu Ala Phe Leu Pro Glu Ser Phe Asp Gly Asp Pro Ala Ser Asn Thr
            35                  40                  45

Ala Pro Leu Gln Pro Glu Gln Leu Gln Val Phe Glu Thr Leu Glu Glu
 50                  55                  60

Ile Thr Gly Tyr Leu Tyr Ile Ser Ala Trp Pro Asp Ser Leu Pro Asp
 65                  70                  75                  80

Leu Ser Val Phe Gln Asn Leu Gln Val Ile Arg Gly Arg Ile Leu His
                85                  90                  95

Asn Gly Ala Tyr Ser Leu Thr Leu Gln Gly Leu Gly Ile Ser Trp Leu
            100                 105                 110

Gly Leu Arg Ser Leu Arg Glu Leu Gly Ser Gly Leu Ala Leu Ile His
            115                 120                 125

His Asn Thr His Leu Cys Phe Val His Thr Val Pro Trp Asp Gln Leu
130                 135                 140

Phe Arg Asn Pro His Gln Ala Leu Leu His Thr Ala Asn Arg Pro Glu
145                 150                 155                 160

Asp Glu Cys Val Gly Glu Gly Leu Ala
            165

<210> SEQ ID NO 22
<211> LENGTH: 142
<212> TYPE: PRT
<213> ORGANISM: Homo Sapiens

<400> SEQUENCE: 22

Cys His Gln Leu Cys Ala Arg Gly His Cys Trp Gly Pro Gly Pro Thr
 1               5                  10                  15

Gln Cys Val Asn Cys Ser Gln Phe Leu Arg Gly Gln Glu Cys Val Glu
                20                  25                  30

Glu Cys Arg Val Leu Gln Gly Leu Pro Arg Glu Tyr Val Asn Ala Arg
            35                  40                  45

His Cys Leu Pro Cys His Pro Glu Cys Gln Pro Gln Asn Gly Ser Val
        50                  55                  60

Thr Cys Phe Gly Pro Glu Ala Asp Gln Cys Val Ala Cys Ala His Tyr
 65                  70                  75                  80
```

```
Lys Asp Pro Pro Phe Cys Val Ala Arg Cys Pro Ser Gly Val Lys Pro
                85                  90                  95
Asp Leu Ser Tyr Met Pro Ile Trp Lys Phe Pro Asp Glu Glu Gly Ala
            100                 105                 110
Cys Gln Pro Cys Pro Ile Asn Cys Thr His Ser Cys Val Asp Leu Asp
        115                 120                 125
Asp Lys Gly Cys Pro Ala Glu Gln Arg Ala Ser Pro Leu Thr
    130                 135                 140
```

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
tgcggatgtc agccactgtg                                               20

<210> SEQ ID NO 24
<211> LENGTH: 19
<212> TYPE: DNA
<213> ORGANISM: Artificial Sequence
<220> FEATURE:
<223> OTHER INFORMATION: Primer

<400> SEQUENCE: 24
gggtgcatcg ggtgacctg                                                19

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
agccactgtg aggcggga                                                 18

<210> SEQ ID NO 26
<211> LENGTH: 25
<212> TYPE: DNA
<213> ORGANISM: Artificial Sequence
<220> FEATURE:
<223> OTHER INFORMATION: Probe

<400> SEQUENCE: 26
ggtgttttcg ggcagaaggc catcc                                         25

<210> SEQ ID NO 27
<211> LENGTH: 29
<212> TYPE: DNA
<213> ORGANISM: Artificial Sequence
<220> FEATURE:
<223> OTHER INFORMATION: Probe

<400> SEQUENCE: 27
aacagccacc agatggtggg gtagatctt                                     29

<210> SEQ ID NO 28
<211> LENGTH: 21
<212> TYPE: DNA
<213> ORGANISM: Artificial Sequence
<220> FEATURE:
<223> OTHER INFORMATION: Primer

```
<400> SEQUENCE: 28
ccgtcaatgt agtgggcaca c                                    21

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
gggtgagcca agggagtttg                                      20

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
gcacactgga tacagttgtc tggtc                                25

<210> SEQ ID NO 31
<211> LENGTH: 27
<212> TYPE: DNA
<213> ORGANISM: Artificial Sequence
<220> FEATURE:
<223> OTHER INFORMATION: Probe

<400> SEQUENCE: 31
tgtgcaggtg atgttcatgg cctgagg                              27

<210> SEQ ID NO 32
<211> LENGTH: 26
<212> TYPE: DNA
<213> ORGANISM: Artificial Sequence
<220> FEATURE:
<223> OTHER INFORMATION: Probe

<400> SEQUENCE: 32
cactctgggt ggcactgtat gcactc                               26

<210> SEQ ID NO 33
<211> LENGTH: 20
<212> TYPE: DNA
<213> ORGANISM: Artificial Sequence
<220> FEATURE:
<223> OTHER INFORMATION: Primer

<400> SEQUENCE: 33
ggacctgcct cacttggttg                                      20

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
caggtggtgc agggaaacct                                      20

<210> SEQ ID NO 35
<211> LENGTH: 21
<212> TYPE: DNA
```

-continued

<213> ORGANISM: Artificial Sequence
<220> FEATURE:
<223> OTHER INFORMATION: Primer

<400> SEQUENCE: 35
ctgcctcact tggttgtgag c                                          21

<210> SEQ ID NO 36
<211> LENGTH: 25
<212> TYPE: DNA
<213> ORGANISM: Artificial Sequence
<220> FEATURE:
<223> OTHER INFORMATION: Probe

<400> SEQUENCE: 36
caatgccagc ctgtccttcc tgcag                                      25

<210> SEQ ID NO 37
<211> LENGTH: 26
<212> TYPE: DNA
<213> ORGANISM: Artificial Sequence
<220> FEATURE:
<223> OTHER INFORMATION: Probe

<400> SEQUENCE: 37
tatccaggag gtgcagggct acgtgc                                     26

<210> SEQ ID NO 38
<211> LENGTH: 24
<212> TYPE: DNA
<213> ORGANISM: Artificial Sequence
<220> FEATURE:
<223> OTHER INFORMATION: Primer

<400> SEQUENCE: 38
gtgtccatgt gacaaagctt atcg                                       24

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39
gatgggaagt ttgccatctt cg                                         22

<210> SEQ ID NO 40
<211> LENGTH: 25
<212> TYPE: DNA
<213> ORGANISM: Artificial Sequence
<220> FEATURE:
<223> OTHER INFORMATION: Primer

<400> SEQUENCE: 40
tctcaatata aacaccccct gacag                                      25

<210> SEQ ID NO 41
<211> LENGTH: 24
<212> TYPE: DNA
<213> ORGANISM: Artificial Sequence
<220> FEATURE:
<223> OTHER INFORMATION: Probe

<400> SEQUENCE: 41
aacaccaact ccagccacgc tctg                                       24

```
<210> SEQ ID NO 42
<211> LENGTH: 24
<212> TYPE: DNA
<213> ORGANISM: Artificial Sequence
<220> FEATURE:
<223> OTHER INFORMATION: Probe

<400> SEQUENCE: 42
agctccgctt gactcagctc accg                                              24

<210> SEQ ID NO 43
<211> LENGTH: 14
<212> TYPE: DNA
<213> ORGANISM: Artificial Sequence
<220> FEATURE:
<223> OTHER INFORMATION: Primer

<400> SEQUENCE: 43
cttgtcgaag tttc                                                         14

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
ccatagctgc ctttatgtct gc                                                22

<210> SEQ ID NO 45
<211> LENGTH: 24
<212> TYPE: DNA
<213> ORGANISM: Artificial Sequence
<220> FEATURE:
<223> OTHER INFORMATION: Primer

<400> SEQUENCE: 45
ctttcgttcc tcagcttctc cttc                                              24

<210> SEQ ID NO 46
<211> LENGTH: 24
<212> TYPE: DNA
<213> ORGANISM: Artificial Sequence
<220> FEATURE:
<223> OTHER INFORMATION: Probe

<400> SEQUENCE: 46
tgatcctcac agctgttgct gtta                                              24

<210> SEQ ID NO 47
<211> LENGTH: 33
<212> TYPE: DNA
<213> ORGANISM: Artificial Sequence
<220> FEATURE:
<223> OTHER INFORMATION: Probe

<400> SEQUENCE: 47
tacagtccag cttagaagac aatacgtcag gaa                                    33

<210> SEQ ID NO 48
<211> LENGTH: 16
<212> TYPE: DNA
<213> ORGANISM: Artificial Sequence
<220> FEATURE:
<223> OTHER INFORMATION: Primer
```

```
<400> SEQUENCE: 48
gtcaactctc tcacac                                                          16

<210> SEQ ID NO 49
<211> LENGTH: 16
<212> TYPE: DNA
<213> ORGANISM: Artificial Sequence
<220> FEATURE:
<223> OTHER INFORMATION: Primer

<400> SEQUENCE: 49
tctaggtgcc ccaagc                                                          16

<210> SEQ ID NO 50
<211> LENGTH: 21
<212> TYPE: DNA
<213> ORGANISM: Artificial Sequence
<220> FEATURE:
<223> OTHER INFORMATION: Primer

<400> SEQUENCE: 50
tagccttcat cacagacaca g                                                    21

<210> SEQ ID NO 51
<211> LENGTH: 27
<212> TYPE: DNA
<213> ORGANISM: Artificial Sequence
<220> FEATURE:
<223> OTHER INFORMATION: Probe

<400> SEQUENCE: 51
gcattactgc atcaaaggga gatgccg                                              27

<210> SEQ ID NO 52
<211> LENGTH: 20
<212> TYPE: DNA
<213> ORGANISM: Artificial Sequence
<220> FEATURE:
<223> OTHER INFORMATION: Probe

<400> SEQUENCE: 52
tcgtggtggc cgagcagacg                                                      20
```